(12) United States Patent
Hagiwara et al.

(10) Patent No.: US 7,432,392 B2
(45) Date of Patent: Oct. 7, 2008

(54) ESTER DERIVATIVES AND MEDICAL USE THEREOF

(75) Inventors: Atsushi Hagiwara, Osaka (JP); Taku Ikenogami, Osaka (JP); Yasuko Mera, Osaka (JP); Yukako Sumida, Osaka (JP); Akio Iida, Osaka (JP); Toshio Taniguchi, Osaka (JP); Mitsuru Takahashi, Osaka (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 11/362,375

(22) Filed: Feb. 27, 2006

(65) Prior Publication Data

US 2006/0205726 A1    Sep. 14, 2006

Related U.S. Application Data

(63) Continuation of application No. PCT/JP2004/012407, filed on Aug. 27, 2004.

(30) Foreign Application Priority Data

Aug. 29, 2003    (JP)    ............... 2003-305877

(51) Int. Cl.
*C07C 69/34* (2006.01)
*C07C 69/66* (2006.01)
*A01N 47/06* (2006.01)
*A61K 31/21* (2006.01)

(52) U.S. Cl. .............. 560/190; 560/177; 514/512; 514/514

(58) Field of Classification Search .............. None
See application file for complete search history.

(56) References Cited

U.S. PATENT DOCUMENTS

| | | |
|---|---|---|
| 5,683,682 A | 11/1997 | Betts |
| 5,827,875 A | 10/1998 | Dickson, Jr. et al. |
| 5,962,440 A | 10/1999 | Sulsky |
| 6,057,339 A | 5/2000 | Gregg |
| 6,121,283 A | 9/2000 | Chang et al. |
| 6,171,599 B1 | 1/2001 | Miyamoto et al. |
| 6,235,730 B1 | 5/2001 | Sato et al. |
| 6,288,234 B1 | 9/2001 | Griffin |
| 6,369,075 B1 | 4/2002 | Ruggeri et al. |
| 6,617,325 B1 | 9/2003 | Lehmann-Lintz et al. |
| 6,713,489 B2 | 3/2004 | Ruggeri et al. |
| 6,818,644 B1 | 11/2004 | Lehmann-Lintz et al. |
| 6,943,185 B2 * | 9/2005 | Susilo et al. .............. 514/365 |
| 2001/0007678 A1 | 7/2001 | Baert |
| 2002/0012706 A1 | 1/2002 | Vladyka, Jr. |
| 2002/0028943 A1 | 3/2002 | Griffin |
| 2002/0032238 A1 | 3/2002 | Priepke et al. |
| 2003/0044528 A1 | 3/2003 | Tanno et al. |
| 2003/0114442 A1 | 6/2003 | Heckel et al. |
| 2004/0058903 A1 | 3/2004 | Takasugi et al. |
| 2005/0075367 A1 | 4/2005 | Hagiwara et al. |
| 2006/0089392 A1 | 4/2006 | Hagiwara et al. |
| 2006/0153913 A1 | 7/2006 | Yamane et al. |

FOREIGN PATENT DOCUMENTS

| | | |
|---|---|---|
| CA | 2 291 471 | 12/1999 |
| CA | 2 324 800 | 10/2000 |
| CA | 2 376 881 | 1/2001 |
| EP | 1099701 | 5/2001 |
| EP | 1 769 793 A1 | 4/2007 |
| JP | 47-25189 | 10/1972 |
| JP | 57-206612 | 2/1982 |
| JP | 3-1288 B | 1/1991 |
| JP | 3-28404 B | 4/1991 |
| JP | 05-097672 | 4/1993 |
| JP | 08-208476 | 8/1996 |
| JP | 9-59159 | 3/1997 |
| JP | 9-309834 | 12/1997 |
| JP | 11-228569 | 8/1999 |
| JP | 11-509238 | 8/1999 |
| JP | 11-246404 | 9/1999 |
| JP | 2000-169395 | 6/2000 |
| JP | 2000-281561 | 10/2000 |
| JP | 2001-172180 | 6/2001 |
| JP | 2002-220345 | 8/2002 |
| JP | 2003-73261 | 3/2003 |
| JP | 2003-509505 | 3/2003 |
| JP | 2003-531099 | 10/2003 |
| JP | 2003-321424 | 11/2003 |
| JP | 2004-10575 | 1/2004 |

(Continued)

OTHER PUBLICATIONS

Hagiwara et al., CAPLUS AN 2003:696857 (Feb. 28, 2003), 2 Pages Only.*

(Continued)

*Primary Examiner*—Kamal Saeed
*Assistant Examiner*—Sun Jae Y Loewe
(74) *Attorney, Agent, or Firm*—Finnegan, Henderson, Farabow, Garrett & Dunner, LLP

(57) ABSTRACT

A therapeutic agent for hyperlipidemia which has no side effects on the liver unlike conventional MTP inhibitors and has excellent MTP inhibitory activity. Also, provided is an ester compound represented by the general formula (1):

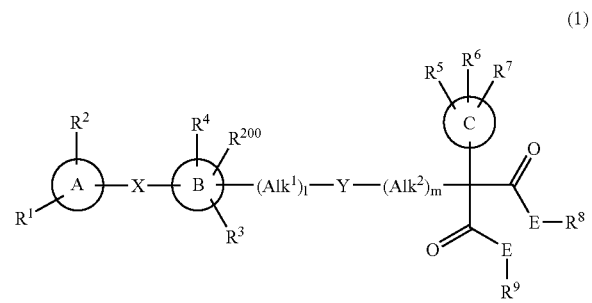

or a pharmaceutically acceptable salt thereof.

11 Claims, No Drawings

FOREIGN PATENT DOCUMENTS

| | | |
|---|---|---|
| JP | 2004-510763 | 4/2004 |
| WO | WO 96/40640 | 12/1996 |
| WO | WO 97/26240 | 7/1997 |
| WO | WO 97/43257 | 11/1997 |
| WO | WO 98/23593 | 6/1998 |
| WO | WO 98/47875 | 10/1998 |
| WO | WO 99/63929 | 12/1999 |
| WO | WO 00/5201 | 2/2000 |
| WO | WO 00/32582 | 6/2000 |
| WO | WO 00/37422 | 6/2000 |
| WO | WO 00/56726 | 9/2000 |
| WO | WO 01/00183 | 1/2001 |
| WO | WO 01/00184 | 1/2001 |
| WO | WO 01/00189 | 1/2001 |
| WO | WO 01/05762 | 1/2001 |
| WO | WO 01/12601 | 2/2001 |
| WO | WO 01/21604 | 3/2001 |
| WO | WO 01/47898 | 7/2001 |
| WO | WO 01/47899 | 7/2001 |
| WO | WO 01/53260 | 7/2001 |
| WO | WO 01/77077 | 10/2001 |
| WO | WO 01/97810 | 12/2001 |
| WO | WO 02/04403 | 1/2002 |
| WO | WO 02/20501 | 3/2002 |
| WO | WO 02/28835 | 4/2002 |
| WO | WO 02/042271 | 5/2002 |
| WO | WO 02/42291 | 5/2002 |
| WO | WO 02/051385 | 7/2002 |
| WO | WO 02/081460 | 10/2002 |
| WO | WO 02/098839 | 12/2002 |
| WO | WO 05/021486 | 3/2005 |
| WO | WO 06/043510 | 4/2006 |
| WO | WO 06/046623 | 5/2006 |

OTHER PUBLICATIONS

Rx for Success, Lipid Levels—The Risk of Arteriosclerosis, Prudential Financial, 2002, 2 pages.*
http://www.nhlbi.nih.gov/health/dci/Diseases/Cad/CAD_WhatIs.html.*
Japan Tobacco Inc. Clinical Development.*
http://cholesterol.about.com/od/treatments/a/mttpinhibitor.htm.*
Aggarwal et al., BMC Cardiovascular Disorders, 2005, 5:30, pp. 1-8.*
http://www.mayoclinic.com/health/arteriosclerosis-atherosclerosis/DS00525/DSECTION=8.*
http://www.mayoclinic.com/health/obesity/DS00314/DSECTION=7.*
Ksander et al., Diaminoindanes as Microsomal Triglyceride Transfer Protein Inhibitors, J. Med. Chem., vol. 44 (26), pp. 4677-4687 (2001).
Robl et al., *Novel Series of Highly Potent Benzimidazole-Based Microsomal Triglyceride Transfer Protein Inhibitors*, J. Med. Chem., vol. 44 (6), pp. 851-856 (2001).
Wetterau et al., Purification and Characterization of Microsomal Triglyceride and Cholesteryl Ester Transfer Protein from Bovine Liver Microsomes, Chem. Phys. Lipids, vol. 38, pp. 205-222 (1985).
Anastasiou, Theordore J., et al., "Syntheses of aminosalicylate-based polyanhydride prodrugs: esters, amides, and azos," Polymer Preprints (American Chemical Society, Division of Polymer Chemistry) 42(2), 121-122 (2001).
Chiou, W.L. et al., Pharmaceutical Application of Solid Dispersion Systems, J. Pharm. Sci. 60 (1971) 1281-1302.
Fischer et al., Journal of the Chemical Society (B), Rates of Base-catalyzed Hydrolysis of Substituted Aryl Benzoates, 1971, pp. 1818-1819.
Shiomi et al., MTP inhibitor decreases plasma cholesterol levels in LDL receptor-deficient WHHL rabbits by lowering the VLDL secrection, European Journal of Pharmacology, vol. 431, pp. 127-131 (2001).
European Search Report of Application No. 04772363.0 dated Jan. 23, 2008.
International Search Report of PCT/JP03/02398 dated Jun. 3, 2003.
International Search Report of PCT/JP2004/012407 dated Feb. 15, 2005.
PCT International Search Report (PCT/JP2005/019744) dated Dec. 13, 2005.
International Search Report (PCT/JP2005/019041) dated Jan. 24, 2006.
SciFinder Scholar, version 2007.1; Chemical Abstracts Service, Columbus, OH; RN 339202-67-4 (accessed Feb. 6, 2008).
SciFinder Scholar, version 2007.1; Chemical Abstracts Service, Columbus, OH; RN 339202-91-4 (accessed Feb. 6, 2008).
SciFinder Scholar, version 2007.1; Chemical Abstracts Service, Columbus, OH; RN 516466-52-7 (accessed Feb. 6, 2008).
SciFinder Scholar, version 2007.1; Chemical Abstracts Service, Columbus, OH; RN 901355-00-8 (accessed Feb. 6, 2008).
SciFinder Scholar, version 2007.1; Chemical Abstracts Service, Columbus, OH; RN 888922-25-6 (accessed Feb. 6, 2008).
SciFinder Scholar, version 2007.1; Chemical Abstracts Service, Columbus, OH; RN 900909-90-2 (accessed Feb. 6, 2008).

* cited by examiner

ESTER DERIVATIVES AND MEDICAL USE THEREOF

This is a continuation of Application No. PCT/JP2004/012407, filed Aug. 27, 2004 and claims the benefit of JP2003-305877, filed Aug. 29, 2003 all of which are incorporated herein by reference.

TECHNICAL FIELD

The present invention relates to a novel ester derivative or a novel carbonate compound, and also relates to a pharmaceutical composition comprising a novel ester derivative or its prodrug or a pharmaceutically acceptable salt thereof, which selectively inhibits microsomal triglyceride transfer protein (hereinafter also abbreviated as MTP) in the small intestine. Further, the present invention relates to an agent for the treatment or prophylaxis of hyperlipidemia, arteriosclerosis, coronary artery diseases, obesity, diabetes or hypertension, comprising a novel ester or a pharmaceutically acceptable salt thereof as an active ingredient which selectively inhibits MTP in the small intestine. In addition, the present invention relates to an agent for the treatment or prophylaxis of hyperlipidemia, arteriosclerosis, coronary artery diseases, obesity, diabetes or hypertension, which has a novel function that has never been known before.

BACKGROUND ART

It has been said that hyperlipidemia, diabetes, hypertension or the like is one of the risk factors for arteriosclerosis. Hyperlipidemia is a condition where the concentration of lipid such as cholesterol is abnormally elevated in the blood. Types of hyperlipidemia, depending on the cause, include primary hyperlipidemia caused by genetic abnormality in enzyme, protein, lipoprotein receptors and the like which participate in the metabolism of low-density lipoprotein (LDL), secondary hyperlipidemia due to various disease or drug administration, and acquired hyperlipidemia basically resulting from overnutrition.

Meanwhile, lipid taken in from food is absorbed in the small intestine by the action of bile acid, and secreted as chylomicron in the blood via lymphatic vessels. The triglyceride (TG) moiety of the secreted chylomicrons is hydrolyzed to free fatty acids by the action of lipoprotein lipase (LPL) existing in capillary vessels to become chylomicron remnants having a high content of cholesteryl ester (CE), which is then absorbed into the liver by the mediation of chylomicron remnant receptor in the liver. Further, in the liver, the incorporated chylomicron remnant and free fatty acids are converted to CE and TG, respectively, which are then associated with apolipoprotein B synthesized on rough surfaced endoplasmic reticulum to form very low density lipoprotein (VLDL). The VLDL is transferred to the Golgi apparatus, modified and secreted outside cells, and it becomes intermediate density lipoprotein (IDL) by the action of LPL. The IDL is converted to LDL by the action of hepatic triglyceride lipase (HTGL), and lipids are distributed to peripheral tissues.

It has long been indicated that, during the above-mentioned formation of chylomicron in the small intestine or VLDL in the liver, a protein having TG- or CE-transfer activity is existing in microsomal fractions of the small intestine or liver. Meanwhile, the protein, i.e. MTP (microsomal triglyceride transfer protein: hereinafter also abbreviated as MTP) was purified and separated from microsomal fractions of bovine liver by Wetterau et al. in 1985 (Wetterau J. R. et al: Chem.Phys.Lipids 38, 205-222 (1985)). MTP, however, began attracting a lot of attention in the field of clinical medicine only after it was reported in 1993 that the cause of abetalipoproteinemia lay in the deficit of MTP. In other word, the disease is characterized in that, while the genes related to apolipoprotein B are normal, apolipoprotein B is hardly detected in the serum, the level of serum cholesterol is 50 mg/dL or lower, the level of serum triglyceride is extremely low. By this finding, it has been shown that MTP is an integral protein involved in the association between apolipoprotein B and TG or CE, i.e. the formation of VLDL or chylomicron, and plays an essential role in secretion thereof.

Since lipid is by nature insoluble in water, lipid in the blood is combined with a hydrophilic protein known as apolipoprotein and exists as so-called lipoprotein. All the VLDL, IDL, LDL or chylomicron, etc. related to hyperlipidemia are a lipoprotein.

MTP exists in the microsome fractions of hepatocytes and intestinal epithelial cells, and catalyses the transfer of TG or CE in cells. In the liver and small intestine, along with the synthesis of apolipoprotein B (apolipoprotein B100 in the liver and apolipoprotein B48 in the small intestine), TG and CE are combined with respective apolipoprotein B by the transfer activity of MTP, and thus VLDL or chylomicron is formed. As a result, those lipoproteins are secreted outside the cells as VLDL in the liver or as chylomicron in the small intestine. It should be said that MTP is indispensable for the construction of those lipoproteins. Namely, if the activity of MTP is blocked, the transfer of lipid such as TG and CE, etc. to apolipoprotein is inhibited, whereby formation of a lipoprotein can be inhibited.

On the other hand, it has been elucidated that LDL in general is closely related to the progression of arteriosclerosis. That is, LDL permeating endothelium of blood vessels is deposited in intercellular matrix of vessel wall, where oxidative denaturation takes place and lipid peroxides or denaturated proteins induce a series of inflammation reactions. Consequently, macrophage emigration in blood vessels leading to lipid deposit or composition of layers of foamy cells, migration or proliferation of smooth muscle cells and increase in intercellular matrix, etc. take place, which leads to the development of arteriosclerosis plaque. On the basis of the above, it is supposed to be possible to prevent or treat arteriosclerosis, coronary artery diseases or hypertension by reducing the level of LDL.

As already mentioned, it is possible to inhibit the formation of lipoprotein such as chylomicron, VLDL, LDL, etc. by inhibiting the action of MTP. Accordingly, it has been expected that it should become possible to control TG, cholesterol and lipoproteins such as LDL, etc. in blood and to control lipid in cells by adjusting the activity of MTP, and therefore, a previously unknown new type agent for the treatment or prophylaxis of hyperlipidemia, arteriosclerosis, coronary artery diseases, diabetes, obesity, or hypertension, and further, an agent for the treatment or prophylaxis of pancreatitis, hypercholesterolemia, hyperglyceridemia, etc. has been expected to be provided.

However, with the development of MTP inhibitors, some cases of fatty liver were reported and concern over hepatotoxicity has been raised. Thus, a novel MTP inhibitor having no side effect such as fatty liver has been strongly desired.

In the conventional manners, combined therapies of various combinations of different antihyperlipidemic drugs have been tried. However, when, for example, a statin-type drug and a resin-type drug are given together, undesirable side effects such as elevated GOT and GPT, constipation, blocking of absorption of vitamins A, D, E and K and the like are observed. On the other hand, when a statin-type drug and a fibrate drug are given together, side effects such as rhabdomyolysis or elevated CPK (creative phosphokinase) are observed. Thus, with regard to a combined therapy for hyperlipidemia, a medicament for a combined administration which can be administered in combination with a conventional antihyperlipidemic drug without causing any above-mentioned side effect has been desired.

Meanwhile, examples of the known compound having MTP inhibitory activity and similar structure are described below.

The following compound is disclosed in WO97/26240.

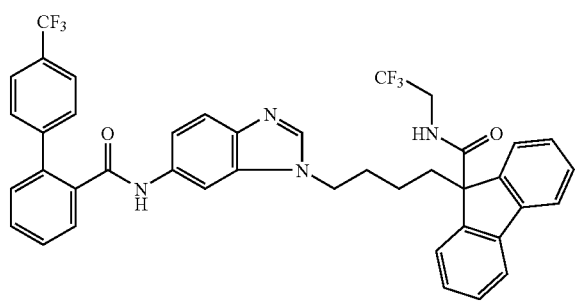

The following compound is disclosed in WO97/43257.

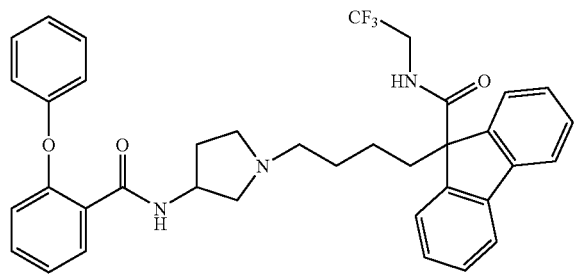

The following compound is disclosed in WO98/23593.

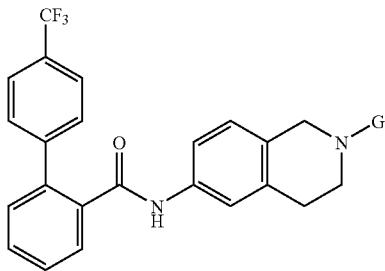

(In the formula, G is phenyl, heterocyclyl, —CH$_2$CN, diphenylmethyl, C$_2$-C$_{12}$ alkyl, C$_2$-C$_{12}$ perfluoroalkyl, C$_3$-C$_8$ cycloalkyl, C$_3$-C$_8$ cycloalkenyl, —(CH$_2$)$_n$—COOH, —(CH$_2$)$_n$—COO-alkyl, etc.)

The following compound is disclosed in WO99/63929.

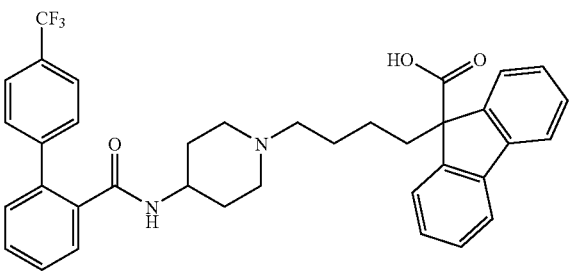

The following compound is disclosed in WO2000/5201.

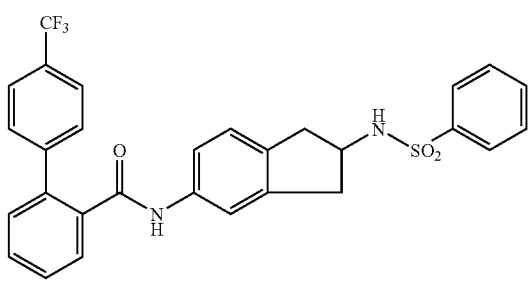

The following compound is disclosed in J. Med. Chem. (2001), 44(6) p. 851-856.

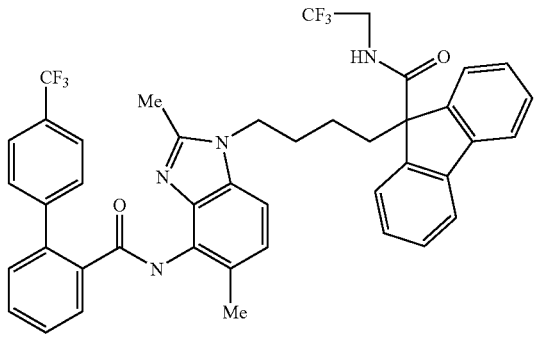

The following compound is disclosed in EP 1099701.

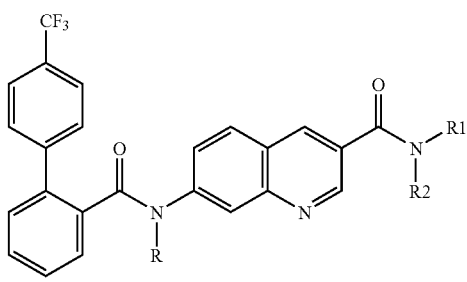

The following compound is disclosed in WO2001/77077.

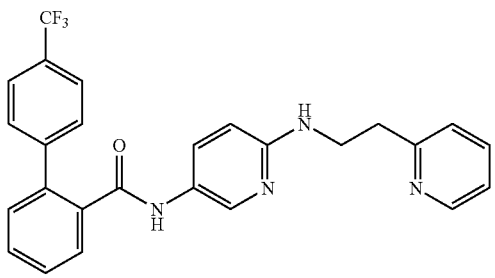

The following compound is disclosed in J. Med. Chem. (2001), 44(6) p. 4677-4687.

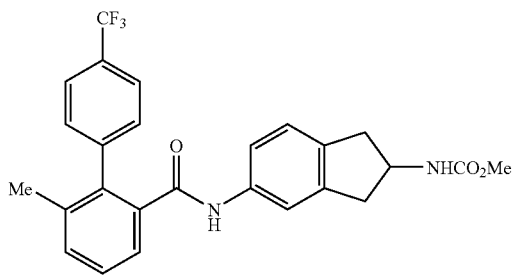

The following compound is disclosed in WO2002/4403.

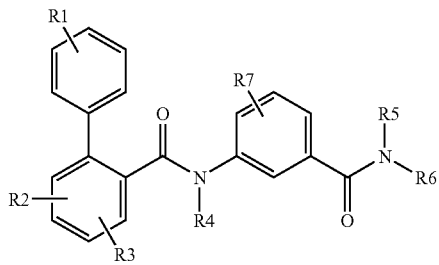

In the above literatures, however, there is no disclosure of a compound comprising ester as the essential structure, much less the disclosure or suggestion of the data indicating that the disclosed compound selectively inhibits MTP in the small intestine while rarely affects MTP in the liver.

Further, WO2002/28835 discloses the following compound represented by the formula:

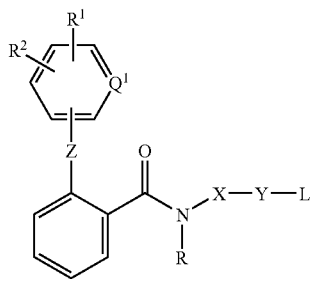

wherein
L is an unsaturated 3- to 10-membered heterocycle which may be substituted by a suitable substituent, Y is -$(A^1)_m$-$(A_2)_n$-$(A^4)_k$—

(in the formula, $A^1$ is lower alkylene or lower alkenylene and these two groups may be substituted by a suitable substituent; $A_2$ is —N($R^3$)—, —CO—N($R^3$)—, —NH—CO—NH—, —CO—O—, —O—, —O—$(CH_2)_2$—N($R^3$)—, —S—, —SO—, or —$SO_2$— (in the formula, $R^3$ is hydrogen or a suitable substituent);

$A^4$ is lower alkylene, lower alkenylene or lower alkynylene; and k, m and n are each independently 0 or 1).

However, the compound disclosed in this patent differs from the compound of the present invention in its structure with respect to the moiety of —Y-L. Further, in this patent, there is no disclosure or suggestion of the data indicating that the disclosed compound selectively inhibits MTP in the small intestine while rarely affects MTP in the liver.

DISCLOSURE OF THE INVENTION

Although the development of new antihyperlipidemic drugs due to its MTP inhibitory activity has been advanced nowadays, those drugs are not satisfactory in terms of their activity or side effect such as fatty liver, etc. Thus, the development of an antihyperlipidemic drug which has little side effect in the liver as has been observed in the previous MTP inhibitors and which has excellent MTP inhibitory activity has been strongly desired. A technical problem to be solved by the present invention is to provide excellent antihyperlipidemic drugs having high MTP inhibitory activity without side effect on the liver which is seen in the conventional MTP inhibitors.

The inventors of the present invention have carried out intensive studies to provide a novel MTP inhibitor causing no above-mentioned side effect such as fatty liver. As a result, they have found that an MTP inhibitor, which selectively inhibits MTP in the small intestine but substantially does not inhibit MTP in the liver, significantly lowers the level of unnecessary TG or cholesterol without causing side effects such as fatty liver, etc. More surprisingly, they have also found that the compound having ester structure represented by the hereinafter mentioned formula (1) is rapidly metabolized in the small intestine, blood or liver, whereby it does not substantially inhibit MTP in the liver, but selectively inhibits MTP only in the small intestine.

To be more specific, according to the conventional drug design concept for the preparation of a prodrug, the carboxylic acid which is the active principle is esterified to improve the absorption rate in the small intestine and is immediately metabolized in blood to reproduce carboxylic acid which is the active principle. On the other hand, a drug design concept that is different from the above concept for the preparation of a prodrug is used in the present invention. Namely, by introducing at least one ester or at least one carbonate in the molecule of a compound having MTP inhibitory activity, the compound is, after it exerts MTP inhibitory activity on mucous membranes of the small intestine, immediately metabolized by an esterase or a metabolic enzyme, etc. in the small intestine, portal vein (blood) and liver to be transformed to corresponding carboxylic acid and alcohol which do not have MTP inhibitory activity. This is completely a new concept, whereby MTP in the liver is not substantially affected and MTP in the small intestine is selectively inhibited.

Further, since the compounds of the present invention show strong MTP inhibitory activity in vitro, they potently inhibit MTP in the small intestine and significantly lower the level of triglyceride and cholesterol in blood. In addition, the compounds of the present invention significantly lower non-HDL cholesterol and, surprisingly, increase plasma HDL cholesterol.

Accordingly, the inventors of the present invention have found that when a compound comprises the ester structure represented by the hereinafter mentioned formula (1), the compound is immediately metabolized in the small intestine, blood or liver after it strongly inhibits MTP in the small intestine and hence MTP in the liver is not substantially inhibited, whereby they have completed the present invention.

Namely, the present invention relates to:

1) an ester compound of the formula (1):

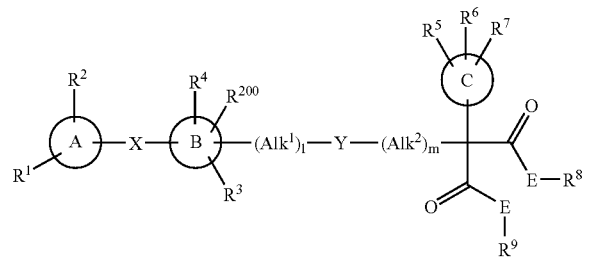

(1)

wherein

R$^1$ and R$^2$ are each independently hydrogen; C$_1$-C$_6$ alkyl; C$_3$-C$_7$ cycloalkyl; C$_1$-C$_6$ alkoxy; halo-C$_1$-C$_6$ alkyl; halo-C$_1$-C$_6$ alkyloxy; optionally substituted C$_6$-C$_{14}$ aryl; optionally substituted C$_7$-C$_{16}$ aralkyl; optionally substituted C$_6$-C$_{14}$ aryloxy; optionally substituted C$_7$-C$_{16}$ aralkyloxy; optionally substituted C$_7$-C$_{15}$ arylcarbonyl; optionally substituted heterocycle; C$_2$-C$_7$ alkoxycarbonyl; halogen; C$_2$-C$_6$ alkenyl; C$_1$-C$_6$ acyl; cyano; —N(R$^{40}$)(R$^{41}$) (wherein R$^{40}$ and R$^{41}$ are each independently hydrogen, C$_1$-C$_6$ alkyl or optionally substituted C$_6$-C$_{14}$ aryl), or —(CH$_2$)$_r$—O—CO—R$^{100}$ (wherein R$^{100}$ is C$_1$-C$_6$ alkyl, C$_1$-C$_6$ alkoxy or C$_2$-C$_{12}$ alkoxyalkyl, and r is 0 or an integer of 1 to 3);

ring A is C$_6$-C$_{14}$ aryl; heterocycle;

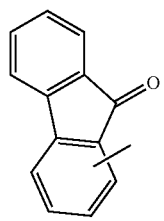 or 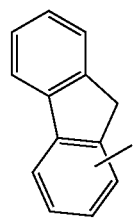 ;

X is —COO—(CH$_2$)$_n$—, —CON(R$_{10}$)—(CH$_2$)$_n$— or —N(R$^{10}$)—CO—(CH$_2$)$_n$-(wherein R$^{10}$ is hydrogen; C$_1$-C$_6$ alkyl or C$_3$-C$_7$ cycloalkyl, and n is 0 or an integer of 1 to 3);

R$^3$, R$^4$ and R$^{200}$ are each independently hydrogen; hydroxyl; halogen; optionally substituted C$_1$-C$_6$ alkyl; C$_1$-C$_6$ alkoxy; halo-C$_1$-C$_6$ alkyl; C$_7$-C$_{16}$ aralkyloxy; C$_1$-C$_6$ acyl; C$_3$-C$_{10}$ alkoxycarbonylalkyl; optionally substituted heterocycle;

—CON(R$^{11}$)(R$^{12}$)

(wherein R$^{11}$ and R$^{12}$ are each independently hydrogen, optionally substituted C$_1$-C$_6$ alkyl, optionally substituted C$_6$-C$_{14}$ aryl, optionally substituted C$_7$-C$_{16}$ aralkyl, C$_1$-C$_6$ alkoxy, or R$^{11}$ and R$^{12}$ taken together with the nitrogen atom to which they are attached may form

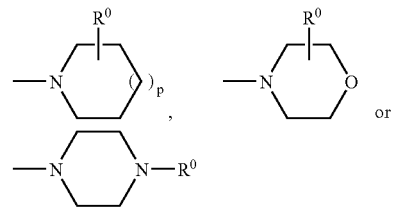

(wherein R$^0$ is hydrogen, hydroxyl, C$_1$-C$_6$ alkyl or C$_1$-C$_6$ acyl, and p is 0 or an integer of 1 or 2);

—(CH$_2$)$_{q'}$—N(R$^{13}$)(R$^{14}$)

(wherein R$^{13}$ and R$^{14}$ are each independently hydrogen; C$_1$-C$_6$ alkyl; C$_2$-C$_7$ alkoxycarbonyl; or C$_1$-C$_6$ acyl; or R$^{13}$ and R$^{14}$ taken together with the nitrogen atom to which they are attached may form

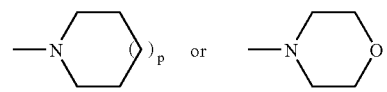

(wherein p has the same meaning as defined above) and q' is 0 or an integer of 1 to 3);

—CO—(R$^{15}$)

(wherein R$^{15}$ is hydroxy, C$_1$-C$_6$ alkyl, C$_1$-C$_6$ alkoxy, optionally substituted C$_6$-C$_{14}$ aryloxy or C$_7$-C$_{16}$ aralkyloxy); or —(CH$_2$)$_{r'}$—O—CO—R$^{100'}$ (wherein R$^{100'}$ is C$_1$-C$_6$ alkyl, C$_1$-C$_6$ alkoxy, C$_2$-C$_{12}$ alkoxyalkyl or —N(R$^{40}$)(R$^{41}$) (wherein R$^{40}$ and R$^{41}$ have each the same meanings as defined above), and r' is 0 or an integer of 1 to 3);

ring B is

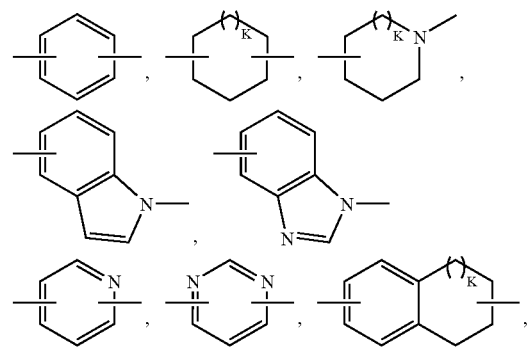

-continued

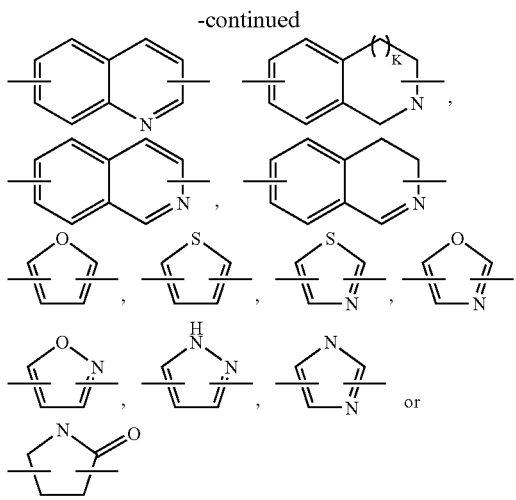

(wherein k is 0 or an integer of 1 to 2); or $R^3$, $R^{10}$ and ring B taken together with the nitrogen atom to which $R^{10}$ is attached may form

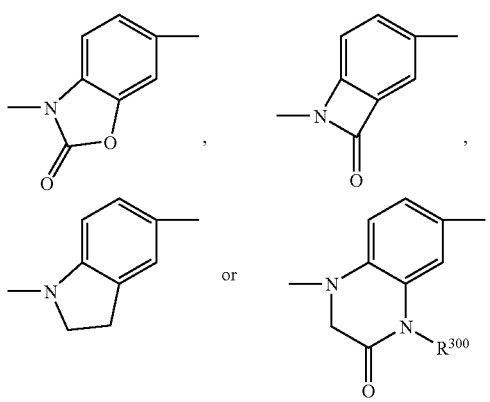

($R^{300}$ is optionally substituted $C_1$-$C_6$ alkyl);
Alk$^1$ is alkanediyl or alkenediyl;
Alk$^2$ is alkanediyl or alkenediyl;
l is 0 or an integer of 1 to 3;
m is 0 or an integer of 1 to 3;
ring C is

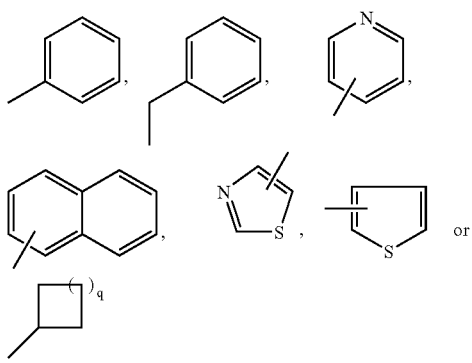

(wherein q is 0 or an integer of 1 to 4);

$R^5$, $R^6$ and $R^7$ are each independently hydrogen; $C_1$-$C_6$ alkyl; $C_1$-$C_6$ alkoxy; $C_2$-$C_7$ alkoxycarbonyl; carboxyl; halogen, cyano; nitro; halo-$C_1$-$C_6$ alkyl; $C_1$-$C_6$ acyl; hydroxy; amino; optionally substituted $C_6$-$C_{14}$ aryl; —(CH$_2$)$_r$—CON($R^{16}$) ($R^{17}$) (wherein $R^{16}$ and $R^{17}$ are each independently hydrogen; $C_1$-$C_6$ alkyl; or halo-$C_1$-$C_6$ alkyl; and r is 0 or an integer of 1 to 3); or —(CH$_2$)$_{r''}$—O—CO—$R^{100''}$ (wherein $R^{100''}$ is $C_1$-$C_6$ alkyl; $C_1$-$C_6$ alkoxy or $C_2$-$C_{12}$ alkoxyalkyl, and r'' is 0 or an integer of 1 to 3);

$R^8$ and $R^9$ are each independently hydrogen, optionally substituted $C_1$-$C_6$ alkyl or optionally substituted $C_6$-$C_{14}$ aryl;

E is —O— or —N($R^{90}$)— wherein $R^{90}$ is hydrogen or $C_1$-$C_6$ alkyl;

Y is —O—CO—O—, —O—CO—, —CO—O—, —CO—O—C($R^{110}$) ($R^{111}$)—O—CO—, —CO—O—C($R^{110}$) ($R^{111}$)—O—CO—O—, —O—CO—O—C($R^{110}$) ($R^{111}$)—O—CO—, —O—CO—C($R^{110}$) ($R^{111}$)—O—, —O—CO—C($R^{110}$) ($R^{111}$)—C($R^{110}$) ($R^{111}$)—O— or —O—C($R^{110}$)($R^{111}$)—CO—O—

(wherein $R^{110}$ and $R^{111}$ are each independently hydrogen or $C_1$-$C_6$ alkyl, provided that when Y is —CO—O—, then $R^3$ is —(CH$_2$)$_r$—O—CO—$R_{100}$, wherein $R^{100'}$ and r' each has the same meaning as defined above;

or a pharmaceutically acceptable salt thereof;

2) the ester compound or a pharmaceutically acceptable salt thereof according to the above 1), wherein ring B is

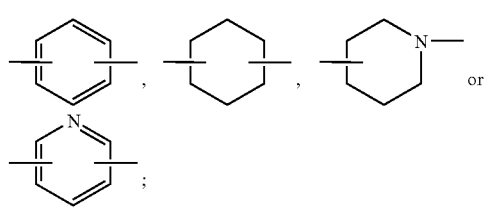

3) the ester compound or a pharmaceutically acceptable salt thereof according to the above 2), wherein ring A is

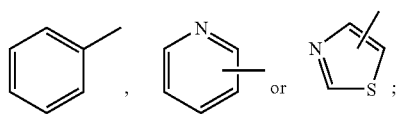

4) the ester compound or a pharmaceutically acceptable salt thereof according to the above 3), wherein X is —CON($R^{10}$)—(CH$_2$)$_n$— in which $R^{10}$ and n each has the same meaning as defined above;

5) the ester compound or a pharmaceutically acceptable salt thereof according to the above 3), wherein X is —COO—(CH$_2$)$_n$— in which n has the same meaning as defined above;

6) the ester compound or a pharmaceutically acceptable salt thereof according to the above 4) or 5), wherein n is 0;

7) the ester compound or a pharmaceutically acceptable salt thereof according to the above 6), wherein Y is —O—CO—O—;

8) the ester compound or a pharmaceutically acceptable salt thereof according to the above 6), wherein Y is —O—CO—;

9) the ester compound or a pharmaceutically acceptable salt thereof according to the above 6), wherein Y is —CO—O—;

10) the ester compound or a pharmaceutically acceptable salt thereof according to the above 6), wherein Y is —O—CO—C($R^{110}$) ($R^{111}$)—O— in which $R^{110}$ and $R^{111}$ each has the same meaning as defined above;

11) the ester compound or a pharmaceutically acceptable salt thereof according to the above 6), wherein Y is —O—CO—C($R^{110}$) ($R^{111}$)—C($R^{110}$) ($R^{111}$)—O— in which $R^{110}$ and $R^{111}$ each has the same meaning as defined above;

12) the ester compound or a pharmaceutically acceptable salt thereof according to the above 6), wherein Y is —O—C($R^{110}$) ($R^{111}$)—CO—O— in which $R^{110}$ and $R^{111}$ each has the same meaning as defined above;

13) the ester compound or a pharmaceutically acceptable salt thereof according to the above 7), 8), 9), 10), 11) or 12) wherein E is —O—, and $R^8$ and $R^9$ are each independently $C_1$-$C_6$ alkyl;

14) the ester compound or a pharmaceutically acceptable salt thereof according to the above 7), 8), 9), 10), 11) or 12) wherein E is —NH—, and $R^8$ and $R^9$ are each independently $C_1$-$C_6$ alkyl;

15) the ester compound according to the above 1), which is represented by the formula (1'):

(1')

wherein $R^{2'}$ and $R^{2''}$ are each independently hydrogen; $C_1$-$C_6$ alkyl; $C_3$-$C_7$ cycloalkyl; $C_1$-$C_6$ alkoxy; halogen; halo-$C_1$-$C_6$ alkyl; halo-$C_1$-$C_6$ alkyloxy; $C_1$-$C_6$ acyl; $C_2$-$C_6$ alkenyl; or cyano; $X_1$ is —O— or —$NR^{10}$ wherein $R^{10}$ has the same meaning as defined above; $R^1$, $R^3$, $R^4$, $R^5$, $R^6$, $R^7$, $R^8$, $R^9$, $R^{200}$, Y, ring C, E, l and m each has the same meaning as defined above, provided that when Y is —CO—O—, then $R^3$ is —(CH$_2$)$_{r'}$—O—CO—$R^{100'}$ in which $R^{100'}$ and r' each has the same meaning as defined above; or a pharmaceutically acceptable salt thereof;

16) the ester compound or a pharmaceutically acceptable salt thereof according to the above 15), wherein $X_1$ is —$NR^{10}$— in which $R^{10}$ has the same meaning as defined above;

17) the ester compound or a pharmaceutically acceptable salt thereof according to the above 15), wherein $X_1$ is —O—;

18) the ester compound or a pharmaceutically acceptable salt thereof according to any one of the above 15) to 17), wherein the substitution position of —(CH$_2$)$_l$— on the benzene ring in the formula (1') is h-position;

19) the ester compound or a pharmaceutically acceptable salt thereof according to anyone of the above 15) to 17), wherein the substitution position of —(CH$_2$)$_l$— on the benzene ring in the formula (1') is i-position;

20) the ester compound or a pharmaceutically acceptable salt thereof according to any one of the above 15) to 19), wherein E is —O—, and $R^8$ and $R^9$ are each independently $C_1$-$C_6$ alkyl;

21) the ester compound or a pharmaceutically acceptable salt thereof according to any one of the above 15) to 19), wherein E is —NH—, and $R^8$ and $R^9$ are each independently $C_1$-$C_6$ alkyl;

22) the ester compound or a pharmaceutically acceptable salt thereof according to any one of the above 15) to 21), wherein the ring C is 23) the ester compound or a pharmaceutically acceptable salt thereof according to the above 22), wherein the ring C is phenyl;

24) the ester compound or a pharmaceutically acceptable salt thereof according to any one of the above 15) to 21), wherein ring C is $C_3$-$C_7$ cycloalkyl;

25) the ester compound or a pharmaceutically acceptable salt thereof according to any one of the above 15) to 21), wherein the ring C is 26) the ester compound or a pharmaceutically acceptable salt thereof according to any one of the above 23) to 25), wherein Y is —O—CO—O—;

27) the ester compound or a pharmaceutically acceptable salt thereof according to any one of the above 23) to 25), wherein Y is —O—CO—;

28) the ester compound or a pharmaceutically acceptable salt thereof according to any one of the above 23) to 25), wherein Y is —CO—O—;

29) the ester compound or a pharmaceutically acceptable salt thereof according to any one of the above 23) to 25), wherein Y is —O—CO—C($R^{110}$) ($R^{111}$)—O— in which $R^{110}$ and $R^{111}$ each has the same meaning as defined above;

30) the ester compound or a pharmaceutically acceptable salt thereof according to any one of the above 23) to 25), wherein Y is —O—CO—C($R^{110}$) ($R^{111}$)—C($R^{110}$) ($R^{111}$)—O— in which $R^{110}$ and $R^{111}$ each has the same meaning as defined above;

31) the ester compound or a pharmaceutically acceptable salt thereof according to any one of the above 23) to 25), wherein Y is —O—C($R^{110}$) ($R^{111}$)—CO—O— in which $R^{110}$ and $R^{111}$ each has the same meaning as defined above;

32) the ester compound or a pharmaceutically acceptable salt thereof according to any one of the above 26) to 31), wherein E is —O—, and $R^8$ and $R^9$ are each independently $C_1$-$C_6$ alkyl;

33) the ester compound or a pharmaceutically acceptable salt thereof according to any one of the above 26) to 31), wherein E is —NH—, and $R^8$ and $R^9$ are each independently $C_1$-$C_6$ alkyl;

34) the ester compound or a pharmaceutically acceptable salt thereof according to the above 1), which is selected from the group consisting of:

2-(2-{3-acetoxy-4-[(4'-trifluoromethylbiphenyl-2-carbonyl)amino]phenyl}acetoxymethyl)-2-phenylmalonic acid diethyl ester, 2-phenyl-2-(2-{3-propionyloxy-4-[(4'-trifluoromethylbiphenyl-2-carbonyl)amino]phenyl}acetoxymethyl)malonic acid diethyl ester, 2-(2-{3-(2-methoxyacetoxy)-4-[(4'-trifluoromethylbiphenyl-2-carbonyl)amino]phenyl}acetoxymethyl)-2-phenylmalonic acid diethyl ester, 2-(2-{2-acetoxy-3-[(4'-trifluoromethylbiphenyl-2-carbonyl)amino]phenyl}acetoxymethyl)-2-phenylmalonic acid diethyl ester, 2-(2-{3-acetoxy-4-[(5-methyl-4'-trifluoromethylbiphenyl-2-carbonyl)amino]phenyl}acetoxymethyl)-2-phenylmalonic acid diethyl ester, 2-(2-{4-[(5-methyl-4'-trifluoromethylbiphenyl-2-carbonyl)amino]-3-propionyloxyphenyl}acetoxymethyl)-2-phenylmalonic acid diethyl ester, 2-(2-{3-butyryloxy-4-[(5-methyl-4'-trifluoromethylbiphenyl-2-carbonyl)amino]phenyl}acetoxymethyl)-2-phenylmalonic acid diethyl ester, 2-(2-{3-acetoxy-4-[methyl-(4'-trifluoromethylbiphenyl-2-carbonyl)amino]phenyl}acetoxymethyl)-2-phenylmalonic acid diethyl ester, 2-{5-dimethylcarbamoyl-2-fluoro-4-[(4'-trifluoromethylbiphenyl-2-carbonyl)amino]phenoxycarbonyloxymethyl}-2-phenylmalonic acid diethyl ester, 2-[4-isopropyl-3-oxo-1-(4'-trifluoromethylbiphenyl-2-carbonyl)-1,2,3,4-tetrahydroquinoxalin-6-yloxycarbonyloxymethyl]-2-phenylmalonic acid diethyl ester, 2-phenyl-2-[1-(4'-trifluorometylbiphenyl-2-carbonyl)-2,3-dihydro-1H-indol-5-yloxycarbonyloxymethyl]malonic acid diethyl ester, 2-{3-dimethylcarbamoyl-4-[(4'-trifluoromethylbiphenyl-2-carbonyl)amino]phenoxycarbonyloxymethyl}-2-phenylmalonic acid diethyl ester, 2-{3-dimethylcarbamoyl-4-[(4'-trifluoromethylbiphenyl-2-carbonyl)amino]benzyloxycarbonyloxymethyl}-2-phenylmalonic acid diethyl ester, 2-{2-chloro-5-dimethylcarbamoyl-4-[(4'-trifluoromethylbiphenyl-2-carbonyl)amino]phenoxycarbonyloxymethyl}-2-phenylmalonic acid diethyl ester, 2-{3-dimethylcarbamoyl-4-[(4'-trifluoromethylbiphenyl-2-carbonyl)amino]phenoxycarbonyloxymethyl}-2-thiophen-2-yl-malonic acid diethyl ester, 2-{3-dimethylcarbamoyl-4-[(5-methyl-4'-trifluoromethylbiphenyl-2-carbonyl)amino]phenoxycarbonyloxymethyl}-2-phenylmalonic acid diethyl ester, 2-{3-dimethylcarbamoyl-4-[(5-methyl-4'-trifluoromethylbiphenyl-2-carbonyl)amino]phenoxycarbonyloxymethyl}-2-thiophen-2-yl-malonic acid diethyl ester, carbonic acid 2,2-bisethylcarbamoyl-2-phenylethyl ester 3-dimetylcarbamoyl-4-[(4'-trifluoromethylbiphenyl-2-carbonyl)amino]phenyl ester, carbonic acid 2,2-bisethylcarbamoyl-2-phenylethyl ester 5-dimethylcarbamoyl-2-fluoro-4-[(4'-trifluoromethylbiphenyl-2-carbonyl)amino]phenyl ester, 2-{3-(ethylmethylcarbamoyl)-4-[(4'-trifluoromethylbiphenyl-2-carbonyl)amino]phenoxycarbonyloxymethyl}-2-phenylmalonic acid diethyl ester, 2-{3-(methylpropylcarbamoyl)-4-[(4'-trifluoromethylbiphenyl-2-carbonyl)amino]phenoxycarbonyloxymethyl}-2-phenylmalonic acid diethyl ester, 2-phenyl-2-{3-(pyrrolidine-1-carbonyl)-4-[(4'-trifluoromethylbiphenyl-2-carbonyl)amino]phenoxycarbonyloxymethyl}phenylmalonic acid diethyl ester, 2-{5-dimethylcarbamoyl-2-methyl-4-[(4'-trifluoromethylbiphenyl-2-carbonyl)amino]phenoxycarbonyloxymethyl}-2-phenylmalonic acid diethyl ester, 2-{3-dimethylcarbamoyl-4-[methyl-(4'-trifluoromethylbiphenyl-2-carbonyl)amino]phenoxycarbonyloxymethyl}-2-phenylmalonic acid diethyl ester, 2-{3-dimethylcarbamoyl-4-[(4'-trifluoromethylbiphenyl-2-carbonyl)amino]phenoxycarbonyloxymethyl}-2-pyridin-2-yl-malonic acid diethyl ester, 2-{3-dimethylcarbamoyl-2,6-difluoro-4-[(4'-trifluoromethylbiphenyl-2-carbonyl)amino]phenoxycarbonyloxymethyl}-2-phenylmalonic acid diethyl ester, 2-{3-dimethylcarbamoyl-2,6-difluoro-4-[(4'-trifluoromethylbiphenyl-2-carbonyl)amino]phenoxycarbonyloxymethyl}-2-pyridin-2-yl-malonic acid diethyl ester, 2-{2-chloro-3-dimethylcarbamoyl-4-[(4'-trifluoromethylbiphenyl-2-carbonyl)amino]phenoxycarbonyloxymethyl}-2-phenylmalonic acid diethyl ester, 2-{3-dimethylcarbamoyl-2,6-difluoro-4-[(4'-trifluoromethylbiphenyl-2-carbonyl)amino]phenoxycarbonyloxymethyl}-2-thiophen-2-yl-malonic acid diethyl ester, 2-{3-dimethylcarbamoyl-2,6-difluoro-4-[(5-methyl-4'-trifluoromethylbiphenyl-2-carbonyl)amino]phenoxycarbonyloxymethyl}-2-thiophen-2-yl-malonic acid diethyl ester, carbonic acid 2,2-bis(ethylmethylcarbamoyl)-2-phenylethyl ester 3-dimethylcarbamoyl-2,6-difluoro-4-[(4'-trifluoromethylbiphenyl-2-carbonyl)amino]phenyl ester, 2-{4-[5,4'-bistrifluoromethylbiphenyl-2-carbonyl)amino]-3-dimethylcarbamoyl-2,6-difluorophenoxycarbonyloxymethyl}-2-thiophen-2-yl-malonic acid diethyl ester, 2-{3-dimethylcarbamoyl-2,6-difluoro-4-[(6-fluoro-4'-trifluoromethylbiphenyl-2-carbonyl)amino]phenoxycarbonyloxymethyl}-2-thiophen-2-yl-malonic acid diethyl ester, 2-{3-dimethylcarbamoyl-2,6-difluoro-4-[(6-methyl-4'-trifluoromethylbiphenyl-2-carbonyl)amino]phenoxycarbonyloxymethyl}-2-thiophen-2-yl-malonic acid diethyl ester, 2-{3-dimethylcarbamoyl-2,6-difluoro-4-[(4-methyl-4'-trifluoromethylbiphenyl-2-carbonyl)amino]phenoxycarbonyloxymethyl}-2-thiophen-2-yl-malonic acid diethyl ester, 2-{3-dimethylcarbamoyl-2,6-difluoro-4-[(6-methoxy-4'-trifluoromethylbiphenyl-2-carbonyl)amino]phenoxycarbonyloxymethyl}-2-thiophen-2-yl-malonic acid diethyl ester, 2-{3-dimethylcarbamoyl-2,6-difluoro-4-[(5-methoxy-4'-trifluoromethylbiphenyl-2-carbonyl)amino]phenoxycarbonyloxymethyl}-2-thiophen-2-yl-malonic acid diethyl ester, 2-{2,6-difluoro-3-(morpholine-4-carbonyl)-4-[(4'-trifluoromethylbiphenyl-2-carbonyl)amino]phenoxycarbonyloxymethyl}-2-thiophen-2-yl-malonic acid diethyl ester, 2-{3-dimethylcarbamoyl-2,6-difluoro-4-[(3-methyl-4'-trifluoromethylbiphenyl-2-carbonyl)amino]phenoxycarbonyloxymethyl}-2-thiophen-2-yl-malonic acid diethyl ester, 2-{3-dimethylcarbamoyl-2,6-difluoro-4-[(3'-fluoro-4'-trifluoromethylbiphenyl-2-carbonyl)amino]phenoxycarbonyloxymethyl}-2-thiophen-2-yl-malonic acid diethyl ester, 2-{2,6-difluoro-3-[(2-methoxyethyl)methylcarbamoyl]-4-[(4'-trifluoromethylbiphenyl-2-carbonyl)amino]phenoxycarbonyloxymethyl}-2-thiophen-2-yl-malonic acid diethyl ester, 2-{2,6-difluoro-3-(methoxycarbonylmethylmethyl-carbamoyl)-4-[(4'-trifluoromethylbiphenyl-2-carbonyl) amino]phenoxycarbonyloxymethyl}-2-thiophen-2-yl-malonic acid diethyl ester,
2-[2,6-difluoro-4-[(5-methyl-4'-trifluoromethylbiphenyl-2-carbonylamino]-3-(morpholine-4-carbonyl)phenoxycarbonyloxymethyl]-2-thiophen-2-yl-malonic acid diethyl ester,
2-{3-dimethylcarbamoyl-2,6-difluoro-4-[(4'-trifluoromethylbiphenyl-2-carbonyl)amino]phenoxycarbonyloxymethyl}-2-thiazol-2-yl-malonic acid diethyl ester,
2-{2,6-difluoro-3-[(2-hydroxyethyl)methylcarbamoyl]-4-[(4'-trifluoromethylbiphenyl-2-carbonyl)amino]phenoxycarbonyloxymethyl}-2-thiophen-2-yl-malonic acid diethyl ester,
2-{3-(4-acetylpiperazine-1-carbonyl)-2,6-difluoro-4-[(4'-trifluoromethylbiphenyl-2-carbonyl)amino]phenoxycarbonyloxymethyl]-2-thiophen-2-yl-malonic acid diethyl ester,
2-{2,6-difluoro-3-[(4-hydroxypiperidine-1-carbonyl)-4-[(4'-trifluoromethylbiphenyl-2-carbonyl)amino]phenoxycarbonyloxymethyl}-2-thiophen-2-yl-malonic acid diethyl ester,
2-{2,6-difluoro-3-methoxy-4-[(4'-trifluoromethylbiphenyl-2-carbonyl)amino]phenoxycarbonyloxymethyl]-2-thiophen-2-yl-malonic acid diethyl ester,
2-{2,6-difluoro-4-[(4'-trifluoromethylbiphenyl-2-carbonyl) amino]phenoxycarbonyloxymethyl}-2-thiophen-2-yl-malonic acid diethyl ester,
2-{3-dimethylcarbamoyloxy-2,6-difluoro-4-[(4'-trifluoromethylbiphenyl-2-carbonyl)amino]phenoxycarbonyloxymethyl}-2-thiophen-2-yl-malonic acid diethyl ester,
2-{3-ethoxy-2,6-difluoro-4-[(4'-trifluoromethylbiphenyl-2-carbonyl)amino]phenoxycarbonyloxymethyl}-2-thiophen-2-yl-malonic acid diethyl ester,
2-{2,6-difluoro-3-isopropoxy-4-[(4'-trifluoromethylbiphenyl-2-carbonyl)amino]phenoxycarbonyloxymethyl}-2-thiophen-2-yl-malonic acid diethyl ester,
2-ethoxycarbonyl-2-phenylpentanedionic acid 5-{3-dimethylcarbamoyl-4-[(4'-trifluoromethylbiphenyl-2-carbonyl) amino]phenyl}ester 1-ethyl ester,
2-(2-{3-dimethylcarbamoyl-4-[(4'-trifluoromethylbiphenyl-2-carbonyl)amino]phenoxy}acetoxymethyl)-2-phenyl-malonic acid diethyl ester,
3-(2,2-bisethylcarbamoyl-2-phenylethoxy)propionic acid 3-dimethylcarbamoyl-4-[(4'-trifluoromethylbiphenyl-2-carbonyl)amino]phenyl ester,
2-ethoxycarbonyl-2-phenylsuccinic acid 4-{3-dimethylcarbamoyl-4-[(4'-trifluoromethylbiphenyl-2-carbonyl) amino]phenyl}ester 1-ethyl ester,
2-ethoxycarbonyl-2-phenylsuccinic acid 4-{3-dimethylcarbamoyl-4-[(4'-trifluoromethylbiphenyl-2-carbonyl) amino]benzyl}ester 1-ethyl ester,
2-ethoxycarbonyl-2-phenylpentanedionic acid 5-{5-dimethylcarbamoyl-2-fluoro-4-[(4'-trifluoromethylbiphenyl-2-carbonyl)amino]phenyl}ester 1-ethyl ester,
2-ethoxycarbonyl-2-phenylpentanedionic acid 5-{3-dimethylcarbamoyl-4-[(4'-trifluoromethylbiphenyl-2-carbonyl) amino]benzyl}ester 1-ethyl ester,
2-ethoxycarbonyl-2-phenylpentanedionic acid 5-{3-dimethylcarbamoyl-4-[(4'-trifluoromethylbiphenyl-2-carbonyl) amino]phenyl}ester 1-ethyl ester,
2-ethoxycarbonyl-2-phenylpentanedionic acid 5-{3-dimethylcarbamoyl-2,6-difluoro-4-[(4'-trifluoromethylbiphenyl-2-carbonyl)amino]phenyl}ester 1-ethyl ester,
2-ethoxycarbonyl-2-phenylpentanedionic acid 5-{2,6-difluoro-3-methylcarbamoyl-4-[(4'-trifluoromethylbiphenyl-2-carbonyl)amino]phenyl}ester 1-ethyl ester,
(2,2-bisethylcarbamoyl-2-phenylethoxy)acetic acid 3-dimethylcarbamoyl-4-[(4'-trifluoromethylbiphenyl-2-carbonyl)amino]phenyl}ester,
(2,2-bisethylcarbamoyl-2-phenylethoxy)acetic acid 3-dimethylcarbamoyl-2,6-difluoro-4-[(4'-trifluoromethylbiphenyl-2-carbonyl)amino]phenyl}ester,
(3,3-bisethylcarbamoyl-3-phenylpropoxy)acetic acid 3-dimethylcarbamoyl-2,6-difluoro-4-[(4'-trifluoromethylbiphenyl-2-carbonyl)amino]phenyl}ester,
6,6-bisethylcarbamoyl-6-thiophen-2-yl-hexanoic acid 3-dimethylcarbamoyl-2,6-difluoro-4-[(4'-trifluoromethylbiphenyl-2-carbonyl)amino]phenyl}ester,
3-(2,2-bisethylcarbamoyl-2-phenylethoxy)propionic acid 3-dimethylcarbamoyl-2,6-difluoro-4-[(4'-trifluoromethylbiphenyl-2-carbonyl)amino]phenyl}ester,
5,5-bisethylcarbamoyl-5-thiophen-2-yl)pentanoic acid 3-dimethylcarbamoyl-2,6-difluoro-4-[(4'-trifluoromethylbiphenyl-2-carbonyl)amino]phenyl}ester,
4,4-bis(ethylmethylcarbamoyl)-4-phenylbutyric acid 3-dimethylcarbamoyl-2,6-difluoro-4-[(4'-trifluoromethylbiphenyl-2-carbonyl)amino]phenyl}ester,
5,5-bis(ethylmethylcarbamoyl)-5-phenylvaleric acid 3-dimethylcarbamoyl-2,6-difluoro-4-[(4'-trifluoromethylbiphenyl-2-carbonyl)amino]phenyl ester,
2-ethoxycarbonyl-2-thiophen-2-ylpentandionic acid 5-{3-dimethylcarbamoyl-4-[(4'-trifluoromethylbiphenyl-2-carbonyl)amino]phenyl}ester 1-ethyl ester,
2-ethoxycarbonyl-2-thiophen-2-ylpentandionic acid 5-{3-dimethylcarbamoyl-4-[(5-methyl-4'-trifluoromethylbiphenyl-2-carbonyl)amino]phenyl}ester 1-ethyl ester,
2-ethoxycarbonyl-2-phenylpentanedionic acid 5-{3-dimethylcarbamoyl-2,6-difluoro-4-[(5-methyl-4'-trifluoromethylbiphenyl-2-carbonyl)amino]phenyl}ester 1-ethyl ester,
2-ethoxycarbonyl-2-pyridin-2-ylsuccunic acid 4-{3-dimethylcarbamoyl-4-[{4'-trifluoromethylbiphenyl-2-carbonyl) amino]benzyl ester 1-ethyl ester, and
(2,2-bisethylcarbamoyl-2-phenylethoxy)acetic acid 3-dimethylcarbamoyl-4-[(4'-trifluoromethylbiphenyl-2-carbonyl)amino]benzyl ester;

35) the ester compound according to the above 35), which is represented by the formula:

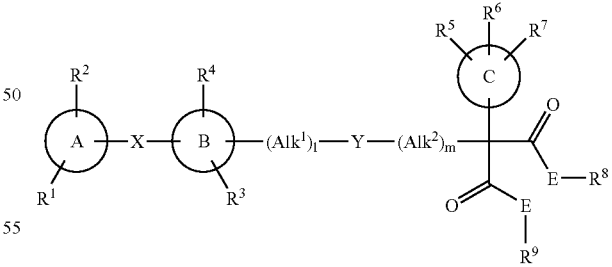

wherein
R$^1$ and R$^2$ are each independently hydrogen; $C_1$-$C_6$ alkyl; $C_3$-$C_7$ cycloalkyl; $C_1$-$C_6$ alkoxy; halo-$C_1$-$C_6$ alkyl; halo-$C_1$-$C_6$ alkyloxy; optionally substituted $C_6$-$C_{14}$ aryl; optionally substituted $C_7$-$C_{16}$ aralkyl; optionally substituted $C_6$-$C_{14}$ aryloxy; optionally substituted $C_7$-$C_{16}$ aralkyloxy; optionally substituted $C_7$-$C_{15}$ arylcarbonyl; optionally substituted heterocycle; $C_2$-$C_7$ alkoxycarbonyl; halogen; $C_2$-$C_6$ alkenyl; cyano; —N(R$^{40}$) (R$^{41}$)

(wherein R⁴⁰ and R⁴¹ are each independently hydrogen or optionally substituted $C_6$-$C_{14}$ aryl) or —(CH²)$_{r}$—O—CO—R¹⁰⁰ (wherein R¹⁰⁰ is $C_1$-$C_6$ alkyl, $C_1$-$C_6$ alkoxy or $C_2$-$C_{12}$ alkoxyalkyl, and r is 0 or an integer of 1 to 3.);

ring A is $C_6$-$C_{14}$ aryl; heterocycle;

X is —COO—(CH₂)$_n$—, —CON(R₁₀)—(CH₂)$_n$— or —N(R¹⁰)—CO—(CH₂)$_n$-(wherein R¹⁰ is hydrogen, $C_1$-$C_6$ alkyl or $C_3$-$C_7$ cycloalkyl, and n is 0 or an integer of 1 to 3);

R³ and R⁴ are each independently hydrogen; hydroxy; halogen; optionally substituted $C_1$-$C_6$ alkyl; $C_1$-$C_6$ alkoxy; halo-$C_1$-$C_6$ alkyl; $C_7$-$C_{16}$ aralkyloxy; $C_1$-$C_6$ acyl; $C_3$-$C_{10}$ alkoxycarbonylalkyl; optionally substituted heterocycle;

—CON(R¹¹) (R¹²)

(wherein R¹¹ and R¹² are each independently hydrogen, $C_1$-$C_6$alkyl, optionally substituted $C_6$-$C_{14}$ aryl, optionally substituted $C_7$-$C_{16}$ aralkyl, or $C_1$-$C_6$ alkoxy, or R¹¹ and R¹² taken together with the nitrogen atom to which they are attached may form (wherein p is 0 or an integer of 1 to 2);

—(CH₂)$_q$—N(R¹³)(R¹⁴)

(wherein R¹³ and R¹⁴ are each independently hydrogen; $C_1$-$C_6$ alkyl; $C_2$-$C_7$ alkoxycarbonyl; or $C_1$-$C_6$ acyl; or R¹³ and R¹⁴ taken together with the nitrogen atom to which they are attached may form (wherein p has the same meaning as defined above), and q is 0 or an integer of 1 to 3);

—CO—(R¹⁵)

(wherein R¹⁵ is hydroxy, $C_1$-$C_6$ alkoxy, optionally substituted $C_6$-$C_{14}$ aryloxy, optionally substituted $C_7$-$C_{16}$ aralkyloxy or optionally substituted $C_1$-$C_6$ alkyl); or —(CH₂)$_{r40}$—O—CO—R¹⁰⁰'

(wherein R¹⁰⁰' is $C_1$-$C_6$ alkyl, $C_1$-$C_6$ alkoxy, or $C_2$-$C_{12}$ alkoxyalkyl, and r' is 0 or an integer of 1 to 3);

ring B is (wherein k is 0 or an integer of 1 to 2); or R³, R¹⁰ and ring B taken together with the nitrogen atom to which R¹⁰ is attached may form Alk¹ is alkanediyl or alkenediyl;
Alk² is alkanediyl or alkenediyl;
l is 0 or an integer of 1 to 3;
m is 0 or an integer of 1 to 3;
ring C is

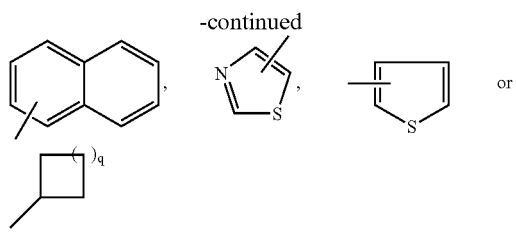

(wherein q is 0 or an integer of 1 to 4);

$R^5$, $R^6$ and $R^7$ are each independently hydrogen; $C_1$-$C_6$ alkyl; $C_1$-$C_6$ alkoxy; $C_2$-$C_7$ alkoxycarbonyl; carboxyl; halogen, cyano; nitro; halo-$C_1$-$C_6$alkyl; $C_1$-$C_6$ acyl; hydroxyl; amino; optionally substituted $C_6$-$C_{14}$ aryl;

—$(CH_2)_r$—$CON(R^{16})(R^{17})$ (wherein $R^{16}$ and $R^{17}$ are each independently hydrogen; $C_1$-$C_6$alkyl; or halo-$C_1$-$C_6$ alkyl, and r is 0 or an integer of 1 to 3); or —$(CH_2)_{r''}$—O—CO—$R^{100''}$ (wherein $R^{100''}$ is $C_1$-$C_6$ alkyl, $C_1$-$C_6$ alkoxy, or $C_2$-$C_{12}$ alkoxyalkyl, and r'' is 0 or an integer of 1 to 3);

$R^8$ and $R^9$ are each independently hydrogen, optionally substituted $C_1$-$C_6$ alkyl, or optionally substituted $C_6$-$C_{14}$ aryl;

E is —O— or —NH—;

Y is —O—CO—O—, —O—CO—, —CO—O—, —CO—O—$C(R^{110})(R^{111})$—O—CO—, —CO—O—$C(R^{110})(R^{111})$—O—CO—O—, or —O—CO—O—$C(R^{110})(R^{111})$—O—CO—, (wherein $R^{110}$ and $R^{111}$ are each independently hydrogen or $C_1$-$C_6$ alkyl, provided that when Y is —CO—O—, then $R^3$ is —$(CH_2)_{r'}$—O—CO—$R^{100'}$ wherein $R^{100'}$ and r' each has the same meaning as defined above;

or a pharmaceutically acceptable salt thereof;

36) the ester compound according to the above 35), which is represented by the formula:

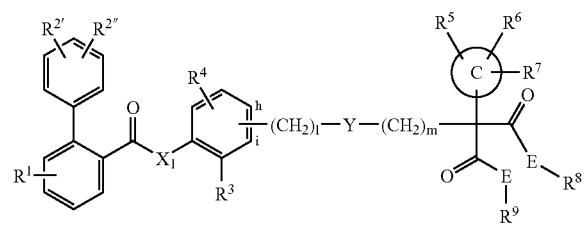

$R^{2'}$ and $R^{2''}$ are each independently hydrogen; $C_1$-$C_6$ alkyl; $C_3$-$C_7$ cycloalkyl; $C_1$-$C_6$ alkoxy; halogen; halo-$C_1$-$C_6$ alkyl; halo-$C_1$-$C_6$ alkyloxy; $C_1$-$C_6$ acyl; $C_2$-$C_6$ alkenyl; or cyano;

$X_1$ is —O— or —$NR^{10}$ ($R^{10}$ has the same meaning as defined above); and R1, R3, R4, R5, R6, R7, R8, R9, Y, ring C, E, l, and m each has the same meaning as defined above;

or a pharmaceutically acceptable salt thereof;

37) a pharmaceutical composition, which comprises the ester compound or a pharmaceutically acceptable salt thereof according to any one of the above 1) to 36), and a pharmaceutically acceptable carrier;

38) an MTP (microsomal triglyceride transfer protein) inhibitor, which comprises the ester compound or a pharmaceutically acceptable salt thereof according to any one of the above 1) to 36) as an active ingredient;

39) an agent for the treatment or prophylaxis of hyperlipidemia, which comprises the ester compound or a pharmaceutically acceptable salt thereof according to any one of the above 1) to 36) as an active ingredient;

40) an agent for the treatment or prophylaxis of arteriosclerosis, which comprises the ester compound or a pharmaceutically acceptable salt thereof according to any one of the above 1) to 36) as an active ingredient;

41) an agent for the treatment or prophylaxis of coronary artery diseases, which comprises the ester compound or a pharmaceutically acceptable salt thereof according to any one of the above 1) to 36) as an active ingredient;

42) an agent for the treatment or prophylaxis of obesity, which comprises the ester compound or a pharmaceutically acceptable salt thereof according to any one of the above 1) to 36) as an active ingredient;

43) an agent for the treatment or prophylaxis of diabetes, which comprises the ester compound or a pharmaceutically acceptable salt thereof according to any one of the above 1) to 36) as an active ingredient;

44) an agent for the treatment or prophylaxis of hypertension, which comprises the ester compound or a pharmaceutically acceptable salt thereof according to any one of the above 1) to 36) as an active ingredient;

45) an agent for the treatment or prophylaxis of hyperlipidemia, arteriosclerosis, coronary artery diseases, obesity, diabetes or hypertension, comprising an MTP inhibitor which is a compound selectively inhibiting MTP (microsomal triglyceride transfer protein) in the small intestine, or a pharmaceutically acceptable salt and having at least one or more carbonate group(s), and a pharmaceutically acceptable carrier;

46) the agent for the treatment or prophylaxis according to the above 45), wherein the MTP inhibitor does not substantially inhibit MTP in the liver but substantially inhibits only MTP in the small intestine;

47) the agent for the treatment or prophylaxis according to the above 45), wherein after the administered MTP inhibitor inhibits MTP in the small intestine, it is metabolized in the small intestine, blood and liver to the amount at which the remaining MTP inhibitor in the liver does not substantially inhibit the MTP in the liver;

48) the agent for the treatment or prophylaxis according to the above 45), wherein after the administered MTP inhibitor inhibits MTP in the small intestine, it is metabolized in the small intestine or blood to the amount at which the remaining MTP inhibitor in the liver does not substantially inhibit the MTP in the liver;

49) the agent for the treatment or prophylaxis according to the above 47) or 48), wherein the remaining MTP inhibitor in the liver is metabolized to the state where TG-releasing activity of the liver is kept at the level of about 80% or more of the normal level;

50) the agent for the treatment or prophylaxis according to any one of the above 45) to 49), wherein the MTP inhibitor according to the above 1) to 36) is a compound having at least one carbonate group;

51) the agent for the treatment or prophylaxis according to any one of the above 45) to 50), wherein after the compound having at least one carbonate group exerts MTP inhibitory activity, the ester moiety of the compound is metabolized in blood to become an inactive substance;

52) the agent for the treatment or prophylaxis according to any one of the above 45) to 51), wherein the MTP inhibitor is an ester compound having at least one carbonate group, or a salt pharmaceutically acceptable salt thereof according to the above 15);

53) a method for the treatment or prophylaxis of hyperlipidemia, arteriosclerosis, coronary artery diseases, obesity, diabetes or hypertension, which comprises administering a compound having at least one or more carbonate group(s) and selectively inhibiting MTP (microsomal triglyceride transfer protein) in the small intestine, or a pharmaceutically acceptable salt thereof;

54) the method according to the above 53), wherein after the compound inhibits MTP in the small intestine, it is metabolized in the small intestine, blood and liver to the amount at which remaining said compound in the liver does not substantially inhibit MTP in the liver;

55) the method according to the above 53), wherein after the compound inhibits MTP in the small intestine, it is metabolized in the small intestine or blood to the amount at which remaining said compound in the liver does not substantially inhibit MTP in the liver;

56) the method according to the above 54) or 55, wherein the remaining compound in the liver is metabolized to the state where TG-releasing activity of the liver is kept at the level of about 80% or more of the normal level;

57) the method according to any one of the above 54) to 56), wherein the ester compound according to any one of the above 1) to 36) is a compound having at least one or more carbonate group(s);

58) the method according to any one of the above 54) to 57), wherein after the compound having at least one or more carbonate group(s) exerts MTP inhibitory activity, the ester moiety of the compound is metabolized in blood to become an inactive substance;

59) the method according to any one of the above 53) to 58), wherein the ester compound or a pharmaceutically acceptable salt thereof according to the above 15) is a compound having at least one or more carbonate group(s);

60) the agent for the treatment or prophylaxis according to any one of the above 45) to 52), wherein the agent is an agent for the treatment or prophylaxis of hyperlipidemia which is used in combination with other antihyperlipidemic drug(s);

61) the agent for the treatment or prophylaxis according to the above 60), wherein other antihyperlipidemic drug is a statin-type drug;

62) the agent for the treatment or prophylaxis according to the above 61), wherein the statin-type drug is one or more drug(s) selected from the group consisting of lovastatin, simvastatin, pravastatin, fluvastatin, atorvastatin and cerivastatin;

63) the agent for the treatment or prophylaxis according to any one of the above 45) to 52), wherein the agent is an agent for the treatment or prophylaxis of obesity which is used in combination with other anti-obesity drug(s);

64) the agent for the treatment or prophylaxis according to the above 63), wherein other anti-obesity drug is mazindol or/and orlistat;

65) the agent for the treatment or prophylaxis according to any one of the above 45) to 52), wherein the agent is an agent for the treatment or prophylaxis of diabetes which is used in combination with other anti-diabetic drug(s);

66) the agent for the treatment or prophylaxis according to the above 65), wherein other anti-diabetic drug is one or more drug(s) selected from the group consisting of insulin preparations, sulfonylurea drugs, insulin secretagogues, sulfonamide drugs, biguanide drugs, α-glucosidase inhibitors and insulin resistance-improving drugs;

67) the agent for the treatment or prophylaxis according to the above 65), wherein other anti-diabetic drug is one or more drug(s) selected from the group consisting of insulin, glibenclamide, tolbutamide, glyclopyramide, acetohexamide, glimepiride, tolazamide, gliclazide, nateglinide, glybuzole, metformin hydrochloride, buformin hydrochloride, boglibose, acarbose and pioglitazone hydrochloride;

68) the agent for the treatment or prophylaxis according to any one of the above 45) to 52), wherein the agent is an agent for the treatment or prophylaxis of hypertension which is used in combination with other anti-hypertension drug(s);

69) the agent for the treatment or prophylaxis according to the above 68), wherein other anti-hypertension drug is one or more drug(s) selected from the group consisting of loop diuretics, angiotensin converting enzyme inhibitors, angiotensin II receptor antagonists, calcium antagonists, β-blockers, α,β-blockers and α-blockers;

70) the agent for the treatment or prophylaxis according to the above 68), wherein other anti-hypertension drug is one or more drug(s) selected from the group consisting of furosemide delayed release, captopril, captopril delayed release, enalapril maleate, alacepril, delapril hydrochloride, silazapril, lisinopril, benazepril hydrochloride, imidapril hydrochloride, temocapril hydrochloride, quinapril hydrochloride, trandolapril, perindopril erbumine, losartan potassium, candesartan cilexetil, nicardipine hydrochloride, nicardipine hydrochloride delayed release, nilvadipine, nifedipine, nifedipine delayed release, benidipine hydrochloride, diltiazem hydrochloride, diltiazem hydrochloride delayed release, nisoldipine, nitrendipine, manidipine hydrochloride, barnidipine hydrochloride, efonidipine hydrochloride, amlodipine besylate, felodipine, cilnidipine, aranidipine, propranolol hydrochloride, propranolol hydrochloride delayed release, pindolol, pindolol delayed release, indenolol hydrochloride, carteolol hydrochloride, carteolol hydrochloride delayed release, bunitrolol hydrochloride, bunitrolol hydrochloride delayed release, atenolol, asebutolol hydrochloride, metoprolol tartrate, metoprolol tartrate delayed release, nipradilol, penbutolol sulfate, tilisolol hydrochloride, carvedilol, bisoprolol fumarate, betaxolol hydrochloride, celiprolol hydrochloride, bopindolol malonate, bevantolol hydrochloride, labetalol hydrochloride, arotinolol hydrochloride, amosulalol hydrochloride, prazosin hydrochloride, terazosin hydrochloride, doxazosin mesylate, bunazocin hydrochloride, bunazocin hydrochloride delayed release, urapidil and phentolamine mesylate;

71) use of the agent for the treatment or prophylaxis according to any one of the above 39) to 52) and other antihyperlipidemic drug(s) for the treatment or prophylaxis of hyperlipidemia;

72) the use according to the above 71), wherein other antihyperlipidemic drug is a statin-type drug;

73) the use according to the above 72), wherein the statin-type drug is one or more drug(s) selected from the group consisting of lovastatin, simvastatin, pravastatin, fluvastatin, atorvastatin and cerivastatin;

74) use of the agent for the treatment or prophylaxis according to any one of the above 39) to 52) and other anti-obesity drug(s) for the treatment or prophylaxis of obesity;

75) the use according to the above 74), wherein other anti-obesity drug is mazindol or/and orlistat;

76) use of the agent for the treatment or prophylaxis according to any one of the above 39) to 52) and other anti-diabetic drug(s) for the treatment or prophylaxis of diabetes;

77) the use according to the above 76), wherein other anti-diabetic drugs are one or more drug(s) selected from the group consisting of insulin preparations, sulfonylurea drugs, insulin secretagogues, sulfonamide drugs, biguanide drugs, α-glucosidase inhibitors and insulin resistance improving drugs;

78) the use according to the above 76), wherein other anti-diabetic drug is one or more drug(s) selected from the group consisting of insulin, glibenclamide, tolbutamide, glyclopyramide, acetohexamide, glimepiride, tolazamide, gliclazide, nateglinide, glybuzole, metformin hydrochloride, buformin hydrochloride, boglibose, acarbose and pioglitazone hydrochloride;

79) use of the agent for the treatment or prophylaxis according to any one of the above 39) to 52) and other anti-hypertension drug(s) for the treatment or prophylaxis of hypertension;

80) the use according to the above 79), wherein other anti-hypertension drug is one or more drug(s) selected from the group consisting of loop diuretics, angiotension converting enzyme inhibitors, angiotension II receptor antagonists, calcium antagonists, beta-blockers, alpha/beta blockers and alpha blockers;

81) the use according to the above 79), wherein other anti-hypertension drug is one or more drug(s) selected from the group consisting of furosemide delayed release, captopril, captopril delayed release, enalapril maleate, alacepril, delapril hydrochloride, silazapril, lisinopril, benazepril hydrochloride, imidapril hydrochloride, temocapril hydrochloride, quinapril hydrochloride, trandolapril, perindopril erbumine, losartan potassium, candesartan cilexetil, nicardipine hydrochloride, nicardipine hydrochloride delayed release, nilvadipine, nifedipine, nifedipine delayed release, benidipine hydrochloride, diltiazem hydrochloride, diltiazem hydrochloride delayed release, nisoldipine, nitrendipine, manidipine hydrochloride, barnidipine hydrochloride, efonidipine hydrochloride, amlodipine besylate, felodipine, cilnidipine, aranidipine, propranolol hydrochloride, propranolol hydrochloride delayed release, pindolol, pindolol delayed release, indenolol hydrochloride, carteolol hydrochloride, carteolol hydrochloride delayed release, bunitrolol hydrochloride, bunitrolol hydrochloride delayed release, atenolol, asebutolol hydrochloride, metoprolol tartrate, metoprolol tartrate delayed release, nipradilol, penbutolol sulfate, tilisolol hydrochloride, carvedilol, bisoprolol fumarate, betaxolol hydrochloride, celiprolol hydrochloride, bopindolol malonate, bevantolol hydrochloride, labetalol hydrochloride, arotinolol hydrochloride, amosulalol hydrochloride, prazosin hydrochloride, terazosin hydrochloride, doxazosin mesylate, bunazocin hydrochloride, bunazocin hydrochloride delayed release, urapidil and phentolamine mesylate;

82) a pharmaceutical composition comprising an effective amount of the ester compound or a pharmaceutically acceptable salt according to any one of the above 1) to 36), a pharmaceutically acceptable, appropriate amount of ethanol and propylene glycol fatty acid ester;

83) the pharmaceutical composition according to the above 82), which comprises 25 to 35% by weight of ethanol and 65 to 75% by weight of propylene glycol fatty acid ester;

84) a capsule formulation comprising the pharmaceutical composition according to the above 82) or 83);

85) the capsule formulation according to the above 84), wherein the capsule formulation is a hard capsule or soft capsule;

86) a biphenyl compound represented by the formula (100):

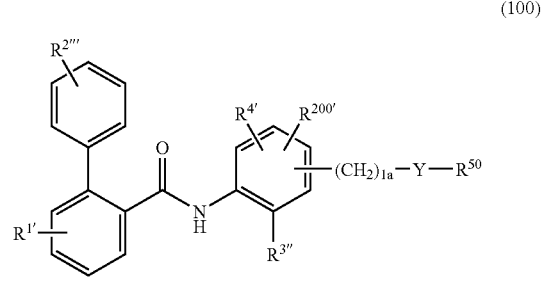

wherein
$R^{1'}$ is hydrogen, $C_1$-$C_6$ alkyl, halogen, halo $C_1$-$C_6$ alkyl, $C_1$-$C_6$ alkoxy or —$(CH_2)_r$—O—CO—$R^{100}$ wherein $R^{100}$ is $C_1$-$C_6$ alkyl, $C_1$-$C_6$ alkoxy or $C_2$-$C_{12}$ alkoxyalkyl, and r is 0 or an integer of 1 to 3;

$R^{2'''}$ is hydrogen, $C_1$-$C_6$ alkyl, halogen, halo-$C_1$-$C_6$ alkyl or $C_2$-$C_6$ alkenyl;

$R^{3''}$ is —CON($R^{11a}$)($R^{12a}$) wherein $R^{11a}$ and $R^{12a}$ are each independently hydrogen, $C_1$-$C_6$ alkyl, optionally substituted $C_6$-$C_{14}$ aryl, optionally substituted $C_7$-$C_{16}$ aralkyl, $C_1$-$C_6$alkoxy, or $R^{11a}$ and $R^{12a}$ may be taken together with the nitrogen to which they are attached to form

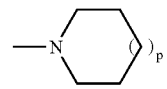

(in which p is 0 or an integer of 1 to 2); or —$(CH^2)_{r'}$—O—CO—$R^{10040}$ wherein $R^{100'}$ is $C_1$-$C_6$ alkyl, $C_1$-$C_6$ alkoxy or $C_2$-$C_{12}$ alkoxyalkyl, and r' is 0 or an integer of 1 to 3;

$R^{4'}$ and $R^{200'}$ are each independently hydrogen, halogen, $C_1$-$C_6$ alkyl or halo-$C_1$-$C_6$ alkyl;

$R^{50}$ is hydrogen, $C_1$-$C_6$alkyl, optionally substituted $C_6$-$C_{14}$ aryl or optionally substituted $C_7$-$C_{16}$ aralkyl;

Y is —O—CO—O—, —O—CO—, —CO—O—, —CO—O—C($R^{110}$)($R^{111}$)—O—CO—, —CO—O—C($R^{110}$)($R^{111}$)—O—CO—O—, —O—CO—O—C($R^{110}$)($R^{111}$)—O—CO—, —O—CO—C($R^{110}$)($R^{111}$)—O—, —O—CO—C($R^{110}$)($R^{111}$)—C($R^{110}$)($R^{111}$)—O— or —O—C($R^{110}$)($R^{111}$)—CO—O— wherein $R^{110}$ and $R^{111}$ are each independently hydrogen or $C_1$-$C_6$ alkyl, provided that when Y is —CO—O—, then $R^{3''}$ is —$(CH_2)_{r'}$—O—CO—$R^{100'}$ wherein $R^{100'}$ and r' each has the same meaning as defined above;

1a is an integer of 1 to 3;

or a pharmaceutically acceptable salt thereof;

87) the biphenyl compound or a pharmaceutically acceptable salt thereof according to the above 86), wherein
$R^{1'}$ is hydrogen,
$R^{2'''}$ is halo-$C_1$-$C_6$ alkyl,
$R^{3''}$ is —CON($R^{11b}$)($R^{12b}$) wherein $R^{11b}$ and $R^{12b}$ are each independently hydrogen or $C_1$-$C_6$ alkyl, or $R^{11b}$ and $R^{12b}$ may be taken together with the nitrogen to which they are attached to form

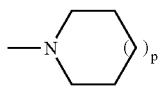

(wherein p is 0 or an integer of 1 to 2); or —$(CH_2)_r$—O—CO—$R^{100'}$ wherein $R^{100'}$ and r' each has the same meaning as defined above;

$R^{4'}$ and $R^{100'}$ are each hydrogen; or $R^{50}$ is hydrogen or $C_1$-$C_6$ alkyl; and 88) a biphenyl compound represented by the formula:

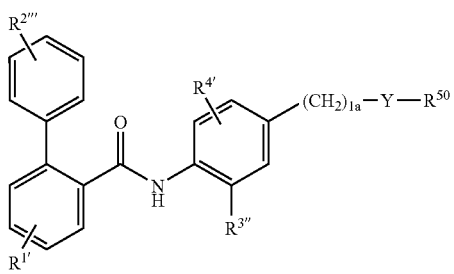

wherein $R^{1'}$ is hydrogen, $C_1$-$C_6$ alkyl, halogen, halo-$C_1$-$C_6$ alkyl, $C_1$-$C_6$ alkoxy or —$(CH_2)_r$—O—CO—$R^{100}$ wherein $R^{100}$ is $C_1$-$C_6$ alkyl, $C_1$-$C_6$ alkoxy or $C_2$-$C_{12}$ alkoxyalkyl, and r is 0 or an integer of 1 to 3;

$R^{2'''}$ is hydrogen, $C_1$-$C_6$ alkyl, halogen, halo-$C_1$-$C_6$ alkyl or $C_2$-$C_6$ alkenyl;

$R^{3''}$ is —$CON(R^{11a})(R^{12a})$ wherein $R^{11a}$ and $R^{12a}$ are each independently hydrogen, $C_1$-$C_6$ alkyl, optionally substituted $C_6$-$C_{14}$ aryl, optionally substituted $C_7$-$C_{16}$ aralkyl, or $C_1$-$C_6$ alkoxy, or $R^{11a}$ and $R^{12a}$ may be taken together with the nitrogen to which they are attached to form

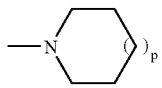

(wherein p is 0 or an integer of 1 to 2); or $(CH_2)_r$—O—CO—$R^{100'}$ wherein $R^{100'}$ is $C_1$-$C_6$ alkyl, $C_1$-$C_6$ alkoxy or $C_2$-$C_{12}$ alkoxyalkyl, and r' is 0 or an integer of 1 to 3;

$R^{4'}$ is hydrogen, halogen, $C_1$-$C_6$ alkyl or halo-$C_1$-$C_6$ alkyl;

$R^{50}$ is hydrogen, $C_1$-$C_6$ alkyl, optionally substituted $C_6$-$C_{14}$ aryl or optionally substituted $C_7$-$C_{16}$ aralkyl;

Y is —O—CO—O—, —O—CO—, —CO—O—, —CO—O—C($R^{110}$)($R^{111}$)—O—CO—, —CO—O—C($R^{110}$)($R^{111}$)—O—CO—O—, or —O—CO—O—C($R^{110}$)($R^{111}$)—O—CO— wherein $R^{110}$ and $R^{111}$ are each independently hydrogen or $C_1$-$C_6$ alkyl, provided that when Y is —CO—O—, then $R^{3''}$ is —$(CH_2)_r$—O—CO—$R^{100'}$ wherein $R^{100'}$ and r' each has the same meaning as defined above;

1a is an integer of 1 to 3;

or a pharmaceutically acceptable salt thereof.

EFFECT OF THE INVENTION

The present invention can provide a novel antihyperlipidemic agent having excellent MTP inhibitory activity without causing side effect to the liver which has been observed in the conventional MTP inhibitors.

BEST MODE FOR CARRYING OUT THE INVENTION

"$C_1$-$C_6$ alkyl" refers to a linear or branched alkyl group of 1 to 6 carbon atoms, including, for example, methyl, ethyl, propyl, isopropyl, butyl, isobutyl, sec-butyl, tert-butyl, pentyl, isopentyl, neopentyl, tert-pentyl, and hexyl, and more preferably a linear or branched $C_1$-$C_4$ alkyl, and especially preferably methyl, ethyl, and isopropyl. In $R^1$, $R^2$, $R^{2'}$ and $R^{2''}$, methyl, ethyl or isopropyl is preferred; in $R^5$, $R^6$, and R7, methyl is preferred; in $R^{10}$, methyl, ethyl or isopropyl is preferred; in $R^{11}$ and $R^{12}$, methyl, ethyl, propyl or isopropyl is preferred; in $R^{13}$ and $R^{14}$, methyl or ethyl is preferred; in $R^{15}$, isopropyl is preferred; in $R^{16}$ and $R^{17}$, methyl or ethyl is preferred; and in $R^{100}$, methyl, ethyl, propyl or isopropyl is preferred.

"Optionally substituted $C_1$-$C_6$ alkyl" refers to a $C_1$-$C_6$ alkyl group which may be substituted by one or two or more substituent(s). Examples of the substituent include, for example, halogen, carboxyl, hydroxy, amino, nitro, cyano, $C_1$-$C_6$ alkoxy, $C_7$-$C_{16}$ aralkyloxy, $C_2$-$C_7$ alkoxycarbonyl, $C_2$-$C_7$ alkoxycarbonyloxy, $C_6$-$C_{14}$ aryl, $C_1$-$C_6$alkylthio (e.g. methylthio, ethylthio, propylthio, butylthio, isobutylthio, etc.), $C_1$-$C_6$ alkylsulfinyl (e.g. methylsulfinyl, ethylsulfinyl, propylsulfinyl, butylsulfinyl, isobutylsulfinyl, etc.), $C_1$-$C_6$ alkylsulfonyl (e.g. methylsulfonyl, ethylsulfonyl, propylsulfonyl, butylsulfonyl, isobutylsulfonyl, etc.), $C_1$-$C_6$ alkylamino (e.g. methylamino, ethylamino, propylamino, butylamino, etc.), $C_2$-$C_7$ acyloxy, acylamino and the like, among which hydroxy is preferable. The number of the substituent(s) is 1 to 5, preferably 1 to 3. A preferable example for $R^3$ and $R^4$ is methyl, ethyl, propyl, isopropyl, butyl or isobutyl, and a preferable example for $R^8$ and $R^9$ is methyl or ethyl.

"$C_3$-$C_7$ cycloalkyl" refers to a cycloalkyl group having 3 to 7 carbon atoms, specifically cyclopropyl, cyclobutyl, cyclopentyl, cyclohexyl, 1-methylcyclohexyl or cycloheptyl. Preferable examples thereof include a cycloalkyl having 3 to 6 carbon atoms, specifically cyclopropyl, cyclobutyl, cyclopentyl or cyclohexyl. More preferable examples thereof include cyclopropyl or cyclohexyl. A preferable example for $R^1$ and $R^2$ includes cyclohexyl; a preferable example for $R^{10}$ includes cyclohexyl; and preferable examples for ring C include cyclopentyl and cyclohexyl.

"$C_1$-$C_6$ alkoxy" refers to a linear or branched alkoxy group having 1 to 6 carbon atom(s), and its example includes methoxy, ethoxy, propoxy, isopropoxy, butoxy, tert-butoxy, pentyloxy, tert-pentyloxy and hexyloxy, etc., preferably an alkoxy having 1 to 4 carbon atom(s), such as methoxy, ethoxy, isopropoxy, butoxy and tert-butoxy, and more preferably methoxy and ethoxy. Preferable examples for $R^1$, $R^2$, $R^{2'}$ and $R^{2''}$ include methoxy, isopropoxy and butoxy; preferable examples for $R^3$ and $R^4$ include methoxy, ethoxy, propoxy and isopropoxy; preferable examples for $R^5$, $R^6$ and $R^7$ include methoxy and ethoxy; a preferable example for $R^{11}$ and $R^{12}$ includes methoxy; and preferable examples for $R^{15}$ include methoxy, ethoxy, propoxy and isopropoxy.

"Halo-$C_1$-$C_6$ alkyl" refers to said $C_1$-$C_6$ alkyl substituted with halogen described below, and its example includes chloromethyl, bromomethyl, fluoromethyl, trifluoromethyl, trichloromethyl, tribromomethyl, trichloroethyl, pentafluoropropyl and chlorobutyl, etc., preferably chloromethyl, bromomethyl, fluoromethyl, trifluoromethyl, trifluoroethyl and trichloromethyl, and especially preferably trifluoromethyl. A preferable example for $R^1$, $R^2$, $R^{2'}$ and $R^{2''}$ includes trifluoromethyl; a preferable example for $R^3$ and $R^4$ includes trifluoromethyl; a preferable example for $R^5$, $R^6$ and $R^7$ includes trifluoromethyl; and preferable examples for $R^{16}$ and $R^{17}$ include trifluoromethyl and trifluoroethyl.

"Halo-$C_1$-$C_6$alkyloxy" refers to a monovalent group wherein the hydrogen atom of the hydroxy group is substituted by the above-mentioned halo-$C_1$-$C_6$alkyl, and includes, for example, chloromethyloxy, bromomethyloxy, fluoromethyloxy, trifluoromethyloxy, trichloromethyloxy, tribromomethyloxy, trichloroethyloxy, pentafluoropropyloxy and chlorobutyloxy, etc., preferably chloromethyloxy, bromomethyloxy, fluoromethyloxy, trifluoromethyloxy and trichloromethyloxy, and especially preferably trifluoromethyloxy. A preferable example for $R^1$, $R^2$, $R^{2'}$ and $R^{2''}$ includes trifluoromethyloxy.

"$C_6$-$C_{14}$ aryl" refers to phenyl, naphthyl or biphenyl, etc., preferably phenyl.

"Optionally substituted $C_6$-$C_{14}$ aryl" refers to a $C_6$-$C_{14}$ aryl which may be substituted by one or two or more substituents (s).

In the "optionally substituted $C_6$-$C_{14}$ aryl", when $C_6$-$C_{14}$ aryl is substituted by two or more substituents, such substituents are not particularly limited, and may be the same or different each other and are arbitrarily positioned. The number of substituents is not particularly limited so long as they are chemically acceptable, while the number is preferably around 1 to 3. Specifically, examples of the substituent include $C_1$-$C_6$ alkyl (e.g. methyl, ethyl, propyl, isopropyl, butyl, tert-butyl, etc.); hydroxyl; $C_1$-$C_6$alkoxy (e.g. methoxy, ethoxy, propoxy, butoxy, etc.); halogen (e.g. fluorine, chlorine, bromine, etc.); nitro; cyano; $C_1$-$C_6$ acyl (e.g. formyl, acetyl, propionyl, etc.); $C_1$-$C_6$ acyloxy (e.g. formyloxy, acetoxy, propionyloxy, etc.); mercapto; $C_1$-$C_6$ alkylthio (e.g. methylthio, ethylthio, propylthio, butylthio, isobutylthio, etc.); amino; $C_1$-$C_6$ alkylamino (e.g. methylamino, ethylamino, propylamino, butylamino, etc.); di($C_1$-$C_6$ alkyl) amino (e.g. dimethylamino, diethylamino, dipropylamino, dibutylamino, etc.); carboxyl; $C_2$-$C_7$ alkoxycarbonyl (e.g. methoxycarbonyl, ethoxycarbonyl, propoxycarbonyl, etc.); amido; trifluoromethyl; $C_1$-$C_6$ alkylsulfonyl(e.g. methylsulfonyl, ethylsulfonyl, etc.); aminosulfonyl; $C_3$-$C_7$ cycloalkyl (e.g. cyclopentyl, cyclohexyl, etc.); phenyl; acylamido (e.g. acetamido, propionylamido, etc.) and the like, among which hydroxy, $C_1$-$C_6$ alkyl, $C_1$-$C_6$ alkoxy, mercapto, $C_1$-$C_6$ alkylthio, halogen, trifluoromethyl, $C_1$-$C_6$ acyl, $C_2$-$C_7$ alkoxycarbonyl or acylamido are preferable.

A preferable example for $R^1$ and $R^2$ includes phenyl which may be substituted with halo-$C_1$-$C_6$alkyl (e.g. trifluoromethyl, etc.), $C_1$-$C_6$ alkyl (e.g. methyl, ethyl, etc.), halogen (e.g. fluorine, chlorine, bromine, etc.), $C_1$-$C_6$alkoxy (e.g. methoxy, etc.), $C_1$-$C_6$ acyl (e.g. acetyl, etc.), $C_2$-$C_6$ alkenyl (e.g. isopropenyl, etc.); or cyano; a preferable example for $R^5$, $R^6$ and $R^7$ includes phenyl which may be substituted with halo-$C_1$-$C_6$ alkyl (e.g. trifluoromethyl, etc.), $C_1$-$C_6$ alkyl (e.g. methyl, etc.), halogen (e.g. chlorine, etc.) or $C_1$-$C_6$ alkoxy (e.g. methoxy, etc.); a preferable example for $R^8$ and $R^9$ includes phenyl; a preferable example for $R^{11}$ and $R^{12}$ includes phenyl; and a preferable example for ring C include phenyl or naphthyl.

"Optionally substituted $C_7$-$C_{16}$ aralkyl" refers to a $C_7$-$C_{16}$ aralkyl which may be substituted by one or two or more substituent(s).

"$C_7$-$C_{16}$ aralkyl" refers to a $C_7$-$C_{16}$ monovalent group wherein the hydrogen atom of the alkyl moiety is substituted by an aryl group, for example, a $C_7$-$C_{16}$ aralkyl wherein the aryl moiety is phenyl (which may be substituted with 1 to 3 substituent(s) mentioned in the above description of aryl) and the alkyl moiety is an alkyl having 1 to 6 carbon atom(s) (e.g. the above-mentioned $C_1$-$C_6$ alkyl). To be more specific, examples thereof include benzyl, phenethyl, phenylpropyl, phenylbutyl and phenylhexyl, etc., among which benzyl or phenylethyl is preferable. A preferable example for $R^1$ and $R^2$ includes benzyl, a preferable example for $R^{11}$ and $R^{12}$ is benzyl; and a preferable example for ring C includes benzyl.

The substituent in the optionally substituted $C_7$-$C_{16}$ aralkyl may be any substituent so long as it does not spoil the purpose of the present invention, and preferably includes those mentioned above for the optionally substituted $C_6$-$C_{14}$ aryl.

"$C_6$-$C_{14}$ aryloxy" refers to phenoxy, naphthyloxy, etc., preferably phenoxy.

"$C_6$-$C_{14}$ aryloxy" refers to a $C_6$-$C_{14}$ aryloxy which may be substituted with 1 or 2 or more substituent (s). Examples of the substituent in the optionally substituted $C_6$-$C_{14}$ aryloxy are preferably those mentioned for the above $C_6$-$C_{14}$ aryl. A preferable example for $R^1$ and $R^2$ is phenoxy, and a preferable example for $R^{15}$ is phenoxy.

"$C_7$-$C_{16}$ aralkyloxy" refers to an arylalkoxy of which alkoxy moiety has 1 to 4 carbon atom(s), including, for example, benzyloxy, phenethyloxy, phenylpropyloxy, phenylbutyloxy, etc., and preferably benzyloxy.

"Optionally substituted $C_7$-$C_{16}$ aralkyloxy" refers to a $C_7$-$C_{16}$ aralkyloxy which may be substituted by one or two or more substituent(s). Examples of the substituent in the optionally substituted $C_7$-$C_{16}$ aralkyloxy are preferably those for the optionally substituted $C_6$-$C_{14}$ aryl mentioned above. A preferable example for $R^1$ and $R^2$ is benzyloxy; a preferable example for $R^3$ is benzyloxy; and a preferable example for $R^{15}$ is benzyloxy.

"Optionally substituted $C_7$-$C_{15}$ arylcarbonyl" refers to, for example, benzoyl, naphthoyl, etc. (wherein the phenyl or naphthyl moiety may be substituted with 1 to 3 substituent(s) mentioned in the above description of aryl), preferably benzoyl. A preferable example for $R^1$ and $R^2$ includes benzoyl. Examples of the substituent for the optionally substituted $C_7$-$C_{15}$ arylcarbonyl are preferably the above substituents in the optionally substituted $C_6$-$C_{14}$ aryl.

"Heterocycle" refers to a 5- to 6-membered heteroaromatic ring, a 5- to 6-membered saturated heterocycle, or a 5- to 6-membered unsaturated heterocycle, any of which contains 1 to 3 heteroatom(s) selected from nitrogen, oxygen and sulfur as an atom constituting the ring other than carbon atom, or a fused heterocyclic ring in which said heterocycle and benzene ring are fused. Specifically, such heterocycles include thiophen-2-yl, thiophen-3-yl, furan-2-yl, furan-3-yl, pyrrol-1-yl, pyrrol-2-yl, pyrrol-3-yl, imidazol-1-yl, imidazol-2-yl, imidazol-4-yl, imidazol-5-yl, pyrazol-1-yl, pyrazol-3-yl, pyrazol-4-yl, thiazol-2-yl, thiazol-4-yl, thiazol-5-yl, oxazol-2-yl, oxazol-4-yl, oxazol-5-yl, isoxazol-3-yl, isoxazol-4-yl, isoxazol-5-yl, pyrimidin-2-yl, pyrimidin-4-yl, pyrimidin-5-yl, pyridin-2-yl, pyridin-3-yl, pyridin-4-yl, pyrrolidin-2-yl, pyrrolidin-3-yl, benzothiophen-2-yl, benzothiophen-3-yl, benzofuran-2-yl, benzofuran-3-yl, indol-2-yl, indol-3-yl, benzimidazol-1-yl, benzimidazol-2-yl, benzothiazol-2-yl, benzoxazol-2-yl, quinolin-2-yl, quinolin-3-yl, quinolin-4-yl, isoquinolin-1-yl, isoquinolin-3-yl, isoquinolin-4-yl, 1,3,4-thiadiazol-2-yl, morpholin-4-yl, etc.

A preferable example for $R^1$ and $R^2$ includes thiophen-3-yl; preferable examples for ring A include imidazol-5-yl, thiazol-5-yl, pyridin-3-yl and pyrrolidin-2-yl; a preferable example for $R^3$ includes thiazol-2-yl; and preferable examples for ring C include pyridin-2-yl, pyridin-3-yl, thiophen-2-yl, thiophen-3-yl and thiazol-2-yl.

"Optionally substituted heterocycle" refers to a heterocyclic group which may be substituted with one or two or more substituent(s) and includes the same substituents as those mentioned in the above description of aryl. The number of substituents is not particularly limited so long as they are chemically acceptable, while the number is preferably around 1 to 3.

"$C_2$-$C_7$ alkoxycarbonyl" refers to an alkoxycarbonyl of which alkyl moiety has 1 to 6 carbon atom(s), such as methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, tert-pentyloxycarbonyl and hexyloxycarbonyl, etc. Preferable examples thereof include methoxycarbonyl, ethoxycarbonyl, propoxycarbonyl and butoxycarbonyl. A preferable example for $R^2$ includes butoxycarbonyl; a preferable example for $R^5$, $R^6$ and $R^7$ includes methoxycarbonyl; and a preferable example for $R^{13}$ and $R^{14}$ includes methoxycarbonyl.

"Halogen" refers to chlorine, bromine, fluorine or the like. Preferable examples for $R^1$ include fluorine and chlorine; preferable examples for $R^{2'}$ and $R^{2''}$ include fluorine, chlorine and bromine; preferable examples for $R^3$ and $R^4$ include chlorine and bromine; and preferable examples for $R^5$, $R^6$ and $R^7$ include fluorine and chlorine.

"$C_2$-$C_6$ alkenyl" refers to a linear or branched alkenyl group having 2 to 6 carbon atoms, and its example includes vinyl, n-propenyl, isopropenyl, n-butenyl, isobutenyl, sec-butenyl, tert-butenyl, n-pentenyl, isopentenyl, neopentenyl, 1-methylpropenyl, n-hexenyl, isohexenyl, 1,1-dimethylbutenyl, 2,2-dimethylbutenyl, 3,3-dimethylbutenyl, 3,3-dimethylpropenyl, 2-ethylbutenyl, etc., and a preferable example for $R^2$, $R^{2'}$, $R^{2''}$ and $R'''$ includes n-propenyl.

"$C_1$-$C_6$ acyl" refers to formyl having one carbon atom, or an alkanoyl having 2 to 6 carbon atoms such as acetyl, propionyl, butyryl or pivaloyl, etc., and its preferable examples include formyl, acetyl and pivaloyl. A preferable example for $R^{2'}$ and $R^{2''}$ includes acetyl; a preferable example for $R^3$ includes formyl; a preferable example for $R^5$, $R^6$ and $R^7$ includes acetyl; and a preferable example for $R^{13}$ and $R^{14}$ includes acetyl. The $C_1$-$C_6$ acyl may include, for example, sulfonylacyl having 1 to 10 carbon atoms such as methanesulfonyl, ethanesulfonyl and benzenesulfonyl, and a phosphonylacyl having 1 to 6 carbon atoms such as methylphosphonyl and ethylphosphonyl.

"$C_3$-$C_{10}$ alkoxycarbonylalkyl" refers to a monovalent group having 3 to 10 carbon atoms, wherein the hydrogen atom of the alkyl moiety is substituted with an alkoxycarbonyl, and said alkyl may be the $C_1$-$C_6$ alkyl mentioned above, and said alkoxycarbonyl may be the $C_2$-$C_7$ alkoxycarbonyl mentioned above. Examples of the $C_3$-$C_{10}$ alkoxycarbonylalkyl includes, for example, methoxycarbonylmethyl, methoxycarbonylethyl, methoxycarbonylpropyl, methoxycarbonylbutyl, ethoxycarbonylmethyl, ethoxycarbonylethyl, ethoxycarbonylpropyl, ethoxycarbonylbutyl, propoxycarbonylmethyl, propoxycarbonylethyl, propoxycarbonylpropyl, propoxycarbonylbutyl, isopropoxycarbonylmethyl, isopropoxycarbonylethyl, isopropoxycarbonylpropyl, isopropoxycarbonylbutyl, butoxycarbonylmethyl, butoxycarbonylethyl, butoxycarbonylpropyl, butoxycarbonylbutyl, isobutoxycarbonylmethyl, isobutoxycarbonylethyl, isobutoxycarbonylpropyl, isobutoxycarbonylbutyl, tert-butoxycarbonylmethyl, tert-butoxycarbonylethyl, tert-butoxycarbonylpropyl, tert-butoxycarbonylbutyl, pentyloxycarbonylmethyl, pentyloxycarbonylethyl, pentyloxycarbonylpropyl, tert-pentyloxycarbonylmethyl, tert-pentyloxycarbonylethyl, tert-pentyloxycarbonylpropyl, hexyloxycarbonylmethyl, hexyloxycarbonylethyl, and hexyloxycarbonylpropyl.

"$C_2$-$C_{12}$ alkoxyalkyl" refers to an alkoxyalkyl of which alkoxy moiety has the same meaning as said alkoxy and alkyl moiety has the same meaning as said alkyl, and its example includes methoxymethyl, ethoxymethyl, propoxymethyl, butoxymethyl, pentyloxymethyl, hexyloxymethyl, ethoxyethyl and methoxyethyl, etc.

"$C_2$-$C_7$ alkoxycarbonyloxy" refers to a monovalent group wherein the hydrogen atom of the hydroxy is substituted with the above $C_2$-$C_7$ alkoxycarbonyloxy, and includes, for example, methoxycarbonyloxy, ethoxycarbonyloxy, propoxycarbonyloxy, isopropoxycarbonyloxy, butoxycarbonyloxy, isobutoxycarbonyloxy, tert-butoxycarbonyloxy, pentyloxycarbonyloxy, tert-pentyloxycarbonyloxy, and hexyloxycarbonyloxy.

"$C_2$-$C_7$ acyloxy" refers to a monovalent group wherein the hydrogen atom of the hydroxy is substituted with an acyl group (e.g. alkanoyl such as acetyl, propionyl, butyryl and pivaloyl), and examples thereof are acetyloxy, propionyloxy, butyryloxy or pivaloyloxy.

"Alkanediyl" has preferably 1 to 6 carbon atom(s), and its example includes methylene, ethane-1,2-diyl, ethane-1,1-diyl, propane-1,3-diyl, butane-1,4-diyl, pentane-1,5-diyl, hexane-1,6-diyl, 1,1-dimethylethane-1,2-diyl, 1,1-diethylethane-1,2-diyl, 2,2-dimethylethane-1,2-diyl, 2,2-diethylethane-1,2-diyl, 1,1-dimethylpropane-1,3-diyl, 1,1-diethylpropane-1,3-diyl, 2,2-dimethylpropane-1,3-diyl, 2,2-diethylpropane-1,3-diyl, 3,3-dimethylpropane-1,3-diyl and 3,3-diethylpropane-1,3-diyl, etc. Preferable examples for $Alk^1$ and $Alk^2$ include methylene, ethane-1,2-diyl, ethane-1,1-diyl, propane-1,3-diyl, etc.

"Alkenediyl" has preferably 2 to 6 carbon atoms, and its example includes ethylene-1,2-diyl, 1-propene-1,3-diyl, 2-propene-1,3-diyl, 1-butene-1,4-diyl, 2-butene-1,4-diyl, 3-butene-1,4-diyl and 1,3-butadiene-1,4-diyl, etc. Preferable examples for $Alk^1$ and $Alk^2$ include ethylene-1,2-diyl, 1-propene-1,3-diyl, 2-propene-1,3-diyl, etc.

The group or substituents as defined above may be further substituted with substituent (s) such as those mentioned above.

"Prodrug" of the compound refers to a derivative of the compound of the present invention, which has a group capable of being chemically or metabolically converted and shows pharmaceutical activity after it is hydrolyzed or solvolyzed or converted under physiological conditions. Since it is fully established in the medical field that what is a group to be degradable or how such a group is introduced into a compound, the technology known per se like these may be used in the present invention.

For example, there may be listed a derivative in which a substituent such as —CO—$C_1$-$C_6$ alkyl, —$CO_2$—$C_1$-$C_6$ alkyl, —CONH—$C_1$-$C_6$ alkyl, —CO—$C_2$-$C_6$ alkenyl, —$CO_2$—$C_2$-$C_6$ alkenyl, —CONH—$C_2$-$C_6$ alkenyl, —CO—$C_6$-$C_{14}$ aryl, —$CO_2$—$C_6$-$C_{14}$ aryl, —CONH—$C_6$-$C_{14}$ aryl, —CO-heterocycle, —$CO_2$-heterocycle, —CONH-heterocycle, etc. (wherein any of said $C_1$-$C_6$ alkyl, $C_2$-$C_6$ alkenyl, $C_6$-$C_{14}$ aryl and heterocycle may be substituted with halogen, $C_1$-$C_6$ alkyl, hydroxy, $C_1$-$C_6$ alkoxy, carboxyl, amino, amino acid residue, —$PO_3H_2$, —$SO_3H$, —CO-polyethyleneglycol residue, —$CO_2$-polyethyleneglycol residue, —CO-polyethyleneglycol monoalkyl ether residue or —$CO_2$-polyethyleneglycol monoalkyl ether residue) is attached to the hydroxy group of the compound.

Also, there may be exemplified a derivative in which a substituent such as —CO—$C_1$-$C_6$ alkyl, —$CO_2$—$C_1$-$C_6$ alkyl, —CO—C$_2$-C$_6$ alkenyl, —CO$_2$—C$_2$-C$_6$ alkenyl, —CO$_2$—C$_6$-C$_{14}$ aryl, —CO—C$_6$-C$_{14}$ aryl, —CO-heterocycle, —CO$_2$-heterocycle, etc. (wherein any of said C$_1$-C$_6$ alkyl, C$_2$-C$_6$ alkenyl, C$_6$-C$_{14}$ aryl and heterocycle may be substituted with halogen, C$_1$-C$_6$ alkyl, hydroxy, C$_1$-C$_6$ alkoxy, carboxyl, amino, amino acid residue, —PO$_3$H$_2$, —SO$_3$H, —CO-polyethyleneglycol residue, —CO$_2$-polyethyleneglycol residue, —CO-polyethyleneglycol monoalkyl ether residue, —CO$_2$-polyethyleneglycol monoalkyl ether residue or —PO$_3$H$_2$, etc.) is attached to the amino group of the compound.

Furthermore, there may be exemplified a derivative in which a substituent such as C$_1$-C$_6$ alkoxy, C$_6$-C$_{14}$ aryloxy, etc. (wherein said C$_1$-C$_6$ alkoxy or C$_6$-C$_{14}$ aryloxy may be substituted with halogen, C$_1$-C$_6$ alkyl, hydroxy, C$_1$-C$_6$ alkoxy, carboxyl, amino, amino acid residue, —PO$_3$H$_2$, —SO$_3$H, polyethyleneglycol residue or polyethyleneglycol monoalkyl ether residue, etc.) is attached to the carboxyl group of the compound.

Detailed description is given below with respect to various substituents.

R$^1$ is preferably hydrogen; C$_1$-C$_6$ alkyl such as methyl, ethyl, etc.; C$_1$-C$_6$ alkoxy such as methoxy, isopropoxy, etc.; halogen such as fluorine, chlorine, etc.; halo-C$_1$-C$_6$ alkyl such as trifluoromethyl, etc.; or C$_2$-C$_6$ alkenyl such as isopropenyl, etc.

R$^2$ is preferably phenyl (which may be substituted with halo-C$_1$-C$_6$ alkyl such as trifluoromethymethyl, etc.; C$_1$-C$_6$ alkyl such as methyl, ethyl, etc.; halogen such as fluoro, chlorine, bromine, etc.; C$_1$-C$_6$ alkyl such as ethyl and isopropyl, etc.; C$_1$-C$_6$ alkoxy such as methoxy, etc.; C$_1$-C$_6$ acyl such as acetyl, etc.; C$_2$-C$_6$ alkenyl such as isopropenyl, etc.; or cyano); C$_1$-C$_6$ alkyl such as ethyl, isopropyl, etc.; C$_3$-C$_7$ cycloalkyl such as cyclohexyl, etc.; C$_1$-C$_6$ alkoxy such as butoxy, etc.; halo-C$_1$-C$_6$ alkyl such as trifluoromethyl, etc.; halo-C$_1$-C$_6$ alkyloxy such as trifluoromethoxy, etc.; C$_7$-C$_{16}$ aralkyl such as benzyl, etc.; C$_6$-C$_{14}$ aryloxy such as phenoxy (of which aryl moiety may be substituted with halo-C$_1$-C$_6$ alkyl such as trifluoromethyl, etc.), etc.; C$_7$-C$_{15}$ arylcarbonyl such as benzoyl (of which aryl moiety may be substituted with halogen such as chlorine, etc.), etc.; heterocycle such as thiophen-3-yl, etc.; C$_2$-C$_7$ alkoxycarbonyl such as butoxycarbonyl, etc.; —N(R$^{40}$)(R$^{41}$) (wherein R$^{40}$ and R$^{41}$ are each independently hydrogen or optionally substituted phenyl); (CH$_2$)$_r$—O—CO—R$^{100}$ (wherein R$^{100}$ is C$_1$-C$_6$ alkyl, C$_1$-C$_6$ alkoxy or C$_2$-C$_{12}$ alkoxyalkyl, and r is 0 or an integer of 1 to 3).

R$^{2'}$ is preferably hydrogen or halogen such as chlorine, etc.

R$^{2''}$ is preferably hydrogen, halo-C$_1$-C$_6$ alkyl such as trifluoromethyl, etc.; C$_1$-C$_6$ alkyl such as methyl, ethyl, etc.; halogen such as fluorine, chlorine, bromine, etc.; C$_1$-C$_6$ alkoxy such as methoxy, etc.; C$_1$-C$_6$ acyl such as methylcarbonyl, etc.; C$_2$-C$_6$ alkenyl such as isopropenyl, etc.; or cyano.

Ring A is preferably

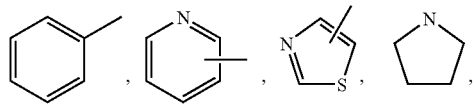

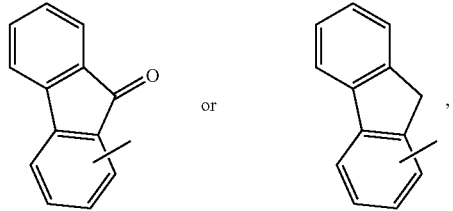

among which phenyl is especially preferred.

X is preferably —COO—, —N(R$^{10}$)CO— or —CON(R$^{10}$)— (wherein R$^{10}$ is hydrogen; C$_1$-C$_6$ alkyl such as methyl, isopropyl, etc.; or C$_3$-C$_7$ cycloalkyl such as cyclohexyl, etc.), among which —COO— or —CONH— is especially preferred.

Ring B is preferably

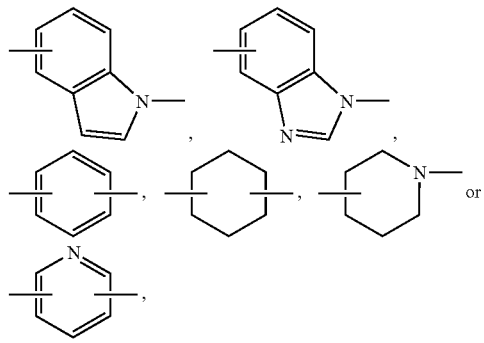

and especially preferably

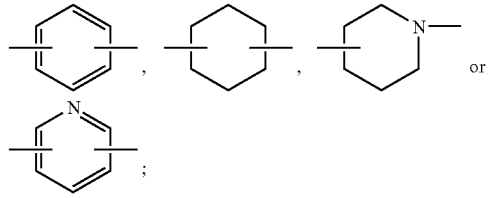

and most preferably

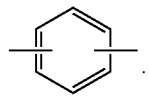.

R$^3$ is preferably hydrogen; hydroxy; halogen such as chlorine, bromine, etc.; C$_1$-C$_6$ alkyl such as methyl, ethyl, isopropyl, isobutyl, etc.; substituted C$_1$-C$_6$ alkyl such as isobutyl substituted with hydroxy, etc.; C$_1$-C$_6$ alkoxy such as methoxy, ethoxy, propoxy, isopropoxy, etc.; halo-C$_1$-C$_6$ alkyl such as trifluoromethyl, etc.; C$_7$-C$_{16}$ aralkyloxy such as benzyloxy, etc.; C$_1$-C$_6$ acyl such as formyl, etc.; optionally substituted heterocycle such as 4-methyl-thiazol-2-yl, etc.; —CON(R$^{11}$)(R$^{12}$) (wherein R$^{11}$ and R$^{12}$ are each independently hydrogen; C$_1$-C$_6$ alkyl such as methyl, ethyl, propyl, isopropyl, etc.; $C_6$-$C_{14}$ aryl such as phenyl, etc.; $C_7$-$C_{16}$ aralkyl such as benzyl, etc.; or $C_1$-$C_6$ alkoxy such as methoxy, etc.; or $R^{11}$ and $R^{12}$ may be taken together with the nitrogen to which they are attached to form

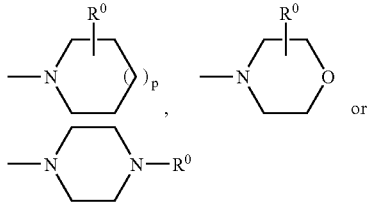

(wherein $R^0$ and p each has the same meaning as defined above)); —N($R^{13}$)($R^{14}$) or —$CH_2$—N($R^{13}$)($R^{14}$) (wherein $R^{13}$ and $R^{14}$ are each independently hydrogen; $C_1$-$C_6$ alkyl such as methyl, ethyl, etc.; $C_2$-$C_7$ alkoxycarbonyl such as methoxycarbonyl, etc.; or $C_1$-$C_6$ acyl such as acetyl, etc.; or $R^{13}$ and $R^{14}$ may be taken together with the nitrogen to which they are attached to form

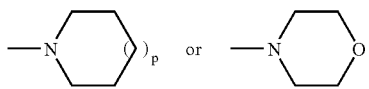

(wherein p has the same meaning as defined above)); or —CO($R^{15}$) (wherein $R^{15}$ is $C_1$-$C_6$ alkyl such as isopropyl, etc.; $C_1$-$C_6$ alkoxy such as methoxy, ethoxy, propoxy, isopropoxy, etc.; $C_7$-$C_{16}$ aralkyloxy such as benzyloxy, etc.; or hydroxy); or —($CH_2$)$_{r'}$—O—CO—$R^{100'}$ (wherein $R^{100'}$ is $C_1$-$C_6$ alkyl, $C_1$-$C_6$ alkoxy or $C_2$-$C_{12}$ alkoxyalkyl, and r' is 0 or an integer of 1 to 3.)). Alternatively, $R^3$, $R^{10}$ and ring B may be taken together with the nitrogen to which $R^{10}$ is attached to form

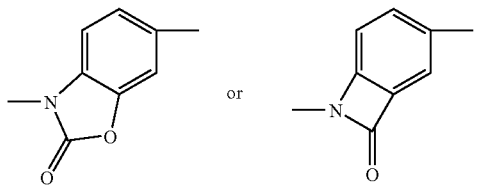

$R^4$ is preferably hydrogen or halogen such as fluorine, chlorine, bromine, etc.
$R^{200}$ is preferably hydrogen or halogen such as fluorine, chlorine, bromine, etc.
Alk1$^1$ is preferably methylene or ethane-1,1-diyl.
l is preferably 0, 1 or 2.
Alk1$^2$ is preferably methylene.
m is preferably 0 or an integer of 1 to 3.
Ring C is preferably phenyl, naphthyl, etc.; $C_3$-$C_7$ cycloalkyl such as cyclopentyl, cyclohexyl, etc.; benzyl, etc.; or pyridine-3-yl, thiophen-3-yl, thiophen-2-yl, thiazol-2-yl, etc.
$R^5$ is preferably hydrogen; $C_1$-$C_6$ alkyl such as methyl, etc.; $C_1$-$C_6$ alkoxy such as methoxy, etc.; halogen such as chlorine, etc.; nitro; amino; $C_6$-$C_{14}$ aryl such as phenyl, etc.; —CON($R^{16}$) ($R^{17}$) or —$CH_2$—CON($R^{16}$) ($R^{17}$) (wherein $R^{16}$ and $R^{17}$ are each independently hydrogen; $C_1$-$C_6$ alkyl such as ethyl, etc., or halo-$C_1$-$C_6$ alkyl such as 2,2,2-trifluoroethyl, etc.); or —($CH_2$)$_{r''}$—O—CO— $R^{100''}$ (wherein $R^{100''}$ is $C_1$-$C_6$ alkyl, $C_1$-$C_6$ alkoxy or $C_2$-$C_{12}$ alkoxyalkyl, and r'' is 0 or an integer of 1 to 3.).

$R^6$ is preferably hydrogen or halogen such as chlorine, etc.
$R^7$ is preferably hydrogen.
$R^8$ and $R^9$ are each independently preferably hydrogen; $C_1$-$C_6$ alkyl such as ethyl, etc.; or $C_6$-$C_{14}$ aryl such as phenyl, etc.

Furthermore preferred embodiments of various substituents and the substitution site will be illustrated below.

$R^1$ is preferably hydrogen, halo-$C_1$-$C_6$ alkyl, $C_1$-$C_6$ alkyl, or —($CH_2$)$_r$—O—CO—$R^{100}$ (wherein $R^{100}$ is $C_1$-$C_6$ alkyl, $C_1$-$C_6$ alkoxy or $C_2$-$C_{12}$ alkoxyalkyl, and r is 0 or an integer of 1 to 3.), among which hydrogen is especially preferred.

$R^2$ is preferably phenyl (which may be substituted with halo-$C_1$-$C_6$ alkyl such as trifluoromethyl, etc.; $C_1$-$C_6$ alkyl such as methyl, etc.; halogen such as chlorine, etc.; or $C_1$-$C_6$ alkoxy such as methoxy, etc.).

$R^{2'}$ is preferably hydrogen.

$R^{2''}$ is preferably hydrogen, halo-$C_1$-$C_6$ alkyl, halogen, $C_1$-$C_6$ alkyl or $C_1$-$C_6$ alkoxy, and trifluoromethyl is especially preferred.

X is preferably —COO— or —CON($R^{10}$)— ($R^{10}$ has the same meaning as defined above), among which —CONH— is especially preferred.

Ring B is preferably phenylene.

$R^3$ is preferably $C_1$-$C_6$ alkyl, $C_1$-$C_6$ alkoxy, —CON($R^{11}$) ($R^{12}$) (wherein $R^{11}$ and $R^{12}$ are each independently preferably hydrogen or $C_1$-$C_6$ alkyl), —CO($R^{15}$) (wherein $R^{15}$ is preferably $C_1$-$C_6$ alkoxy) or —($CH_2$)$_{r'}$—O—CO—$R^{100'}$ (wherein $R^{100'}$ is $C_1$-$C_6$ alkyl, $C_1$-$C_6$ alkoxy or $C_2$-$C_{12}$ alkoxyalkyl, and r' is 0 or an integer of 1 to 3.).

$R^4$ is preferably hydrogen, fluorine or methyl, and especially preferably hydrogen or fluorine.

$R^{200}$ is preferably hydrogen, fluorine or methyl, and especially preferably hydrogen or fluorine.

Alk$^1$ is preferably methylene.

Alk$^2$ is preferably methylene.

l is preferably 0 or 1, especially preferably 1.

m is preferably 1 or 2.

Ring C is preferably phenyl, pyridin-3-yl, thiophen-3-yl, thiophen-2-yl and thiazol-2-yl, among which phenyl is especially preferred.

$R^5$, $R^6$ and $R^7$ each is preferably hydrogen, halogen, $C_1$-$C_6$ alkyl, or —($CH_2$)$_{r''}$—O—CO—$R^{100''}$ (wherein $R^{100''}$ is $C_1$-$C_6$ alkyl, $C_1$-$C_6$ alkoxy or $C_2$-$C_{12}$ alkoxyalkyl, and r'' is 0 or an integer of 1 to 3.), among which hydrogen is especially preferred.

$R^8$ and $R^9$ each is preferably hydrogen, $C_1$-$C_6$ alkyl, or $C_6$-$C_{14}$ aryl, among which $C_1$-$C_6$ alkyl is especially preferred.

The substitution site of —($CH_2$)$_l$— on the benzene ring in the formula (1') is preferably h-position.

Y is preferably —O—CO—O—, —O—CO—, or —CO—O—. In the case where Y is —CO—O—C($R^{110}$) ($R^{111}$)—O—CO—, —CO—O—C($R^{110}$) ($R^{111}$)—O—CO—O—, —O—CO—O—C($R^{110}$) ($R^{111}$)—O—CO—, —O—CO—C($R^{110}$) ($R^{111}$)—O—, —O—C($R^{110}$) ($R^{111}$)—C($R^{110}$) ($R^{111}$)—O— or —O—C($R^{110}$) ($R^{111}$)—CO—O—, $R^{110}$ and $R^{111}$ are each preferably hydrogen.

Among the compounds (1) of the present invention, a preferable compound can be represented by the formula (1'):

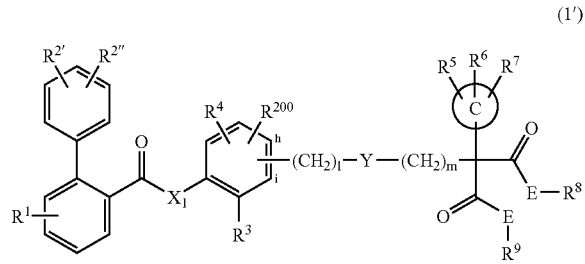

(1')

(wherein all the symbols have the same meanings as defined above).

A more preferable compound of the present invention is an ester compound selected from the group consisting of:

2-(2-{3-acetoxy-4-[(4'-trifluoromethylbiphenyl-2-carbonyl)amino]phenyl}acetoxymethyl)-2-phenylmalonic acid diethyl ester, 2-phenyl-2-(2-{3-propionyloxy-4-[(4'-trifluoromethylbiphenyl-2-carbonyl)amino]phenyl}acetoxymethyl)malonic acid diethyl ester, 2-(2-{3-(2-methoxyacetoxy)-4-[(4'-trifluoromethylbiphenyl-2-carbonyl)amino]phenyl}acetoxymethyl)-2-phenylmalonic acid diethyl ester, 2-(2-{2-acetoxy-3-[(4'-trifluoromethylbiphenyl-2-carbonyl)amino]phenyl}acetoxymethyl)-2-phenylmalonic acid diethyl ester, 2-(2-{3-acetoxy-4-[(5-methyl-4'-trifluoromethylbiphenyl-2-carbonyl)amino]phenyl}acetoxymethyl)-2-phenylmalonic acid diethyl ester, 2-(2-{4-[(5-methyl-4'-trifluoromethylbiphenyl-2-carbonyl)amino]-3-propionyloxyphenyl}acetoxymethyl)-2-phenylmalonic acid diethyl ester, 2-(2-{3-butyryloxy-4-[(5-methyl-4'-trifluoromethylbiphenyl-2-carbonyl)amino]phenyl}acetoxymethyl)-2-phenylmalonic acid diethyl ester, 2-(2-{3-acetoxy-4-[methyl-(4'-trifluoromethylbiphenyl-2-carbonyl)amino]phenyl}acetoxymethyl)-2-phenylmalonic acid diethyl ester, 2-{5-dimethylcarbamoyl-2-fluoro-4-[(4'-trifluoromethylbiphenyl-2-carbonyl)amino]phenoxycarbonyloxymethyl}-2-phenylmalonic acid diethyl ester, 2-[4-isopropyl-3-oxo-1-(4'-trifluoromethylbiphenyl-2-carbonyl)-1,2,3,4-tetrahydroquinoxalin-6-yloxycarbonyloxymethyl]-2-phenylmalonic acid diethyl ester, 2-phenyl-2-[1-(4'-trifluorometylbiphenyl-2-carbonyl)-2,3-dihydro-1H-indol-5-yloxycarbonyloxymethyl]malonic acid diethyl ester, 2-{3-dimethylcarbamoyl-4-[(4'-trifluoromethylbiphenyl-2-carbonyl)amino]phenoxycarbonyloxymethyl}-2-phenylmalonic acid diethyl ester, 2-{3-dimethylcarbamoyl-4-[(4'-trifluoromethylbiphenyl-2-carbonyl)amino]benzyloxycarbonyloxymethyl}-2-phenylmalonic acid diethyl ester, 2-{2-chloro-5-dimethylcarbamoyl-4-[(4'-trifluoromethylbiphenyl-2-carbonyl)amino]phenoxycarbonyloxymethyl}-2-phenylmalonic acid diethyl ester, 2-{3-dimethylcarbamoyl-4-[(4'-trifluoromethylbiphenyl-2-carbonyl)amino]phenoxycarbonyloxymethyl}-2-thiophen-2-yl-malonic acid diethyl ester, 2-{3-dimethylcarbamoyl-4-[(5-methyl-4'-trifluoromethylbiphenyl-2-carbonyl)amino]phenoxycarbonyloxymethyl}-2-phenylmalonic acid diethyl ester, 2-{3-dimethylcarbamoyl-4-[(5-methyl-4'-trifluoromethylbiphenyl-2-carbonyl)amino]phenoxycarbonyloxymethyl}-2-thiophen-2-yl-malonic acid diethyl ester, carbonic acid 2,2-bisethylcarbamoyl-2-phenylethyl ester 3-dimetylcarbamoyl-4-[(4'-trifluoromethylbiphenyl-2-carbonyl)amino]phenyl ester, carbonic acid 2,2-bisethylcarbamoyl-2-phenylethyl ester 5-dimethylcarbamoyl-2-fluoro-4-[(4'-trifluoromethylbiphenyl-2-carbonyl)amino]phenyl ester, 2-{3-(ethylmethylcarbamoyl)-4-[(4'-trifluoromethylbiphenyl-2-carbonyl)amino]phenoxycarbonyloxymethyl}-2-phenylmalonic acid diethyl ester, 2-{3-(methylpropylcarbamoyl)-4-[(4'-trifluoromethylbiphenyl-2-carbonyl)amino]phenoxycarbonyloxymethyl}-2-phenylmalonic acid diethyl ester, 2-phenyl-2-{3-(pyrrolidine-1-carbonyl)-4-[(4'-trifluoromethylbiphenyl-2-carbonyl)amino]phenoxycarbonyloxymethyl}phenylmalonic acid diethyl ester, 2-{5-dimethylcarbamoyl-2-methyl-4-[(4'-trifluoromethylbiphenyl-2-carbonyl)amino]phenoxycarbonyloxymethyl}-2-phenylmalonic acid diethyl ester 2-{3-dimethylcarbamoyl-4-[methyl-(4'-trifluoromethylbiphenyl-2-carbonyl)amino]phenoxycarbonyloxymethyl}-2-phenylmalonic acid diethyl ester, 2-{3-dimethylcarbamoyl-4-[(4'-trifluoromethylbiphenyl-2-carbonyl)amino]phenoxycarbonyloxymethyl}-2-pyridin-2-yl-malonic acid diethyl ester, 2-{3-dimethylcarbamoyl-2,6-difluoro-4-[(4'-trifluoromethylbiphenyl-2-carbonyl)amino]phenoxycarbonyloxymethyl}-2-phenylmalonic acid diethyl ester, 2-{3-dimethylcarbamoyl-2,6-difluoro-4-[(4'-trifluoromethylbiphenyl-2-carbonyl)amino]phenoxycarbonyloxymethyl}-2-pyridin-2-yl-malonic acid diethyl ester, 2-{2-chloro-3-dimethylcarbamoyl-4-[(4'-trifluoromethylbiphenyl-2-carbonyl)amino]phenoxycarbonyloxymethyl}-2-phenylmalonic acid diethyl ester, 2-{3-dimethylcarbamoyl-2,6-difluoro-4-[(4'-trifluoromethylbiphenyl-2-carbonyl)amino]phenoxycarbonyloxymethyl}-2-thiophen-2-yl-malonic acid diethyl ester, 2-{3-dimethylcarbamoyl-2,6-difluoro-4-[(5-methyl-4'-trifluoromethylbiphenyl-2-carbonyl)amino]phenoxycarbonyloxymethyl}-2-thiophen-2-yl-malonic acid diethyl ester, carbonic acid 2,2-bis(ethylmethylcarbamoyl)-2-phenylethylester 3-dimethylcarbamoyl-2,6-difluoro-4-[(4'-trifluoromethylbiphenyl-2-carbonyl)amino]phenyl ester, 2-{4-[5,4'-bistrifluoromethylbiphenyl-2-carbonyl)amino]-3-dimethylcarbamoyl-2,6-difluorophenoxycarbonyloxymethyl}-2-thiophen-2-yl-malonic acid diethyl ester, 2-{3-dimethylcarbamoyl-2,6-difluoro-4-[(6-fluoro-4'-trifluoromethylbiphenyl-2-carbonyl)amino]phenoxycarbonyloxymethyl}-2-thiophen-2-yl-malonic acid diethyl ester, 2-{3-dimethylcarbamoyl-2,6-difluoro-4-[(6-methyl-4'-trifluoromethylbiphenyl-2-carbonyl)amino]phenoxycarbonyloxymethyl}-2-thiophen-2-yl-malonic acid diethyl ester, 2-{3-dimethylcarbamoyl-2,6-difluoro-4-[(4-methyl-4'-trifluoromethylbiphenyl-2-carbonyl)amino]phenoxycarbonyloxymethyl}-2-thiophen-2-yl-malonic acid diethyl ester, 2-{3-dimethylcarbamoyl-2,6-difluoro-4-[(6-methoxy-4'-trifluoromethylbiphenyl-2-carbonyl)amino]phenoxycarbonyloxymethyl}-2-thiophen-2-yl-malonic acid diethyl ester, 2-{3-dimethylcarbamoyl-2,6-difluoro-4-[(5-methoxy-4'-trifluoromethylbiphenyl-2-carbonyl)amino]phenoxycarbonyloxymethyl}-2-thiophen-2-yl-malonic acid diethyl ester, 2-{2,6-difluoro-3-(morpholine-4-carbonyl)-4-[(4'-trifluoromethylbiphenyl-2-carbonyl)amino]phenoxycarbonyloxymethyl}-2-thiophen-2-yl-malonic acid diethyl ester, 2-{3-dimethylcarbamoyl-2,6-difluoro-4-[(3-methyl-4'-trifluoromethylbiphenyl-2-carbonyl)amino]phenoxycarbonyloxymethyl}-2-thiophen-2-yl-malonic acid diethyl ester, 2-{3-dimethylcarbamoyl-2,6-difluoro-4-[(3'-fluoro-4'-trifluoromethylbiphenyl-2-carbonyl)amino]phenoxycarbonyloxymethyl}-2-thiophen-2-yl-malonic acid diethyl ester, 2-{2,6-difluoro-3-[(2-methoxyethyl)methylcarbamoyl]-4-[(4'-trifluoromethylbiphenyl-2-carbonyl)amino]phenoxycarbonyloxymethyl}-2-thiophen-2-yl-malonic acid diethyl ester, 2-{2,6-difluoro-3-(methoxycarbonylmethylmethylcarbamoyl)-4-[(4'-trifluoromethylbiphenyl-2-carbonyl)amino]phenoxycarbonyloxymethyl}-2-thiophen-2-yl-malonic acid diethyl ester, 2-[2,6-difluoro-4-[(5-methyl-4'-trifluoromethylbiphenyl-2-carbonylamino]-3'-(morpholine-4-carbonyl)phenoxycarbonyloxymethyl]-2-thiophen-2-yl-malonic acid diethyl ester, 2-{3-dimethylcarbamoyl-2,6-difluoro-4-[(4'-trifluoromethylbiphenyl-2-carbonyl)amino]phenoxycarbonyloxymethyl}-2-thiazol-2-yl-malonic acid diethyl ester, 2-{2,6-difluoro-3-[(2-hydroxyethyl)methylcarbamoyl]-4-[(4'-trifluoromethylbiphenyl-2-carbonyl)amino]phenoxycarbonyloxymethyl}-2-thiophen-2-yl-malonic acid diethyl ester, 2-{3-(4-acetylpiperazine-1-carbonyl)-2,6-difluoro-4-[(4'-trifluoromethylbiphenyl-2-carbonyl)amino]phenoxycarbonyloxymethyl]-2-thiophen-2-yl-malonic acid diethyl ester, 2-{2,6-difluoro-3-[(4-hydroxypiperidine-1-carbonyl)-4-[(4'-trifluoromethylbiphenyl-2-carbonyl)amino]phenoxycarbonyloxymethyl}-2-thiophen-2-yl-malonic acid diethyl ester, 2-{2,6-difluoro-3-methoxy-4-[(4'-trifluoromethylbiphenyl-2-carbonyl)amino]phenoxycarbonyloxy methyl]-2-thiophen-2-yl-malonic acid diethyl ester, 2-{2,6-difluoro-4-[(4'-trifluoromethylbiphenyl-2-carbonyl)amino]phenoxycarbonyloxymethyl}-2-thiophen-2-yl-malonic acid diethyl ester, 2-{3-dimethylcarbamoyloxy-2,6-difluoro-4-[(4'-trifluoromethylbiphenyl-2-carbonyl)amino]phenoxycarbonyloxymethyl)-2-thiophen-2-yl-malonic acid diethyl ester, 2-{3-ethoxy-2,6-difluoro-4-[(4'-trifluoromethylbiphenyl-2-carbonyl)amino]phenoxycarbonyloxymethyl}-2-thiophen-2-yl-malonic acid diethyl ester, 2-{2,6-difluoro-3-isopropoxy-4-[(4'-trifluoromethylbiphenyl-2-carbonyl)amino]phenoxycarbonyloxymethyl}-2-thiophen-2-yl-malonic acid diethyl ester, 2-ethoxycarbonyl-2-phenylpentanedionic acid 5-{3-dimethylcarbamoyl-4-[(4'-trifluoromethylbiphenyl-2-carbonyl)amino]phenyl}ester 1-ethyl ester, 2-(2-{3-dimethylcarbamoyl-4-[(4'-trifluoromethylbiphenyl-2-carbonyl)amino]phenoxy}acetoxymethyl)-2-phenyl-malonic acid diethyl ester, 3-(2,2-bisethylcarbamoyl-2-phenylethoxy)propionic acid 3-dimethylcarbamoyl-4-[(4'-trifluoromethylbiphenyl-2-carbonyl)amino]phenyl ester, 2-ethoxycarbonyl-2-phenylsuccinic acid 4-{3-dimethylcarbamoyl-4-[(4'-trifluoromethylbiphenyl-2-carbonyl)amino]phenyl}ester 1-ethyl ester, 2-ethoxycarbonyl-2-phenylsuccinic acid 4-{3-dimethylcarbamoyl-4-[(4'-trifluoromethylbiphenyl-2-carbonyl)amino]benzyl}ester 1-ethyl ester, 2-ethoxycarbonyl-2-phenylpentanedionic acid 5-{5-dimethylcarbamoyl-2-fluoro-4-[(4'-trifluoromethylbiphenyl-2-carbonyl)amino]phenyl}ester 1-ethyl ester, 2-ethoxycarbonyl-2-phenylpentanedionic acid 5-{3-dimethylcarbamoyl-4-[(4'-trifluoromethylbiphenyl-2-carbonyl)amino]benzyl}ester 1-ethyl ester, 2-ethoxycarbonyl-2-phenylpentanedionic acid 5-{3-dimethylcarbamoyl-4-[(4'-trifluoromethylbiphenyl-2-carbonyl)amino]phenyl}ester 1-ethyl ester, 2-ethoxycarbonyl-2-phenylpentanedionic acid 5-{3-dimethylcarbamoyl-2,6-difluoro-4-[(4'-trifluoromethylbiphenyl-2-carbonyl)amino]phenyl}ester 1-ethyl ester, 2-ethoxycarbonyl-2-phenylpentanedionic acid 5-{2,6-difluoro-3-methylcarbamoyl-4-[(4'-trifluoromethylbiphenyl-2-carbonyl)amino]phenyl}ester 1-ethyl ester, (2,2-bisethylcarbamoyl-2-phenylethoxy)acetic acid 3-dimethylcarbamoyl-4-[(4'-trifluoromethylbiphenyl-2-carbonyl)amino]phenyl}ester, (2,2-bisethylcarbamoyl-2-phenylethoxy)acetic acid 3-dimethylcarbamoyl-2,6-difluoro-4-[(4'-trifluoromethylbiphenyl-2-carbonyl)amino]phenyl}ester, (3,3-bisethylcarbamoyl-3-phenylpropoxy)acetic acid 3-dimethylcarbamoyl-2,6-difluoro-4-[(4'-trifluoromethylbiphenyl-2-carbonyl)amino]phenyl}ester, 6,6-bisethylcarbamoyl-6-thiophen-2-yl-hexanoic acid 3-dimethylcarbamoyl-2,6-difluoro-4-[(4'-trifluoromethylbiphenyl-2-carbonyl)amino]phenyl}ester, 3-(2,2-bisethylcarbamoyl-2-phenylethoxy)propionic acid 3-dimethylcarbamoyl-2,6-difluoro-4-[(4'-trifluoromethylbiphenyl-2-carbonyl)amino]phenyl}ester, 5,5-bisethylcarbamoyl-5-thiophen-2-yl)pentanoic acid 3-dimethylcarbamoyl-2,6-difluoro-4-[(4'-trifluoromethylbiphenyl-2-carbonyl)amino]phenyl}ester, 4,4-bis(ethylmethylcarbamoyl)-4-phenylbutyric acid 3-dimethylcarbamoyl-2,6-difluoro-4-[(4'-trifluoromethylbiphenyl-2-carbonyl)amino]phenyl}ester, 5,5-bis(ethylmethylcarbamoyl)-5-phenylvaleric acid 3-dimethylcarbamoyl-2,6-difluoro-4-[(4'-trifluoromethylbiphenyl-2-carbonyl)amino]phenyl ester, 2-ethoxycarbonyl-2-thiophen-2-ylpentandionic acid 5-{3-dimethylcarbamoyl-4-[(4'-trifluoromethylbiphenyl-2-carbonyl)amino]phenyl}ester 1-ethyl ester, 2-ethoxycarbonyl-2-thiophen-2-ylpentandionic acid 5-{3-dimethylcarbamoyl-4-[(5-methyl-4'-trifluoromethylbiphenyl-2-carbonyl)amino]phenyl}ester 1-ethyl ester, 2-ethoxycarbonyl-2-phenylpentanedionic acid 5-{3-dimethylcarbamoyl-2,6-difluoro-4-[(5-methyl-4'-trifluoromethylbiphenyl-2-carbonyl)amino]phenyl}ester 1-ethyl ester, 2-ethoxycarbonyl-2-pyridin-2-ylsuccunic acid 4-{3-dimethylcarbamoyl-4-[{4'-trifluoromethylbiphenyl-2-carbonyl)amino]benzyl ester 1-ethyl ester, and (2,2-bisethylcarbamoyl-2-phenylethoxy)acetic acid 3-dimethylcarbamoyl-4-[(4'-trifluoromethylbiphenyl-2-carbonyl)amino]benzyl ester.

Further, examples of furthermore preferable compounds include 2-{3-dimethylcarbamoyl-4-{[6-trifluoromethyl-2-(4-trifluoromethylphenyl)pyridine-3-carbonyl]amino}phenoxycarbonyloxymethyl}-2-phenylmalonic acid diethyl ester, 2-{3-dimethylcarbamoyl-4-{[6-methyl-2-(4-trifluoromethylphenyl)pyridine-3-carbonyl]amino}phenoxycarbonyloxymethyl)-2-phenylmalonic acid diethyl ester, 2-{3-dimethylcarbamoyl-4-{[6-methyl-2-(4-trifluoromethylphenyl)pyridine-3-carbonyl]amino}phenoxycarbonyloxymethyl)-2-pyridin-2-yl-malonic acid diether ester, 2-{4-dimethylcarbamoyl-5-[(4'-trifluoromethylbiphenyl-2-carbonyl)amino]pyridin-2-yloxycarbonyloxymethyl}-2-phenyl-malonic acid diethyl ester, 2-(3-dimethylcarbamoyl-4-{[2-(4-trifluoromethylphenyl)pyridine-3-carbonyl]amino}phenoxycarbonyloxy-methyl)-2-phenylmalonic acid diethyl ester, 2-(3-dimethylcarbamoyl-4-{[2-methylamino-4-(4-trifluoromethylphenyl)pyrimidine-5-carbonyl]amino}phenoxycarbonyloxymethyl)-2-phenylmalonic acid diethyl ester, 2-(4-{[2-dimethylamino-4-(4-trifluoromethylphenyl)pyrimidine-5-carbonyl]amino}-3-dimethylcarbamoylphenoxycarbonyloxymethyl)-2-phenylmalonic acid diethyl ester, 2-(3-dimethylcarbamoyl-2,6-difluoro-4-{[6-methyl-2-(trifluoromethylphenyl)pyridine-3-carbonyl]amino}phenoxycarbonyloxymethyl)-2-thiophen-2-yl-malonic acid diethyl ester, and 2-ethoxycarbonyl-2-phenylpentanedionic acid 5-{4-dimethylcarbamoyl-5-[(4'-trifluoromethylbiphenyl-2-carbonyl)amino]pyridin-2-yl}ester 1-ethyl ester.

The compounds of the present invention may include hydrates or solvates, depending on the case, and may further include their metabolites. Furthermore, the compounds of the present invention include racemates and optically active compounds. The optically active compounds are preferably those wherein one of enantiomers is in enantiomer excess of about 90% or higher, more preferably in enantiomer excess of about 99% or higher.

The term "pharmaceutically acceptable salt" includes various inorganic acid addition salts such as hydrochloride, hydrobromide, sulphate, phosphate and nitrate, etc.; various organic acid addition salts such as acetate, propionate, succinate, glycolate, lactate, malate, oxalate, tartrate, citrate, maleate, fumarate, methanesulfonate, benzensulfonate, p-toluenesulfonate and ascorbate, etc.; various salts with an amino acid such as aspartate and glutamate, etc., and alkali salts thereof such as sodium salt and potassium salt, although it is not limited thereto.

The expression "MTP in the small intestine" refers to the MTP existing in small intestinal epithelial cells.

The expression "MTP in the liver" refers to the MTP existing in hepatic cells.

The expression "selectively inhibit MTP in the small intestine" means the level of inhibition is at least about 5 times higher, preferably about 10 times higher, than MTP inhibition in other parts of body such as liver and heart, especially liver. To be more specific, on the basis of S9 metabolic stability test, it means that in the test using human or hamster S9 the remaining rate of unaltered form 10 minutes after the treatment with small intestine S9 is about 10 times or more higher than that in the case of the treatment with liver S9.

The expression "it is metabolized to the amount at which the remaining MTP inhibitor in the liver does not substantially inhibit the MTP in the liver" means that almost all of the orally administered MTP inhibitors are metabolized to an inactive metabolite before arriving at the liver or at the moment of arriving at the liver and show substantially no MTP inhibitory activity in the liver, i.e. the MTP inhibitors are converted to those that do not substantially inhibit TG release from the liver. More specifically, it means the condition where TG-releasing activity of the liver is kept at the level of about 80% or more, preferably about 90% or more, more preferably 100% of the normal level. In terms of metabolism, it means that the ratio of inactive metabolite to unaltered form in portal vein blood is approximately 8 or more to 1 one hour after the oral administration to hamsters, i.e. about 80% or more of the agent (compound) is metabolized before arriving at the liver, or on the basis of liver S9 metabolic stability test, it means that 10 minutes after the test using human or hamster S9 the remaining rate of unaltered form is about 20% or less, preferably about 10% or less, more preferably about 8% or less.

The expression "MTP inhibitor does not substantially inhibit MTP in the liver" has essentially the same meaning with the above "it is metabolized to the amount at which the remaining MTP inhibitor in the liver does not substantially inhibit the MTP in the liver", and means the condition where TG-releasing activity of the liver is kept at the level of about 80% or more, preferably about 90% or more, more preferably 100% of the normal level.

As "pharmaceutically acceptable carrier", various organic or inorganic carrier materials which are conventionally used as formulation material are used, and it is formulated as excipient, lubricant, binder, disintegrating agent, solvent, solubilizer, suspending agent, isotonizing agent, buffer, soothing agent, etc. If desired, pharmaceutical additives such as preservative, antioxidant, coloring agent, sweetening agent, etc. may be also used. Preferable examples of said excipient include lactose, sucrose, D-mannitol, starch, crystalline cellulose, light anhydrous silicic acid, etc. Preferable examples of said lubricant include magnesium stearate, calcium stearate, talc, colloidal silica, etc. Preferable examples of said binder include crystalline cellulose, sucrose, D-mannitol, dextrin, hydroxypropyl cellulose, hydroxypropyl methylcellulose, polyvinylpyrrolidone, etc. Preferable examples of said disintegrating agent include starch, carboxymethylcellulose, carboxymethylcellulose calcium, crosscarmellose sodium, sodium carboxymethylstarch, etc. Preferable examples of said solvent include water for injection, alcohol, propylene glycol, macrogol, sesame-seed oil, corn oil, propylene glycol fatty acid ester, etc. Preferable examples of said solubilizer include polyethyleneglycol, propyleneglycol, D-mannitol, benzyl benzoate, ethanol, trisaminomethane, cholesterol, triethanolamine, sodium carbonate, sodium citrate, etc. Preferable examples of said suspending agent include surfactants (e.g. stearyl triethanolamine, sodium lauryl sulfate, lauryl aminopropionic acid, lecithin, benzalkonium chloride, benzethonium chloride, glycerin monostearate, etc), polyvinyl alcohol, polyvinylpyrrolidone, carboxymethylcellulose sodium, methylcellulose, hydroxymethyl cellulose, etc. Preferable examples of said isotonizing agent include sodium chloride, glycerin, D-mannitol, etc. Preferable examples of said buffer include phosphate, acetate, carbonate, citrate, etc. Preferable examples of said soothing agent include benzyl alcohol, etc. Preferable examples of said preservative include paraoxybenzoic acid esters, chlorobutanol, benzyl alcohol, phenethyl alcohol, dehydroacetic acid, sorbic acid, etc. Preferable examples of said antioxidant include sulfites, ascorbic acid, etc. Preferable examples of said sweetening agent include aspartame, saccharin sodium, stevia, etc. Preferable examples of said coloring agent include food colors such as food yellow No. 5, food red No. 2 and food blue No. 2, lake colors for food, iron oxide, etc.

When the compounds of the present invention is used as an agent for the treatment or prevention of hyperlipidemia or arteriosclerosis, they can be administered systemically or locally, and orally or parenterally. Though the dose may vary depending on the age, body weight, symptoms, therapeutic effect, etc., the dose per adult is in the range of 0.1 mg to 1 g per one dose and can be administered one to several times per day. Also, the compounds of the present invention can be administered to human beings as well as animals other than human beings, especially mammals, for the treatment or prevention of said diseases. In a similar manner as above, the compounds of the present invention is also used as an agent for the treatment or prevention of coronary artery disease, obesity, diabetes, or hypertension.

In the formulation of the compounds of the present invention into solid compositions and liquid compositions for oral administration or injections, etc., for parenteral administration, there may be added appropriate additives such as diluents, dispersants, adsorbents, solubilizers, etc. In addition, the composition of the present invention may take the known form such as tablets, pills, powders, granules, suppositories, injections, eye drops, solutions, capsules, troches, aerosols, elixirs, suspensions, emulsions, syrups, etc.

In the case where the pharmaceutical composition of the present invention are solid preparations such as tablets, pills, powders, granules, etc., an additive includes, for example, lactose, mannitol, glucose, hydroxypropyl cellulose, microcrystalline cellulose, starch, polyvinylpyrrolidone, magnesium aluminometasilicate and powdery silicic anhydride. In the case where the compounds of the present invention are formulated into tablets or pills, they may be coated with a gastroenteric or enteric coating film containing a substance such as white sugar, gelatin, hydroxypropyl cellulose and hydroxymethyl cellulose phthalate. Furthermore, the tablets or pills may be multi-layered tablets comprising two or more layers.

As the pharmaceutical compositions of the present invention, there are also exemplified capsules in which are filled liquid, semi-solid or solid contents prepared by dissolving the compounds of the present invention or its pharmaceutically acceptable salt in a solvent and adding an additive thereto. Examples of said solvents are purified water, ethanol, vegetable oil, etc., among which ethanol or a mixture of purified water and ethanol is preferably used. Any additives commonly used in the preparation of capsules can be used without any particular limitation. Such additives include, for example, propylene glycol fatty acid esters; low molecular weight polyethylene glycols such as polyethylene glycol 200 to 600, etc., glycerine fatty acid esters thereof, and medium chain fatty acid triglycerides thereof; alcohols/polyols such as stearyl alcohol, cetanol, polyethylene glycol, etc., or esters thereof; lipids such as sesame oil, soy bean oil, peanut oil, corn oil, hydrogenated oil, paraffin oil, bleached wax; fatty acids such as triethyl citrate, triacetin, stearic acid, palmitic acid, myristic acid, etc., and derivatives thereof. These additives are suitable for preparing liquid or semi-solid contents. In the capsules of the present invention, propylene glycol fatty acid esters are preferable as such an additive. Examples of the propylene glycol fatty acid esters are propylene glycol monocaprylate (Capmul PG-8 (Brand name), Sefol 218 (Brand name), Capryo 190 (Brand name), propylene glycol monolaurate (Lauroglycol FCC (Brand name), propylene glycol monooleate (Myverol P-O6 (Brand name)), propylene glycol myristate, propylene glycol monostearate, propylene glycol lisinolate (Propymuls (Brand name)), propylene glycol dicaprylate/dicaprate (Captex (Trademark) 200 (Brand name)) propylene glycol dilaurate, propylene glycol distearate and propylene glycol dioctanoate (Captex (Trademark) 800 (Brand name)). Although there is no particular limitation to the materials constituting the capsules of the present invention, they include, for example, polysaccharides derived from natural products such as agar, alginic acid salt, starch, xanthan, dextran, etc; proteins such as gelatin, casein, etc.; chemically processed products such as hydroxystarch, pullulan, hydroxypropyl cellulose, hydroxypropyl methylcellulose, polyvinyl alcohol or derivatives thereof, polyacryl derivatives, polyvinylpyrrolidone or derivatives thereof, polyethylene glycol, etc.

In the case where the pharmaceutical compositions of the present invention are liquid formulations for oral administration such as pharmaceutically acceptable emulsions, solubilizers, suspensions, syrups, and elixirs, etc., diluents to be used include, for example, purified water, ethanol, vegetable oils, emulsifiers, etc. In addition to such diluents, auxiliary agents such as wetting agents, suspending agents, sweeteners, condiments, flavors and antiseptics may be added to said liquid formulations.

In the case where the pharmaceutical compositions of the present invention are parenteral formulations such as injections, there are employed sterilized aqueous or non-aqueous solutions, solubilizers, suspending agents, emulsifiers, etc. Examples of the aqueous solutions, solubilizers and suspending agents include distilled water for injections, physiological saline, cyclodextrin, and derivatives thereof; organic amines such as triethanolamine, diethanolamine, monoethanolamine, triethylamine, etc.; and inorganic alkaline solutions. When aqueous solutions are employed, for example, propylene glycol, polyethylene glycol or vegetable oils such as olive oil, or alcohols such as ethanol may be further added. Further, surfactants (for mixed micelle formation) such as polyoxyethylene hydrogenated castor oils and sucrose fatty acid esters, or lecithin or hydrogenated lecithin (for liposome formation), etc. can be used as a solubilizer. Furthermore, with regard to the parenteral formulations of the present invention, they may be formulated into emulsions comprising non-aqueous solubilizers such as vegetable oils, together with lecithin, polyoxyethylene hydrogenated castor oil or polyoxyethylene-polyoxypropylene glycol, etc.

Further, the present invention provides a pharmaceutical composition having a new function which has not been known for the treatment or prophylaxis of hyperlipidemia, arteriosclerosis, coronary artery diseases, obesity, diabetes or hypertension. That is, the agent for the treatment or prevention of said diseases in accordance with the present invention is characterized by selectively inhibiting MTP (microsomal triglyceride transfer protein) in the small intestine. Above all, a pharmaceutical composition or an agent which does not substantially inhibit MTP in the liver, but inhibits only MTP in the small intestine is desirable. Specifically, it is preferable that MTP inhibition of the agent in the liver is approximately ⅓ or less, preferably ¹⁄₁₀₀ or less when compared to that in the small intestine as estimated in terms of $ED_{50}$ or $ED_{20}$.

As one preferred embodiment of the therapeutic or prophylactic agents of the present invention for said diseases, they inhibit MTP in the small intestine, and they are then metabolized in the small intestine, blood, and liver to the amount at which the residual agent arriving at the liver does not substantially inhibit MTP in the liver. It is particularly preferable that, when 300 mg/kg of the compound of the present invention is administered orally, the rate of liver TG release inhibition exerted by the residual compound reaching the liver is about 20% or less, preferably less than about 10%, more preferably about 0%. Specifically, it is desirable that the agent has about 40% or less, preferably about 20% or less inhibition rate of liver TG release when assayed by the method of Test Example 4 which will be hereinafter mentioned.

The pharmaceutical compositions or agents of the present invention can be used in combination with other pharmaceutical compositions or agents. As other agents, there may be exemplified drugs for the treatment or prophylaxis of hyperlipidemia, arteriosclerosis, coronary artery disease, obesity, diabetes, or hypertension, and they can be used alone or in combination with two or more kinds of said drugs.

Examples of the agents for the treatment of hyperlipidemia include a statin-type drug, more specifically, lovastatin, simvastatin, pravastatin, fluvastatin, atorvastatin and cerivastatin.

Examples of the agents for the treatment and/or prophylaxis of obesity include mazindol and olristat.

Examples of the agents for the treatment and/or prophylaxis of diabetes include insulin preparations, sulfonylurea drugs, insulin secretion-promotor drugs, sulfonamide drugs, biguanide drugs, α-glucosidase inhibitors, insulin resistance-improving drugs, etc., more specifically insulin, glibenclamid, tolbutamide, glyclopyramide, acetohexamide, glimepiride, tolazamide, gliclazide, nateglinide, glibuzol, metformin hydrochloride, buformin hydrochloride, voglibose, acarbose, pioglitazone hydrochloride, etc.

Examples of the agents for the treatment and/or prophylaxis of hypertension include loop diuretics, angiotensin converting enzyme inhibitors, angiotensin II receptor antagonists, calcium antagonists, β-blockers, α, β-blockers and α-blockers, and more specifically, furosemide delayed release, captopril, captopril delayed release, enalapril maleate, alacepril, delapril hydrochloride, silazapril, lisinopril, benazepril hydrochloride, imidapril hydrochloride, temocapril hydrochloride, quinapril hydrochloride, trandolapril, perindopril erbumine, losartan potassium, candesartan cilexetil, nicardipine hydrochloride, nicardipine hydrochloride delayed release, nilvadipine, nifedipine, nifedipine delayed release, benidipine hydrochloride, diltiazem hydrochloride, diltiazem hydrochloride delayed release, nisoldipine, nitrendipine, manidipine hydrochloride, barnidipine hydrochloride, efonidipine hydrochloride, amlodipine besylate, felodipine, cilnidipine, aranidipine, propranolol hydrochloride, propranolol hydrochloride delayed release, pindolol, pindolol delayed release, indenolol hydrochloride, carteolol hydrochloride, carteolol hydrochloride delayed release, bunitrolol hydrochloride, bunitrolol hydrochloride delayed release, atenolol, asebutolol hydrochloride, metoprolol tartrate, metoprolol tartrate delayed release, nipradilol, penbutolol sulfate, tilisolol hydrochloride, carvedilol, bisoprolol fumarate, betaxolol hydrochloride, celiprolol hydrochloride, bopindolol malonate, bevantolol hydrochloride, labetalol hydrochloride, arotinolol hydrochloride, amosulalol hydrochloride, prazosin hydrochloride, terazosin hydrochloride, doxazosin mesylate, bunazocin hydrochloride, bunazocin hydrochloride delayed release, urapidil, and phentolamine mesylate, etc.

There is no particular limitation on the timing for the administration of pharmaceutical compositions, agents, or combination drugs according to the present invention, and they may be administered simultaneously or intermittently to the subjects. The amount of such drugs for combination use can be determined based on their clinical doses, and can be chosen appropriately depending on the subjects, age, body weight, symptom, medication time, dosage form, administration route, combination, etc. There is no particular limitation on the dosage form of the drugs for combination use, and it may be sufficient that the pharmaceutical compositions or agents and other drugs for combination use according to the present invention are combined at the time of administration.

The compounds of the present invention can be prepared by the method known per se.

Next, a production method for preparing a compound represented by the formula (1) will be illustrated below as an example, but it is to be understood that the production method of the present invention is not limited thereto.

In addition, when the subsequent reaction is carried out, the functional groups other than those to be reacted may be optionally protected in a previous stage and may be deprotected in an appropriate stage.

Further, the reaction in each step may be carried out in the usual manner, and separation and purification may be conducted by the appropriate selection or combination of conventional methods such as crystallization, recrystallization, column chromatography, preparative HPLC, etc.

Production Method 1

Among the compounds of the formula (1), a method for producing compounds in which X is —CONH—$(CH_2)_n$— and Y is —CO—O— will be illustrated below.

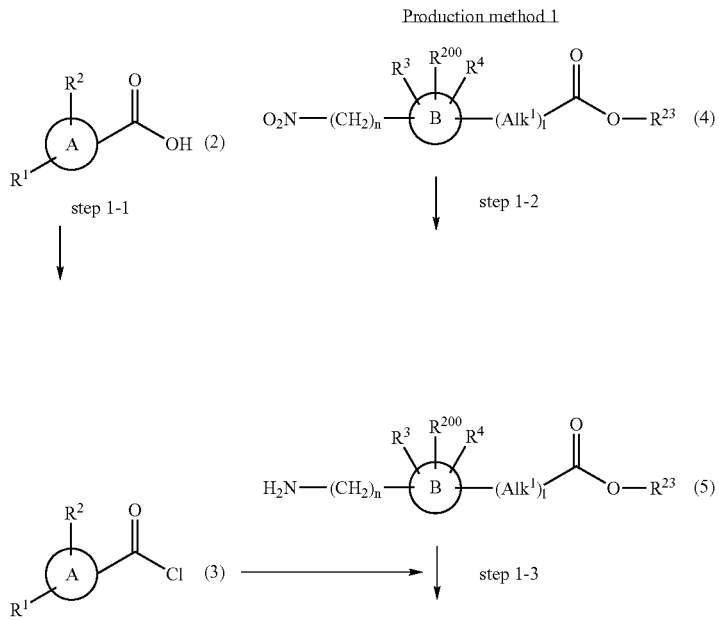

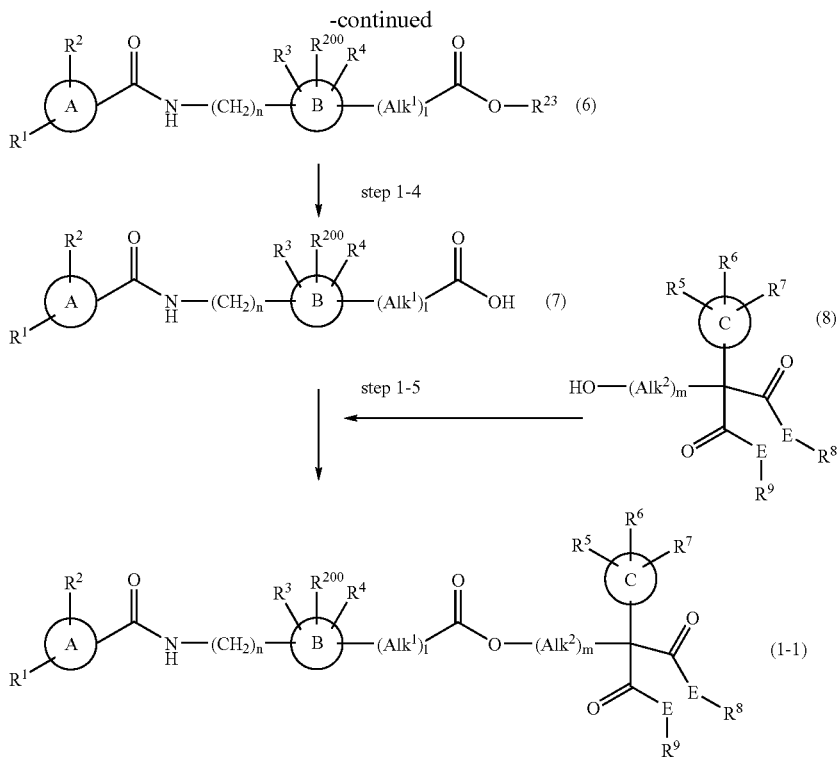

In the above reaction scheme, $R^1$, $R^2$, $R^3$, $R^4$, $R^5$, $R^6$, $R^7$, $R^8$, $R^9$, $R^{200}$, l, m, n, $Alk^1$, $Alk^2$, E, ring A, ring B, and ring C each has the same meaning as defined above, and $R^{23}$ is $C_1$-$C_6$ alkyl.

Step 1-1

A carboxylic acid of the formula (2) is reacted with oxalyl chloride or thionyl chloride in a solvent to give an acid chloride of the formula (3).

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; and esters such as ethyl acetate, methyl acetate, butyl acetate, etc., and they may be used solely or in combination thereof. Preferred solvents in the present reaction include methylene chloride, chloroform or toluene, all of which contain a catalytic amount of N,N-dimethylformamide.

The reaction temperature is about −20° C. to 120° C., preferably about 0° C. to room temperature.

The reaction time is about 10 minutes to 8 hours, preferably about 30 minutes to 4 hours.

The compound of the formula (2) can be easily prepared by the conventional method.

Step 1-2

This step is a general reduction method for the nitro group attached directly to the aromatic ring. A nitro compound of the formula (4) is hydrogenated in a solvent in the presence of a catalyst to give a compound of the formula (5).

The solvent used in the reaction includes, for example, ethers such as tetrahydrofuran, dioxane, 1,2-dimethoxyethane, etc.; alcohols such as methanol, ethanol, isopropyl alcohol, t-butanol, etc.; and esters such as ethyl acetate, methyl acetate, butyl acetate, etc.; and they are used solely or in combination thereof. Preferred solvents in the present reaction include alcohols such as methanol, ethanol, isopropyl alcohol, t-butanol, etc., and a mixture of said alcohol solvent and tetrahydrofuran and/or water.

The catalyst used in the reaction includes, for example, palladium-carbon, palladium hydroxide, Raney-Ni, platinum oxide, etc., and among which palladium-carbon or reduced iron is preferred.

The reaction temperature is about 0° C. to 120° C., preferably about room temperature to 100° C.

The reaction time is about 30 minutes to 8 days, preferably about one hour to 96 hours.

The compound of the formula (4) can be easily prepared by the conventional method.

Step 1-3

This step is a general condensation reaction between acid chlorides and amines. An acid chloride of the formula (3) is preferably condensed with an amine of the formula (5) in a solvent in the presence of a base to give a compound of the formula (6).

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; and esters such as ethyl acetate, methyl acetate, butyl acetate, etc., and they can be used solely or in combination thereof. Preferred solvents in the present reaction include methylene chloride, chloroform, toluene, ethyl acetate and tetrahydrofuran.

Examples of the bases used in the present invention include organic bases such as triethylamine, pyridine, N-methylmorpholine, etc.; alkali metal hydroxides such as lithium hydroxide, sodium hydroxide, potassium hydroxide, etc.; and alkali metal carbonates such as sodium carbonate, potassium carbonate, sodium bicarbonate, potassium bicarbonate, etc., among which triethylamine, sodium hydroxide or sodium bicarbonate is preferable.

The reaction temperature is about 0° C. to 80° C., preferably about 0° C. to room temperature.

The reaction time is about 10 minutes to 48 hours, preferably about 30 minutes to 24 hours.

In the case of a compound of the formula (5) wherein $R^{23}$ is hydrogen, a compound of the formula (7) can be prepared by one step of condensation between an aminocarboxylic acid and an acid chloride (Schotten-Baumann reaction).

Alternatively, a compound of the formula (6) can be prepared by using a condensing agent (e.g. WSC-HOBT, DCC-HOBT) for a compound of the formula (2) and a compound of the formula (5). Further, a compound of the formula (6) may be synthesized by converting a compound of the formula (2) into its mixed anhydride, followed by the reaction with a compound of the formula (5) in the presence of a base.

Step 1-4

This step is a general ester hydrolysis reaction using an alkali. An ester compound of the formula (6) is hydrolyzed in a solvent in the presence of an acid or a base to give a compound of the formula (7).

The solvent used in the reaction includes, for example, ethers such as diethyl ether, tetrahydrofuran, dioxane, 1,2-dimethoxyethane, diglyme, etc.; alcohols such as methanol, ethanol, isopropyl alcohol, etc.; and water; and they can be used solely or in combination thereof. Preferred solvents in the present reaction include a mixture of tetrahydrofuran and ethanol or methanol.

Examples of the bases are aqueous solutions of alkali metal carbonates such as sodium carbonate, potassium carbonate, etc., or aqueous solutions of alkali metal hydroxides such as lithium hydroxide, sodium hydroxide, potassium hydroxide, etc., among which sodium hydroxide or lithium hydroxide is preferable. Examples of the acids are hydrochloric acid, sulfuric acid, and nitric acid.

The reaction temperature is about 0° C. to 120° C., preferably about room temperature to 80° C.

The reaction time is about 1 hour to 24 hours, preferably about 2.5 hours to 12 hours.

Step 1-5

This step is a general condensation reaction of a carboxylic acid with an alcohol.

A carboxylic acid of the formula (7) is condensed with an alcohol of the formula (8) in a solvent in the presence of a base and a condensing agent to give a compound of the formula (1-1) which is one of the objective compounds. Alternatively, a carboxylic acid may be converted into its activated derivative such as acid chloride and acid anhydride, followed by the reaction with an alcohol optionally in the presence of a base.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; esters such as ethyl acetate, methyl acetate, butyl acetate, etc.; polar solvents such as acetone, N,N-dimethylformamide, dimethyl sulfoxide, etc.; and they can be used solely or in combination thereof. Preferred solvents in the present reaction include tetrahydrofuran, acetone, methylene chloride and N,N-dimethylformamide.

Examples of the bases used in the reaction include organic bases such as triethylamine, pyridine, dimethylaminopyridine, N-methylmorpholine, etc., among which dimethylaminopyridine is preferred.

Examples of the condensing agents used in the reaction include 1-ethyl-3-(3'-dimethylaminopropyl)carbodiimide hydrochloride (WSC.HCl), dicyclohexylcarbodiimide (DCC), etc. among which 1-ethyl-3-(3'-dimethylaminopropyl)carbodiimide hydrochloride is preferred.

The reaction temperature is about 0° C. to 80° C., preferably about 0° C. to room temperature.

The reaction time is about 1 hour to 48 hours, preferably about 3 hours to 24 hours.

The compound of the formula (8) can be easily prepared by the conventional method or the method known per se.

In addition, a compound of the formula (1-1) wherein $R^3$ is hydroxyl may be prepared by subjecting a compound of the formula (1-1) wherein $R^3$ is $C_1$-$C_6$ alkoxy or $C_7$-$C_{16}$ aralkyloxy, to dealkylation or dearalkylation (debenzylation) respectively.

Further, the acylation of the hydroxyl group gives a compound wherein $R^3$ is —$(CH_2)_{r'}$—O—CO—$R^{100}$ (wherein r' is 0 and $R^{100}$ has the same meaning as defined above).

Production Method 1a

Production method 1a

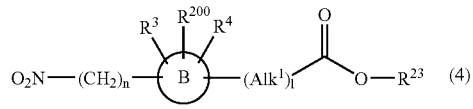

step 1 a-1

-continued
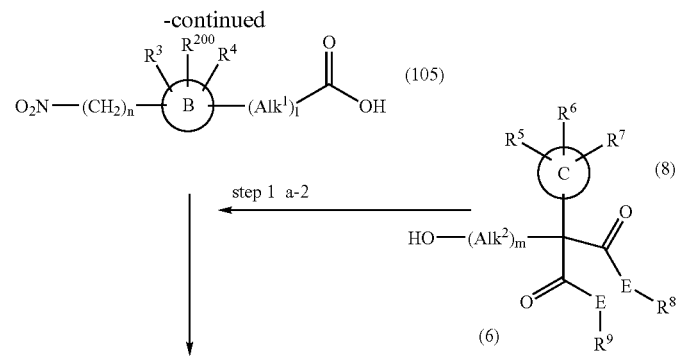
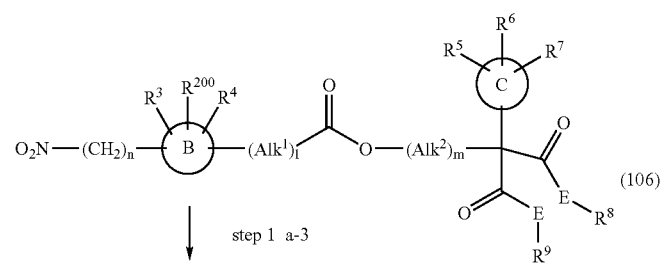
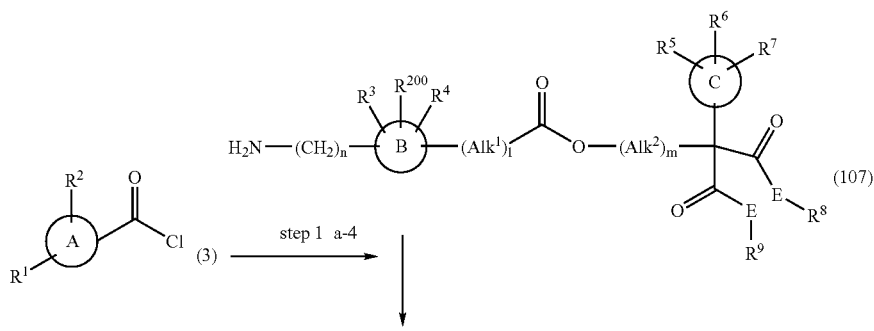
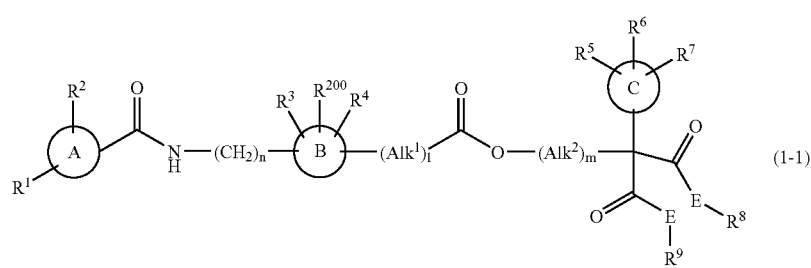

In the above reaction scheme, $R^1$, $R^2$, $R^3$, $R^4$, $R^5$, $R^6$, $R^7$, $R^8$, $R^9$, $R^{23}$, $R^{200}$, l, m, n, $Alk^1$, $Alk^2$, E, ring A, ring B, and ring C each has the same meaning as defined above.

Step 1a-1

A compound of the formula (105) can be prepared from a compound of the formula (4) in a similar manner to Step 1-4 of Production Method 1.

Step 1a-2

A compound of the formula (106) can be prepared by condensing a carboxylic acid of the formula (105) with an amine of the formula (107) with an acid chloride of the formula (3) in a similar manner to Step 1-3 of Production Method 1.

Production Method 2

Among the compounds represented by the formula (1), a method for producing compounds in which X is —COO—$(CH_2)_n$— and Y is —CO—O— will be illustrated below.

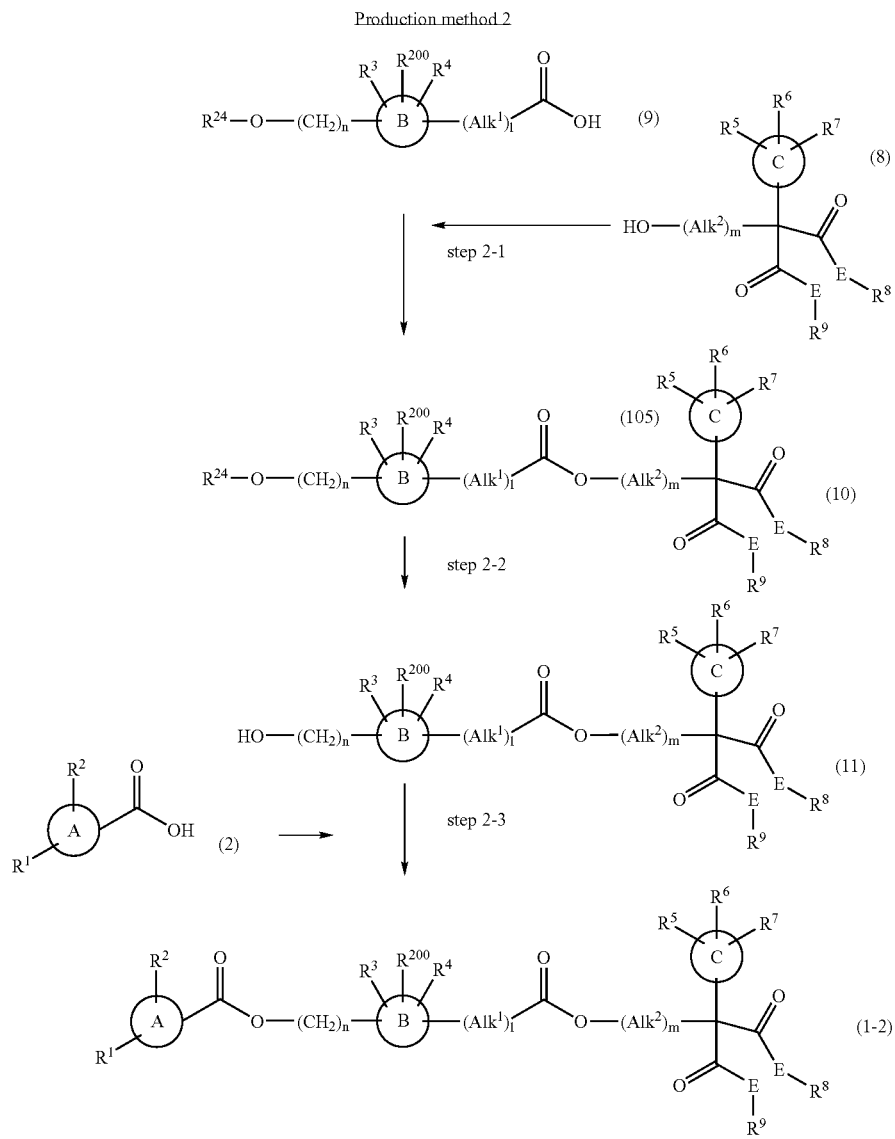

alcohol of the formula (8) in a similar manner to Step 1-5 of Production Method 1.

Step 1a-3

A compound of the formula (107) can be prepared from a compound of the formula (106) in a similar manner to Step 1-2 of Production Method 1.

Step 1a-4

A compound of the formula (1-1) which is one of the objective compounds can be prepared by condensing an In the above reaction scheme, $R^1$, $R^2$, $R^3$, $R^4$, $R^5$, $R^6$, $R^7$, $R^8$, $R^9$, $R^{200}$, l, m, n, $Alk^1$, $Alk^2$, E, ring A, ring B, and ring C each has the same meaning as defined above, and $R^{24}$ is a hydroxyl-protecting group (e.g. benzyl, p-methoxybenzyl, tert-butyl, trialkylsilyl, etc.).

Step 2-1

This step is a condensation reaction of a carboxylic acid with an alcohol similar to Step 1-5 of Production Method 1. A compound of the formula (10) can be prepared by condensing a carboxylic acid of the formula (9) with an alcohol of the formula (8) in a solvent preferably in the presence of a base and a condensing agent.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; esters such as ethyl acetate, methyl acetate, butyl acetate, etc.; polar solvents such as acetone, N,N-dimethylformamide, dimethyl sulfoxide, water, etc.; and they can be used solely or in combination thereof. Preferred solvents in the present reaction include tetrahydrofuran, methylene chloride and N,N-dimethylformamide.

Examples of the bases used in the reaction include organic bases such as triethylamine, pyridine, dimethylaminopyridine, N-methylmorpholine, etc., among which dimethylaminopyridine is preferred.

Examples of the condensing agents used in the reaction include 1-ethyl-3-(3'-dimethylaminopropyl)carbodiimide hydrochloride (WSC.HCl), dicyclohexylcarbodiimide (DCC), etc., among which 1-ethyl-3-(3'-dimethylaminopropyl)carbodiimide hydrochloride is preferred.

The reaction temperature is about 0° C. to 80° C., preferably about 0° C. to room temperature.

The reaction time is about 2 hours to 48 hours, preferably about 6 hours to 24 hours.

The compound of the formula (9) can be easily prepared according to the conventional method or the method known per se.

Step 2-2

This step is a general deprotection method for hydroxy groups. For example, when $R^{24}$ is benzyl in a compound of the formula (10), the compound of the formula (10) is hydrogenated in a solvent in the presence of a catalyst to give a compound of the formula (11).

The solvent used in the reaction includes, for example, ethers such as tetrahydrofuran, dioxane, 1,2-dimethoxyethane, diglyme, etc.; alcohols such as methanol, ethanol, isopropyl alcohol, t-butanol, etc.; and esters such as ethyl acetate, methyl acetate, butyl acetate, etc.; and they can be used solely or in combination thereof. Preferred solvents in the present reaction are alcohols such as methanol, ethanol, isopropyl alcohol, t-butanol, etc.

Examples of the catalyst used in the reaction include palladium carbon, palladium hydroxide, Raney-Ni, platinum oxide, etc., among which palladium carbon is preferred.

The reaction temperature is about 0° C. to 80° C., preferably about 0° C. to room temperature.

The reaction time is about 1 hour to 16 hours, preferably about 2 hours to 8 hours.

Step 2-3

This step is a condensation reaction between a carboxylic acid and an alcohol similar to Step 1-5 of Production Method 1. A compound of the formula (11) is condensed with an alcohol of the formula (2) in a solvent preferably in the presence of a base and a condensing agent to give a compound of the formula (1-2) which is one of the objective compounds.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; esters such as ethyl acetate, methyl acetate, butyl acetate, etc.; and polar solvents such as acetone, N,N-dimethylformamide, dimethyl sulfoxide, etc., and they can be used solely or in combination thereof. Preferred solvents in the present reaction are tetrahydrofuran, methylene chloride, dimethylformamide, etc.

Examples of the bases used in the reaction include organic bases such as triethylamine, pyridine, dimethylaminopyridine, N-methylmorpholine, etc., among which dimethylaminopyridine is preferred.

Examples of the condensing agents used in the reaction include 1-ethyl-3-(3'-dimethylaminopropyl)carbodiimide hydrochloride (WSC.HCl), dicyclohexylcarbodiimide (DCC), etc., among which 1-ethyl-3-(3'-dimethylaminopropyl)carbodiimide hydrochloride is preferred.

The reaction temperature is about 0° C. to 80° C., preferably about 0° C. to room temperature.

The reaction time is about 2 hours to 48 hours, preferably about 6 hours to 24 hours.

As an alternative of Production Method 2, a carboxylic acid ester compound derived from a compound of the formula (9) (wherein $R^{24}$ is p-methoxybenzyl and the carboxyl group is protected by benzyl ester) is subjected to removal of the p-methoxybenzyl group with 2,3-dichloro-5,6-dicyanobenzoquinone (DDQ), etc., followed by condensation with a compound of the formula (2). After removal of the benzyl group from the resulting compound, the deprotected compound is condensed with a compound of the formula (8) to give a compound of the formula (1-2) which is one of the objective compounds.

Production Method A

The following is an example of the method for producing a compound of the formula (1) wherein ring B and its substituent, $Alk^1$, and l are taken together to form

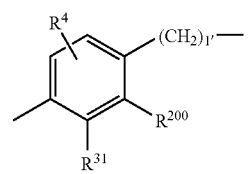

wherein $R^4$ and $R^{200}$ each has the same meaning as defined above, $R^{31}$ is $C_1$-$C_6$ alkyl, and l' is 1.

Production method A

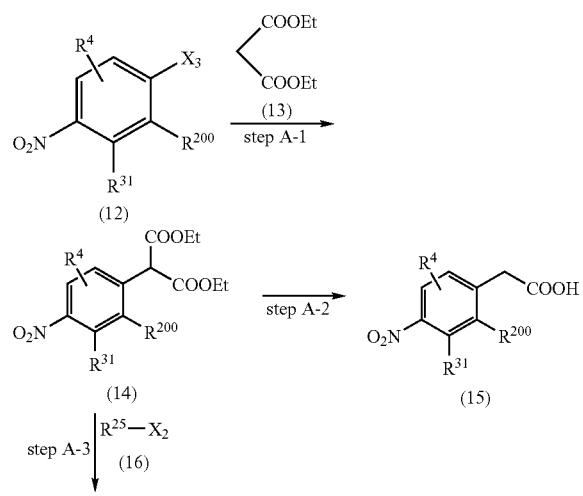

-continued

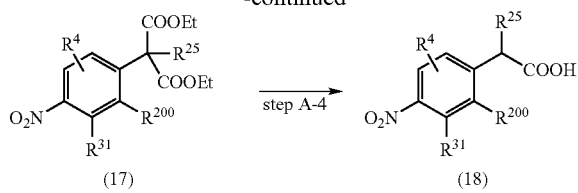

In the above reaction scheme, $R^{31}$, $R^4$ and $R^{200}$ each has the same meaning as defined above; $R^{25}$ is $C_{1-6}$ alkyl; $X_2$ and $X_3$ each is halogen; and Et is ethyl.

Step A-1

A compound of the formula (14) can be prepared by reacting a compound of the formula (12) with a malonic acid ester of the formula (13) in a solvent in the presence of a base.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; alcohols such as methanol, ethanol, isopropyl alcohol, t-butanol, etc.; and polar solvents such as N,N-dimethylformamide, dimethyl sulfoxide, etc., and they can be used solely or in combination thereof. A preferred solvent in the present reaction is N,N-dimethylformamide.

Examples of the bases used in the reaction include alkali metal hydrides such as sodium hydride, potassium hydride, etc.; alkali metal alkoxides such as sodium ethoxide, sodium methoxide, potassium t-butoxide, etc.; alkali metal amides such as sodium amide, lithium bistrimethylsilylamide, etc.; and alkali metal carbonates such as sodium carbonate, potassium carbonate, etc., among which sodium hydride is preferable.

The reaction temperature is about 0° C. to 120° C., preferably about room temperature to 100° C.

The reaction time is about 30 minutes to 24 hours, preferably about 1 hour to 12 hours.

Step A-2

This step is a hydrolysis reaction of esters, followed by decarboxylation. A compound of the formula (15) can be prepared by stirring a compound of the formula (14) under heating in a solvent in the presence of a base.

The solvent used in the reaction includes, for example, ethers such as diethyl ether, tetrahydrofuran, dioxane, 1,2-dimethoxyethane, diglyme, etc.; alcohols such as methanol, ethanol, isopropyl alcohol, t-butanol, etc.; and water; and they can be used solely or in combination thereof. Preferred solvents in the present reaction are a mixture of an alcohol and water.

Examples of the bases used in the reaction include alkali metal carbonates such as sodium carbonate, potassium carbonate, etc., and alkali metal hydroxides such as lithium hydroxide, sodium hydroxide, potassium hydroxide, etc., among which sodium hydroxide or potassium hydroxide is preferred.

The reaction temperature is about 0° C. to 150° C., preferably about 60° C. to 120° C.

The reaction time is about 10 minutes to 12 hours, preferably about 30 minutes to 6 hours.

In accordance with the Steps 1a-2, 1a-3 and 1a-4 of the Production Method 1a, compounds of the present invention can be prepared from a compound of the formula (15) obtained in the above Step A-2.

An example in the case where $Alk^1$ is a branched alkanediyl or alkenediyl will be illustrated below.

Step A-3

A compound of the formula (17) can be prepared by reacting a compound of the formula (14) with a compound of the formula (16) in a solvent in the presence of a base.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; alcohols such as methanol, ethanol, isopropyl alcohol, t-butanol, etc.; and polar solvents such as N,N-dimethylformamide, dimethyl sulfoxide, etc., and they can be used solely or in combination thereof. Preferred solvents in the present reaction are N,N-dimethylformamide, etc.

Examples of the bases used in the reaction include alkali metal hydrides such as sodium hydride, potassium hydride, etc.; alkali metal alkoxides such as sodium ethoxide, sodium methoxide, potassium t-butoxide, etc.; alkali metal carbonates such as sodium carbonate, potassium carbonate, sodium bicarbonate, potassium bicarbonate, etc.; alkali metal hydroxides such as lithium hydroxide, sodium hydroxide, potassium hydroxide, etc.; alkali metal carboxylates such as sodium acetate, potassium acetate, etc.; and alkali metal phosphates such as sodium phosphate, potassium phosphate, etc., among which sodium hydride is preferred.

The reaction temperature is about 0° C. to 120° C., preferably about room temperature to 100° C.

The reaction time is about 10 minutes to 24 hours, preferably about 30 minutes to 12 hours.

Step A-4

In a similar manner to Step A-2, a compound of the formula (18) can be prepared from a compound of the formula (17).

In accordance with the Steps 1a-2, 1a-3 and 1a-4 of the Production Method 1a, the compounds of the present invention can be prepared from a compound of the formula (18) obtained in the above Step A-4.

Production Method B

The following is an example of the method for producing a compound of the formula (1) wherein ring B and its substituent, $Alk^1$, and l are taken together to form

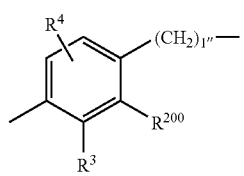

wherein $R^3$, $R^4$ and $R^{200}$ each has the same meaning as defined above, and 1" is 2 or 3.

Production method B l" = 2

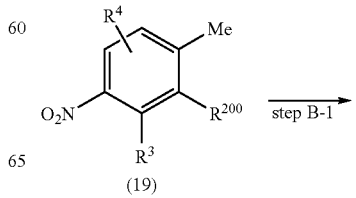

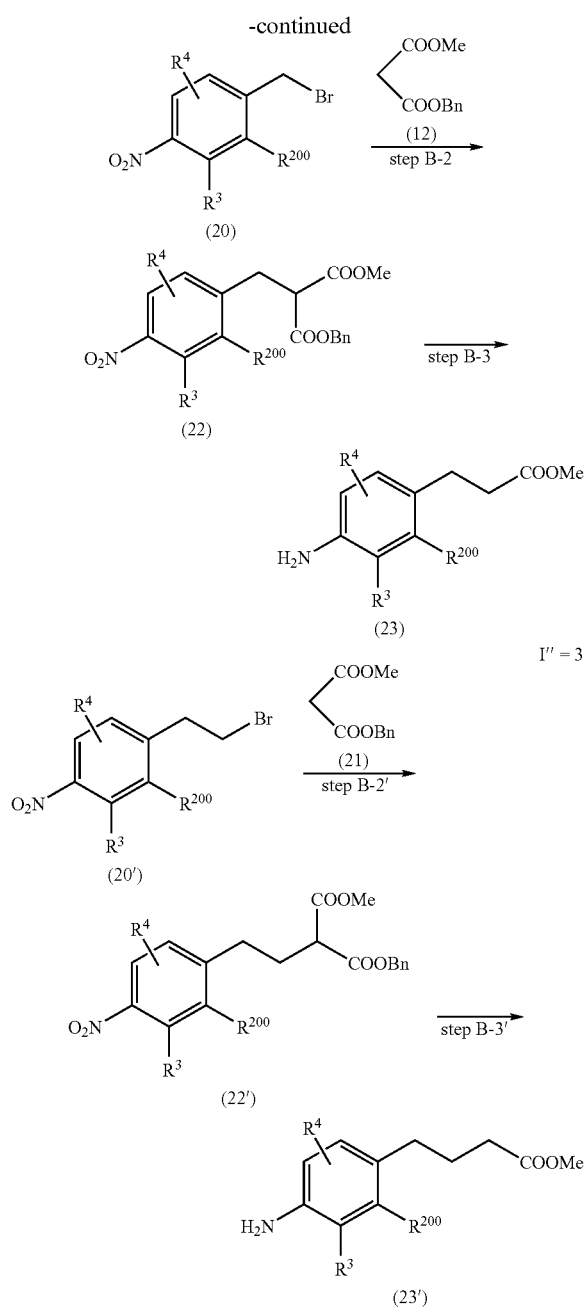

The brominating agent used in the reaction includes, for example, bromine, N-bromosuccinimide, etc., among which N-bromosuccinimide is preferred.

The reaction temperature is about room temperature to 120° C., preferably about 60° C. to 100° C.

The reaction time is about 10 minutes to 8 hours, preferably about 30 minutes to 4 hours.

Step B-2

In a similar manner to Step A-1 of Production Method A, a compound of the formula (22) can be prepared by reacting a compound of the formula (20) with a compound of the formula (21).

Step B-2'

In a similar manner to Step A-1 of Production Method A, a compound of the formula (22') can be prepared by reacting a compound of the formula (20') (prepared from a compound of the formula (15) or a compound of the formula (22) via several steps) with a compound of the formula (21').

Step B-3

A compound of the formula (23) can be prepared by hydrogenating a compound of the formula (22) for debenzylation in a solvent, followed by decarboxylation.

The solvent used in the reaction includes, for example, ethers such as diethyl ether, tetrahydrofuran, dioxane, 1,2-dimethoxyethane, diglyme, etc.; alcohols such as methanol, ethanol, isopropyl alcohol, t-butanol, etc.; and water; and they can be used solely or in combination thereof. Preferred solvents in the present reaction are alcohols.

Examples of the catalyst used for the debenzylation include palladium carbon, palladium hydroxide, Raney-Ni, platinum oxide, etc., among which palladium carbon is preferred.

The reaction temperature in the debenzylation is preferably about room temperature to 80° C., and the reaction temperature in the decarboxylation is preferably 10° C. to 150° C.

The reaction time in the debenzylation is about 1 hour to 16 hours, preferably about 2 hours to 8 hours, and the reaction time in the decarboxylation is about 5 minutes to 4 hours, preferably about 10 minutes to 2 hours.

Step B-3'

In a similar manner to Step B-3 of Production Method B, a compound of the formula (23') can be prepared from a compound of the formula (22').

In accordance with the Steps 1-3, 1-4 and 1-5 of the Production Method 1, the compounds of the present invention can be prepared from a compound of the formula (23) or (23') obtained in Step B-3 or B-3'.

Production Method C

The following is an example of the method for producing a compound of the formula (1) wherein ring B and its substituent, $Alk^1$, and l are taken together to form In the above reaction scheme, $R^3$, $R^4$ and $R^{200}$ each has the same meaning as defined above; Me is methyl; and Bn is benzyl.

Step B-1

A compound of the formula (20) can be prepared by reacting a compound of the formula (19) with a brominating agent in a solvent in the presence of a radical initiator (for example, 2,2'-azobisisobutyronitrile or benzoyl peroxide).

The solvent used in the reaction includes, for example, hydrocarbons such as benzene, etc., and halogenated hydrocarbons such as methylene chloride, chloroform, carbon tetrachloride, 1,2-dichloroethane, etc., and they can be used solely or in combination thereof. Preferred solvents in the present reaction are methylene chloride or carbon tetrachloride.

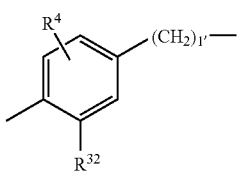

wherein $R^4$ has the same meaning as defined above; $R^{32}$ is —CON($R^{11}$)($R^{12}$) in which $R^{11}$ and $R^{12}$ each has the same meaning as defined above, and l' is 1.

Production method C

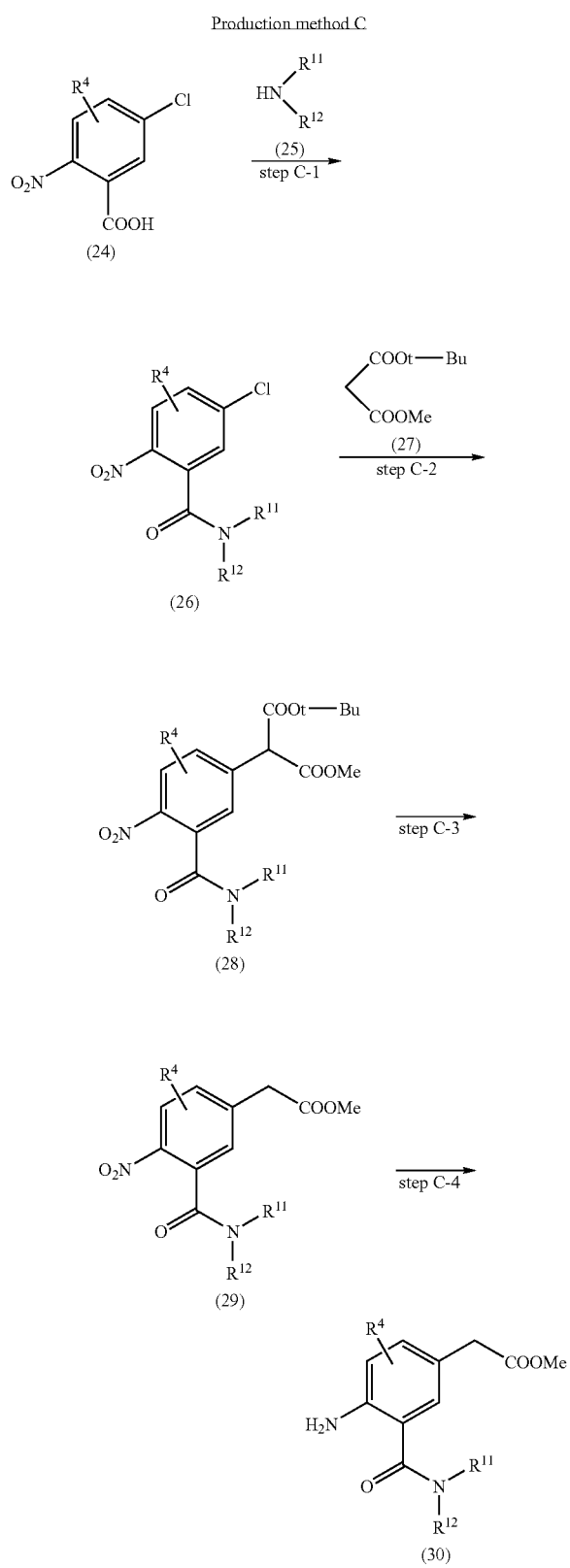

Step C-1

An acid chloride can be prepared from a compound of the formula (24) in a similar manner to Step 1-1 of Production Method 1. The resulting acid chloride is reacted with a compound of the formula (25) in a similar manner to Step 1-3 of Production Method 1 to give a compound of the formula (25).

Also, a compound of the formula (26) can be prepared by condensing a compound of the formula (24) with a compound of the formula (25) using a condensing agent (for example, WSC, HOBT). Alternatively, a compound of the formula (24) is converted into its mixed anhydride, followed by reaction with a compound of the formula (25) in the presence of a base, thereby to give a compound of the formula (26).

Step C-2

In a similar manner to Step A-1 of Production Method A, a compound of the formula (28) can be prepared by reacting a compound of the formula (26) with a compound of the formula (27).

Step C-3

A compound of the formula (29) can be prepared by treating a compound of the formula (28) with an acid (trifluoroacetic acid, toluenesulfonic acid, methanesulfonic acid, etc.) in the presence or absence of a solvent under heating or at room temperature to convert the tert-butyl ester moiety into the carboxylic acid moiety, followed by decarboxylation.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; alcohols such as methanol, ethanol, isopropyl alcohol, t-butanol, etc.; halogenated hydrocarbons such as methylene chloride, chloroform, carbon tetrachloride, 1,2-dichloroethane, etc.; and water; and they can be used solely or in combination thereof. Preferred solvents in the present reaction are methylene chloride, chloroform or toluene.

The reaction temperature is about 0° C. to 120° C., preferably about room temperature to 100° C.

The reaction time is about 1 hour to 24 hours, preferably about 2 hours to 12 hours.

Step C-4

In a similar manner to Step 1-2 of Production Method 1, a compound of the formula (30) can be prepared from a compound of the formula (29).

In accordance with the Steps 1-3,1-4 and 1-5 of Production Method 1, the compounds of the present invention can be prepared from a compound of the formula (30) obtained in the above Step C-4.

Production Method C'

The following is an example of the method for producing a compound of the formula (1) wherein ring B and its substituent, $Alk^1$, and 1 are taken together to form

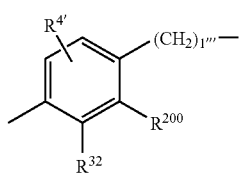

In the above reaction scheme, $R^4$, $R^{11}$ and $R^{12}$ each has the same meaning as defined above; Me is methyl; and t-Bu is tert-butyl.

wherein $R^{4'}$ is halogen; $R^{32}$ is —$CON(R^{11})(R^{12})$ in which $R^{11}$ and $R^{12}$ each has the same meaning as defined above; 1''' is 0; and $R^{200}$ has the same meaning as defined above.

Production method C'

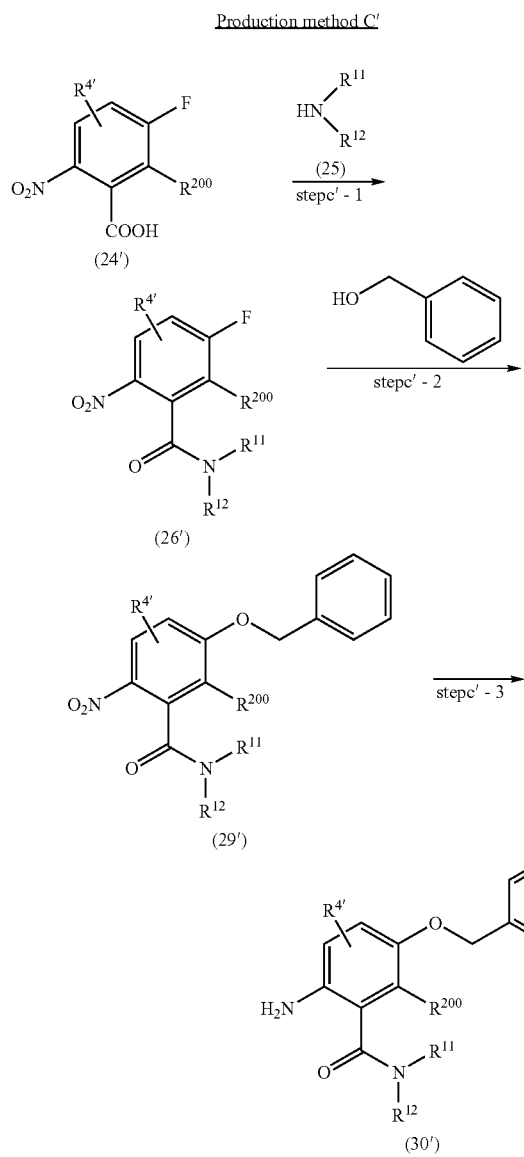

In the above reaction scheme, $R^{4'}$ is halogen, and $R^{11}$, $R^{12}$ and $R^{200}$ each has the same meaning as defined above.

Step C'-1
In a similar manner to Step C-1 of Production Method C, a compound of the formula (26') can be prepared from a compound of the formula (24').

Step C'-2
In a similar manner to Step C-2 of Production Method C, a compound of the formula (29') can be prepared by reacting a compound of the formula (26') with benzyl alcohol.

Step C'-3
In a similar manner to Step C-4 of Production Method C, a compound of the formula (30') can be prepared from a compound of the formula (29').

The compounds of the present invention can be prepared by debenzylating the compound (30') obtained in the Step C'-3 and condensing the debenzylated compound with a compound of the formula (3) in accordance with the Step 1-3 of Production Method 1, followed by condensation with a compound of the formula (89) according to the Step 3-5.

Production Method C''

The following is an example of the method for producing a compound of the formula (1) wherein ring B and its substituent, $Alk^1$, and l are taken together to form

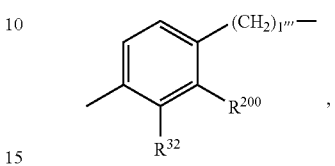

wherein $R^{32}$ is —$CON(R^{11})(R^{12})$ in which $R^{11}$ and $R^{12}$ each has the same meaning as defined above; and $R^{200}$ and $l'''$ each has the same meaning as defined above.

Production method C''

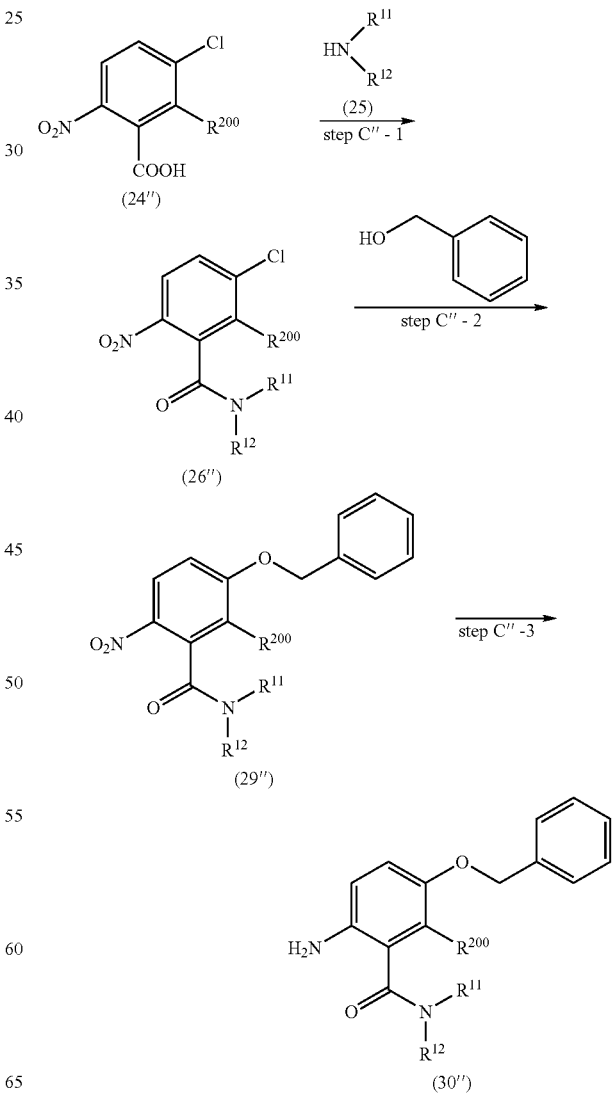

In the above reaction scheme, $R^{11}$, $R^{12}$ and $R^{200}$ each has the same meaning as defined above).

Step C"-1

In a similar manner to Step C-1 of Production Method C, a compound of the formula (26") can be prepared from a compound of the formula (24").

Step C"-2

In a similar manner to Step C-2 of Production Method C, a compound of the formula (29") can be prepared by reacting a compound of the formula (26") with benzyl alcohol.

Step C"-3

In a similar manner to Step C-4 of Production Method C, a compound of the formula (30") can be prepared from a compound of the formula (29").

Production Method C'''

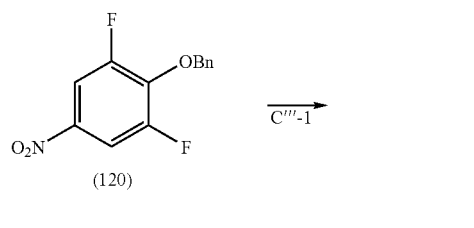
(120)

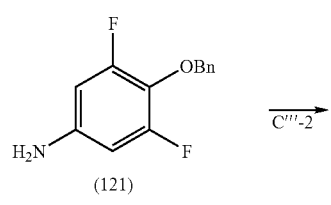
(121)

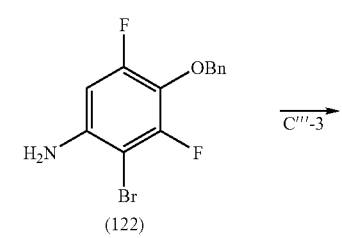
(122)

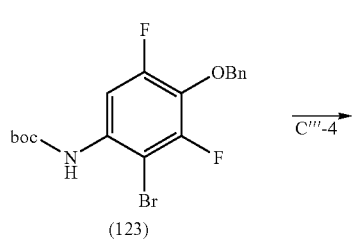
(123)

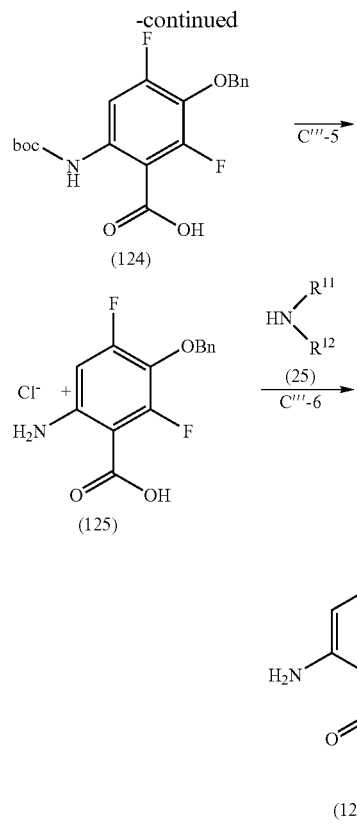
(124)
(125)
(126)

In the above reaction scheme, Bn is benzyl, boc is tert-butoxycarbonyl, and $R^{11}$ and $R^{12}$ each has the same meaning as defined above.

Step C'''-1

This step is a general method for converting the nitro group attached directly to the aromatic ring, into an amino group. A compound of the formula (121) can be prepared by reducing a compound of the formula (120) in a solvent in the presence of a reducing agent and an acid.

The solvent used in the reaction includes, for example, ethers such as diethyl ether, tetrahydrofuran, dioxane, 1,2-dimethoxyethane, diglyme, etc.; alcohols such as methanol, ethanol, isopropyl alcohol, etc.; and water; and they can be used solely or in combination thereof. A preferable example of such solvents in the present reaction is a mixed solvent of ethanol-tetrahydrofuran-acetic acid.

The acid used in the reaction includes, for example, hydrochloric acid, acetic acid, ammonium chloride, etc.

The reducing agent used in the reaction includes, for example, iron, zinc, tin, etc.

The reaction temperature is about 0° C. to 150° C., preferably about room temperature to 120° C.

Step C'''-2

This step is a selective monobromination at o-position of the aniline derivatives. A compound of the formula (122) can be prepared by reacting a compound of the formula (121) with a brominating agent.

The solvent used in the reaction includes, for example, ethers such as diethyl ether, tetrahydrofuran, dioxane, 1,2-dimethoxyethane, diglyme, etc.; and alcohols such as methanol, ethanol, isopropyl alcohol, etc.; and they can be used solely or in combination thereof. A preferable example of such solvents in the present reaction is tetrahydrofuran.

Preferred brominating agents are N-bromosuccinimide or bromine.

The reaction temperature is about 0° C. to 150° C., preferably about room temperature to 120° C.

Step C'''-3

This step is an introduction of tert-butoxycarbonyl group as an aniline-protecting group.

A compound of the formula (123) can be prepared by reacting a compound of the formula (122) with di-tert-butoxycarbonate in a solvent in the presence of a base.

The solvent used in the reaction includes, for example, ethers such as diethyl ether, tetrahydrofuran, dioxane, 1,2-dimethoxyethane, diglyme, etc.; and they can be used solely or in combination thereof. A preferable example of such solvents in the present reaction is tetrahydrofuran.

The base used in the reaction includes, for example, alkali metal hydroxides such as sodium hydroxide, potassium hydride, etc.; alkali metal alkoxides such as sodium ethoxide, sodium methoxide, potassium tert-butoxide, etc.; and organic bases such as triethylamine, pyridine, 4-dimethylaminopyridine, N-methylmorpholine, etc., among which 4-dimethylaminopyridine is preferred.

The reaction temperature is about 0° C. to 100° C., preferably about room temperature to 10° C.

In the case where two tert-butoxycarbonyl groups are introduced into a compound, such compound may be converted into a mono-tert-butoxycarbonyl compound by treatment with a base such as potassium carbonate and sodium carbonate in methanol.

Step C'''-4

This step is a method for converting the bromine atom on the benzene ring into the lithio group with an alkyl lithium, followed by conversion into the carboxyl group using carbon dioxide. A compound of the formula (124) can be prepared by reacting a compound of the formula (123) in a solvent in the presence of n-butyl lithium using dry-ice as a carbon dioxide source.

The solvent used in the reaction includes, for example, ethers such as diethyl ether, tetrahydrofuran, dioxane, 1,2-dimethoxyethane, diglyme, etc.; and they can be used solely or in combination thereof. A preferable example of such solvents in the present reaction is tetrahydrofuran.

The reaction temperature is about −150° C. to −50° C., and the reaction is performed preferably about −70° C., and then the reaction temperature is raised slowly to room temperature.

Step C'''-5

This step is a deprotection method of removing the tert-butoxycarbonyl group for the protected aniline into the free aniline. A compound of the formula (125) can be prepared by reacting a compound of the formula (124) in a solvent in the presence of an acid.

The solvent used in the reaction includes, for example, ethers such as diethyl ether, tetrahydrofuran, dioxane, 1,2-dimethoxyethane, diglyme, etc.; esters such as ethyl acetate, etc.; and hydrocarbons such as benzene, etc.; and they can be used solely or in combination thereof. Preferred solvents in the present reaction are tetrahydrofuran or ethyl acetate.

The acid used in the reaction includes, for example, hydrochloric acid, trifluoroacetic acid, tosic acid, etc.

The reaction temperature is about 0° C. to 100° C., preferably about room temperature to 60° C.

Step C'''-6

This step is a general conversion reaction of carboxylic acids and amides into dimethylamides using a condensing agent. A compound of the formula (126) can be prepared by reacting a compound of the formula (125) with a compound of the formula (25) in a solvent in the presence of a condensing agent.

The solvent used in the reaction includes, for example, ethers such as diethyl ether, tetrahydrofuran, dioxane, 1,2-dimethoxyethane, diglyme, etc.; dimethylformamide; and methylene chloride, etc; and they can be used solely or in combination thereof.

The condensing agent used in the reaction include a combination of DCC or WSC.HCl (1-ethyl-3-(3'-dimethylaminopropyl)carbodiimide hydrochloride) and HOBT (1-ethylhydroxybenzotriazole dicyclohexylcarbodiimide (DCC).

In the case where dimethylamine hydrochloride is used, the reaction is performed in the presence of a tertiary amine such as triethylamine. It is preferred to carry out the reaction at room temperature in DMF in the presence of triethylamine using a combination of dimethylamine hydrochloride and WSC.HCl and HOBT.

Production Method D

The following is an example of the method for preparing a compound of the formula (1) wherein ring B and its substituent, $Alk^1$, and 1 are taken together to form

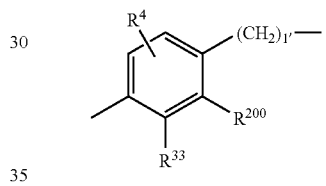

wherein $R^4$ and $R^{200}$ each has the same meaning as defined above, $R^{33}$ is $C_{1-6}$ alkoxy or $C_{7-16}$ aralkyloxy, and 1' is 1.

Production method D

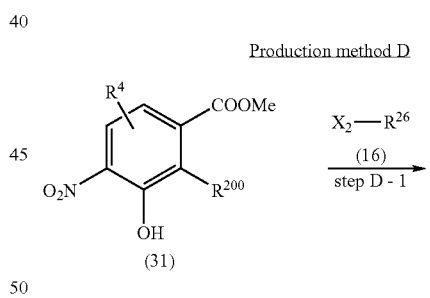

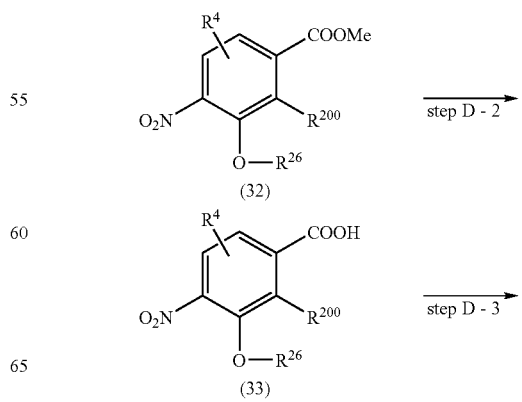

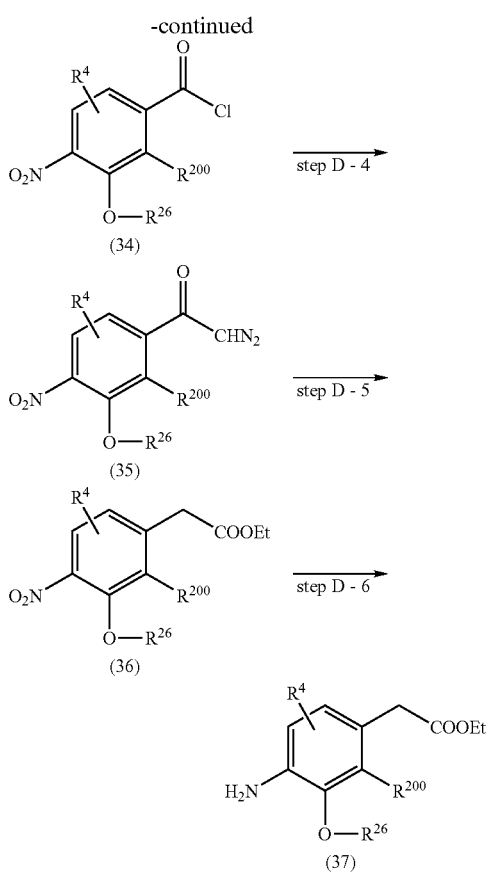

In the above reaction scheme, $R^4$, $R^{200}$, $X_2$, Me and Et each has the same meaning as defined above, and $R^{26}$ is $C_{1-6}$ alkyl or $C_{7-16}$ aralkyl.

Step D-1

A compound of the formula (32) can be prepared by reacting a compound of the formula (31) with a compound of the formula (16) in a solvent in the presence of a base.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; esters such as ethyl acetate, methyl acetate, butyl acetate, etc.; and polar solvents such as acetone, N,N-dimethylformamide, dimethyl sulfoxide, etc.; and they can be used solely or in combination thereof. A preferred solvents in the present reaction is N,N-dimethylformamide.

Examples of the bases used in the reaction include alkali metal hydrides such as sodium hydride, potassium hydride, etc., and alkali metal carbonates such as sodium carbonate, potassium carbonate, sodium bicarbonate, potassium bicarbonate, etc., among which sodium hydride is preferred.

The reaction temperature is about 0° C. to 100° C., preferably about room temperature to 80° C.

The reaction time is about 2 hour to 48 hours, preferably about 6 hours to 24 hours.

Step D-2

A compound of the formula (33) can be prepared by hydrolyzing a compound of the formula (32) in a solvent in the presence of a base.

The solvent used in the reaction includes, for example, ethers such as diethyl ether, tetrahydrofuran, dioxane, 1,2-dimethoxyethane, diglyme, etc.; alcohols such as methanol, ethanol, isopropyl alcohol, etc.; and water, and they can be used solely or in combination thereof. Preferred solvents in the present reaction are tetrahydrofuran or a mixture of tetrahydrofuran and ethanol or methanol.

Examples of the bases used in the reaction include alkali metal carbonates such as sodium carbonate, potassium carbonate, etc.; aqueous solutions of alkali metal hydroxides such as lithium hydroxide, sodium hydroxide, potassium hydroxide, etc., among which sodium hydroxide is preferred.

The reaction temperature is about 0° C. to 120° C., preferably about room temperature to 80° C.

The reaction time is about 1 hour to 24 hours, preferably about 2.5 hours to 12 hours.

Step D-3

In a similar manner to Step 1-1 of Production Method 1, a compound of the formula (34) can be prepared from a compound of the formula (33).

Step D-4

This step is a conversion reaction from acid chlorides to diazoketones. A compound of the formula (35) can be prepared by reacting a compound of the formula (34) with diazomethane in a solvent in the presence of a base.

The solvent used in the reaction includes, for example, ethers such as diethyl ether, tetrahydrofuran, dioxane, 1,2-dimethoxyethane, diglyme, etc., and they can be used solely or in combination thereof. Preferred solvents in the present reaction are diethyl ether or tetrahydrofuran.

Examples of the bases used in the reaction include organic bases such as triethylamine, pyridine, dimethylaminopyridine, N-methylmorpholine, etc., among which triethylamine is preferred.

The reaction temperature is about −20° C. to 50° C., preferably about 0° C. to room temperature.

The reaction time is about 2 hours to 48 hours, preferably about 6 hours to 24 hours.

Step D-5

This process is one carbon homologation (Arndt-Eistert synthesis) by α-diazoketone rearrangement (Wolff rearrangement). A compound of the formula (35) is reacted by use of a silver catalyst (for example, silver benzoate, silver oxide) in an alcohol in the presence of a base to give a compound of the formula (36).

The solvent (also served as the reaction reagents) used in the reaction includes, for example, alcohols such as methanol, ethanol, isopropyl alcohol, t-butanol, etc., and they can be used solely or in combination thereof. Preferred solvents (also served as the reaction reagents) in the present reaction are methanol or ethanol.

Examples of the bases used in the reaction include organic bases such as triethylamine, pyridine, dimethylaminopyridine, N-methylmorpholine, etc., among which triethylamine is preferred.

The reaction temperature is about room temperature to 120° C., preferably about 60° C. to 120° C.

The reaction time is about 2 hours to 36 hours, preferably about 4 hours to 18 hours.

Step D-6

In a similar manner to Step 1-2 of Production Method 1, a compound of the formula (37) can be prepared from a compound of the formula (36).

In accordance with the Steps 1-3,1-4 and 1-5 of the above Production Method 1, the compounds of the present invention can be prepared from a compound of the formula (37) obtained in the above Step D-6. The resulting compound of the present invention is further subjected to the reactions of Step 2-2 of Production Method 2, whereby the substituent —OR$^{26}$ can be converted into —OH.

Further, a compound of the formula (1) wherein $R^3$, $R^4$ or $R^{200}$ is —O—CO—X$_4$—R$^{100''''}$) can be prepared by reacting the resulting alcohol or phenol compound with a compound of the formula:

Cl—CO—X$_4$—R$^{100''''}$ (wherein X$_4$ is —O— or —CH$_2$—, and R$^{100''''}$ is C$_1$-C$_6$ alkyl or C$_1$-C$_6$ alkoxy) in a solvent (e.g. toluene, ethyl acetate, etc.) preferably in the presence of a base (e.g. triethylamine, etc.)

Production Method E

The following is an example of the method for preparing a compound of the formula (1) wherein ring B and its substituent, Alk$^1$, and l are taken together to form

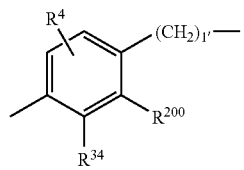

wherein $R^4$ and $R^{200}$ each has the same meaning as defined above, $R^{34}$ is —N(R$^{13}$)(R$^{14}$) in which $R^{13}$ and $R^{14}$ each has the same meaning as defined above, and l' is 1.

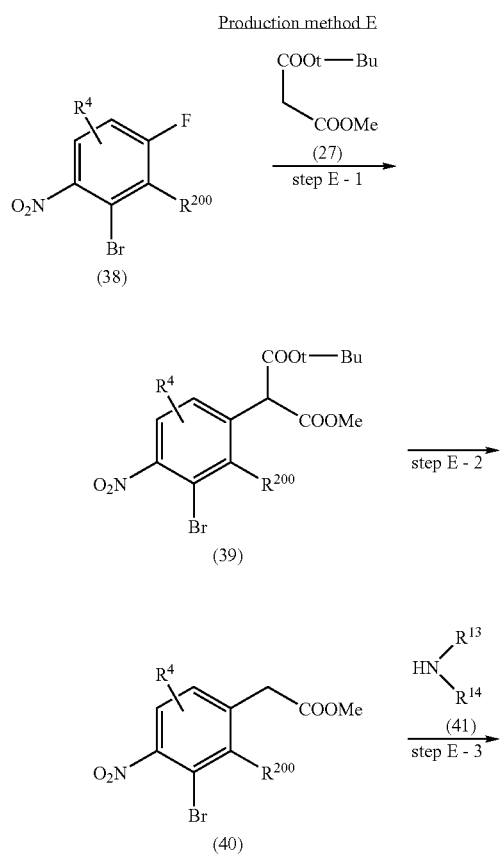

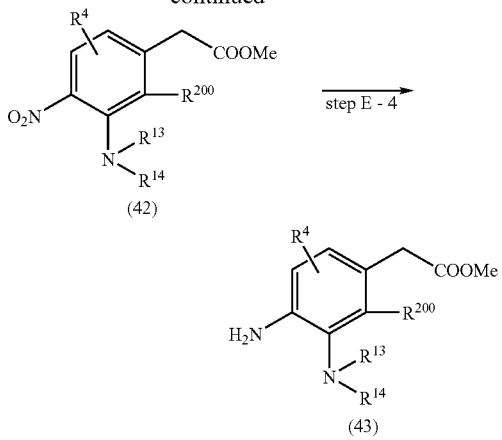

In the above reaction scheme, $R^4$, $R^{13}$, $R^{14}$, $R^{200}$, Me and t-Bu each has the same meaning as defined above.

Step E-1

In a similar manner to Step A-1 of Production Method A, a compound of the formula (39) can be prepared by reacting a compound of the formula (38) with a compound of the formula (27).

Step E-2

In a similar manner to Step C-3 of Production Method C, a compound of the formula (40) can be prepared from a compound of the formula (39).

Step E-3

A compound of the formula (42) can be prepared by reacting a compound of the formula (40) with a compound of the formula (41) with or without a solvent and in the presence of a base.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; alcohols such as methanol, ethanol, isopropyl alcohol, t-butanol, etc.; esters such as ethyl acetate, methyl acetate, butyl acetate, etc.; and polar solvents such as N,N-dimethylformamide, dimethyl sulfoxide, etc.; and they can be used solely or in combination thereof. A preferred solvent in the present reaction is tetrahydrofuran.

Examples of the bases used in the reaction include organic bases such as triethylamine, pyridine, dimethylaminopyridine, N-methylmorpholine, etc., among which triethylamine or a mixture of triethylamine and dimethylaminopyridine is preferred.

The reaction temperature is about 0° C. to 120° C., preferably about room temperature to 100° C.

The reaction time is about 2 hours to 48 hours, preferably about 6 hours to 24 hours.

Step E-4

In a similar manner to Step 1-2 of Production Method 1, a compound of the formula (43) can be prepared from a compound of the formula (42).

In accordance with the Steps 1-3, 1-4 and 1-5 of the above Production Method 1, the compounds of the present invention can be prepared from a compound of the formula (43) obtained in the above Step E-4.

Production Method F

The following is an example of the process for preparing a compound of the formula (1) wherein ring B and its substituent, $Alk^1$, and 1 are taken together to form

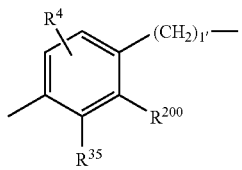

wherein $R^4$ and $R^{200}$ each has the same meaning as defined above, and $R^{35}$ is —COO($R^{25}$) in which $R^{25}$ is $C_1$-$C_6$ alkyl, and l' is 1.

Production method F

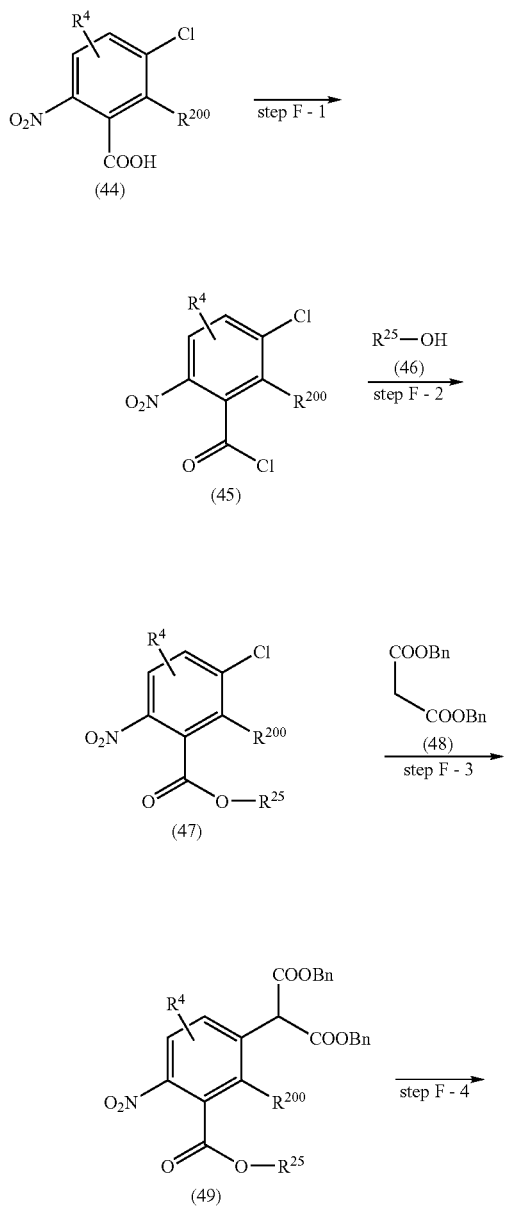

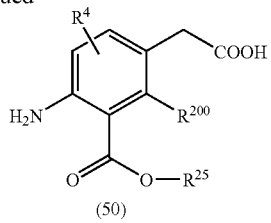

In the above reaction scheme, $R^4$, $R^{25}$, $R^{200}$ and Bn each has the same meaning as defined above.

Step F-1

In a similar manner to Step 1-1 of Production Method 1, a compound of the formula (45) can be prepared from a compound of the formula (44).

Step F-2

A compound of the formula (47) can be prepared by reacting a compound of the formula (45) with a compound of the formula (46) in a solvent in the presence of a base.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; and esters such as ethyl acetate, methyl acetate, butyl acetate, etc.; and they can be used solely or in combination thereof. A preferred solvent in the present reaction is tetrahydrofuran.

Examples of the bases used in the reaction include organic bases such as triethylamine, pyridine, dimethylaminopyridine, N-methylmorpholine, etc., among which triethylamine is preferred.

The reaction temperature is about −30° C. to 80° C., preferably about −20° C. to room temperature.

The reaction time is about 2 hours to 48 hours, preferably about 6 hours to 24 hours.

Step F-3

In a similar manner to Step A-1 of Production Method A, a compound of the formula (49) can be prepared by reacting a compound of the formula (47) with a compound of the formula (48).

Step F-4

A compound of the formula (49) was reacted in a similar manner to Step 1-2 of Production Method 1, followed by debenzylation and decarboxylation to give a compound of the formula (50).

In accordance with the alternative process described in Step 1-3 and Step 1-5 of Production Method 1, the compounds of the present invention can be prepared from a compound of the formula (50) obtained in the above Step F-4.

Production Method G

The following is an example of the process for preparing a compound of the formula (1) wherein ring B and its substituent, $Alk^1$, and 1 are taken together to form

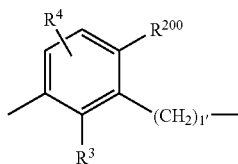

wherein $R^3$, $R^4$ and $R^{200}$ each has the same meaning as defined above and l' is 1.

Production method G

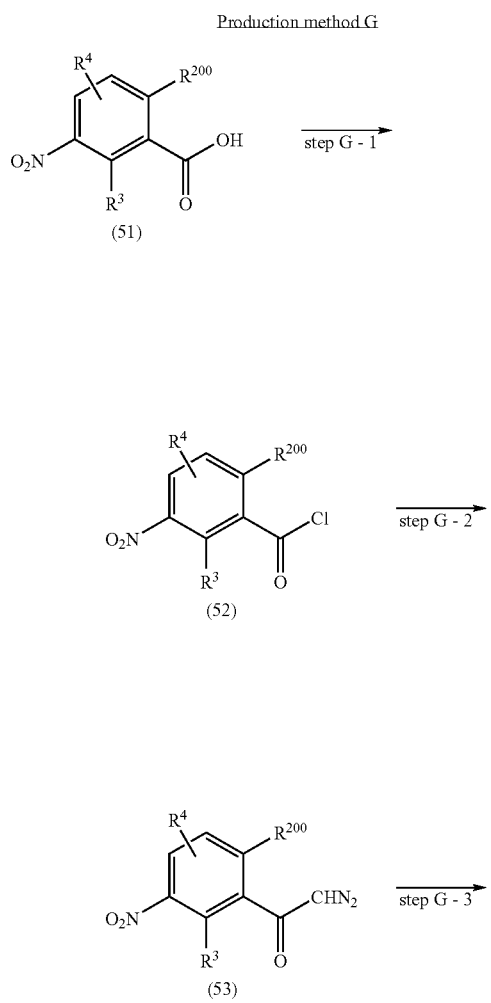

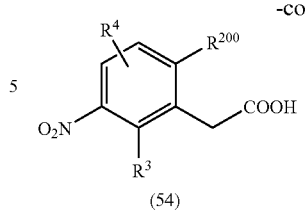

In the above reaction scheme, $R^3$, $R^4$, $R^{200}$ and Et each has the same meaning as defined above.

Step G-1

In a similar manner to Step 1-1 of Production Method 1, a compound of the formula (52) can be prepared from a compound of the formula (51).

Step G-2

In a similar manner to Step D-4 of Process D, a compound of the formula (53) can be prepared from a compound of the formula (52).

Step G-3

In a similar manner to Step D-5 of Production Method D, a compound of the formula (54) can be prepared from a compound of the formula (53).

Step G-4

In a similar manner to Step D-6 of Production Method D, a compound of the formula (55) can be prepared from a compound of the formula (54).

In accordance with Steps 1-3, 1-4 and 1-5 of the above Production Method 1, the compounds of the present invention can be prepared from a compound of the formula (55) obtained above in Step G-4.

Step G-5

In a similar manner to Step 1-4 of the above Production Method 1, a compound of the formula (55') can be prepared from a compound of the formula (54).

In accordance with Steps 1a-2, 1a-3 and 1a-4 of the above Production Method 1a, the compounds of the present invention can be prepared from a compound of the formula (55') obtained in the above Step G-5.

Production Method H

The following is an example of the process for preparing a compound of the formula (1) wherein ring B and its substituent, $Alk^1$, and 1 are taken together to form

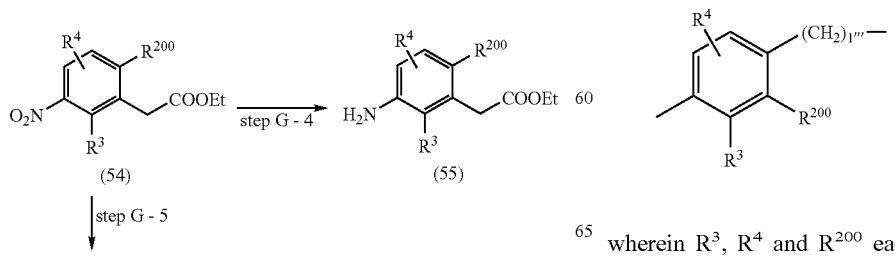

wherein $R^3$, $R^4$ and $R^{200}$ each has the same meaning as defined above and l''' is 0.

Production method H
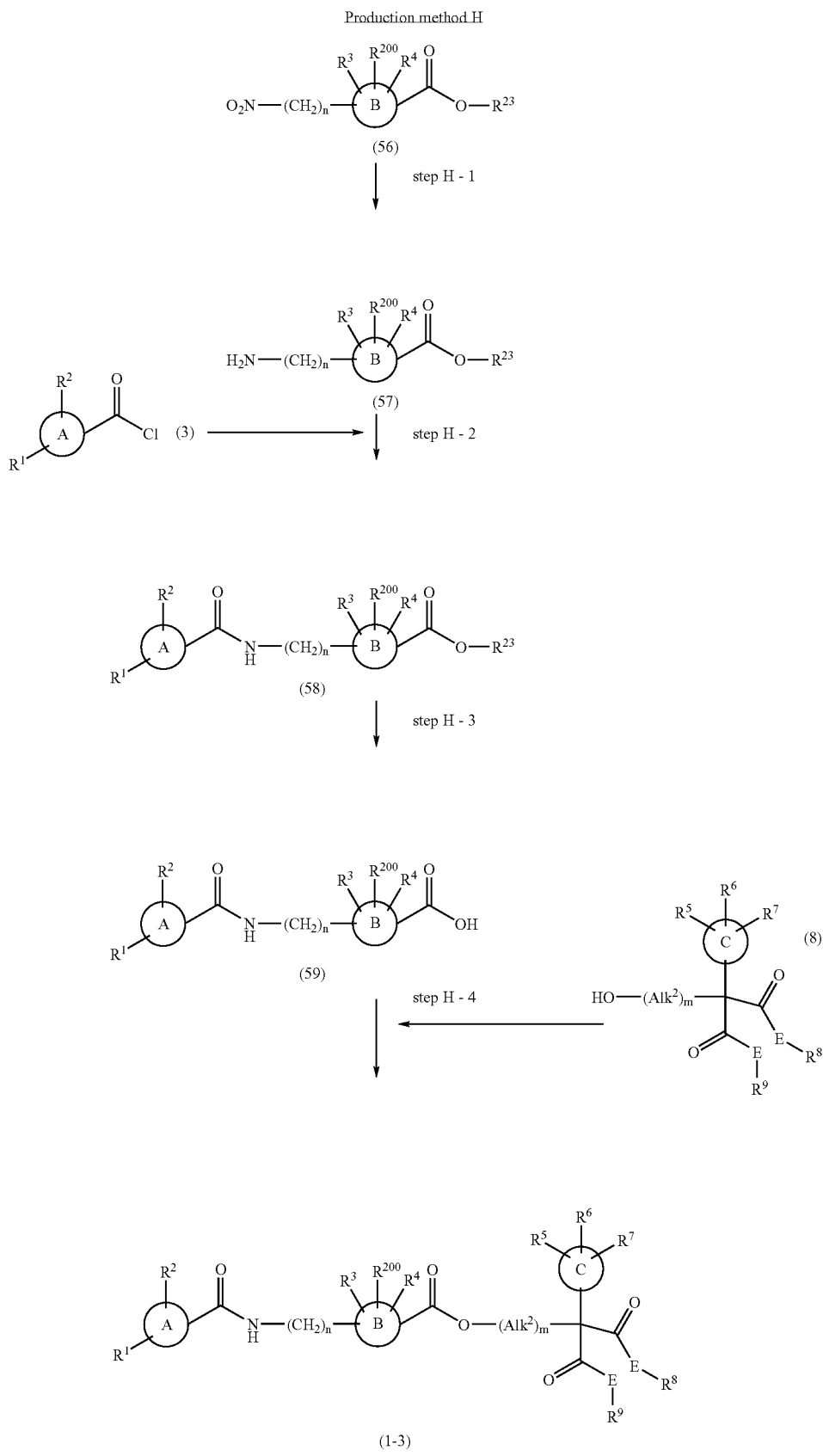

In the above reaction scheme, $R^1$, $R^2$, $R^3$, $R^4$, $R^5$, $R^6$, $R^7$, $R^8$, $R^9$, $R^{23}$, $R^{200}$, $Alk^2$, E, ring A, ring B, ring C, m has the same meaning as defined above.

Step H-1

In a similar manner to Step 1-2 of Production Method 1, a compound of the formula (57) can be prepared from a compound of the formula (56).

Step H-2

In a similar manner to Step 1-3 of Production Method 1, a compound of the formula (58) can be prepared by reacting a compound of the formula (57) obtained in Step of H-1 (or commercially available product) with a compound of the formula (3).

Step H-3

In a similar manner to Step 1-4 of Production Method 1, a compound of the formula (59) can be prepared from a compound of the formula (58).

Step H-4

In a similar manner to Step 1-5 of Production Method 1, a compound of the formula (1-3) which is one of the objective compounds can be prepared by reacting a compound of the formula (59) with a compound of the formula (8).

Production Method I

The following is an example of the process for preparing a compound of the formula (1) wherein ring B and its substituent, $Alk^1$, and l are taken together to form

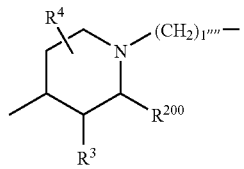

wherein $R^3$, $R^4$ and $R^{200}$ each has the same meaning as defined above and l'''' is 1 to 3).

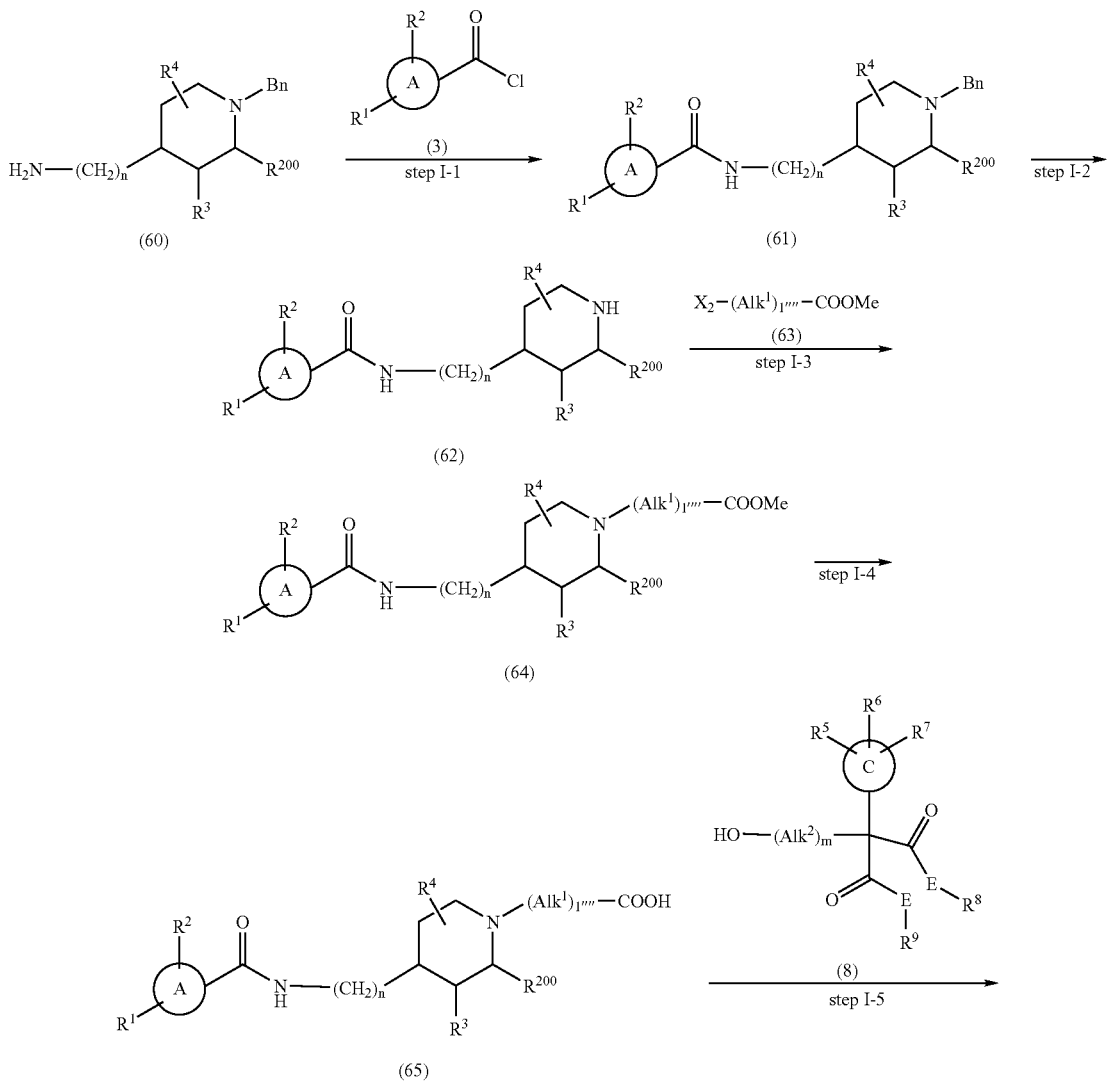

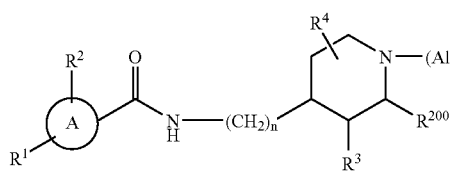

(1-4)

In the above reaction scheme, $R^1$, $R^2$, $R^3$, $R^4$, $R^5$, $R^6$, $R^7$, $R^8$, $R^9$, $R^{200}$, l'''', m, n, E, ring A, ring C, Bn, Me, $Alk^1$, $Alk^2$ and $X_2$ each has the same meaning as defined above.

Step I-1

In a similar manner to Step 1-3 of Production Method 1, a compound of the formula (61) can be prepared by reacting a compound of the formula (60) with a compound of the formula (3).

Step I-2

Under conditions similar to Step 1-2 of Production Method 1, with the proviso that palladium hydroxide is used as a catalyst, a compound of the formula (62) can be prepared from a compound of the formula (61).

Step I-3

A compound of the formula (64) can be prepared by reacting a compound of the formula (62) with a compound of the formula (63) in a solvent in the presence of a base. Alternatively, $X_2$-$(Alk^1)_{l''''}$—COOEt (in the formula, $X_2$, $Alk^1$, l'''' and Et each has the same meaning as defined above) may be used in place of a compound of the formula (63).

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; alcohols such as methanol, ethanol, isopropyl alcohol, t-butanol, etc.; esters such as ethyl acetate, methyl acetate, butyl acetate, etc.; polar solvents such as acetone, N,N-dimethylformamide, dimethyl sulfoxide, etc.; and they can be used solely or in combination thereof. A preferred solvent in the present reaction is N,N-dimethylformamide.

Examples of the bases used in the reaction include alkali metal hydrides such as sodium hydride, potassium hydride, etc.; alkali metal alkoxides such as sodium ethoxide, sodium methoxide, potassium t-butoxide, etc.; alkali metal carbonates such as sodium carbonate, potassium carbonate, etc.; alkali metal hydroxides such as lithium hydroxide, sodium hydroxide, potassium hydroxide, etc.; alkali metal carboxylates such as sodium acetate, potassium acetate, etc.; and alkali metal phosphates such as sodium phosphate, potassium phosphate, etc., among which potassium carbonate or sodium hydride is preferred.

The reaction temperature is about 0° C. to 150° C., preferably about room temperature to 100° C.

The reaction time is about 1 hour to 48 hours, preferably about 2 hours to 24 hours.

Step I-4

In a similar manner to Step 1-4 of Production Method 1, a compound of the formula (65) can be prepared from a compound of the formula (64).

Step I-5

In a similar manner to Step 1-5 of Production Method 1, a compound of the formula (1-4) which is one of the objective compounds can be prepared by reacting a compound of the formula (65) with a compound of the formula (8).

Production Method J

The following is an example of the method for preparing a compound of the formula (1) wherein ring B and its substituent, $Alk^1$, and 1 are taken together to form

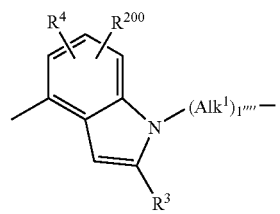

wherein $R^3$, $R^4$, $R^{200}$, l'''' and $Alk^1$ each has the same meaning as defined above.

Production method J

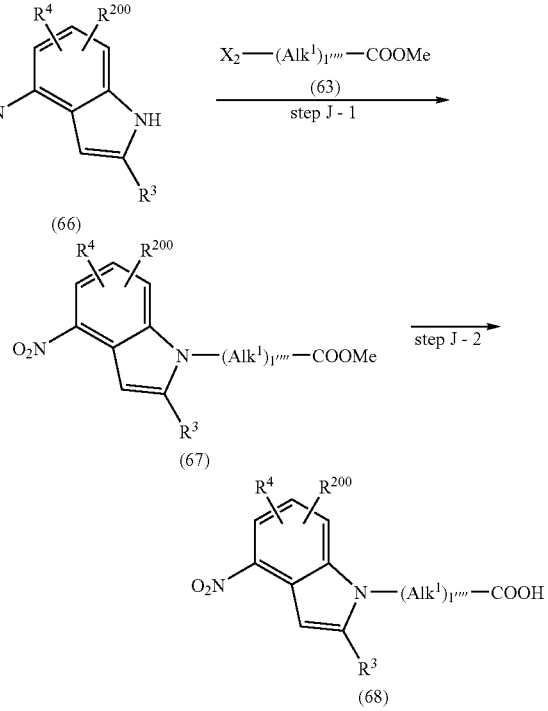

In the above reaction scheme, $R^3$, $R^4$, $R^{200}$, Me, $Alk^1$, $l''''$ and $X_2$ each has the same meaning as defined above.

Step J-1

In a similar manner to Step I-3 of Production Method I, a compound of the formula (67) can be prepared by reacting a compound of the formula (66) with a compound of the formula (63). Alternatively, $X_2\text{-}(Alk^1)_{l''''}\text{—COOEt}$ (in the formula $X_2$, $Alk^1$, $l''''$ and Et each has the same meaning as defined above) may be used in place of a compound of the formula (63).

Step J-2

In accordance with the Step I-4 of Production Method I, a compound of the formula (68) can be prepared from a compound of the formula (67).

In a similar manner to Steps 1a-2, 1a-3 and 1a-4 of Production Method 1a, the compounds of the present invention can be prepared from a compound of the formula (68) obtained in the above Step J-2.

Production Method K

The following is an example of the method for preparing a compound of the formula (1) wherein ring B and its substituent, $Alk^1$, and l are taken together to form

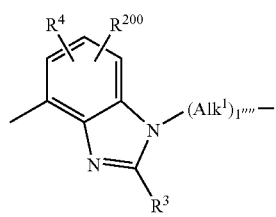

wherein $R^3$, $R^4$, Me, $R^{200}$, $l''''$, and $Alk^1$ each has the same meaning as defined above.

Production method K

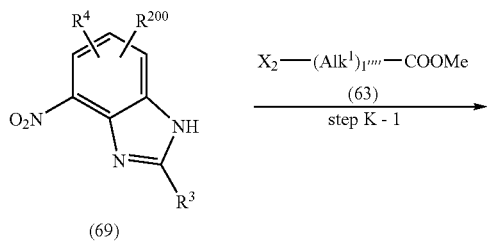

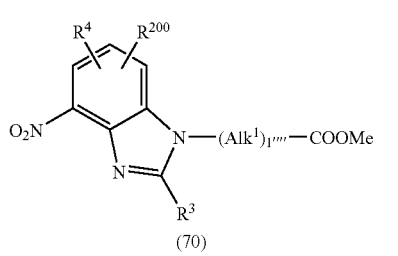

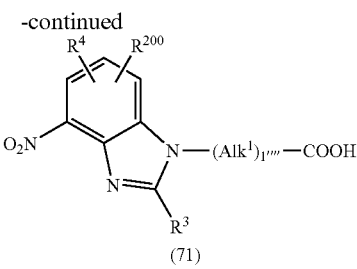

In the above reaction scheme, $R^3$, $R^4$, $R^{200}$, Me, $l''''$, $Alk^1$ and $X_2$ each has the same meaning as defined above.

Step K-1

In a similar manner to Step I-3 of Production Method I, a compound of the formula (70) can be prepared by reacting a compound of the formula (69) with a compound of the formula (63). Alternatively, $X_2\text{-}(Alk^1)_{l''''}\text{—COOEt}$ (in the formula $X_2$, $Alk^1$, $l''''$ and Et each has the same meaning as defined above) may be used in place of a compound of the formula (63).

Step K-2

In a similar manner to Step I-4 of Production Method I, a compound of the formula (71) can be prepared from a compound of the formula (70).

In accordance with the Steps 1a-2, 1a-3 and 1a-4 of the above Production Method 1a, the compounds of the present invention can be prepared from a compound of the formula (71) obtained in the above Step K-2.

Production Method L

The following is an example of the process for preparing a compound of the formula (1) wherein X, ring B, the substituent on the ring B, $Alk^1$ and l are taken together to form

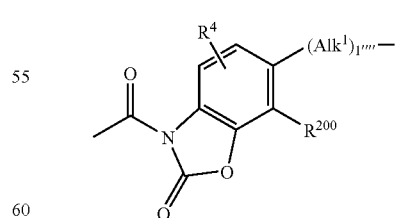

wherein $R^4$, $R^{200}$, $l''''$ and $Alk^1$ each has the same meaning as defined above.

Production method L

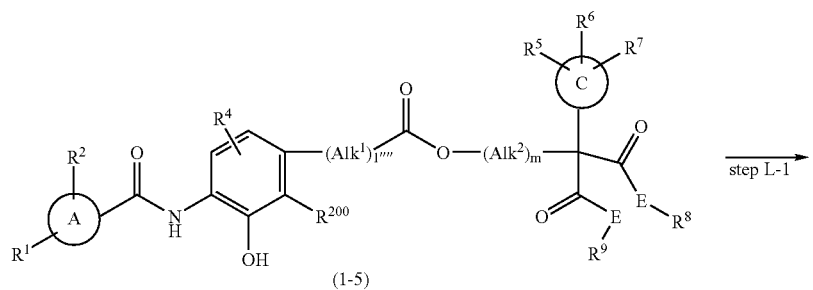

(1-5)

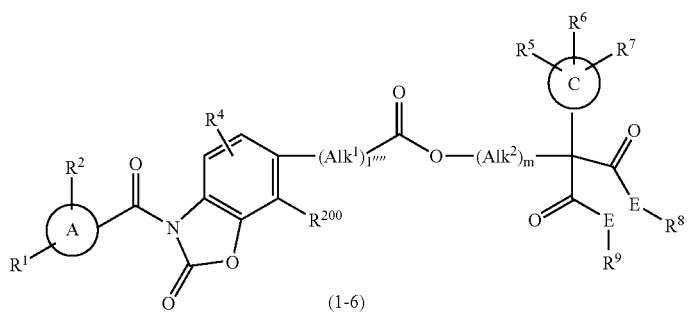

(1-6)

In the above reaction scheme, $R^1$, $R^2$, $R^4$, $R^5$, $R^6$, $R^7$, $R^8$, $R^9$, $R^{200}$, l'''', m, E, ring A, ring C, $Alk^1$ and $Alk^2$ each has the same meaning as defined above.

Step L-1

A compound obtained in accordance with Steps 1-3, 1-4, and 1-5 of the Production Method 1 from a compound (wherein $R^{26}$ is benzyl) obtained in the Production Method D is debenzylated, and the resultant compound of the formula (1-5) is reacted with a phosgene equivalent reagent (for example, triphosgene or diphosgene, etc.) in a solvent in the presence of a base to give a compound of the formula (1-6).

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; and they can be used solely or in combination thereof. A preferred solvent in the present reaction is chloroform.

Examples of the bases used in the reaction include The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; and they can be used solely or in combination thereof. A preferred solvent in the present reaction is chloroform.

Examples of the bases used in the reaction include organic bases such as triethylamine, pyridine, dimethylaminopyridine, N-methylmorpholine, etc., among which triethylamine is preferred.

The reaction temperature is about −20° C. to 100° C., preferably about 0° C. to room temperature.

The reaction temperature is about −20° C. to 100° C., preferably about 0° C. to room temperature.

The reaction time is about 10 minutes to 4 hours, preferably about 30 minutes to 2 hours.

Production Method L'

The following is an example of the process for preparing a compound of the formula (1) wherein X, ring B, and the substituent on the ring B are taken together to form the group of the formula:

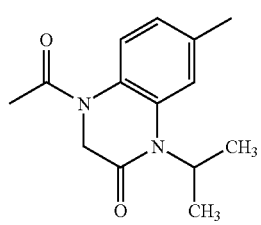

Production method L'

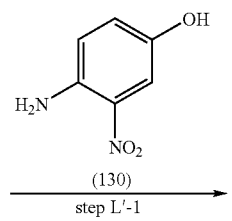

(130)

$\xrightarrow{\text{step L'-1}}$ (3)

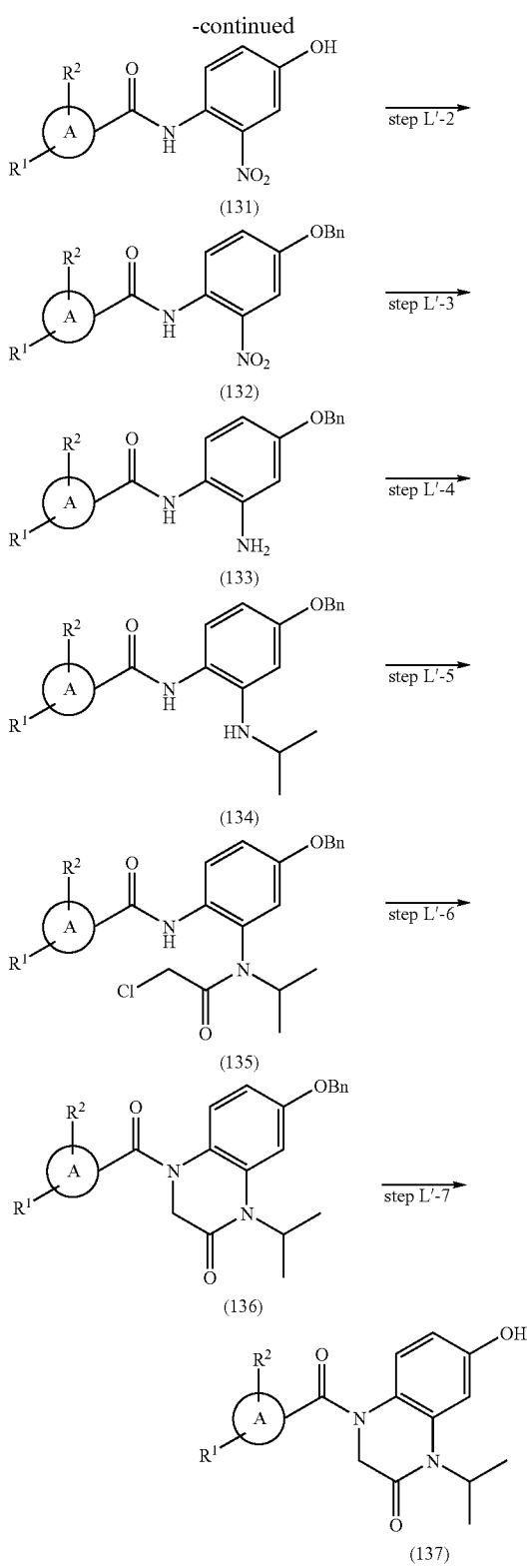

the formula (131) can be prepared by reacting a compound of the formula (3) with a compound of the formula (130) in a solvent in the presence of a base.

The solvent used in the reaction includes, for example, ethers such as diethyl ether, tetrahydrofuran, dioxane, 1,2-dimethoxyethane, diglyme, etc.; toluene; dimethylfomamide; ethyl acetate; and water, etc.; and they can be used solely or in combination thereof.

Examples of the bases used in the reaction include inorganic bases such as sodium carbonate, potassium carbonate, sodium bicarbonate, etc.; and organic bases such as triethylamine, pyridine, 4-dimethylaminopyridine, etc., among which sodium bicarbonate is preferred.

The reaction temperature is about 0° C. to 100° C., preferably about 0° C. to room temperature.

Step L'-2

This step is a protection method wherein phenol is converted into benzyl ether. A compound of the formula (132) can be prepared by reacting a compound of the formula (131) with a benzyl halide (e.g. benzyl bromide) in a solvent in the presence of a base.

The solvent used in the reaction includes, for example, ethers such as diethyl ether, tetrahydrofuran, dioxane, 1,2-dimethoxyethane, diglyme, etc.; toluene; dimethylfomamide; and ethyl acetate, etc.; and they can be used solely or in combination thereof.

Examples of the bases used in the reaction include inorganic bases such as alkali metal hydrides (e.g. sodium hydride, potassium hydride, etc.), alkali metal alkoxides such as sodium ethoxide, sodium methoxide, etc.; and organic bases such as triethylamine, pyridine, 4-dimethylaminopyridine, etc., among which potassium carbonate is preferred.

The reaction temperature is about 0° C. to 100° C., preferably about 0° C. to room temperature.

Step L'-3

This step is a reduction method for the nitro group attached directly to the aromatic ring into an amino group. A compound of the formula (133) can be prepared by subjecting a compound of the formula (132) to reduction reaction in a solvent.

The solvent used in the reaction includes, for example, ethers such as diethyl ether, tetrahydrofuran, dioxane, 1,2-dimethoxyethane, diglyme, etc.; alcohols such as methanol, ethanol, isopropyl alcohol, etc.; toluene; dimethylfomamide; ethyl acetate; water, etc.; and they can be used solely or in combination thereof. If necessary, acetic acid, hydrochloric acid or aqueous ammonium chloride may be used in combination with said solvents.

The reducing agent used in the reaction includes, for example, iron, zinc, tin, etc.

The reaction temperature is about 0° C. to 150° C., preferably room temperature to 120° C.

Step L'-4

This step is a reductive amination using aniline and ketone or aldehyde. A compound of the formula (134) can be prepared by subjecting a compound of the formula (133) to reductive amination in a solvednt.

The solvent used in the reaction includes, for example, dichloromethane, dichloroethane, chloroform, etc., and they can be used solely or in combination thereof.

The reducing agent used in the reaction includes, for example, hydrides such as sodium triacetoxy borohydride, sodium borohydride, sodium cyanoborohydride, etc.

The reaction temperature is about 0° C. to 50° C., preferably 0° C. to room temperature.

Step L'-5

This step is an N-halo-acetylation method for aniline. A compound of the formula (135) can be prepared by reacting a In the above reaction scheme, $R^1$, $R^2$ and Bn each has the same meaning as defined above.

Step L'-1

This step is a general amide conversion method by the reaction between acid chlorides and amines. A compound of compound of the formula (134) with chloroacetyl chloride in a solvent in the presence of a base.

The solvent used in the reaction includes, for example, dichloromethane, DMF, ethyl acetate, tetrahydrofuran, toluene, etc., and they can be used solely or in combination thereof.

Examples of the bases used in the reaction include alkali metal hydrides such as sodium hydride, potassium hydride, etc., alkali metal alkoxides such as sodium ethoxide, sodium methoxide, potassium t-butoxide, etc.; and organic bases such as triethylamine, pyridine, 4-dimethylaminopyridine, etc., among which tirethylamine is preferred.

The reaction temperature is about 0° C. to 50° C., preferably 0° C. to room temperature.

Step L'-6

This step is a cyclization reaction between haloacetylamide and the intramolecular nitrogen atom existing in the amide. A compound of the formula (136) can be prepared by subjecting a compound of the formula (135) to a cyclization reaction in a solvent in the presence of an additive and a base.

The solvent used in the reaction includes, for example, DMF, tetrahydrofuran, etc.

The additive includes sodium iodide, potassium iodide, tetrabutyl ammonium iodide, etc.

The reaction temperature is about 0° C. to 50° C., preferably room temperature to 60° C.

Step L'-7

This step is a deprotection reaction by hydrogenation of the benzyl ether of a phenol compound. Compound (137) can be prepared by hydrogenating a compound of the formula (136) in a solvent in the presence of a reducing agent.

The solvent used in the reaction includes, for example, ethanol, methanol, THF, ethyl acetate, etc.

The reducing agent includes, for example, palladium carbon, Raney-Ni, etc.

The reaction temperature is 0° C. to 100° C., preferably room temperature to 60° C.

Production Method M

The following is an example of the method for preparing a compound of the formula (1) wherein X is —CON($R^{10}$)—($CH_2$)n —($R^{10}$ is other than hydrogen).

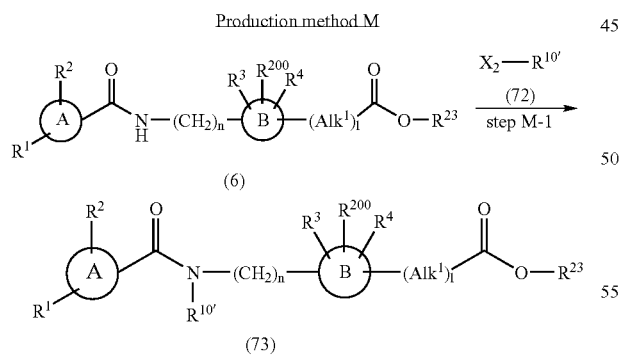

Production method M

In the above reaction scheme, $R^1$, $R^2$, $R^3$, $R^4$, $R^{23}$, $R^{200}$, l n, $X_2$, ring A, ring B, and $Alk^1$ each has the same meaning as defined above, and $R^{10'}$ is $C_1$-$C_6$ alkyl or $C_3$-$C_7$ cycloalkyl.

Step M-1

A compound of the formula (73) can be prepared by reacting a compound of the formula (6) obtained in the Step 1-3 of Production Method 1 with a compound of the formula (72) in a solvent in the presence of a base.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; esters such as ethyl acetate, methyl acetate, butyl acetate, etc.; and polar solvents such as acetone, N,N-dimethylformamide, dimethyl sulfoxide, etc.; and they can be used solely or in combination thereof. A preferred solvent in the present reaction is N,N-dimethylformamide.

Examples of the bases used in the reaction include alkali metal hydrides such as sodium hydride, potassium hydride, etc.; alkali metal alkoxides such as sodium ethoxide, sodium methoxide, potassium t-butoxide, etc.; alkali metal carbonates such as sodium carbonate, potassium carbonate, etc.; alkali metal carboxylates such as sodium acetate, potassium acetate, etc.; and alkali metal phosphates such as sodium phosphate, potassium phosphate, etc., among which sodium hydride is preferred.

The reaction temperature is about 0° C. to 100° C., preferably about room temperature to 80° C.

The reaction time is about 1 hour to 24 hours, preferably about 2 hours to 8 hours.

In accordance with the above Steps 1-4 and 1-5, the compounds of the present invention can be prepared from a compound of the formula (73) obtained in the above Step M-1.

Production Method N

The following is an example of the method for preparing a compound of the formula (1) wherein -E-$R^8$— and -E-$R^9$— are each —NH—($R^{25}$) (wherein $R^{25}$ is $C_1$-$C_6$ alkyl).

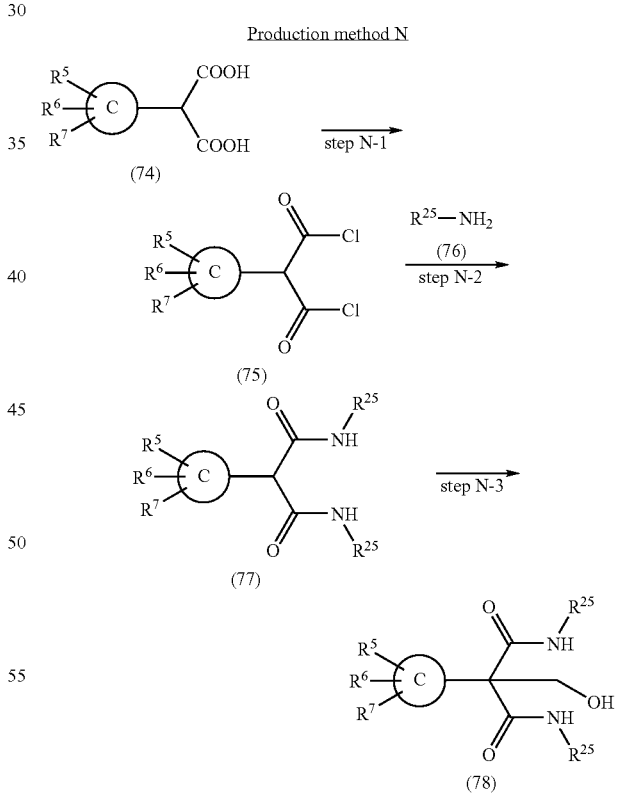

Production method N

In the above reaction scheme, $R^5$, $R^6$, $R^7$, $R^{25}$ and ring C each has the same meaning as defined above.

Step N-1

A compound of the formula (75) can be prepared by reacting a compound of the formula (74) with thionyl chloride or oxalyl chloride in a solvent.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; and esters such as ethyl acetate, methyl acetate, butyl acetate, etc.; and they can be used solely or in combination thereof. A preferred solvent used in the present reaction is toluene containing a catalytic amount of N,N-dimethylformamide.

The reaction temperature is about room temperature to 120° C., preferably about 50° C. to 100° C.

The reaction time is about 10 minutes to 6 hours, preferably about 30 minutes to 3 hours.

Step N-2

A compound of the formula (77) can be prepared by reacting a compound of the formula (75) with a compound of the formula (76) in a solvent in the presence of a base.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; and esters such as ethyl acetate, methyl acetate, butyl acetate, etc.; and they can be used solely or in combination thereof. Preferred solvents in the present reaction are methylene chloride or tetrahydrofuran.

Examples of the bases used in the reaction include organic bases such as triethylamine, pyridine, dimethylaminopyridine, N-methylmorpholine, etc., among which triethylamine is preferred.

The reaction temperature is about −40° C. to 60° C., preferably about −30° C. to room temperature.

The reaction time is about 2 hours to 48 hours, preferably about 6 hours to 24 hours.

Step N-3

A compound of the formula (78) can be prepared by reacting a compound of the formula (77) with paraformaldehyde or formalin without or in a solvent in the presence of a catalytic amount of a base.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; alcohols such as methanol, ethanol, isopropyl alcohol, t-butanol, etc.; esters such as ethyl acetate, methyl acetate, butyl acetate, etc.; and polar solvents such as N,N-dimethylformamide, dimethyl sulfoxide, etc.; and they can be used solely or in combination thereof. A preferred solvent in the present reaction is tetrahydrofuran.

Examples of the bases used in the reaction include alkali metal hydrides such as sodium hydride, potassium hydride, etc.; alkali metal alkoxides such as sodium ethoxide, sodium methoxide, potassium t-butoxide, etc.; alkali metal hydroxides such as sodium hydroxide, potassium hydroxide, lithium hydroxide, etc.; alkali metal carbonates such as sodium carbonate, potassium carbonate, etc.; and organic bases such as triethylamine, diethylamine, pyridine, etc., among which potassium t-butoxide, sodium ethoxide or potassium hydroxide is preferred.

The reaction temperature is about 0° C. to 100° C., preferably about room temperature to 80° C.

The reaction time is about 10 minutes to 24 hours, preferably about 30 minutes to 12 hours.

In accordance with the above Production Method 1, Production Method 1a or Production Method 2, the compounds of the present invention can be prepared using a compound of the formula (78) obtained in the above Step N-3 in place of a compound of the formula (8).

Production Method O

The following is an example of the method for preparing a compound of the formula (1) wherein -E-$R^8$ and -E-$R^9$— are each —O($R^{25}$)(wherein $R^8$ and $R^9$ are each is $C_1$-$C_6$ alkyl).

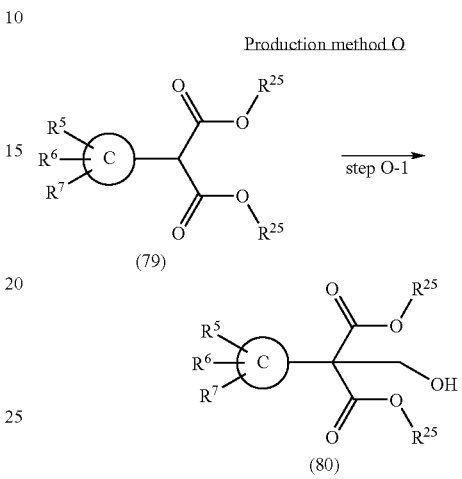

Production method O

In the above reaction scheme, $R^5$, $R^6$, $R^7$, $R^{25}$ and ring C each has the same meaning as defined above.

Step O-1

In a similar manner to Step N-3 of Production Method N, a compound of the formula (80) can be prepared from a compound of the formula (79).

In accordance with the above Production Method 1, Production Method 1a and Production Method 2, the compounds of the present invention can be prepared using a compound of the formula (80) obtained in the above Step O-1 in place of a compound of the formula (8).

Production Method P

The following is an example of the method for preparing a compound of the formula (1) wherein $Alk^2$ is methylene, and m is 2 or 3. In this method, tert-butyldimethylsilyl (TBS) may be used in place of benzyl (Bn).

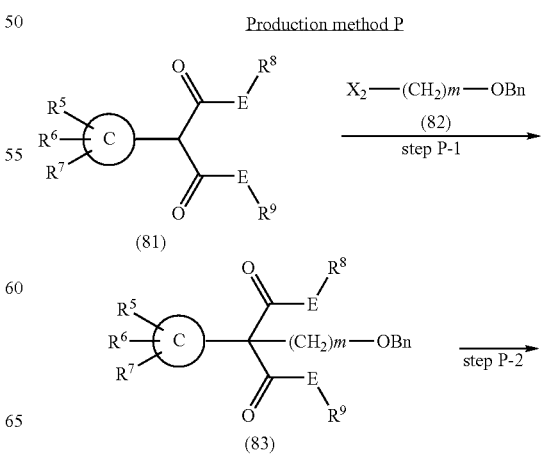

Production method P

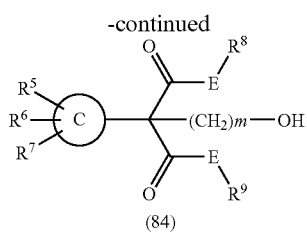

(84)

In the above reaction scheme, $R^5$, $R^6$, $R^7$, $R^8$, $R^9$, E, $X_2$, m, Bn and ring C each has the same meaning as defined above.

Step P-1

A compound of the formula (83) can be prepared by reacting a compound of the formula (81) with a compound of the formula (82) in a solvent in the presence of a base.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; alcohols such as methanol, ethanol, isopropyl alcohol, t-butanol, etc.; esters such as ethyl acetate, methyl acetate, butyl acetate, etc.; and polar solvents such as N,N-dimethylformamide, dimethyl sulfoxide, etc.; and they can be used solely or in combination thereof. Preferred solvents in the present reaction are N,N-dimethylformamide or tetrahydrofuran.

Examples of the bases used in the reaction include alkali metal hydrides such as sodium hydride, potassium hydride, etc.; alkali metal alkoxides such as sodium ethoxide, sodium methoxide, potassium t-butoxide, etc.; alkali metal carbonates such as sodium carbonate, potassium carbonate, etc.; and organoalkali metals such as lithium diisopropylamide, etc., among which sodium hydride or lithium diisopropylamide is preferred.

The reaction temperature is about 0° C. to 100° C., preferably about room temperature to 80° C.

The reaction time is about 30 minutes to 48 hours, preferably about 2 hours to 24 hours.

Step P-2

In a similar manner to Step 2-2 of Production Method 2, a compound of the formula (84) can be prepared from a compound of the formula (83).

In accordance with the above Production Method 1, Production Method 1a and Production Method 2, the compounds of the present invention can be prepared using a compound of the formula (84) obtained in the above Step P-2 in place of a compound of the formula (8).

Production Method 3

The following is an example of the method for preparing a compound of the formula (1) wherein X is —CONH—$(CH_2)_n$— and Y is —O—CO—C— or —O—CO—.

Production method 3

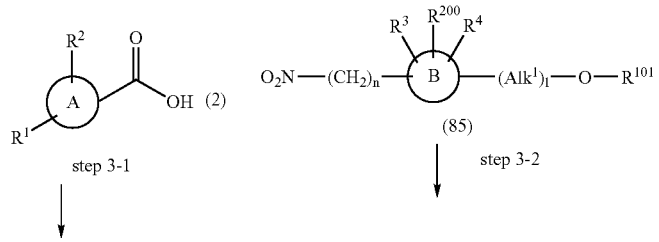

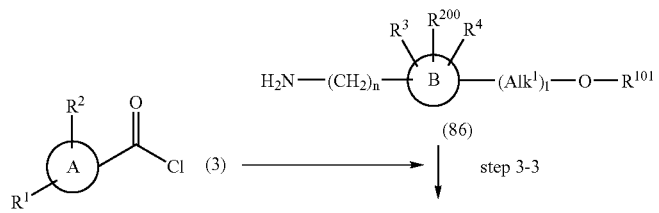

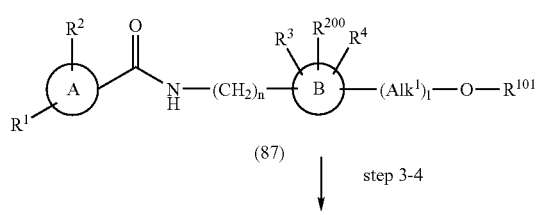

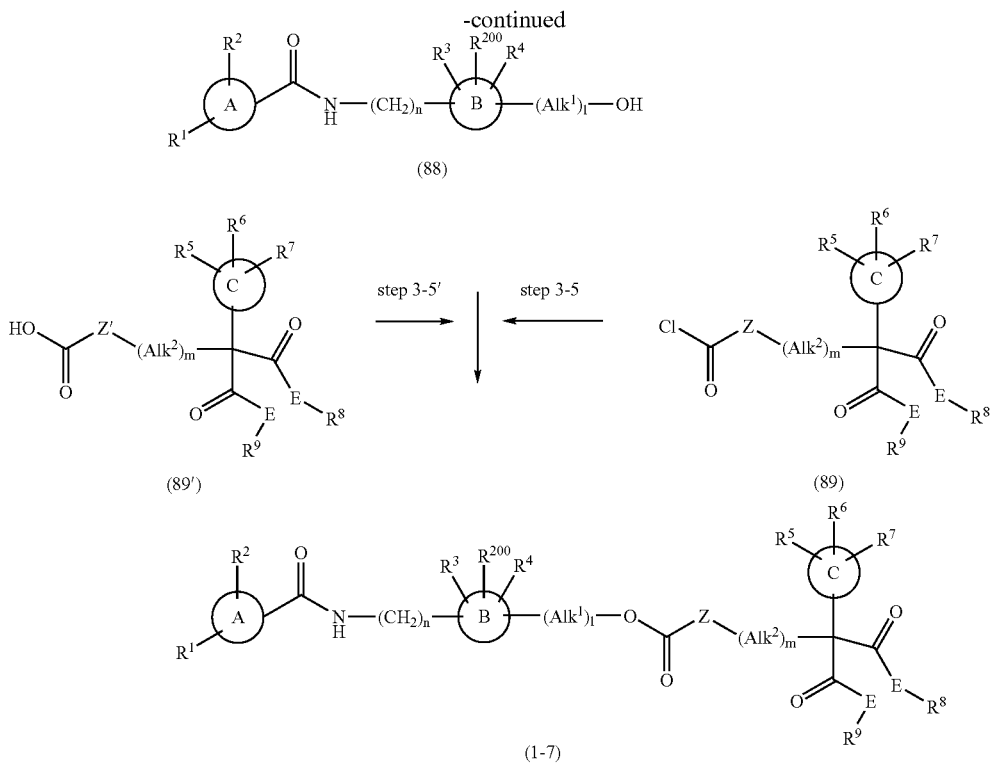

In the above reaction scheme, $R^1$, $R^2$, $R^3$, $R^4$, $R^5$, $R^6$, $R^7$, $R^8$, $R^9$, $R^{200}$, l, m, n, $Alk^1$, $Alk^2$, E, ring A, ring B, and ring C each has the same meaning as defined above; $R^{101}$ is $C_1$-$C_6$ alkyl or benzyl; Z is —$CH_2$— or —O—; and Z' is —$CR_2$—.

Step 3-1

In a similar manner to Step 1-1, an acid chloride compound of the formula (3) can be prepared from a carboxylic acid compound of the formula (2).

Step 3-2

A compound of the formula (86) can be prepared by reducing a compound of the formula (85) with a reducing agent in a solvent.

The solvent used in the reaction includes, for example, alcohols such as methanol, ethanol, isopropyl alcohol, etc., and acetic acid; and they can be used solely or in combination thereof. If necessary, acetic acid or hydrochloric acid may be used in combination with said solvents. A preferred solvent in the present reaction is ethanol.

The reducing agent used in the reaction includes, for example, iron dust and tin chloride, among which zinc dust is preferred.

The reaction temperature is about 0° C. to 200° C., preferably room temperature to 120° C.

Step 3-3

In a similar manner to Step 1-3, a compound of the formula (87) can be prepared by reacting a compound of the formula (86) with a compound of the formula (3).

Step 3-4

In a similar manner to Step 1-4 or by catalytic reduction, a compound of the formula) can be prepared from a compound of the formula (85). The catalytic reduction can be carried out according to the conventional method, for example, by hydrogenating a compound of the formula (87) in the presence of a catalyst such as palladium black, palladium hydroxide, Raney Ni, platinum oxide, etc, preferably palladium carbon.

The solvent used in the reaction includes, for example, ethers such as diethyl ether, tetrahydrofuran, dioxane, 1,2-dimethoxyethane, diglyme, etc.; alcohols such as methanol, ethanol, isopropyl alcohol, t-butanol, etc.; and esters such as ethyl acetate, methyl acetate, butyl acetate, etc.; and they can be used solely or in combination thereof. Preferred solvents in the present reaction are alcohols such as methanol, ethanol, isopropyl alcohol, t-butanol, etc., and a mixed solvent of said alcohol solvent and tetrahydrofuran and/or water.

The reaction temperature is about 0° C. to 120° C., preferably room temperature to 100° C.

The reaction time is about 30 minutes to 8 days, preferably about 1 hour to 96 hours.

Step 3-5

This step is a general condensation method between alcohols and acid chlorides. A compound of the formula (1-7) which is one of the objective compounds can be prepared by condensing an alcohol compound of the formula (88) with an acid chloride compound of the formula (89) in a solvent in the presence of a base.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; and esters such as ethyl acetate, methyl acetate, butyl acetate, etc.; and they can be used solely or in combination thereof. Preferred solvents in the present reaction are tetrahydrofuran and methylene chloride.

The base used in the reaction includes, for example, organic bases such as triethylamine, pyridine, dimethylaminopyridine, N-methylmorpholine, etc.

The reaction temperature is about 0° C. to 80° C., preferably 0° C. to room temperature 100° C.

In addition, the compound of the formula (85) can be easily prepared by the conventional method or the method known per se. The compound of the formula (89) can be prepared by Production Methods Q, R, and S hereinafter described.

Step 3-5'

This step is a general condensation reaction between alcohols and carboxylic acids. A compound of the formula (1-7) wherein Z is —CH$_2$—, which is one of the objective compounds, can be prepared by condensing a compound of the formula (88) with a compound of the formula (89') in a solvent in the presence of a condensing agent.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; and esters such as ethyl acetate, methyl acetate, butyl acetate, etc.; and they can be used solely or in combination thereof. A preferred solvent in the present reaction is acetone.

The condensing agent used in the reaction includes WSC, DCC, etc, among which WSC is preferred.

The reaction temperature is about 0° C. to 80° C., preferably about 0° C. to room temperature.

Production Method 4

The following is an example of the method for preparing a compound of the formula (1) wherein X is —CONH—(CH$_2$)$_n$— and Y is —O—C(R$^{110'}$) (R$^{111'}$)—CO—O- (wherein R$^{110'}$ and R$^{111'}$ are each hydrogen).

Production method 4

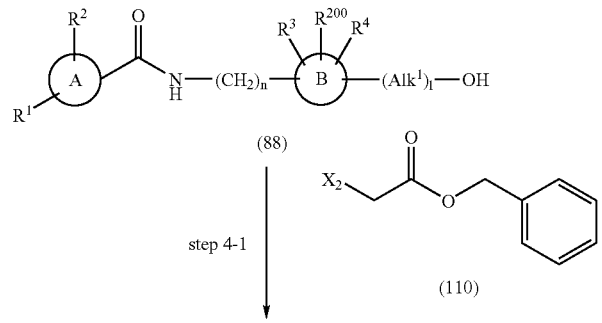

(88)

(110)

step 4-1

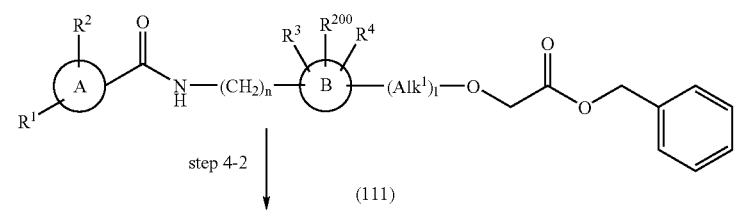

(111)

step 4-2

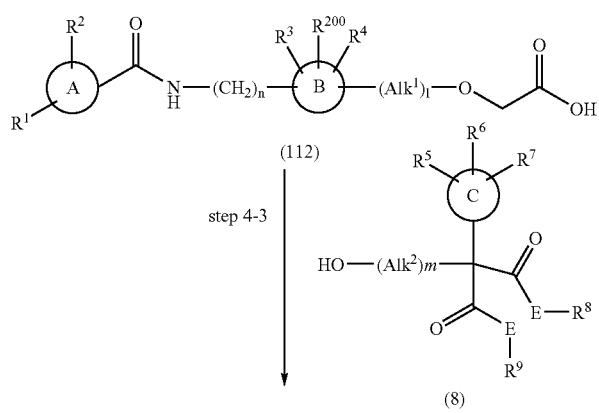

(112)

step 4-3

(8)

-continued

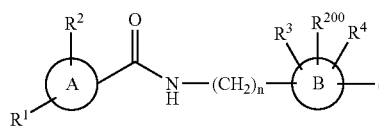

(1-8)

In the above reaction scheme, $R^1$, $R^2$, $R^3$, $R^4$, $R^5$, $R^6$, $R^7$, $R^8$, $R^9$, $R^{200}$, $X_2$, $Alk^1$, $Alk^2$, m, n, E, ring A, ring B, and ring C each has the same meaning as defined above.

Step 4-1

A compound of the formula (111) can be prepared by reacting a compound of the formula (88) obtained in the Step 3-4 with a compound of the formula (110) in a solvent in the presence of a base.

The solvent used in the reaction includes, for example, ethers such as diethyl ether, tetrahydrofuran, dioxane, 1,2-dimethoxyethane, diglyme, etc.; and water; etc.; and they can be used solely or in combination thereof. A preferred solvent in the present reaction is tetrahydrofuran.

Examples of the bases used in the reaction include alkali metal carbonates such as sodium carbonate, potassium carbonate, etc.; and alkali metal hydroxides such as lithium hydroxide, sodium hydroxide, potassium hydroxide, etc., and sodium hydride is preferred.

The reaction temperature is about 0° C. to 120° C., preferably 0° C. to 100° C.

The reaction time is about 1 to 24 hours, preferably about 2 to 12 hours.

In addition, the reaction smoothly proceeds using a reaction aid such as tetrabutyl ammonium iodide, etc.

Step 4-2

In a similar manner to Step 3-4, a compound of the formula (112) can be prepared from a compound of the formula (111).

Step 4-3

In a similar manner to Step 3-5', a compound of the formula (1-8) which is one of the objective compounds can be prepared by reacting a compound of the formula (112) with a compound of the formula (8).

Production method Q

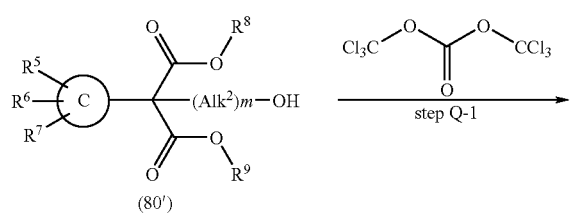

(80')

-continued

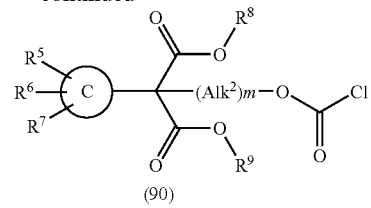

(90)

In the above reaction scheme, $R^5$, $R^6$, $R^7$, $R^8$, $R^9$, $Alk^2$, m and ring C each has the same meaning as defined above.

Step Q-1

A compound of the formula (90) can be prepared by reacting a compound of the formula (80') with triphosgene in a solvent such as toluene, methylene chloride, etc.

Production Method R

Production method R

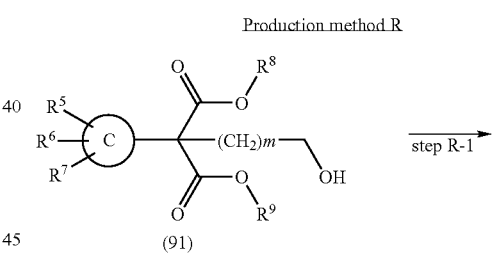

(91)

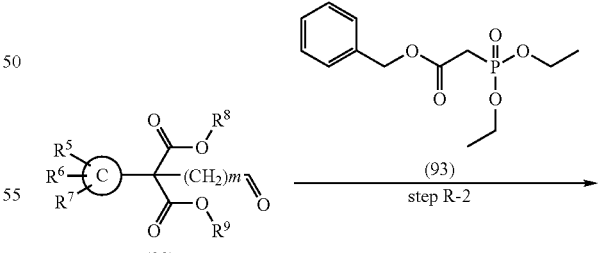

(92)

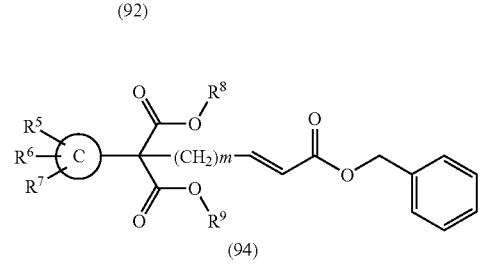

(94)

-continued

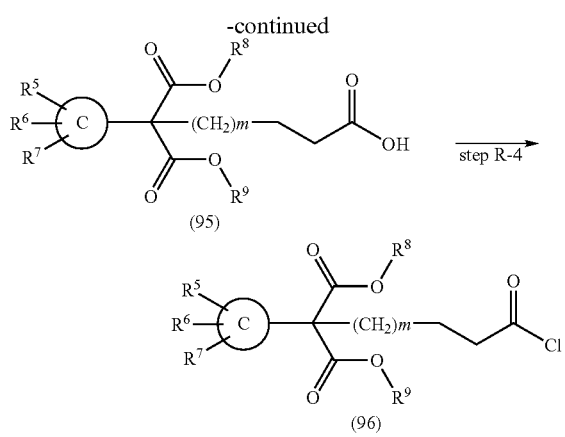

In the above reaction scheme, $R^5$, $R^6$, $R^7$, $R^8$, $R^9$, m and ring C each has the same meaning as defined above.

Step R-1

A compound of the formula (92) can be prepared by treating a compound of the formula (91) with an oxidizing reagent in a solvent.

The solvent used in the reaction includes, for example, ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; esters such as ethyl acetate, methyl acetate, butyl acetate, etc.; and polar solvents such as acetonitrile, N,N-dimethylformamide, dimethyl sulfoxide, etc., and they can be used solely or in combination thereof. A preferred solvent in the present reaction is acetonitrile.

The oxidizing reagent used in the reaction includes, for example, Dess-Martin reagent, etc.

Step R-2

A compound of the formula (94) can be prepared by reacting a compound of the formula (92) with a Horner-Emmons reagent (e.g. a compound of the formula (93)) in a solvent in the presence of a base.

The solvent used in the reaction includes, for example, ethers such as diethyl ether, tetrahydrofuran, dioxane, 1,2-dimethoxyethane, diglyme, etc.; alcohols such as methanol, ethanol, isopropyl alcohol, t-butanol, etc.; hydrocarbons such as benzene, toluene, hexane, xylene, etc.; and polar solvents such as acetonitrile, N,N-dimethylformamide, dimethyl sulfoxide, etc. and they can be used solely or in combination thereof. A preferred solvent in the present reaction is N,N-dimethylformamide.

Examples of the bases used in the reaction include alkali metal hydrides such as sodium hydride, potassium hydride, etc.; and alkali metal alkoxides such as sodium ethoxide, sodium methoxide, potassium t-butoxide, etc., among which sodium hydride is preferred.

Step R-3

This step is a general hydrogenation reaction permitting simultaneous debenzylation. For example, a compound of the formula (95) can be prepared by hydrogenation of a compound of the formula (94) in a solvent in the presence of a catalyst.

The solvent used in the reaction includes, for example, ethers such as diethyl ether, tetrahydrofuran, dioxane, 1,2-dimethoxyethane, diglyme, etc.; alcohols such as methanol, ethanol, isopropyl alcohol, t-butanol, etc.; and esters such as ethyl acetate, methyl acetate, butyl acetate, etc., and they can be used solely or in combination thereof. A preferred solvent in the present reaction is tetrahydofuran.

The catalyst used in the reaction includes, for example, palladium carbon, palladium hydroxide, Raney Ni, platinum oxide, etc., among which palladium carbon is preferred.

Step R-4

This step is a general conversion method of carboxylic acids into acid chlorides. A compound of the formula (96) can be prepared by reacting a compound of the formula (95) with a chlorinating agent in a solvent.

The solvent used in the reaction includes, for example, ethers such as diethyl ether, tetrahydrofuran, dioxane, 1,2-dimethoxyethane, diglyme, etc.; hydrocarbons such as benzene, toluene, etc.; halogenated hydrocarbons such as methylene chloride, chloroform, carbon tetrachloride, 1,2-dichloroethane, etc.; and esters such as ethyl acetate, methylacetate, butyl acetate, etc., and they can be used solely or in combination thereof. A preferred solvent in the present reaction is toluene.

The chlorinating agent used in the reaction includes, for example, thionyl chloride, oxalyl chloride, phosphorus pentachloride, etc., among which thionyl chloride is preferred.

Production Method S

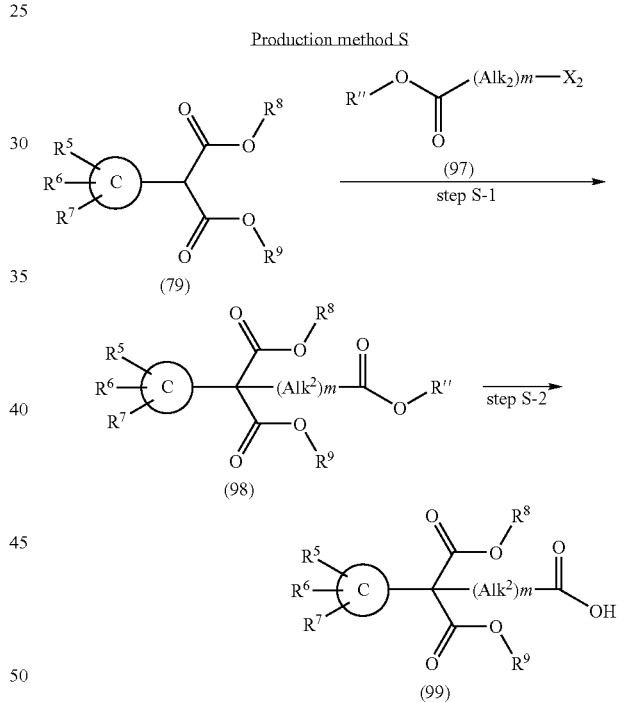

In the above reaction scheme, R" is $C_1$-$C_6$ alkyl, and $R^5$, $R^6$, $R^7$, $R^8$, $R^9$, $Alk^2$, m, $X_2$ and ring C each has the same meaning as defined above.

Step S-1

In a similar manner to Step P-1 of Production Method P, a compound of the formula (98) can be prepared by reacting a compound of the formula (79) with a compound of the formula (97).

Step S-2

In a similar manner to Step 1-4 of Production Method 1, a compound of the formula (99) can be prepared from a compound of the formula (98).

According to the above Production method, the compounds of the formula (1) can be prepared. Further, the compounds of the present invention when Y is —CO—O—C(R$^{110}$)—(R$^{111}$)—O—CO—, —CO—O—C(R$^{110}$) (R$^{111}$)—O—CO—O or —O—CO—O—C(R$^{110}$) (R$^{111}$)—O—CO— can be prepared according to the above Production Methods 1 to 3, and the known production methods.

Production Method T

The following is an example of the method for preparing a compound of the formula (1) wherein Y is —O—C(R$^{110}$)(R$^{111}$)—C(R$^{110}$)(R$^{111}$)—.

Production method T

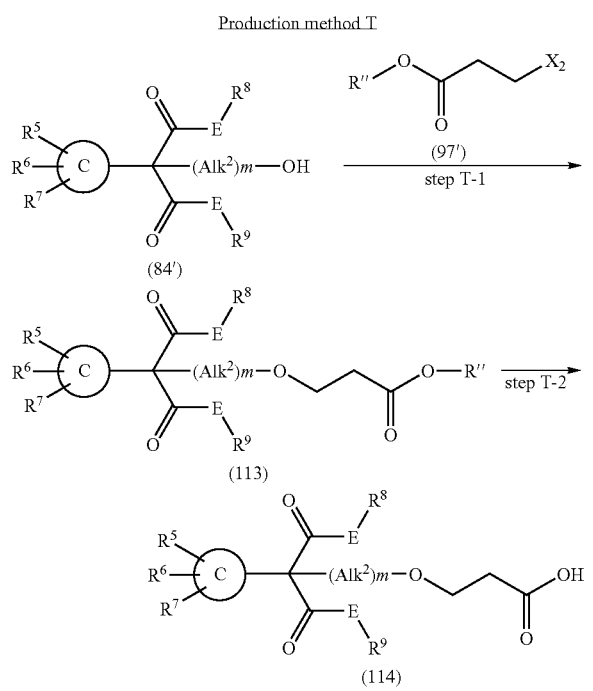

In the above reaction scheme, R'', R$^5$, R$^6$, R$^7$, R$^8$, R$^9$, Alk$^2$, X$_2$, m, E and ring C each has the same meaning as defined above.

Step T-1

A compound of the formula (113) can be prepared by reacting a compound of the formula (84') with a compound of the formula (97') in a solvent in the presence of a base. The solvent used in the reaction includes, for example, ethers such as diethyl ether, tetrahydrofuran, dioxane, 1,2-dimethoxyethane, diglyme, etc., and they can be used solely or in combination thereof. A preferred solvent in the present reaction is tetrahydrofuran.

Examples of the bases used in the reaction include alkali metal carbonates such as sodium carbonate, potassium carbonates, etc., or alkali metal hydroxides such as lithium hydroxide, sodium hydroxides, potassium hydroxide, etc., and sodium hydride is preferred.

The reaction temperature is about 0° C. to 120° C., preferably 0° C. to 60° C.

The reaction time is about 1 to 24 hours, preferably about 2 to 12 hours.

The reaction smoothly proceeds using a reaction aid such as tetrabutyl ammonium iodide, etc.

Step T-2

In a similar manner to Step 1-4, a compound of the formula (114) can be prepared from a compound of the formula (113).

The biphenyl compounds of the formula (100) or salts thereof are new.

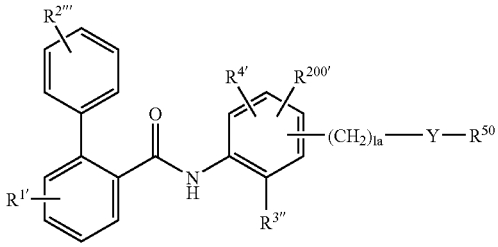

In the above formula, R$^{1'}$ is hydrogen; C$_1$-C$_6$ alkyl; halogen; halo-C$_1$-C$_6$ alkyl; C$_1$-C$_6$ alkoxy; or —(CH$^2$)$_r$—O—CO—R$^{100}$ (wherein R$^{100}$ is C$_1$-C$_6$ alkyl, C$_1$-C$_6$ alkoxy, or C$_2$-C$_{12}$ alkoxyalkyl, and r is 0 or an integer of 1 to 3);

R$^{2'''}$ is hydrogen; C$_1$-C$_6$ alkyl; halogen; halo-C$_1$-C$_6$ alkyl; or C$_2$-C$_6$ alkenyl; R$^{3''}$ is —CON(R$^{11a}$) (R$^{12a}$) wherein R$^{11a}$ and R$^{12a}$ are each independently hydrogen; C$_1$-C$_6$ alkyl, optionally substituted C$_6$-C$_{14}$ aryl; optionally substituted C$_7$-C$_{16}$ aralkyl; or C$_1$-C$_6$ alkoxy, or R$^{11a}$ and R$^{12a}$ may be taken together with the adjacent nitrogen atom to which they are attached to form

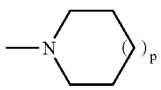

wherein p is 0 or an integer of 1 to 2; or —(CH$_2$)$_{r'}$—O—CO$_7$R$^{100'}$ wherein R$^{100'}$ is C$_1$-C$_6$ alkyl, C$_1$-C$_6$ alkoxy, or C$_2$-C$_{12}$ alkoxyalkyl, and r' is 0 or an integer of 1 to 3;

R$^{4'}$ and R$^{200'}$ are each independently hydrogen, halogen, C$_1$-C$_6$ alkyl, or halo-C$_1$-C$_6$ alkyl;

R$^{50}$ is hydrogen, C$_1$-C$_6$ alkyl, optionally substituted C$_6$-C$_{14}$ aryl, or optionally substituted C$_7$-C$_{16}$ aralkyl;

Y is —O—CO—O—, —O—CO—, —CO—O—, —CO—O—C(R$^{110}$) (R$^{111}$)—O—CO—, —CO—O—C(R$^{110}$) (R$^{111}$)—O—CO—O—, —O—CO—O—C(R$^{110}$) (R$^{111}$)—O—CO—, —O—CO—C(R$^{110}$) (R$^{111}$)—O—, —O—CO—C(R$^{110}$) (R$^{111}$)—C(R$^{110}$) (R$^{111}$)—O—, or —O—C(R$^{110}$)(R$^{111}$)—CO—O— wherein R$^{110}$ and R$^{111}$ are each independently hydrogen or C$_1$-C$_6$ alkyl, provided that when Y is —CO—O—, then R$^{3''}$ is —(CH$_2$)$_{r'}$—O—CO—R$^{100'}$ wherein R$^{100'}$ and r' are each has the same meaning as defined above; and la is an integer of 1 to 3.

EXAMPLES

The present invention is illustrated in detail by the following Examples and Reference Examples, but it is to be understood that the present invention is not limited thereto. In the Examples and Reference Examples, Me is methyl, Et is ethyl, tBu is tbutyl, and TBS is tert-butyldimethylsilyl.

Reference Example 1 a) Phenylmalonic Acid Dichloride

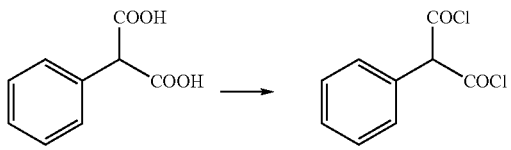

Thionyl chloride (13.7 mL) was added dropwise to a mixture of phenylmalonic acid dichloride (11.31 g) and N,N-dimethylformamide (230 μL) under ice-cooling, The mixture was stirred at 80° C. for 70 minutes, and concentrated in vacuo. The residue was evaporated azeotropically together with toluene, and dried in vacuo to give the title compound (11.61 g).

b) Phenylmalonic Acid Diethylamide

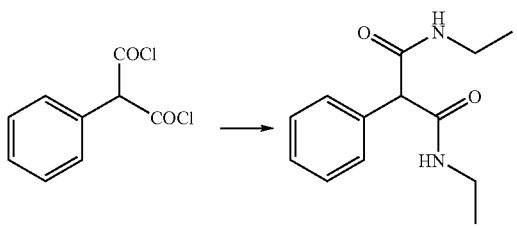

The phenylmalonic acid dichloride (8.99 g) obtained in Reference Example 1a) was added dropwise to a mixture of ethylamine/tetrahydrofuran (2M, 45.5 mL), triethylamine (13.9 mL) and methylene chloride (80 mL) at −20° C. The reaction temperature was elevated to room temperature, and the mixture was stirred overnight. After addition of 3N hydrochloric acid, the reaction solution was diluted with ethyl acetate, and the organic phase was washed successively with saturated brine, saturated aqueous sodium bicarbonate solution, and saturated brine, dried over sodium sulfate, and then concentrated to give a solid. The solid was washed with ethyl acetate-hexane to give the title compound (4.85 g) as a white powder.

c) 2-Hydroxymethyl-2-phenylmalonic acid diethylamide

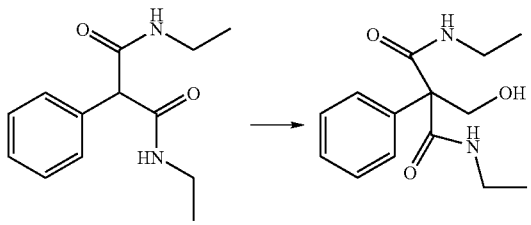

Phenylmalonic acid diethylamide (2.34 g) obtained in Reference Example 1 b) and paraformamide (390 mg) were suspended in tetrahydrofuran (20 mL), and to this suspension was added potassium hydroxide (catalytic amount). After stirring for 5 hours, the reaction solution was concentrated to remove the solvent, and the residue was chromatographed on silica gel (ethyl acetate:hexane=1:1) to give the title compound (2.31 g).

d) 4'-Trifluoromethylbiphenyl-2-carboxylic acid chloride

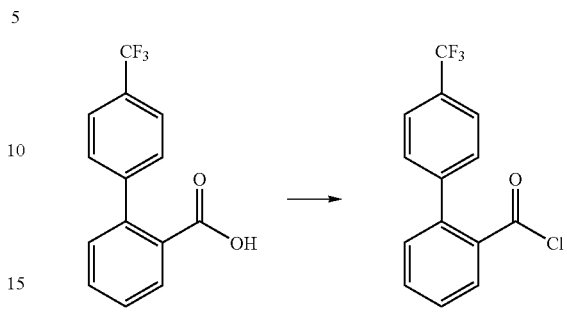

Oxalyl chloride (2.43 mL) was added dropwise to a mixture of 4'-trifluoromethylbiphenyl-2-carboxylic acid (5.06 g), dimethylformamide (catakytic amount) and methylene chloride (30 mL) under ice-cooling. The reaction mixture was stirred at room temperature for 100 minutes, and concentrated to remove the solvent. The residue was evaporated azeotropically together with toluene, and dried in vacuo to give the title compound (5.40 g).

Reference Example 1-2 a) Diethyl 2-hydroxymethyl-2-phenylmalonate

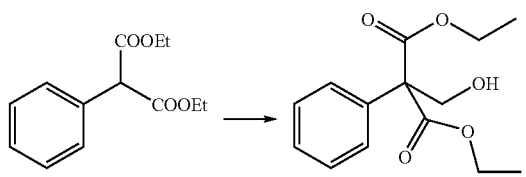

Paraformaldehyde (720 mg) was suspended in diethyl phenylmalonate (4.73 g), and potassium hydroxide (catalytic amount) was added thereto at 60° C. After stirring for 1.5 hours, the reaction solution was purified by chromatograophy on silica gel (ethyl acetate:hexane=1:5 to 1:2) to give the title compound (4.96 g).

Reference Example 1-3 a) Diethyl 2-(3-methyl-4-nitrophenyl)malonate

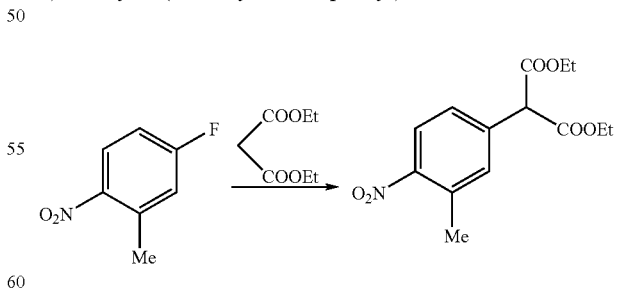

Sodium hydride (60% in mineral oil; 0.599 g) was suspended in dimethylformamide (10 mL), and to this was added dropwise a solution of diethyl malonate (2.00 g) in dimethylformamide (10 mL) under ice-cooling. After the foam generation was finished, a solution of 4-fluoro-2-methylnitrobenzene (1.94 g) in dimethylformamide (5 mL)

was added thereto. The reaction temperature was raised to 100° C., the mixture was stirred for 6 hours. The resulting reaction mixture was concentrated, acidified with 1N hydrochloric acid, and extracted with ethyl acetate. The extract was washed successively with water and saturated brine, dried over sodium sulfate, concentrated, and purified by column chromatography on silica gel (ethyl acetate:hexane=1:5) to give the title compound (1.65 g) as a yellow oil.

Reference Example 2 a) Methyl 3-ethoxy-4-nitrobenzoate

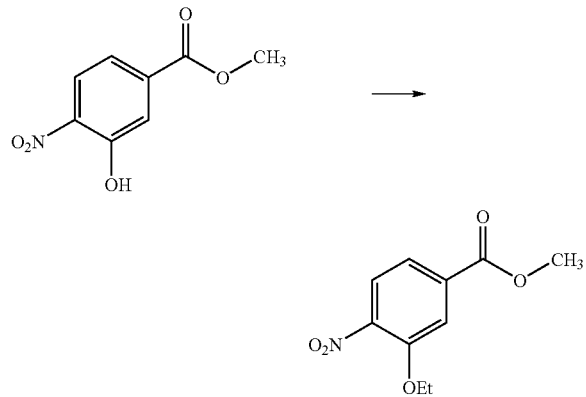

To a suspension of sodium hydride (60% in mineral oil; 1.20 g) in dimethylformamide (50 mL) was added methyl 3-hydroxy-4-nitrobenzoate (4.93 g) under ice-cooling, and the mixture was stirred for 30 minutes at room temperature. After addition of ethyl iodide (4.4 mL), the mixture was stirred at 60° C. overnight. The reaction solution was cooled down to room temperature, poured into saturated aqueous ammonium chloride solution, and extracted with ethyl acetate-tetrahydrofuran. The extract was washed with saturated aqueous ammonium chloride solution and saturated brine, dried over sodium sulfate, and concentrated to yield a solid. The solid was washed with ethyl acetate-hexane to give methyl 3-ethoxy-4-nitrobenzoate (3.30 g) as a pale yellow solid.

b) 3-Ethoxy-4-nitrobenzoyl chloride

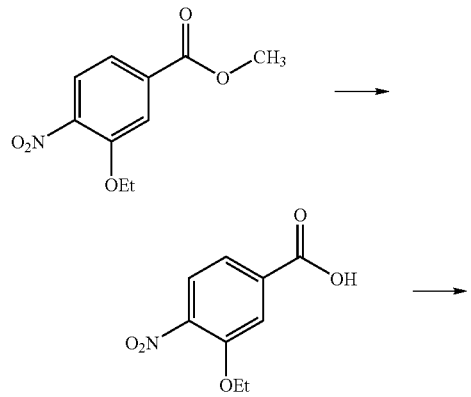

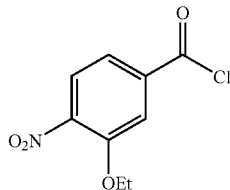

3-Ethoxy-4-nitrobenzoyl chloride was obtained from the methyl 3-ethoxy-4-nitrobenzoate obtained in Reference Example 2a) by the conventional method.

c) 2'-Diazo-3-ethoxy-4-nitroacetophenone

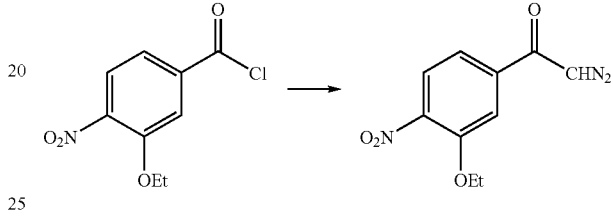

To a mixed solution of a solution of diazomethane in diethyl ether (0.35 M, 64 ml) and triethylamine (3.12 mL) was added dropwise a diethyl ether solution (30 mL) of 3-ethoxy-4-nitrobenzoyl chloride (2.06 g) obtained in Reference Example 2 b), under ice-cooling. The mixture was stirred for 2 hours under ice-cooling, and after the reaction temperature was raised to room temperature, the mixture was stirred overnight. After addition of acetic acid (1 mL), the reaction solution was stirred at room temperature for one hour, concentrated in vacuo to remove the solvent, and purified by column chromatography on silica gel (hexane:ethyl acetate=5:2) to give the title compound (1.80 g) as a yellow solid.

d) Ethyl 3-ethoxy-4-nitrophenylacetate

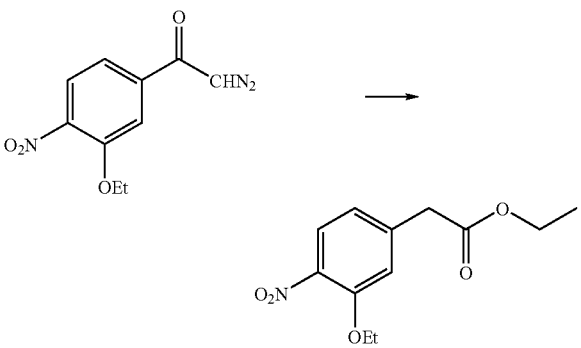

To a solution of 2'-diazo-3-ethoxy-4-nitroacetophenone (1.80 g) in ethanol (25 mL) obtained in Reference Example 2 c) was added dropwsie (10 times portionwise) a solution of silver benzoate (270 mg) in triethylamine (2.7 mL) under heating at reflux.

The mixture was refluxed for 9 hours, and the reaction solution was filtered through a Celite pad and the filtrate was concentrated. The concentrate was diluted with diethyl ether, washed successively with 10% aqueous sodium carbonate solution, water, and saturated brine, drived over sodium sulfate, and purified by column chromatography on silica gel (hexane:ethyl acetate=4:1) to give the title compound (1.27 g) as a yellow solid.

e) Ethyl 4-amino-3-ethoxyphenylacetate

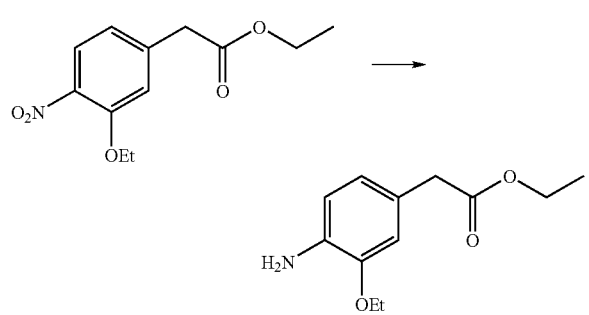

Methyl 3-ethoxy-4-nitroacetate (1.27 g) obtained in Reference Example 2 d) was subjected to the same reaction as in Example 2 c) to give the title compound (1.12 g) as a brown oil.

f) 2-(2-{3-Ethoxy-4-[(4'-trifluoromethylbiphenyl-2-carbonyl)amino]phenyl}acetoxymethyl)-2-phenylmalonic acid diethyl ester

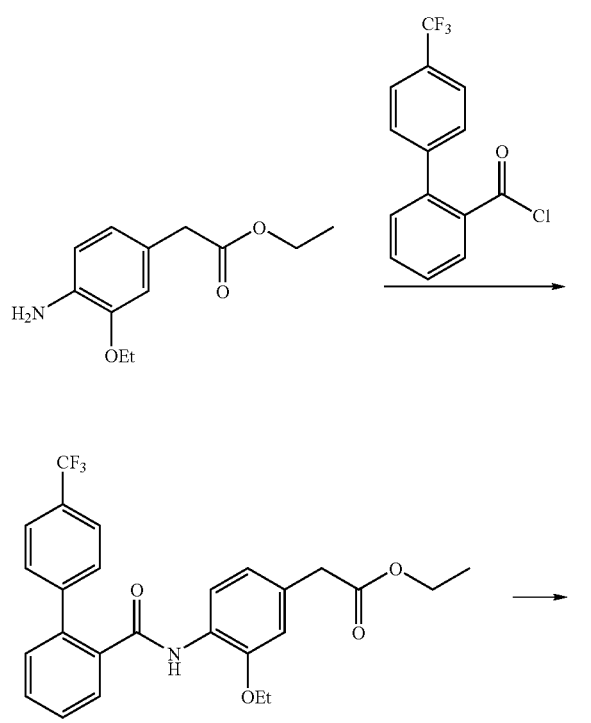

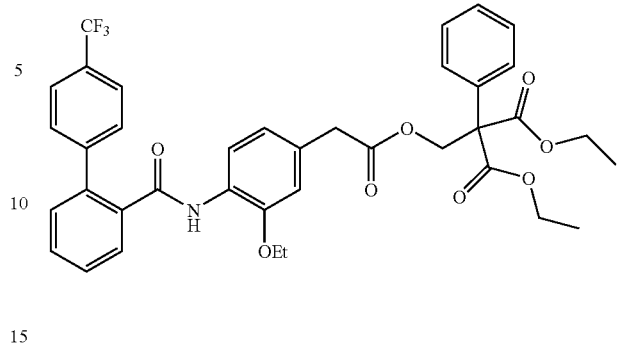

Ethyl 4-amino-3-ethoxyphenylacetate obtained in Reference Example 2e) was subjected to the above reaction to give the title compound (0.159 g).

Reference Example 2-2

{3-Benzyloxy-4-[(4'-trifluoromethylbiphenyl-2-carbonyl)amino]phenyl}acetic acid 2,2-bisethylcarbamoyl-2-phenylethyl ester The title copmpound (see Table 1) was obtained similarly as in Reference Example 2, provided that the nitro group was reduced with iron powder.

Reference Example 2-3

{3-Hydroxy-4-[(4'-trifluoromethylbiphenyl-2-carbonyl)amino]phenyl}acetic acid 2,2-bisethylcarbamoyl-2-phenylethyl ester

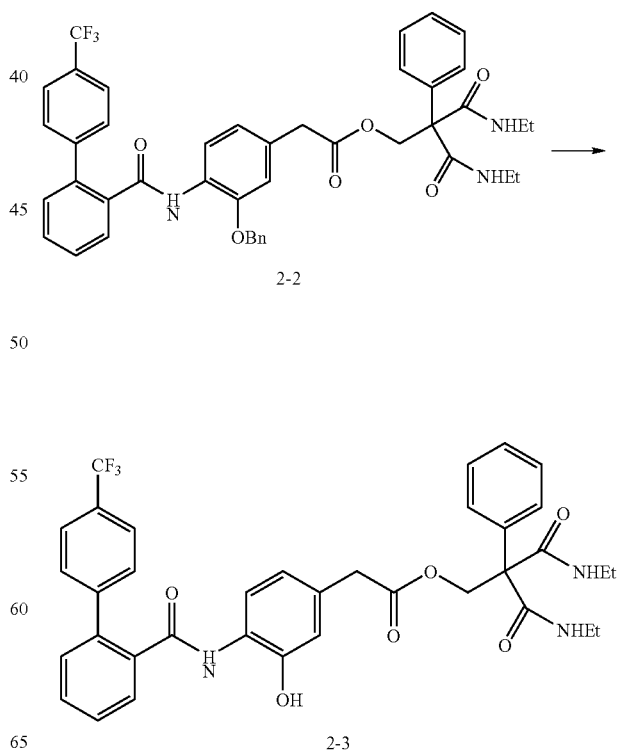

{3-Benzyloxy-4-[(4'-trifluoromethylbiphenyl-2-carbonyl)amino]phenyl}acetic acid 2,2-bisethylcarbamoyl-2-phenyl ethyl ester (300 mg) obtained in Reference Example 2-2 (provided that the nitro group was reduced using zinc dust) was treated in a similar manner to Example 1 a) to give the title compound (244 mg)(see Table 1).

Reference Examples 2-4 to 2-7

Compounds of Reference Examples 2-4 to 2-7 were obtained in a similar manner to Reference Examples 2 to 2-3. The compounds obtained were shown in Tables 1 to 2.

TABLE 1

| Reference Example | Structure | NMR (δ, 300MHz, CDCl$_3$) |
|---|---|---|
| 2 | 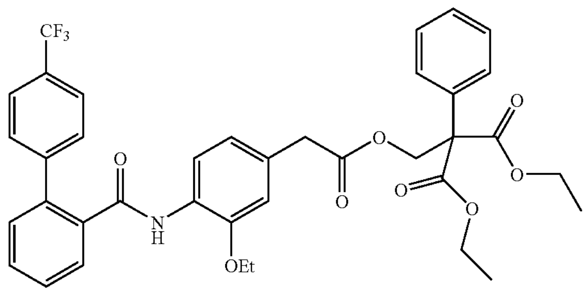 | — |
| 2-2 | 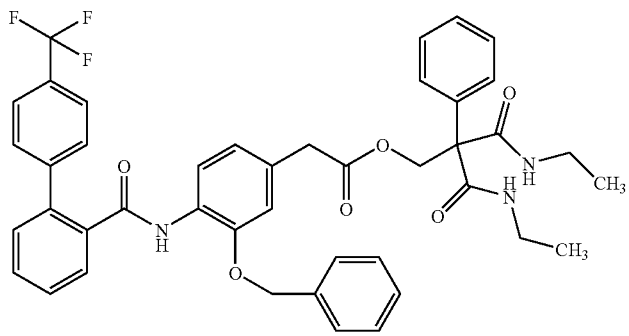 | 1.04 (6H, t, J=7.2Hz), 3.23 (4H, dq, J=7.2, 7.2Hz), 3.52 (2H, s), 4.82-4.86 (4H, m), 6.70-7.79 (16H, m), 7.71 (1H, br.s), 7.78 (1H, dd, J=7.1, 1.9Hz), 8.40 (1H, d, J=8.3Hz) |
| 2-3 | 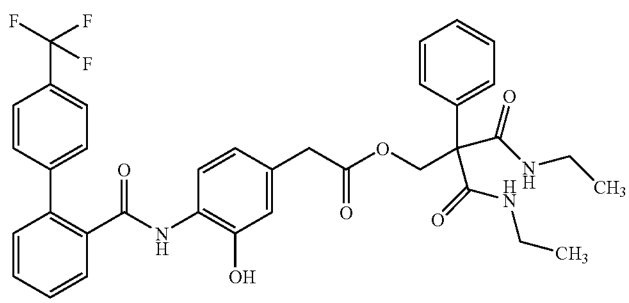 | 1.05 (6H, t, J=7.2Hz), 3.23 (4H, dq, J=7.2, 7.2Hz), 3.48 (2H, s), 4.83 (2H, s), 6.48 (1H, d, J=7.9Hz), 6.55 (1H, dd, J=7.9, 1.9Hz), 6.77 (1H, d, J=1.5Hz), 7.17-7.86 (15H, m), 8.58 (1H, s) |
| 2-4 | 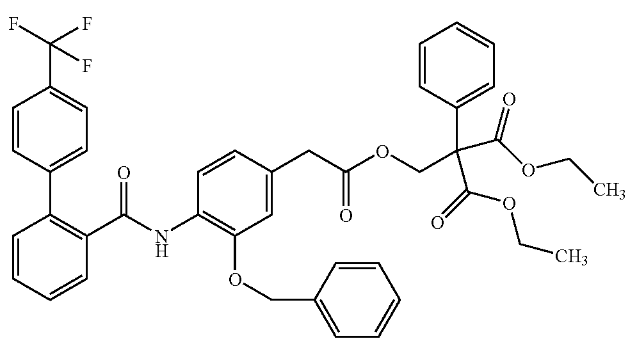 | 1.19 (6H, t, J=7.1Hz), 3.49 (2H, s), 4.17 (4H, q, J=7.1Hz), 4.78 (2H, s), 4.83 (2H, s), 6.70 (1H, d, J=1.9Hz), 6.78 (1H, dd, J=8.3, 1.5Hz), 7.21-7.57 (12H, m), 7.70 (1H, br.s), 7.77 (1H, dd, J=7.2, 1.9Hz), 8.38 (1H, d, J=8.3Hz) |

TABLE 1-continued

| Reference Example | Structure | NMR (δ, 300MHz, CDCl₃) |
|---|---|---|
| 2-5 | 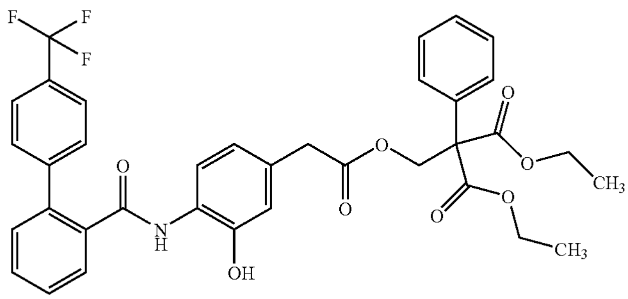 | 1.20 (6H, t, J=7.2Hz), 3.47 (2H, s), 4.19 (4H, q, J=7.2Hz), 4.82 (2H, s), 6.29 (1H, d, J=7.9Hz), 6.57 (1H, dd, J=7.9, 1.9Hz), 6.79 (1H, d, J=1.9Hz), 7.18 (1H, br.s), 7.28-7.74 (11H, m), 7.86 (1H, dd, J=7.9, 1.5Hz), 8.39 (1H, s) |

TABLE 2

| Reference Example | Structure | NMR (δ, 300MHz, CDCl₃) |
|---|---|---|
| 2-6 | mp 123.5-125.5 | 1.21 (6H, t, J=7.2Hz), 3.61 (2H, s), 4.21 (4H, q, J=7.2Hz), 4.85 (2H, s), 6.73 (1H, d, J=7.5Hz), 6.85 (1H, d, J=7.5Hz), 6.91 (1H, d, J=7.5Hz), 7.29 (5H, s), 7.42-7.64 (6H, m), 7.69 (2H, d, J=7.9Hz), 7.81-7.87 (1H, m), 8.54 (1H, brs). |
| 2-7 | 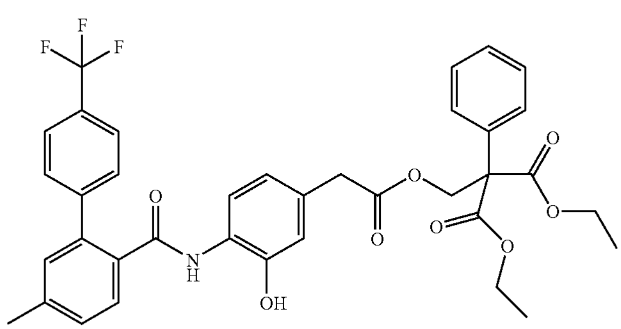 | 1.20 (6H, t, J=7.2Hz), 2.47 (3H, s), 3.46 (2H, s), 4.19 (4H, q, J=7.2Hz), 4.81 (2H, s), 6.22 (1H, d, J=7.9Hz), 6.56 (1H, dd, J=1.5Hz, J=7.9Hz), 6.78 (1H, d, J=1.5Hz), 7.11 (1H, brs), 7.22-7.40 (7H, m), 7.58 (2H, d, J=7.9Hz), 7.73 (2H, d, J=7.9Hz), 7.78 (1H, d, J=7.9Hz), 8.54 (1H, brs). |

Reference Example 3 a) 2-(3-Bromo-4-nitrophenyl)malonic acid tert-butyl ester methyl ester

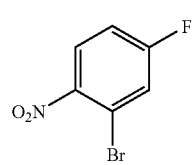 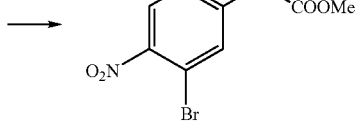

Sodium hydride (60% in mineral oil; 0.985 g) is suspended in N,N-dimehylforamamide (20 mL), and to this suspension was added dropwise a solution of tert-butyl methyl malonic acid ester (4.29 g) in N,N-dimethylformamide (5 mL) under ice-cooling. After completion of the foam generation, a solution of 2-bromo-4-fluoro-1-nitrobenzene (2.71 g) in N,N-dimethylformamide (5 mL) was dropwise added thereto at the same temperature, and the mixture was stirred at 60° C. for 3 hours. The reaction mixture was concentrated, neutralized with 1N hydrochloric acid, and extracted with ethyl acetate. The extract was washed with saturated brine, dried over sodium sulfate, and concentrated. The residue was purified by column chromatography on silica gel (ethyl acetate: hexane=1:4 to 5) to give the title compound (7.54 g) as an oil.

b) 3-(Bromo-4-nitrophenyl)acetic acid methyl ester

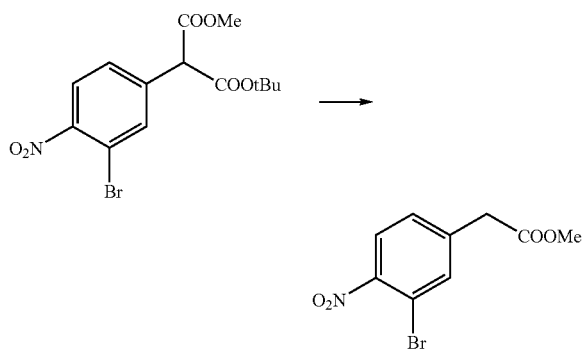

2-(3-Bromo-4-nitrophenyl)malonic acid tert-butyl ester methyl ester (1.18 g) obtained in Reeference Example 3a) was dissolved in chloroform (10 mL), and to this solution was added trifluoroacetic acid (10 g) under ice-cooling. The mixture was stirred at room temperature for 5 hours. The reaction mixture was poured portinwise into ice and saturated aqueous sodium bicarbonate, and extracted with ethyl acetate. The extract was washed with water and saturated brine, dried over sodium sulfate, and concentrated to give the title compound (0.820 g) as a pale yellow oil.

Reference Example 4 a) 4-Benzyloxy-3,5-difluorophenylamine

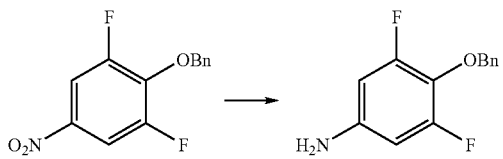

2-Benzyloxy-1,3-difluoro-5-nitrobenzene (4.5 g) was treated in a similar manner to Example 2-c) to give 4-benzyloxy-3,5-difluorophenylamine (3.0 g).

b) 4-Benzyloxy-2-bromo-3,5-difluorophenylamine

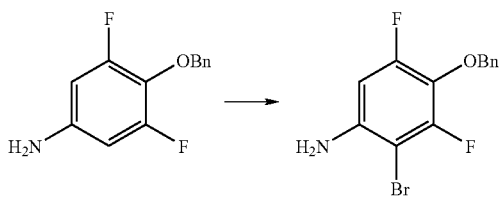

To a solution of 4-benzyloxy-3,5-difluorophenylamine (3.0 g) in THF (30 mL) was added N-bromosuccinimide (2.32 g) under ice-cooling, and the mixture was stirred for 30 minutes. Conc. Hydrochloric acid (2 mL) was added to the reaction mixture to precipitate a solid. The solid was collected by filtration and dried. The dried solid was dissolved in water, and the solution was added with saturated aqueous sodium bicarbonate, and then extracted with ethyl acetate. The extract was dried over sodium sulfate and concentrated to give 4-benzyloxy-2-bromo-3,5-difluorophenylamine (3.33 g).

c) (4-Benzyloxy-2-bromo-3,5-difluorophenyl)carbamic acid tert-butyl ester

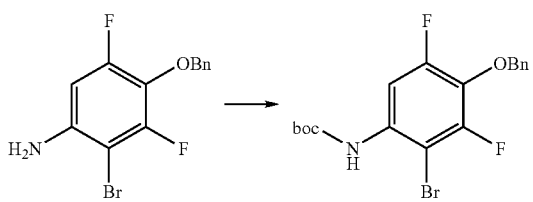

(In the above formulae, boc is t-butoxycarbonyl)

To a solution of 4-benzyloxy-2-bromo-3,5-difluorophenylamine (3.33 g) in THF (35 mL) were added di-tert-butylcarbonate (6.95 g) and 4-dimethylaminopyridine (130 mg), and the mixture was heated under reflux for 2 hours. The reaction mixture was allowed to stand for cooling to room temperature, and concentrated. The residue was diluted with ethyl acetate and washed with 0.5N hydrochloric acid and saturated aqueous brine, dried over sodium sulfate and concentrated. The residue was purified by column chromatography on silica gel (hexane:ethyl acetate=20:1) to give (4-benzyloxy-2-bromo-3,5-difluorophenyl)carbamic acid tert-butyl ester (3.9 g).

d) 3-Benzyloxy-6-tert-butoxycarbonylamino-2,4-difluorobenzenecarboxylic acid

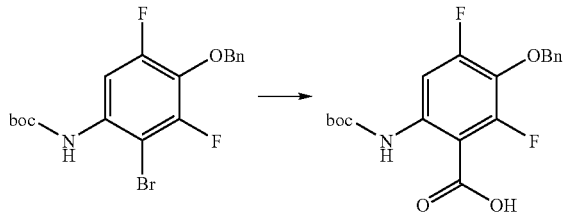

A solution of (4-benzyloxy-2-bromo-3,5-difluorophenyl)carbamic acid tert-butyl ester (3.8 g) in THF (40 mL) was cooled in a dry ice-acetone bath, and thereto was added dropwise 1.6 M n-butyl lithium/hexane solution (12.7 mL). After stirring for 30 minutes, dry ice was added portionwise to the reaction mixture, and the resulting mixture was stirred for 1 hour. The dry-ice acetone bath was removed and 2N hydrochloric acid was added portionwise to the reaction mixture. The reaction solution was diluted with ethyl acetate, and the extract was washed with water and saturated brine, dried over sodium sulfate, and concentrated to give 3-benzyloxy-6-tert-butoxycarbonylamino-2,14-difluorobenzenecarboxylic acid (3.53 g) as a crude product.

e) 6-Amino-3-benzyloxy-2,4-difluorobenzenecarboxylic acid hydrochloride

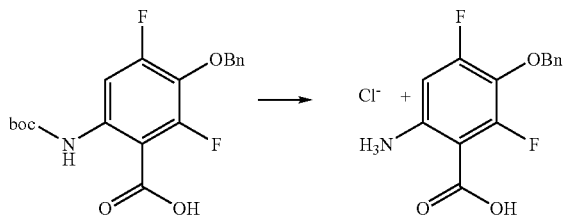

4N Hydrochloric acid-ethyl acetate (35 mL) was added to 3-benzyloxy-6-tert-butoxycarbonylamino-2,4-difluorobenzenecarboxylic acid (3.53 g), and the mixture was stirred at 60° C. for 1 hour. The reaction mixture was cooled down to room temperature, and the resultant precipitated solid was collected by filtration and dried to give 6-amino-3-benzyloxy-2,4-difluorobenzenecarboxylic acid hydrochloride (2.08 g).

f) 6-Amino-3-benzyloxy-2,4-difluoro-N,N-dimethylbenzamide

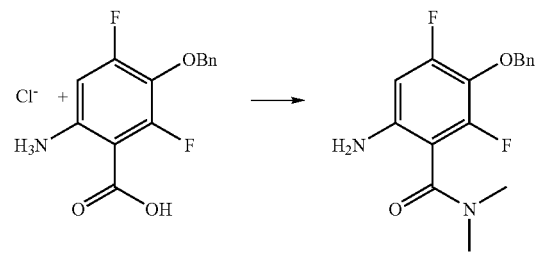

To a solution of 6-amino-3-benzyloxy-2,4-difluorobenzenecarboxylic acid hydrochloride (2.07 g) in DMF (30 mL) were added dimethylamine hydrochloride (1.07 g), 1-hydroxybenzotriazole (1.51 g), 1-ethyl-3-(3-dimethylaminopropyl)carbodiimide hydrochloride (1.89 g) and triethylamine (2.0 g), and the mixture was stirred at room temperature for 4 hours. The reaction mixture was diluted with ethyl acetate, washed successively with water, saturated aqueous sodium bicarbonate, water and brine, dried over sodium sulfate and purified by column chromatography (hexane:ethyl acetate=1:2) on silica gel to give 6-amino-3-benzyloxy-2,4-difluoro-N,N-dimethylbenzamide (1.19 g).

Example 1

2-(2-{3-acetoxy-4-[(4'-trifluoromethyl-biphenyl-2-carbonyl)amino]phenyl}acetoxymethyl)-2-phenyl-malonic acid diethyl ester a) 2-(2-{3-hydroxy-4-[(4'-trifluoromethyl-biphenyl-2-carbonyl)amino]phenyl}acetoxymethyl)-2-phenyl-malonic acid diethyl ester

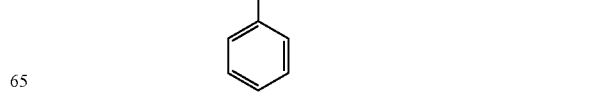

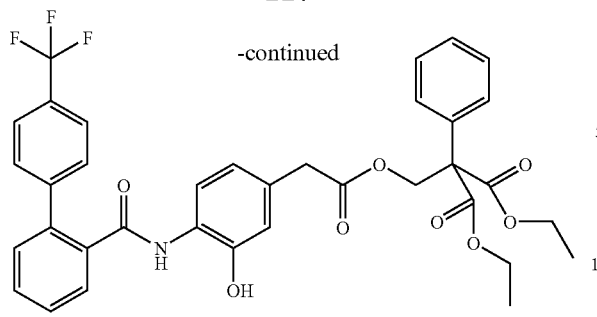

2-(2-{3-Benzyloxy-4-[(4'-trifluoromethyl-biphenyl-2-carbonyl)amino]phenyl}acetoxymethyl)-2-phenylmalonic acid diethyl ester (Reference Example 2-4) (0.310 g) was dissolved in methanol, and palladium carbon (0.04 g) was added thereto. The mixture was hydrogenated at normal pressure for 2 hours. The reaction solution was filtered through a Celite, and the filtrate was concentrated to give the title compound as a colorless non-crystalline substance (0.245 g).

b) 2-(2-{3-acetoxy-4-[(4'-trifluoromethyl-biphenyl-2-carbonyl)amino]phenyl}acetoxymethyl)-2-phenyl-malonic acid diethyl ester

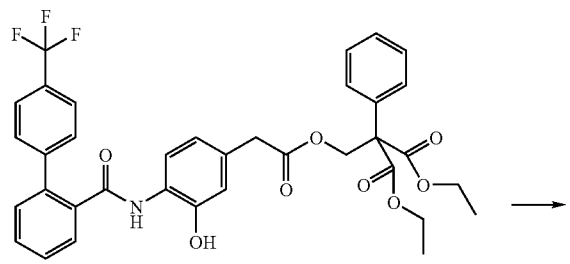

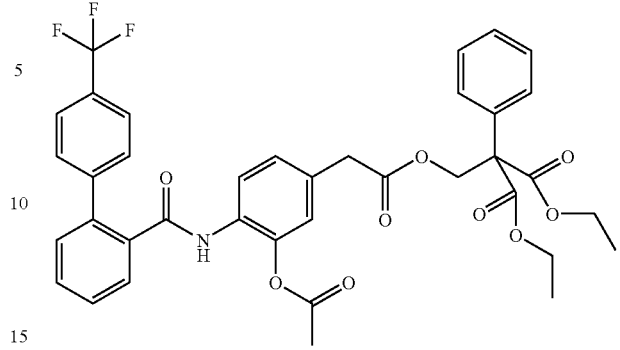

2-(2-{3-Hydroxy-4-[(4'-trifluoromethyl-biphenyl-2-carbonyl)amino]phenyl}acetoxymethyl)-2-phenylmalonic acid diethyl ester (0.200 g) obtained in Example 1-a) was dissolved in toluene (4 mL), and to this solution was added triethylamine (0.040 g). After dropwise addition of a solution of acetyl chloride (0.026 g) in toluene (1 mL), the resultant mixture was stirred at room temperature for 1 hour. The reaction solution was diluted with toluene (5 mL) and washed with saturated aqueous sodium bicarbonate (5 mL), 1N hydrochloric acid (5 mL) and water (5 mL). The toluene layer was concentrated and the residue was purified by column chromatography on silica gel (ethyl acetate:hexane=2:3) to give the title compound (0.165 g) as a colorless crystal. The physicochemical properties of the product are shown in Table 3 below.

Examples 1-2 to 1-8

Compounds of Examples 1-2 to 1-8 as shown in Tables 3 and 4 were prepared according to the procedure of Example 1 or by the conventional method.

TABLE 3

| Example | Structure | NMR (δ, 300MHz, CDCl$_3$) |
|---|---|---|
| 1 | mp 102-105 | 1.21 (6H, t, J=7.2Hz), 2.13 (3H, s), 3.51 (2H, s), 4.21 (4H, q, J=7.2Hz), 4.83 (2H, s), 6.93 (1H, brs), 7.03 (1H, d, J=7.9Hz), 7.14 (1H, brs), 7.30 (5H, s), 7.41-7.78 (8H, m), 8.13 (1H, d, J=7.9Hz). |

TABLE 3-continued
| Example | Structure | NMR (δ, 300MHz, CDCl₃) |
|---|---|---|
| 1-2 | 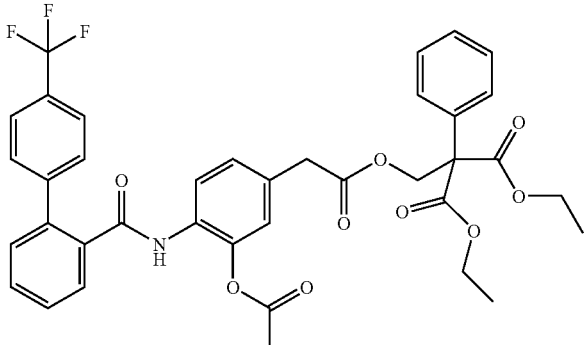<br>mp 98-103 | 1.18 (3H, t, J=7.5Hz),<br>1.21 (3H, t, J=7.2Hz),<br>2.41 (2H, q, J=7.5Hz), 3.51 (2H, s),<br>4.20 (4H, q, J=7.2Hz),<br>4.83 (2H, s), 6.94 (1H, brs),<br>7.03 (1H, d, J=7.9Hz),<br>7.10 (1H, brs),<br>7.30 (5H, s), 7.39-7.77 (8H, m),<br>8.10 (1H, d, J=9.1Hz). |
| 1-3 | 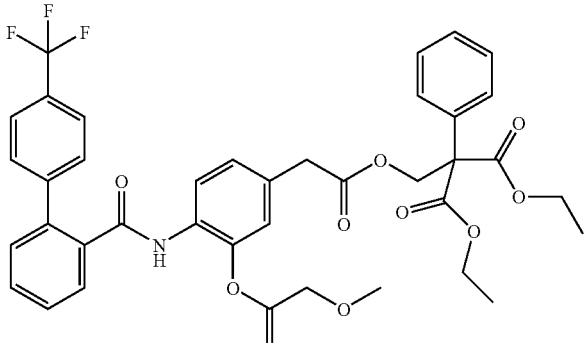<br>mp 104-108 | 1.21 (6H, t, J=7.2Hz), 3.39 (3H, s),<br>3.49 (2H, s), 3.99 (2H, s),<br>4.21 (4H, q, J=7.2Hz),<br>4.84 (2H, s), 6.81 (1H, d, J=1.9Hz),<br>7.04 (1H, dd, J=1.9Hz, J=8.7Hz),<br>7.30 (5H, s), 7.40-7.73 (7H, m),<br>8.17 (1H, d, J=8.3Hz),<br>8.40 (1H, brs). |
| 1-4 | 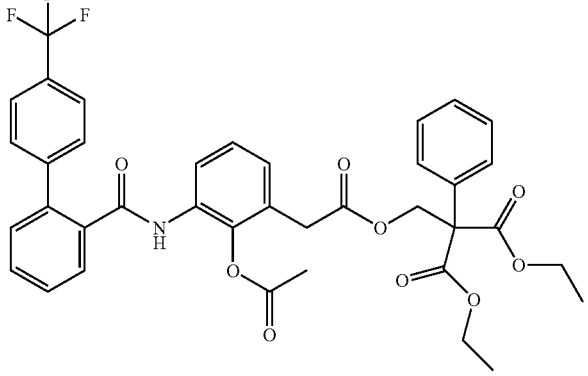 | 1.19 (6H, t, J=7.2Hz), 2.10 (3H, s),<br>3.42 (2H, s), 4.17 (4H, q, J=7.2Hz),<br>4.78 (2H, s), 6.99 (1H, d, J=7.5Hz),<br>7.12 (1H, brs), 7.16 (1H,<br>d, J=7.5Hz),<br>7.28 (5H, s), 7.41-7.72 (8H, m),<br>7.97 (1H, d, J=9.1Hz). |

TABLE 3-continued
| Example | Structure | NMR (δ, 300MHz, CDCl₃) |
|---|---|---|
| 1-5 | 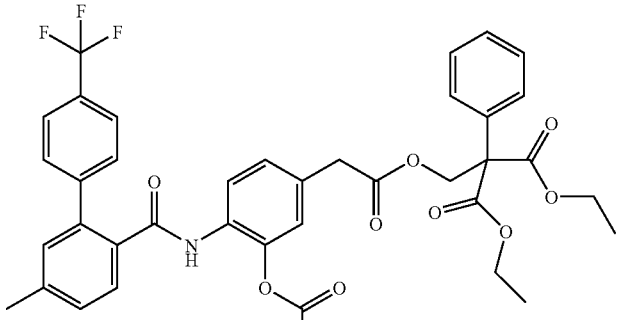 mp 74-77 | 1.20 (6H, t, J=7.2Hz), 2.13 (3H, s), 2.46 (3H, s), 3.50 (2H, s), 4.20 (4H, q, J=7.2Hz), 4.82 (2H, s), 6.92 (1H, brs), 7.02 (1H, d, J=8.3Hz), 7.12 (1H, brs), 7.20-7.37 (7H, m), 7.50-7.70 (5H, m), 8.15 (1H, d, J=7.9Hz). |
TABLE 4
| Example | Structure | NMR (δ, 300MHz, CDCl₃) |
|---|---|---|
| 1-6 | 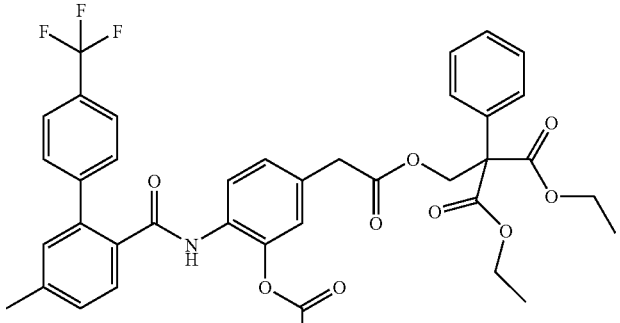 mp 112-115 | 1.18 (3H, t, J=7.5Hz), 1.20 (6H, t, J=7.2Hz), 2.42 (2H, q, J=7.5Hz), 2.46 (3H, s), 3.50 (2H, s), 4.21 (4H, q, J=7.2Hz), 4.83 (2H, s), 6.93 (1H, brs), 7.01 (1H, d, J=8.7Hz), 7.15 (1H, s), 7.20-7.37 (7H, m), 7.50-7.70 (5H, m), 8.12 (1H, d, J=8.7Hz). |
| 1-7 | 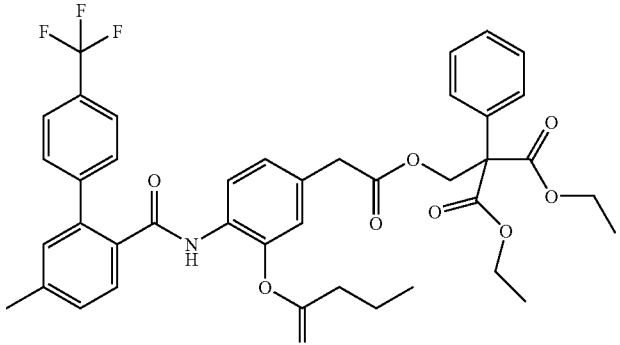 mp 101-103 | 0.98 (3H, t, J=7.5Hz), 1.20 (6H, t, J=7.2Hz), 1.60-1.81 (2H, m), 2.37 (2H, t, J=7.5Hz), 2.46 (3H, s), 3.50 (2H, s), 4.20 (4H, q, J=7.2Hz), 4.82 (2H, s), 6.92 (1H, brs), 7.02 (1H, d, J=8.3Hz), 7.15 (1H, brs), 7.21-7.35 (8H, m), 7.52-7.67 (5H, m). |

TABLE 4-continued

| Example | Structure | NMR (δ, 300MHz, CDCl₃) |
|---|---|---|
| 1-8 | 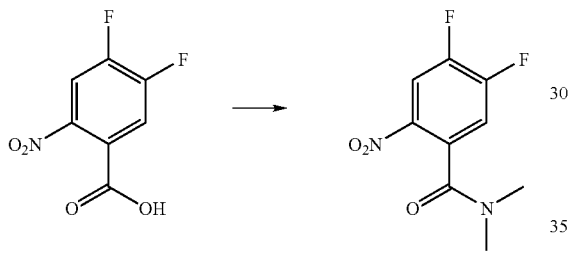 | 1.22 (6H, t, J=7.2Hz), 2.19-2.22 (3H, m), 2.71-3.10 (3H, m), 3.40-3.54 (2H, m), 4.18-4.23 (4H, m), 4.83 (2H, s), 6.59-6.66 (2H, m), 7.02-7.09 (2H, m), 7.30-7.72 (12H, m). |

Example 2
2-{5-Dimethylcarbamoyl-2-fluoro-4-[(4'-trifluoromethyl-biphenyl-2-carbonyl)amino]phenoxycarbonyloxymethyl}-2-phenylmalonic acid diethyl ester a) 4,5-Difluoro-N,N-dimethyl-2-nitrobenzamide

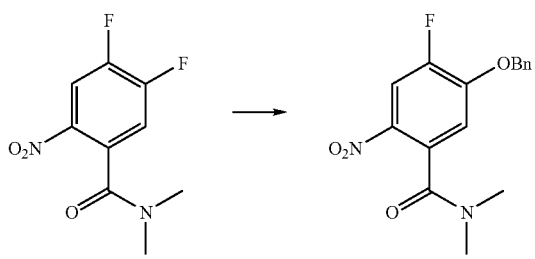

To a solution of 4,5-difluoro-2-nitrobenzenecarboxylic acid (5.37 g) in toluene (15 mL) was added oxalyl chloride (4.7 g) under ice-cooling, and DMF (one drop) was added thereto. The mixture was stirred at room temperature for 1 hour, and concentrated in vacuo. The residue was diluted with toluene, and added dropwise to a mixture of 50% aqueous dimethylamine (3.58 g), toluene (30 mL), sodium bicarbonate (3.34 g) and water (30 mL) under ice-cooling, and the resulting mixture was stirred overnight at room temperature. After addition of water, the reaction solution was extracted with ethyl acetate, and the extract was washed successively with 1N hydrochloric acid and saturated brine, dried over sodium slfate and concentrated. The residue was purified by column chromatography on silica gel (hexane:ethyl acetate=4:3) to give 4,5-difluoro-N,N-dimethyl-2-nitrobenzamide (5.4 g).

b)
5-Benzyloxy-4-fluoro-N,N-dimethyl-2-nitrobenzamide

Sodium hydride (209 mg) was suspended in DMF (10 mL), and to this suspension were added benzyl alcohol (564 mg) and a solution of 4,5-difluoro-N,N-dimethyl-2-nitrobenzamide (1.0 g) in DMF (3 mL). The mixture was stirred at 50° C. for 2 hours, and then cooled with ice. After addition of 10% aqueous citric acid, the reaction mixture was extracted with ethyl acetate and the extract was washed with water and aqueous brine, dried over sodium sulfate, and concentrated. The residue was purified by column chromatography on silica gel (hexane:ethyl acetate=4:3) to give 5-benzyloxy-4-fluoro-N,N-dimethyl-2-nitrobenzamide (1.06 g).

c)
2-Amino-5-benzyloxy-4-fluoro-N,N-dimethylbenzamide

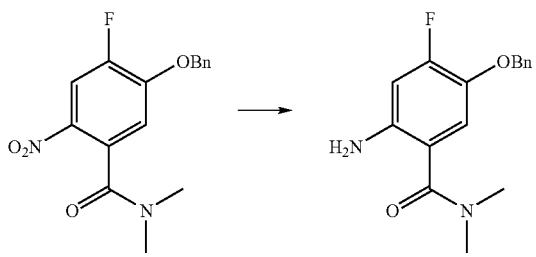

To a solution of 5-benzyloxy-4-fluoro-N,N-dimethyl-2-nitrobenzamide (1.06 g) in THF (3 mL) were added ethanol (12 mL) and water (1.5 mL), and to the solution were added ammonium chloride (893 mg) and reduced iron (933 mg). The resultant mixture was heated under reflux for 2 hours, allowed to stand for cooling to room temperature, and filtered through a Celite. The filtrate was concentrated and the residue was diluted with ethyl acetate. The extract was washed with successively with saturated aqueous sodium bicarbonate, water, and saturated brine, dried over sodium sulfate, and concentrated to give 2-amino-5-benzyloxy-4-fluoro-N,N-dimethylbenzamide (984 mg) as a crude product.

d) 4'-Trifluoromethylbiphenyl-2-carboxylic acid (4-benzyloxy-2-dimethylcarbamoyl-5-fluorophenyl) amide

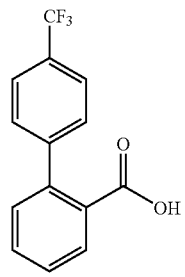

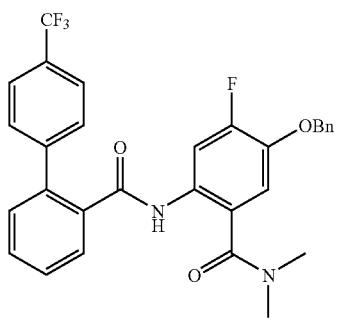

To a solution of 4'-trifluorobiphenyl-2-carboxylic acid (1.07 g) in toluene (3 mL) were added oxalyl chloride (1.02 g) and DMF (one drop) under ice-cooling, and the mixture was stirred at room temperature for 1 hour. The reaction solution was concentrated in vacuo and the residue was diluted with chloroform. The diluted solution was added dropwise to a solution of 2-amino-5-benzyloxy-4-fluoro-N,N-dimethylbenzamide (970 mg) and triethylamine (676 mg) in chloroform (10 mL) under ice-cooling, and the mixture was stirred overnight at room temperature. The reaction solution was diluted with chloroform, and the extract was washed successively with 1N hydrochloric acid and saturated brine, dried over sodium sulfate and concentrated. The residue was purified by column chromatography on silica gel (hexane:ethyl acetate=1:1) to give 4'-trifluoromethylbiphenyl-2-carboxylic acid (4-benzyloxy-2-dimethylcarbamoyl-5-fluorophenyl) amide (1.49 g).

e) 4'-trifluoromethylbiphenyl-2-carboxylic acid (2-dimethylcarbamoyl-5-fluoro-4-hydroxyphenyl) amide

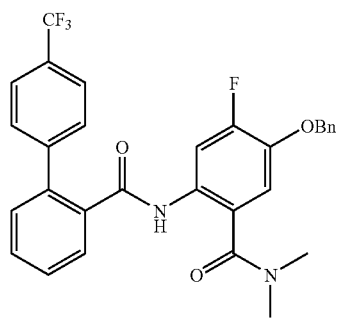

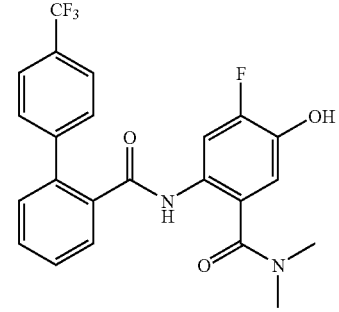

To a solution of 4'-trifluoromethylbiphenyl-2-carboxylic acid (4-benzyloxy-2-dimethylcarbamoyl-5-fluorophenyl) amide (1.48 g) in a mixed solvent of THF (10 mL) and methanol (10 mL) was added 7.5% palladium carbon (200 mg). The mixture was stirred at room temperature for 3 hours under hydrogen atmosphere. The reaction solution was filtered through a celite to remove the catalyst, and the filtrate was concentrated to give 4'-trifluoromethylbiphenyl-2-carboxylic acid (2-dimethylcarbamoyl-5-fluoro-4-hydroxyphenyl)amide (1.09 g).

f) 2-{5-Dimethylcarbamoyl-2-fluoro-4-[(4'-trifluoromethylbiphenyl-2-carbonyl)amino]phenoxycarbonyloxymethyl}-2-phenylmalonic acid diethyl ester

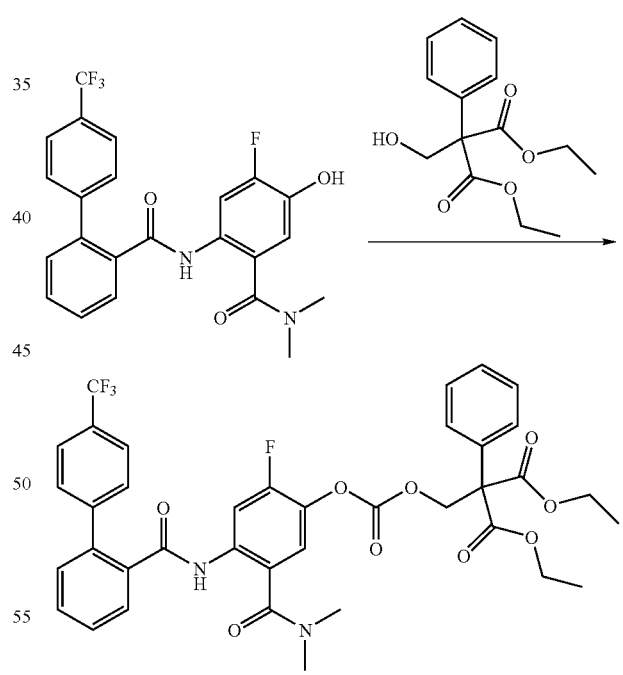

To a solution of diethyl 2-hydroxymethyl-2-phenylmalonate (179 mg) and N,N-dimethylaniline (122 mg) in chloroform was added triphosgene (80 mg) under ice-cooling, and the mixture was stirred at room temperature, and after 3 hours, added dropwise to a solution of 4'-trifluoromethylbiphenyl-2-carboxylic acid (2-dimethylcarbamoyl-5-fluoro-4-hydroxyphenyl)amide (200 mg) and triethylamine (68 mg) in THF under ice-cooling. The mixture was stirred at room temperature for 2 hours, and then diluted with ethyl acetate.

The extract was washed successively with saturated aqueous sodium bicarbonate and saturated brine, dried over sodium sulfate, and concentrated. The residue was purified by column chromatography on silica gel (hexane:ethyl acetate=1:1) to give 2-{5-dimethylcarbamoyl-2-fluoro-4-[(4'-trifluoromethylbiphenyl-2-carbonyl)amino]phenoxycarbonyloxymethyl}-2-phenylmalonic acid diethyl ester (88 mg).

Example 2-2

2-[4-Isopropyl-3-oxo-1-(4'-trifluoromethylbiphenyl-2-carbonyl)-1,2,3,4-tetrahydroquinoxalin-6-yloxycarbonyloxymethyl]-2-phenylmalonic acid diethyl ester a) 4'-Trifluoromethylbiphenyl-2-carboxylic acid (4-hydroxy-2-nitrohenyl)amide

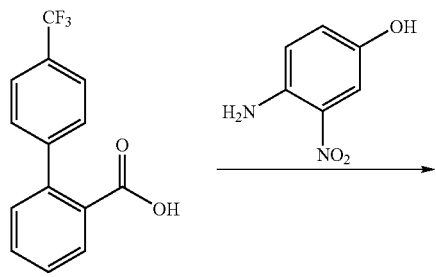

To a solution of 4'-trifluoromethylbiphenyl-2-carboxylic acid (1.9 g) in toluene (3 mL) was added oxalyl chloride (1.25 mL) and DMF (one drop) under ice-cooling, and the mixture was stirred at room temperature for 1 hour. The reaction solution was concentrated in vacuo, and the residue was diluted with ethyl acetate and then added dropwise to a solution of 4-amino-3-nitrophenol (1.0 g), ethyl acetate (10 mL) and sodium bicarbonate (654 mg) in water (10 mL) under ice-cooling. The mixture was stirred at room temperature for 1 hour and diluted with ethyl acetate. The extract was washed successively with 1N hydrochloric acid and saturated brine, dried over sodium sulfate, and concentrated. The residue was purified by column chromatography on silica gel (hexane: ethyl acetate=3:1) to give 4'-trifluoromethylbiphenyl-2-carboxylic acid (4-hydroxy-2-nitrohenyl)amide (474 mg).

b) 4'-Trifluoromethylbiphenyl-2-carboxylic acid (4-benzyloxy-2-nitrophenyl)amide

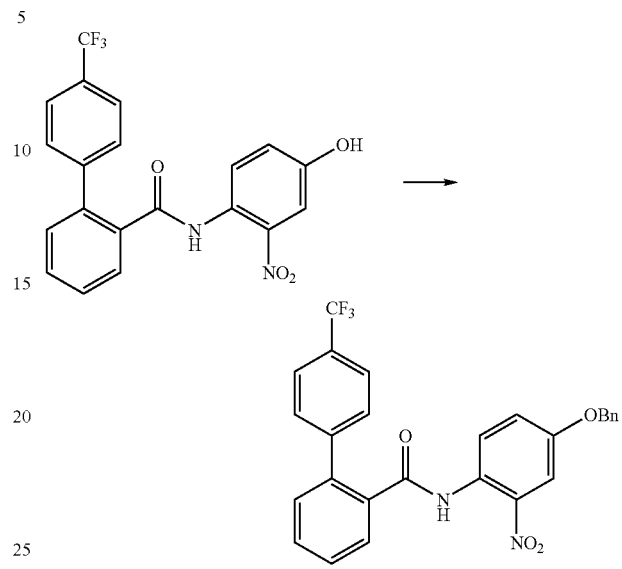

To a solution of 4'-trifluoromethylbiphenyl-2-carboxylic acid (4-hydroxy-2-nitrohenyl)amide (469 mg) in DMF (10 mL) were added potassium carbonate (177 mg) and benzyl bromide (219 mg), and the mixture was stirred at room temperature overnight. The reaction solution was diluted with ethyl acetate, and the extract was washed with water and saturated brine, dried over sodium sulfate and concentrated to give 4'-trifluoromethylbiphenyl-2-carboxylic acid (4-benzyloxy-2-nitrophenyl)amide (582 mg).

c) 4'-Trifluoromethylbiphenyl-2-carboxylic acid (2-amino-4-benzyloxyphenyl)amide

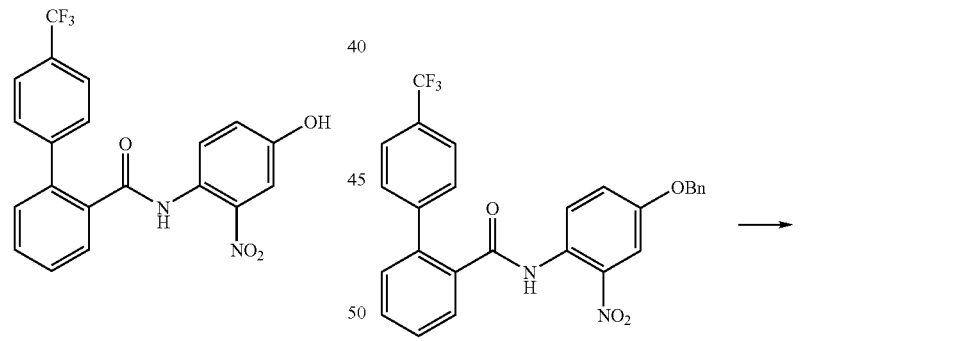

4'-Trifluoromethylbiphenyl-2-carboxylic acid (2-amino-4-benzyloxyphenyl)amide (398 mg) was obtained by treating 4'-trifluoromethylbiphenyl-2-carboxylic acid (4-benzyloxy-2-nitrophenyl)amide (578 mg) in a similar manner to Example 2c).

d) 4'-Trifluoromethylbiphenyl-2-carboxylic acid (2-amino-4-benzyloxy-2-isopropylaminophenyl) amide

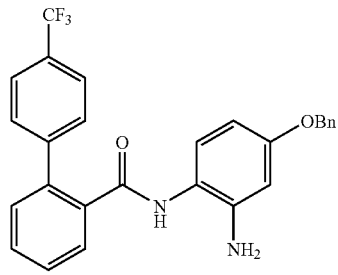

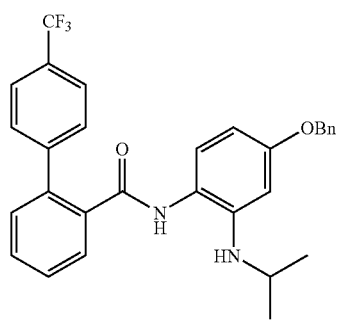

To a solution of 4'-trifluoromethylbiphenyl-2-carboxylic acid (2-amino-4-benzyloxyphenyl)amide (410 mg) in dichloromethane were successively added acetone (57 mg), acetic acid (80 mg) and sodium triacetoxyborohydride (282 mg), and the mixtrure was stirred overnight at room temperature. After addition of saturated aqueous sodium bicarbonate, the reaction solution was extracted with chloroform. The extract was dried over sodium sulfatge and concentrated. The residue was purified by column chromatography on silica gel (hexane:ethyl acetate=3:1) to give 4'-trifluoromethylbiphenyl-2-carboxylic acid (2-amino-4-benzyloxy-2-isopropylaminophenyl)amide (289 mg).

e) 4'-Trifluoromethylbiphenyl-2-carboxylic acid {4-benzyloxy-2-[(2-chloroacetyl)isopropylamino] phenyl}amide

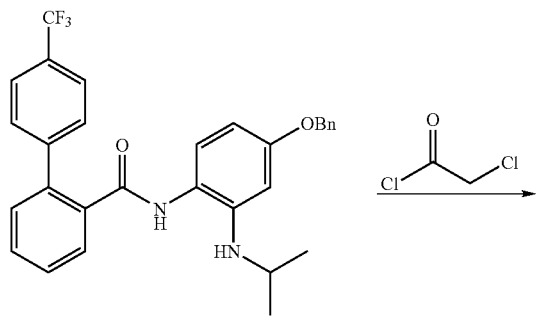

-continued

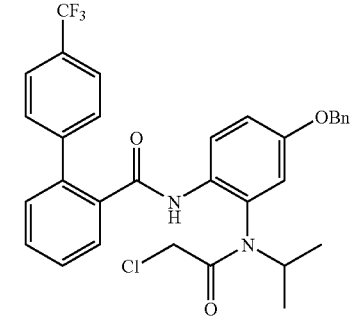

To a solution of 4'-trifluoromethylbiphenyl-2-carboxylic acid (2-amino-4-benzyloxy-2-isopropylaminophenyl)amide (140 mg) and triethylamine (42 mg) in chloroform was added chloroacetyl chloride (48 mg) under ice-cooling, and the mixture was stirred at room temperature for 2 hours. After addition of water to the reaction solution, it is extracted with chloroform. The extract was dried over sodium sulfate and then concentrated. The residue was purified by column chromatography on silica gel (hexane:ethyl acetate=3:1) to give 4'-trifluoromethylbiphenyl-2-carboxylic acid {4-benzyloxy-2-[(2-chloroacetyl)isopropylamino]phenyl}amide (140 mg).

f) 7-Benzyloxy-1-isopropyl-4-(4'-trifluoromethylbiphenyl-2-carbonyl)-3,4-dihydro-1H-quinoxalin-2-one

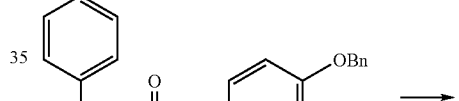

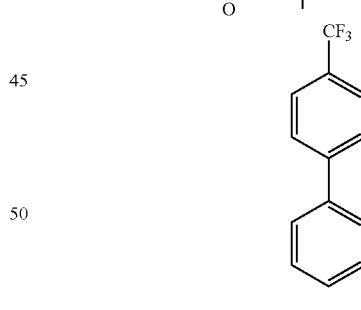

To a solution of 4'-trifluoromethylbiphenyl-2-carboxylic acid {4-benzyloxy-2-[(2-chloroacetyl)isopropylamino]phenyl}amide (134 mg) in DMF (2 mL) were added potassium carbonate (48 mg) and sodium iodide (one spatula), and he mixture was stirred at 80° C. for 2 hours. The reaction solution was allowed to stand for cooling to room temperature, and diluted with ethyl acetate. The extract was washed with water and saturated brine, dried over sodium sulfate and concentrated. The residue was purified by column chromatography on silica gel (hexane:ethyl acetate=3:1) to give 7-benzyloxy-1-isopropyl-4-(4'-trifluoromethylbiphenyl-2-carbonyl)-3,4-dihydro-1H-quinoxalin-2-one (118 mg).

131 g) 7-Hydroxy-1-isopropyl-4-(4'-trifluoromethylbiphenyl-2-carbonyl)-3,4-dihydro-1H-quinoxalin-2-one

132 h) 2-[4-isopropyl-3-oxo-1-(4'-trifluoromethylbiphenyl-2-carbonyl)-1,2,3,4-tetrahydroquinoxalin-6-yloxycarbonyloxymethyl]-2-phenylmalonic acid diethyl ester

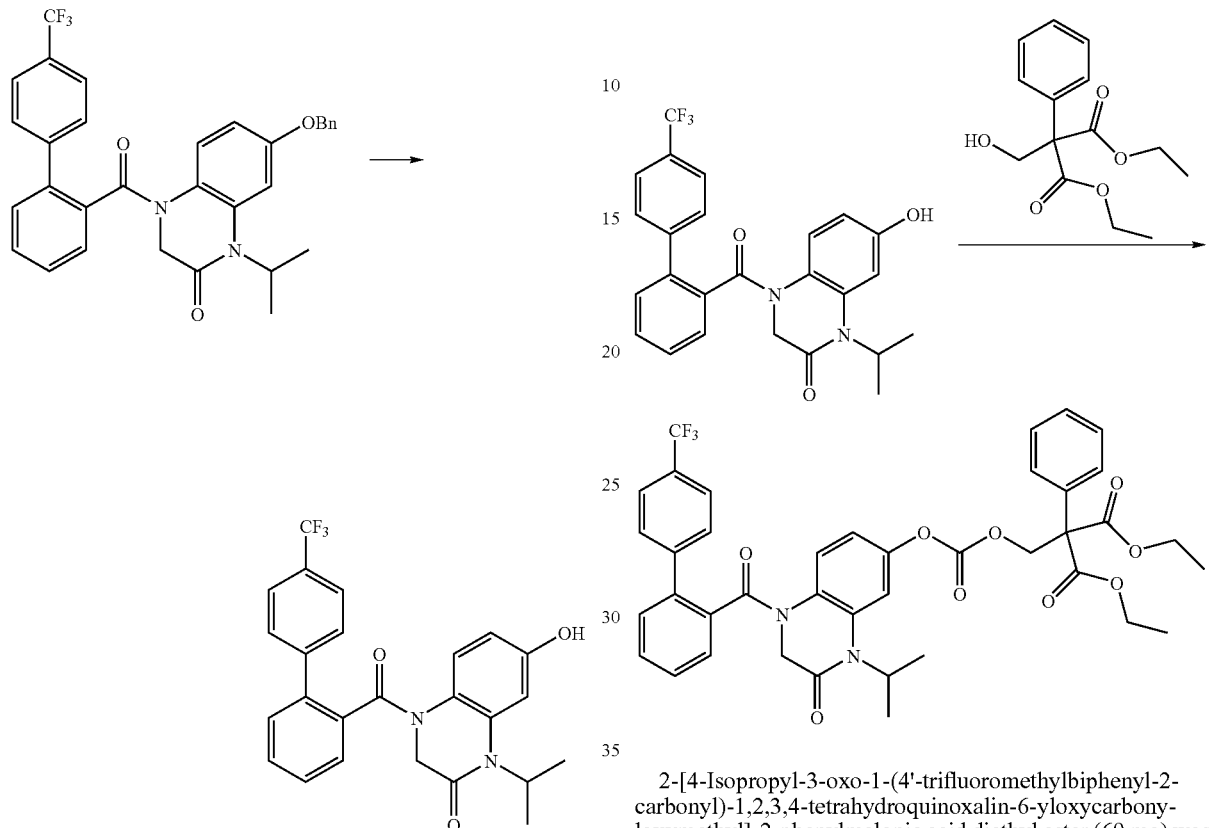

7-Hydroxy-1-isopropyl-4-(4'-trifluoromethylbiphenyl-2-carbonyl)-3,4-dihydro-1H-quinoxalin-2-one (91 mg) was obtained by treating 7-benzyloxy-1-isopropyl-4-(4'-trifluoromethylbiphenyl-2-carbonyl)-3,4-dihydro-1H-quinoxalin-2-one (111 mg) in a similar manner to Example 2 e).

2-[4-Isopropyl-3-oxo-1-(4'-trifluoromethylbiphenyl-2-carbonyl)-1,2,3,4-tetrahydroquinoxalin-6-yloxycarbonyloxymethyl]-2-phenylmalonic acid diethyl ester (69 mg) was obtained by treating 7-hydroxy-1-isopropyl-4-(4'-trifluoromethylbiphenyl-2-carbonyl)-3,4-dihydro-1H-quinoxalin-2-one (82 mg) in a similar manner to Example 2 f).

Examples 2-3 to 2-52

Compounds of Examples 2-4 to 2-52 shown in Tables 5 to 15 were prepared in a similar manner to Example 2 or Example 2-2 or by the known method.

TABLE 5

| Example | Structure | NMR (δ, 300MHz, CDCl$_3$) |
|---|---|---|
| 2 | (structure shown)<br>mp 129-131° C. | 1.27 (6H, t, J=7.1Hz), 2.87 (6H, brs), 4.25-4.33 (4H, m), 4.96 (2H, s), 6.97 (1H, d, J=8.1Hz), 7.33-7.62 (12H, m), 7.69 (1H, dd, J=7.6, 1.4Hz), 8.45 (1H, d, J=12.7Hz), 9.43 (1H, s). |

TABLE 5-continued

| Example | Structure | NMR (δ, 300MHz, CDCl₃) |
|---|---|---|
| 2-2 | 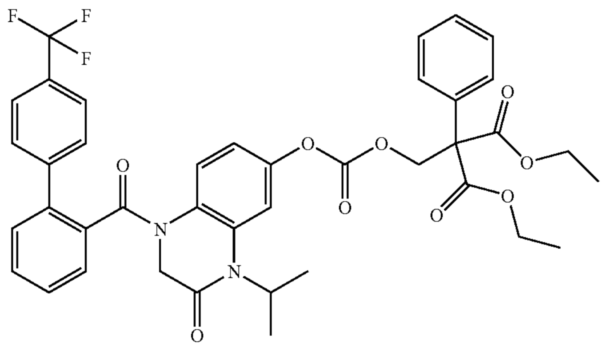 | 1.28 (6H, t, J=7.2Hz), 1.30-1.40 (3H, m), 3.48-3.83 (3H, m), 4.26-4.39 (4H, m), 6.12-6.53 (3H, m), 6.87-7.06 (3H, m), 7.33-7.77 (10H, m). |
| 2-3 | 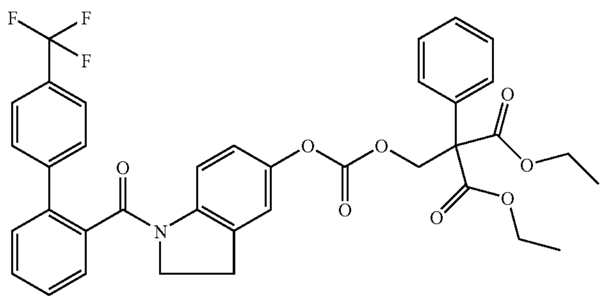 | 1.28 (6H, t, J=7.2Hz), 2.27-4.14 (4H, m), 4.29 (2H, q, J=7.2Hz), 4.30 (2H, q, J=7.2Hz), 4.95 (2H, s), 5.54 (0.5H, d, J=9.3Hz), 6.46-7.67 (15H, m), 8.21 (0.5H, d, J=9.3Hz). |
| 2-4 | mp 59-61° C. | 1.27 (6H, t, J=7.2Hz), 2.85 (3H, brs), 2.93 (3H, brs), 4.29 (2H, q, J=7.2Hz), 4.30 (2H, q, J=7.2Hz), 4.95 (2H, s), 6.95 (1H, d, J=3.0Hz), 7.14 (1H, dd, J=3.0, 9.0Hz), 7.32-7.72 (13H, m), 8.41 (1H, d, J=9.0Hz), 9.15 (1H, brs). |
| 2-5 | 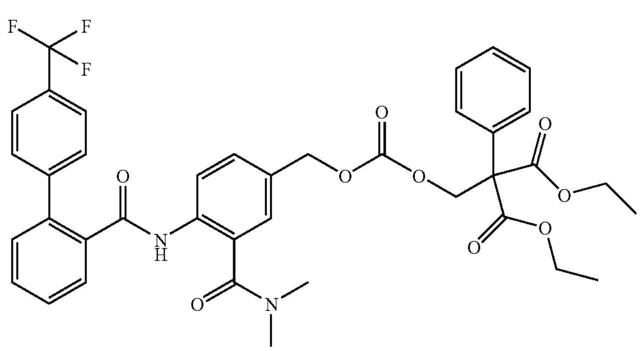 | 1.22 (6H, t, J=7.2Hz), 2.82 (3H, brs), 2.94 (3H, brs), 4.20-4.27 (4H, m), 4.24 (2H, s), 5.02 (2H, s), 7.15 (1H, d, J=2.1Hz), 7.29-7.39 (7H, m), 7.14-7.62 (6H, m), 7.68 (1H, dd, J=7.5, 1.4Hz), 8.41 (1H, d, J=8.6Hz), 9.18 (1H, s). |

TABLE 6

| Example | Structure | NMR (δ, 300MHz, CDCl₃) |
|---|---|---|
| 2-6 | 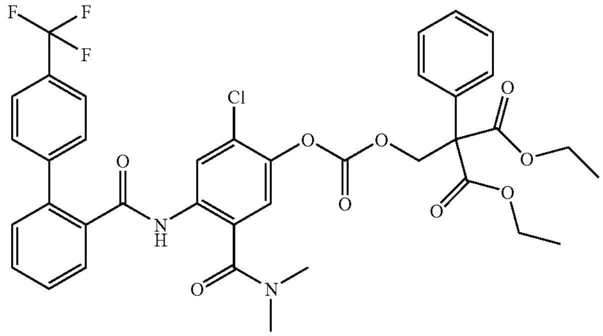 | 1.28 (6H, t, J=7.3Hz), 2.89 (6H, brs), 4.25-4.35 (4H, m), 4.98 (2H, s), 6.96 (1H, s), 7.34-7.72 (13H, m), 8.68 (1H, s), 9.32 (1H, s). |
| 2-7 | 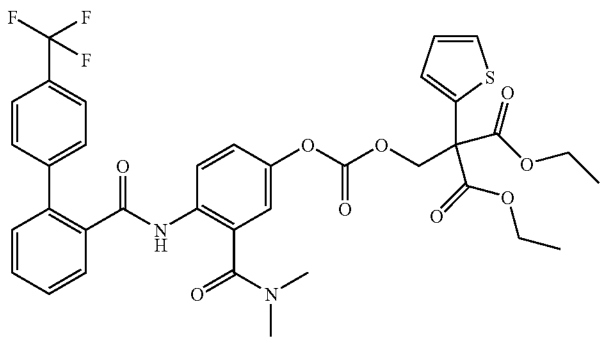 | 1.28 (6H, t, J=7.2Hz), 2.85 (3H, brs), 2.93 (3H, brs), 4.30 (4H, q, J=7.2Hz)), 4.96 (2H, s), 6.96 (1H, d, J=3.2Hz), 7.01 (1H, t, J=3.2Hz), 7.08-7.71 (11H, m), 8.43 (1H, d, J=9.0Hz), 9.15 (1H, brs). |
| 2-8 | 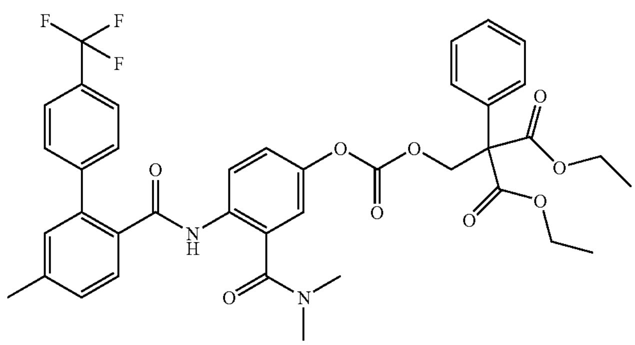 | 1.27 (6H, t, J=7.4Hz), 2.44 (3H, s), 2.85 (3H, brs), 2.93 (3H, brs), 4.29 (4H, q, J=7.4Hz), 4.95 (2H, s), 6.90 (1H, d, J=2.7Hz), 7.12 (1H, dd, J=2.7Hz, J=9.1Hz), 7.19 (1H, brs), 7.23-7.39 (8H, m), 7.54-7.69 (5H, m), 8.42 (1H, d, J=9.1Hz), 9.12 (1H, s). |
| 2-9 | mp 92-97° C. | 1.28 (6H, t, J=7.4Hz), 2.44 (3H, s), 2.86 (3H, brs), 2.93 (3H, brs), 4.30 (4H, q, J=7.4Hz), 4.96 (2H, s), 6.95 (1H, d, J=2.6Hz), 7.01 (1H, dd, J=2.6Hz, J=8.4Hz), 7.09-7.37 (7H, m), 7.54-7.64 (5H, m), 8.42 (1H, d, J=8.4Hz), 9.12 (1H, s). |

TABLE 6-continued

| Example | Structure | NMR (δ, 300MHz, CDCl₃) |
|---|---|---|
| 2-10 | 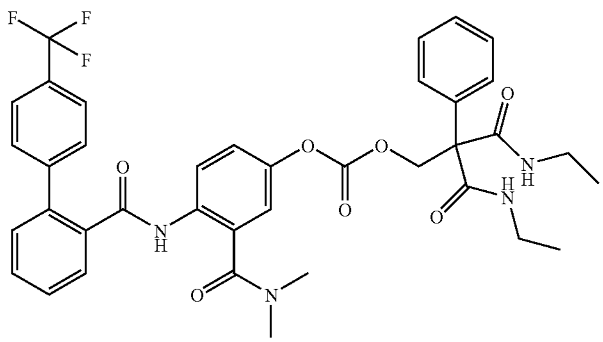 | 1.15 (6H, t, J=7.2Hz), 2.86 (3H, brs), 2.94 (3H, brs), 3.35 (4H, dt, J=13.2, 7.2Hz), 4.95 (2H, s), 6.96 (1H, d, J=2.8Hz), 7.10-7.17 (3H, m), 7.27-7.62 (12H, m), 7.67 (1H, dd, J=7.7, 1.4Hz), 8.41 (1H, d, J=9.0Hz), 9.14 (1H, s). |

TABLE 7

| Example | Structure | NMR (δ, 300MHz, CDCl₃) |
|---|---|---|
| 2-11 | 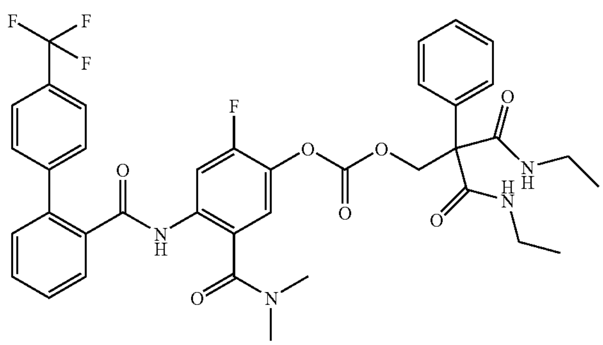 | 1.15 (6H, t, J=7.3Hz), 2.89 (6H, brs), 3.35 (4H, dt, J=12.7, 7.3Hz), 4.97 (2H, s), 7.00 (1H, d, J=8.1Hz), 7.11-7.18 (2H, m), 7.26-7.70 (14H, m), 8.46 (1H, d, J=12.5Hz), 9.44 (1H, s). |
| 2-12 | mp 117-20° C. | 1.20-1.38 (3H, m), 1.27 (6H, t, J=7.2Hz), 2.85 (3H, brs), 3.16-3.42 (2H, m), 4.25-4.33 (4H, m), 4.95 (2H, s), 6.95 (1H, brs), 7.12 (1H, dd, J=9.8, 2.8Hz), 7.34-7.65 (13H, m), 8.33 (1H, d, J=9.1Hz), 8.93-9.11 (1H, m). |
| 2-13 | mp 101–105° C. | 0.74-0.93 (3H, m), 1.27 (6H, t, J=7.2Hz), 1.50-1.59 (2H, m), 2.84-3.35 (5H, m), 4.23-4.35 (4H, m), 4.95 (2H, s), 6.95 (1H, brs), 7.12 (1H, dd, J=9.1, 2.8Hz), 7.34-7.64 (13H, m), 8.33 (1H, brs), 8.93-9.11 (1H, m). |

TABLE 7-continued
| Example | Structure | NMR (δ, 300MHz, CDCl₃) |
|---|---|---|
| 2-14 | 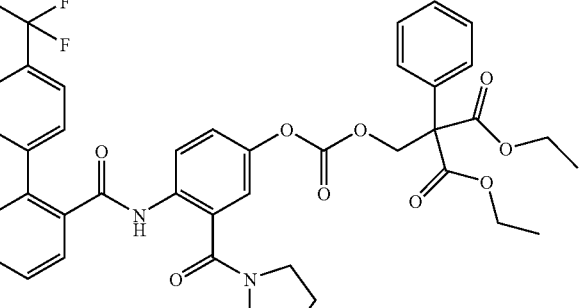 mp 132-134° C. | 1.27 (6H, t, J=7.2Hz), 1.82-1.87 (2H, m), 1.90-1.95 (2H, m), 3.38 (2H, t, J=6.3Hz), 3.50 (2H, t, J=6.3Hz), 4.23-4.35 (4H, m), 4.95 (2H, s), 7.10-7.13 (2H, m), 7.31-7.61 (12H, m), 7.67 (1H, dd, J=7.5, 1.4Hz), 8.39 (1H, d, J=9.7Hz), 9.86 (1H, s). |
| 2-15 | 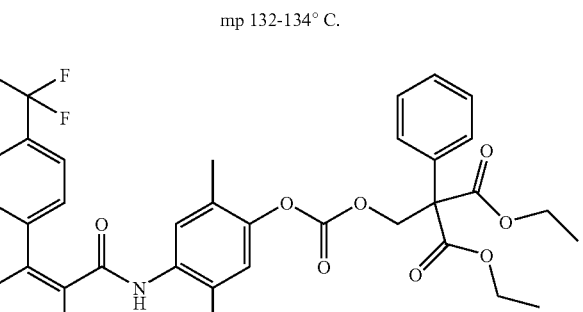 | 1.27 (6H, t, J=7.1Hz), 2.17 (3H, s), 2.87 (6H, brs), 4.23-4.34 (4H, m), 4.94 (2H, s), 6.85 (1H, s), 7.32-7.62 (12H, m), 7.68 (1H, dd, J=7.3, 1.6Hz), 8.32 (1H, s), 9.29 (1H, s). |
TABLE 8
| Example | Structure | NMR (δ, 300MHz, CDCl₃) |
|---|---|---|
| 2-16 | 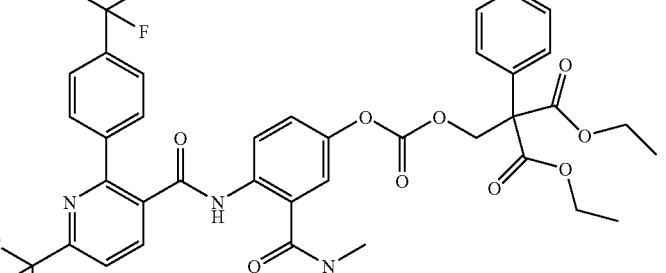 | 1.28 (6H, t, J=7.5Hz), 2.86 (6H, s), 4.30 (4H, q, J=7.5Hz)), 4.96 (2H, s), 6.99 (1H, d, J=2.7Hz), 7.19 (1H, dd, J=2.7Hz, J=8.5Hz), 7.37 (5H, brs), 7.69 (2H, d, J=7.9Hz), 7.79 (1H, d, J=7.4Hz), 7.92 (2H, d, J=7.9Hz), 8.20 (1H, d, J=7.4Hz), 8.46 (1H, d, J=8.5Hz), 9.57 (1H, brs). |
| 2-17 | 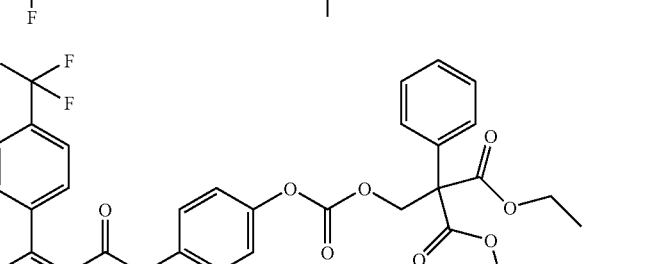 | 1.12-1.29 (6H, m), 2.92-3.26 (9H, m), 4.24-4.35 (4H, m), 4.93-4.96 (2H, m), 6.63-6.78 (2H, m), 7.05-7.12 (2H, m), 7.30-7.52 (8H, m), 7.61-7.71 (4H, m). |

TABLE 8-continued
| Example | Structure | NMR (δ, 300MHz, CDCl₃) |
|---|---|---|
| 2-18 | 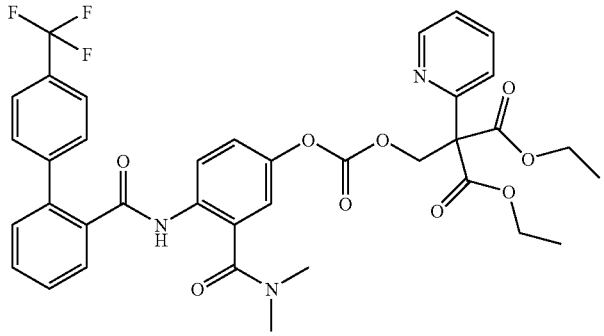<br>mp 62-66° C. | 1.27 (6H, t, J=7.1Hz), 2.87 (3H, brs), 2.94 (3H, brs), 4.30 (4H, q, J=7.1Hz), 5.11 (2H, s), 6.99 (1H, d, J=2.9Hz), 7.15 (1H, dd, J=2.9Hz, J=9.2Hz), 7.22-7.75 (11H, m), 8.42 (1H, d, J=9.2Hz), 8.55 (1H, m), 9.17 (1H, s). |
| 2-19 | 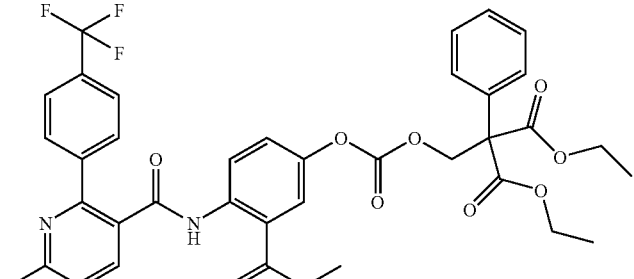<br>mp 147-49° C. | 1.28 (6H, t, J=7.2Hz), 2.67 (3H, s), 2.85 (6H, brs), 4.30 (4H, q, J=7.2Hz), 4.31 (2H, q, J=7.2Hz), 4.96 (2H, s), 6.95 (1H, d, J=2.5Hz), 7.16 (1H, dd, J=2.5Hz, J=9.2Hz), 7.27 (1H, d, J=7.9Hz), 7.37 (5H, brs, 7.65 (2H, d, J=7.9Hz), 7.85 (2H, d, J=7.9Hz), 7.91 (1H, d, J=7.9Hz), 8.48 (1H, d, J=9.2Hz), 9.29 (1H, brs). |
| 2-20 | 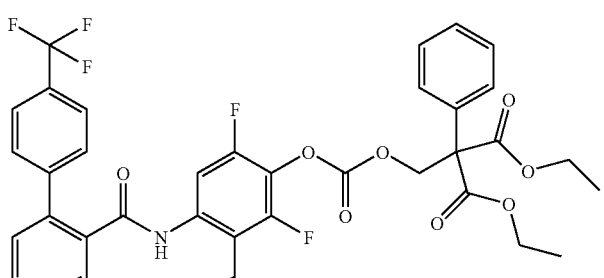<br>mp 132-35° C. | 1.28 (6H, t, J=7.2Hz), 2.73 (3H, d, J=2.8Hz), 2.95 (3H, s), 4.24-4.35 (4H, m), 4.97 (1H, d, J=10.6Hz), 5.01 (1H, d, J=10.6Hz), 7.31-7.40 (6H, m), 7.47-7.57 (4H, m), 7.63-7.67 (3H, m), 8.27 (1H, dd, J=12.3, 1.6Hz), 8.93 (1H, s). |

TABLE 9

| Example | Structure | NMR (δ, 300MHz, CDCl₃) |
|---|---|---|
| 2-21 | 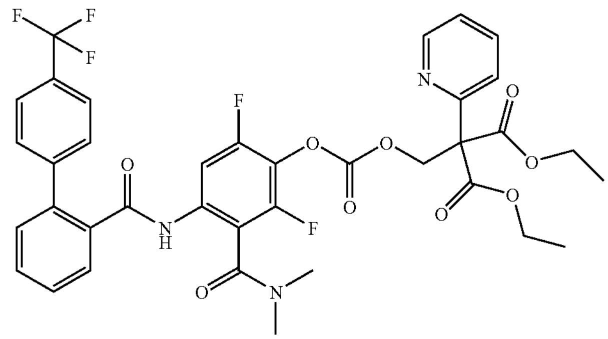 | 1.27 (6H, t, J=7.2Hz), 2.74 (3H, d, J=3.3Hz), 2.94 (3H, s), 4.26-4.32 (4H, m), 5.12 (1H, d, J=10.2Hz), 5.18 (1H, d, J=10.2Hz), 7.22-7.72 (11H, m), 8.24-8.27 (1H, m), 8.52-8.53 (1H, m), 8.92 (1H, s). |
| 2-22 | 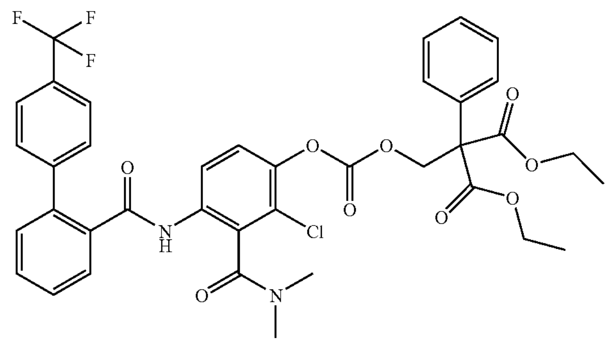 | 1.28 (6H, t, J=7.3Hz), 2.62 (3H, s), 2.96 (3H, s), 4.25-4.35 (4H, m), 4.98 (1H, d, J=14.6Hz), 5.01 (1H, d, J=14.6Hz), 7.15-7.68 (14H, m), 7.88 (1H, s), 8.16 (1H, d, J=9.2Hz). |
| 2-23 | mp 140–142° C. | 1.27 (6H, t, J=7.1Hz), 2.67 (3H, s), 2.86 (6H, brs), 4.30 (4H, q, J=7.1Hz), 5.12 (2H, s), 6.99 (1H, d, J=2.8Hz), 7.17 (1H, dd, J=2.8Hz, J=9.1Hz), 7.27 (2H, d, J=7.9Hz), 7.55-7.77 (4H, m), 7.85 (2H, d, J=7.9Hz), 7.91 (1H, d, J=7.9Hz), 8.48 (1H, d, J=9.1Hz), 8.55 (1H, m), 9.29 (1H, brs). |
| 2-24 | mp 142-143° C. | 1.27 (6H, t, J=7.2Hz), 2.83 (3H, s), 2.94 (3H, s), 4.23-4.34 (4H, m), 4.95 (2H, s), 6.85 (1H, s), 7.31-7.71 (13H, m), 8.71 (1H, s), 9.37 (1H, s). |

TABLE 9-continued

| Example | Structure | NMR (δ, 300MHz, CDCl₃) |
|---|---|---|
| 2-25 | 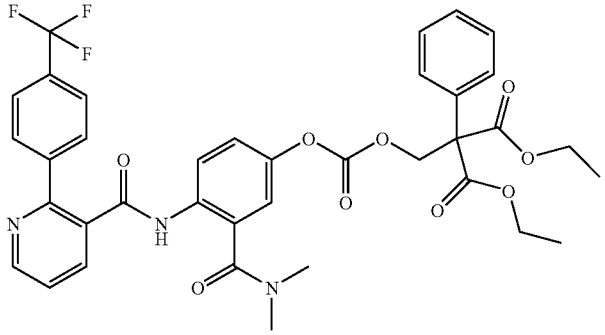 mp 116-120° C. | 1.28 (6H, t, J=7.4Hz), 2.86 (6H, brs), 4.30 (2H, q, J=7.4Hz)), 4.31 (2H, q, J=7.4Hz), 4.96 (2H, s), 6.97 (1H, d, J=2.8Hz), 7.18 (1H, dd, J=2.8Hz, J=9.0Hz), 7.37 (5H, brs), 7.42 (1H, dd, J=4.6Hz, J=7.8Hz), 7.66 (2H, d, J=7.9Hz), 7.87 (2H, d, J=7.9Hz), 8.03 (1H, dd, J=1.8Hz, J=7.8Hz), 8.48 (1H, d, J=9.0Hz), 8.81 (1H, dd, J=1.8Hz, J=4.6Hz), 9.37 (1H, brs). |

TABLE 10

| Example | Structure | NMR (δ, 300MHz, CDCl₃) |
|---|---|---|
| 2-26 | 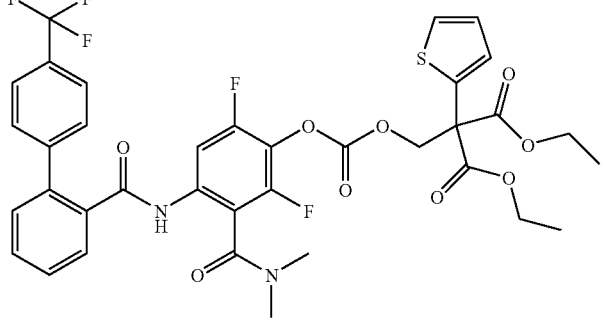 mp 114-117° C. | 1.29 (6H, t, J=7.1Hz), 2.75 (3H, d, J=3.4Hz), 2.96 (3H, s), 4.25-4.36 (4H, m), 4.98 (1H, d, J=14.3Hz), 5.02 (1H, d, J=14.3Hz), 7.01 (1H, dd, J=4.9, 3.8Hz), 7.11 (1H, dd, J=3.8, 2.1Hz), 7.34-7.42 (2H, m), 7.47-7.68 (7H, m), 8.29 (1H, dd, J=12.1, 1.9Hz), 8.94 (1H, s). |
| 2-27 | 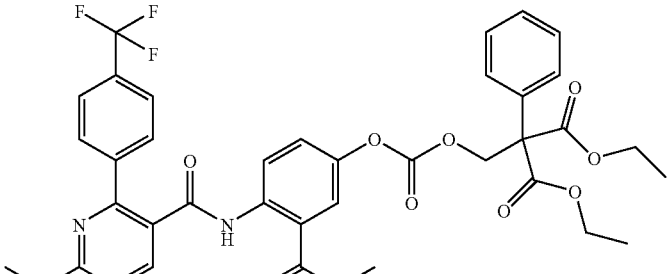 mp 107–112 | 1.20-1.34 (6H, m), 2.88 (6H, brs), 3.10 (3H, d, J=4.8Hz), 4.22-4.36 (4H, m), 4.96 (2H, s), 5.49 (1H, d, J=4.8Hz), 6.96 (1H, d, J=2.7Hz), 7.15 (1H, dd, J=2.7Hz, J=9.0Hz), 7.33-7.40 (5H, brs), 7.66 (2H, d, J=7.9Hz), 7.84 (2H, brs), 8.47 (1H, d, J=9.0Hz), 8.67 (1H, brs), 9.33 (1H, brs). |

TABLE 10-continued
| Example | Structure | NMR (δ, 300MHz, CDCl₃) |
|---|---|---|
| 2-28 | 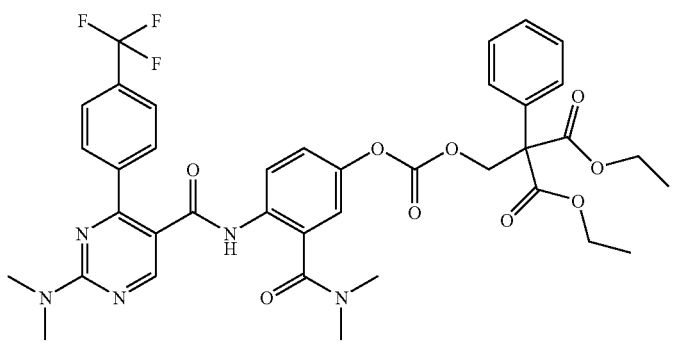 mp 148-162° C. | 1.28 (6H, t, J=7.3Hz), 2.87 (3H, s), 3.29 (3H, s), 4.30 (4H, q, J=7.3Hz), 4.96 (2H, s), 6.96 (1H, brs), 7.11-7.20 (1H, m), 7.37 (5H, brs), 7.65 (2H, d, J=7.9Hz), 7.86 (2H, d, J=7.9Hz), 8.49 (1H, d, J=9.0Hz), 8.69 (1H, s), 9.28 (1H, brs). |
| 2-29 | 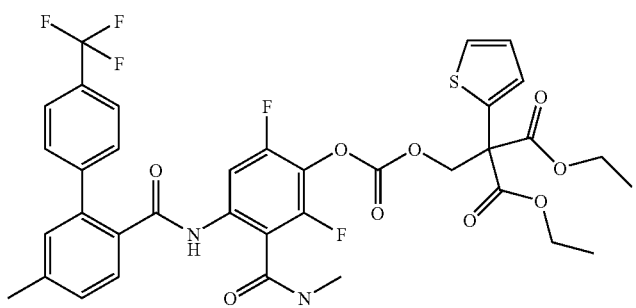 mp 141-43° C. | 1.29 (6H, t, J=7.1Hz), 2.45 (3H, s), 2.75 (3H, d, J=3.4Hz), 2.96 (3H, s), 4.25-4.35 (4H, m), 4.99 (1H, d, J=14.7Hz), 5.02 (1H, d, J=14.7Hz), 7.01 (1H, dd, J=4.9, 3.4Hz), 7.11 (1H, dd, J=3.7, 1.1Hz), 7.29-7.36 (2H, m), 7.54-7.65 (5H, m), 8.28 (1H, dd, J=12.4, 1.8Hz), 8.91 (1H, s). |
| 2-30 | 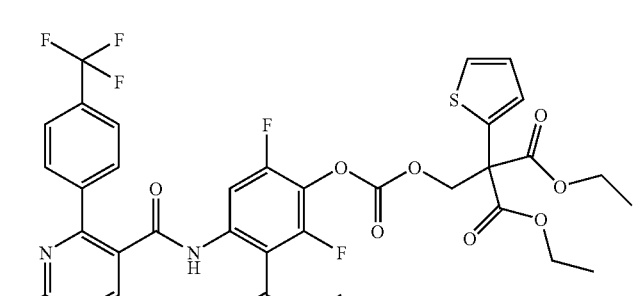 mp 149-151° C. | 1.29 (6H, t, J=7.2Hz), 2.67 (3H, s), 2.72 (3H, d, J=3.4Hz), 2.87 (3H, s), 4.26-4.36 (4H, m), 4.99 (1H, d, J=14.6Hz), 5.03 (1H, d, J=14.6Hz), 7.01 (1H, dd, J=5.3, 3.8Hz), 7.11 (1H, dd, J=3.8, 1.1Hz), 7.29 (1H, s), 7.35 (1H, dd, J=5.3, 1.5Hz), 7.66-7.91 (5H, m), 8.33 (1H, dd, J=12.1, 1.9Hz), 9.02 (1H, s). |

TABLE 11

| Example | Structure | NMR (δ, 300MHz, CDCl₃) |
|---|---|---|
| 2-31 | 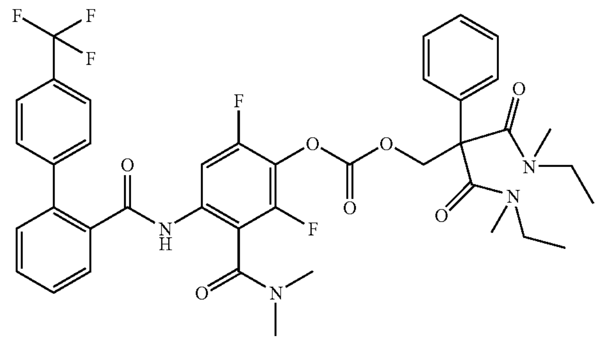 | 0.98-1.24 (6H, m), 2.74 (3H, d, J=3.0Hz), 2.85-3.00 (6H, m), 3.35-3.55 (4H, m), 4.80-4.95 (2H, m), 7.28-7.68 (13H, m), 8.27 (1H, d, J=12.0Hz), 8.95 (1H, s). |
| 2-23 | mp 117-122° C. | 1.29 (6H, t, J=7.0Hz), 2.75 (3H, d, J=3.6Hz), 2.96 (3H, brs), 4.31 (4H, q, J=7.0Hz), 4.99 (1H, d, J=9.5Hz), 5.02 (1H, d, J=9.5Hz), 6.97-7.04 (1H, m), 7.07-7.14 (1H, m), 7.35 (1H, d, J=5.3Hz), 7.59 (2H, d, J=7.9Hz), 7.65-7.73 (3H, m), 7.74-7.83 (2H, m), 8.25 (1H, d, J=11.2Hz), 9.11 (1H, brs). |
| 2-33 | mp 161-65° C. | 1.29 (6H, t, J=7.1Hz), 2.77 (3H, d, J=2.9Hz), 3.03 (3H, brs), 4.30 (2H, q, J=7.1Hz), 4.31 (2H, d, J=7.1Hz), 4.98 (1H, d, J=10.0Hz), 5.02 (1H, d, J=10.0Hz), 6.97-7.03 (1H, m), 7.07-7.13 (1H, m), 7.24-7.36 (2H, m), 7.43-7.51 (2H, m), 7.55 (2H, d, J=7.9Hz), 7.67 (1H, d, J=7.9Hz), 8.18 (1H, d, J=12.5Hz), 9.03 (1H, brs). |
| 2-34 | mp 129-137° C. | 1.29 (6H, t, J=7.4Hz), 2.11 (3H, s), 2.83 (3H, d, J=2.9Hz), 3.10 (3H, brs), 4.30 (4H, q, J=7.4Hz), 4.97 (1H, d, J=9.5Hz), 5.01 (1H, d, J=9.5Hz), 6.97-7.02 (1H, m), 7.08-7.12 (1H, m), 7.34 (1H, d, J=4.3Hz), 7.36-7.48 (5H, m), 7.58-7.69 (2H, m), 8.05 (1H, d, J=11.5Hz), 8.93 (1H, brs). |

TABLE 11-continued
| Example | Structure | NMR (δ, 300MHz, CDCl₃) |
|---|---|---|
| 2-35 | 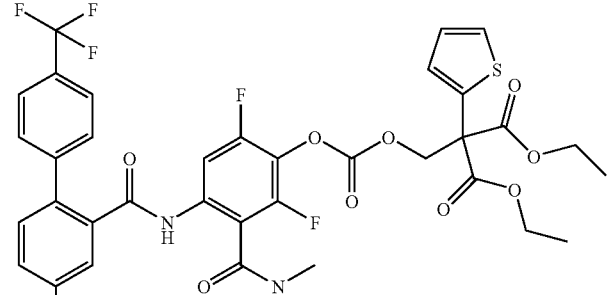 mp 147-157° C. | 1.29 (6H, t, J=7.2Hz), 2.45 (3H, s), 2.71 (3H, d, J=2.9Hz), 2.93 (3H, brs), 4.30 (2H, q, J=7.2Hz), 4.31 (2H, q, J=7.2Hz), 4.98 (1H, d, J=10.0Hz), 5.01 (1H, d, J=10.0Hz), 6.98-7.03 (1H, m), 7.08-7.13 (1H, m), 7.23-7.40 (3H, m), 7.47 (1H, brs), 7.55 (2H, d, J=7.9Hz), 7.63 (2H, d, J=7.9Hz), 8.28 (1H, d, J=11.4Hz), 8.85 (1H, brs). |
TABLE 12
| Example | Structure | NMR (δ, 300MHz, CDCl₃) |
|---|---|---|
| 2-36 | 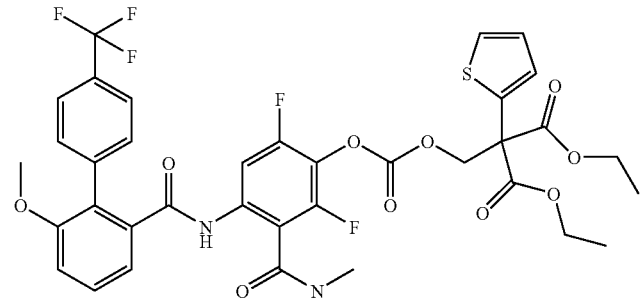 mp 148-153° C. | 1.28 (6H, t, J=7.2Hz), 2.77 (3H, d, J=3.4Hz), 3.04 (3H, s), 3.78 (3H, s), 4.25-4.35 (4H, m), 4.97 (1H, d, J=14.7Hz), 5.02 (1H, d, J=14.7Hz), 6.99-7.11 (3H, m), 7.21-7.35 (2H, m), 7.42-7.62 (5H, m), 8.15 (1H, dd, J=12.1, 1.5Hz), 8.82 (1H, s). |
| 2-37 | 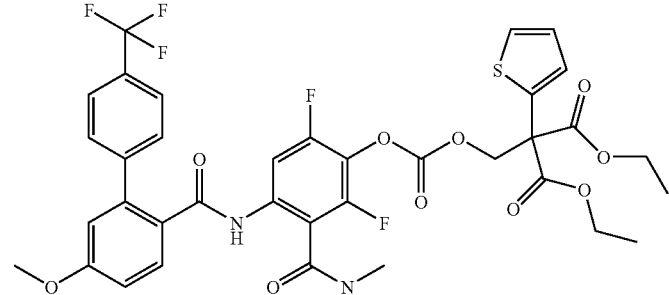 mp 123-132° C. | 1.29 (6H, t, J=7.2Hz), 2.77 (3H, d, J=2.6Hz), 2.98 (3H, s), 3.88 (3H, s), 4.27-4.33 (4H, m), 5.00 (1H, d, J=3.8Hz), 6.87-7.11 (4H, m), 7.35 (1H, d, J=4.9Hz), 7.54-7.66 (5H, m), 8.27 (1H, d, J=12.1Hz), 8.94 (1H, s). |

TABLE 12-continued
| Example | Structure | NMR (δ, 300MHz, CDCl₃) |
|---|---|---|
| 2-38 | 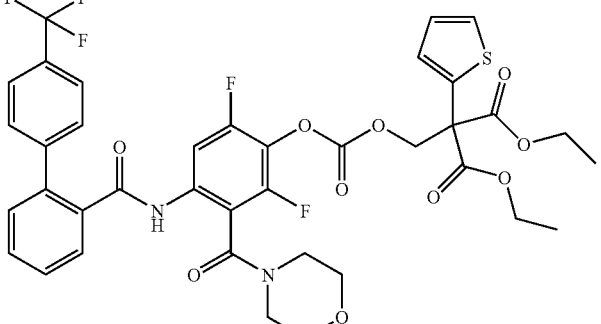\nmp 99-14 | 1.29 (6H, t, J=7.2Hz), 3.00-3.80 (8H, m), 4.30 (4H, q, J=7.2Hz), 4.98 (1H, d, J=10.6Hz), 5.03 (1H, d, J=10.6Hz), 6.98-7.03 (1H, m), 7.08-7.12 (1H, m), 7.32-7.70 (9H, m), 5.15 (1H, d, J=11.7Hz), 8.94 (1H, brs). |
| 2-39 | 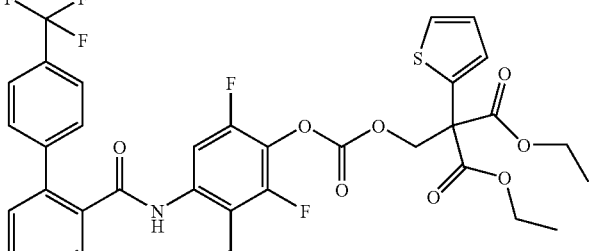\nmp 148-152° C. | 1.29 (6H, t, J=7.2Hz), 2.45 (3H, s), 2.64 (3H, d, J=2.6Hz), 2.93 (3H, s), 4.25-4.36 (4H, m), 4.99 (1H, d, J=14.7Hz), 5.02 (1H, d, J=14.7Hz), 7.01 (1H, dd, J=8.6, 3.7Hz), 7.11 (1H, dd, J=3.7, 1.1Hz), 7.19-7.43 (4H, m), 7.56-7.64 (4H, m), 8.12 (1H, dd, J=12.1, 1.5Hz), 8.64 (1H, s). |
| 2-40 | 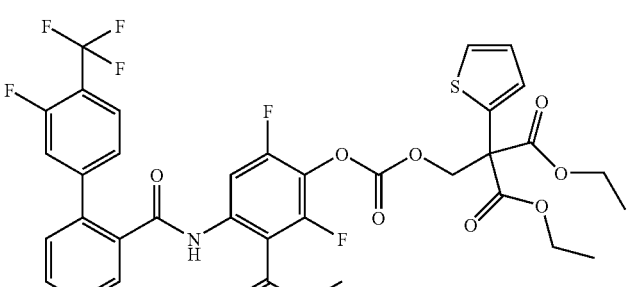\nmp 115-119° C. | 1.29 (6H, t, J=7.1Hz), 2.82 (3H, d, J=3.4Hz), 3.01 (3H, s), 4.26-4.36 (4H, m), 4.99 (1H, d, J=14.3Hz), 5.03 (1H, d, J=14.3Hz), 7.01 (1H, dd, J=4.9, 3.4Hz), 7.11 (1H, dd, J=3.4, 1.2Hz), 7.29-7.39 (4H, m), 7.50-7.69 (4H, m), 8.25 (1H, dd, J=12.1, 1.9Hz), 9.11 (1H, s). |

TABLE 13

| Example | Structure | NMR (δ, 300MHz, CDCl₃) |
|---|---|---|
| 2-41 | 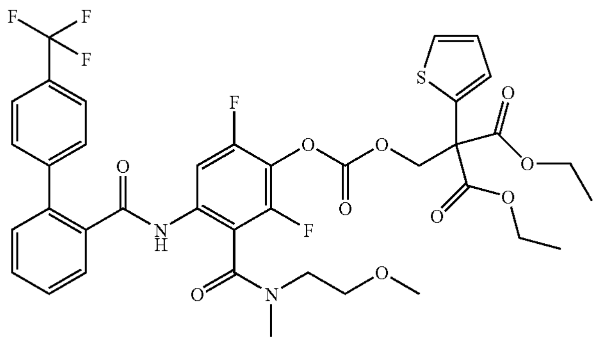 | 1.26 (6H, t, J=7.2Hz), 2.79-3.12 (6H, m), 3.38-3.76 (4H, m), 4.24-4.32 (4H, m), 4.94-5.01 (2H, m), 6.99-7.31 (2H, m), 7.31-7.64 (9H, m), 7.98-8.18 (1H, m), 8.77-8.79 (1H, m). |
| 2-42 | 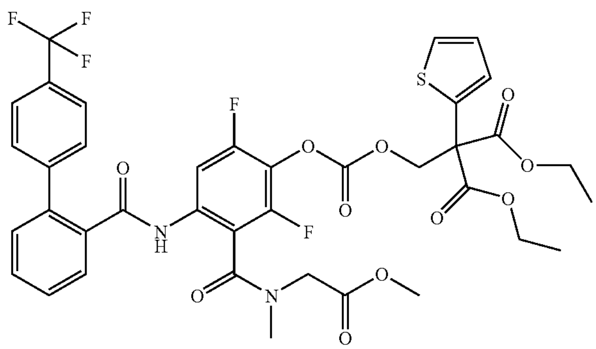 | 1.25-1.29 (6H, m), 2.84-3.06 (3H, m), 3.62-3.66 (3H, m), 3.79-4.46 (5H, m), 4.94-5.00 (2H, m), 6.97-7.09 (2H, m), 7.23-7.66 (9H, m), 8.02-8.19 (1H, m), 8.78-8.89 (1H, m). |
| 2-43 | 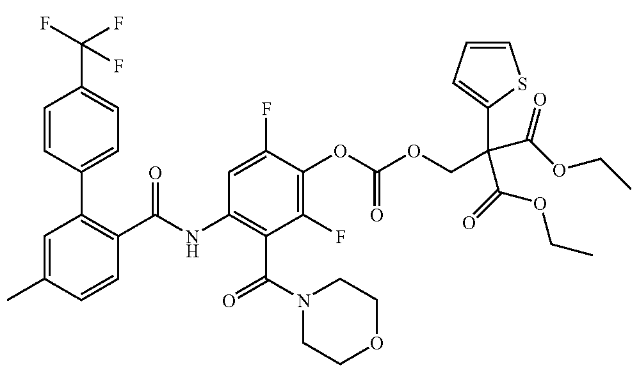 | 1.29 (6H, t, J=7.2Hz), 2.45 (3H, s), 3.00-3.79 (8H, m), 4.30 (4H, q, J=7.2Hz), 4.98 (1H, d, J=9.5Hz), 5.02 (1H, d, J=9.5Hz), 6.97-7.03 (1H, m), 7.08-7.12 (1H, m), 7.17-7.36 (3H, m), 7.48-7.68 (5H, m), 8.08-8.18 (1H, m), 8.92 (1H, brs). |
| 2-44 | mp 95-102° C. | 1.28 (6H, t, J=7.2Hz), 2.74 (3H, d, J=3.0Hz), 2.95 (3H, s), 4.26-4.37 (4H, m), 5.21 (2H, s), 7.39-7.68 (9H, m), 7.83 (1H, d, J=3.0Hz), 8.27 (1H, dd, J=12.0, 1.5Hz), 8.93 (1H, s). |

TABLE 13-continued
| Example | Structure | NMR (δ, 300MHz, CDCl₃) |
|---|---|---|
| 2-45 | 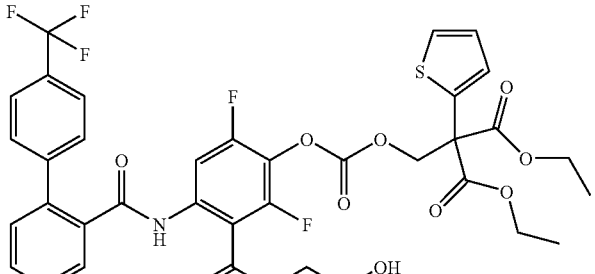 mp 93-00° C. | 1.29 (6H, t, J=7.1Hz), 2.00-2.15 (1H, m), 2.85-3.80 (7H, m), 4.22-4.36 (4H, m), 4.93-5.08 (2H, m), 6.99-7.11 (2H, m), 7.33-7.67 (9H, m), 7.93-8.08 (1H, m), 8.77 (1H, s). |
TABLE 14
| Example | Structure | NMR (δ, 300MHz, CDCl₃) |
|---|---|---|
| 2-46 | 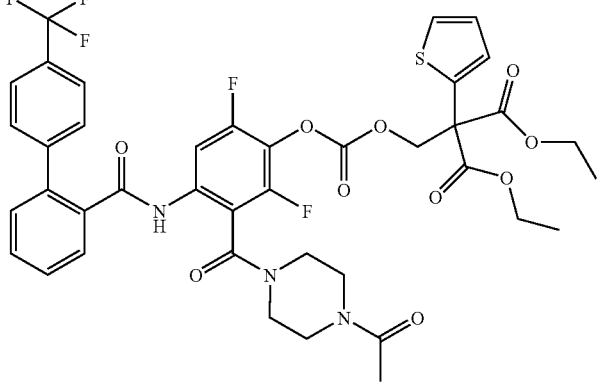 | 1.29 (6H, t, J=7.1Hz), 2.11-2.14 (3H, m), 2.94-3.86 (8H, m), 4.27-4.34 (4H, m), 4.95-5.06 (2H, m), 7.01 (1H, dd, J=9.0, 3.7Hz), 7.10-7.11 (1H, m), 7.33-7.66 (9H, m), 8.08-8.19 (1H, m), 8.82-8.91 (1H, m). |
| 2-47 | 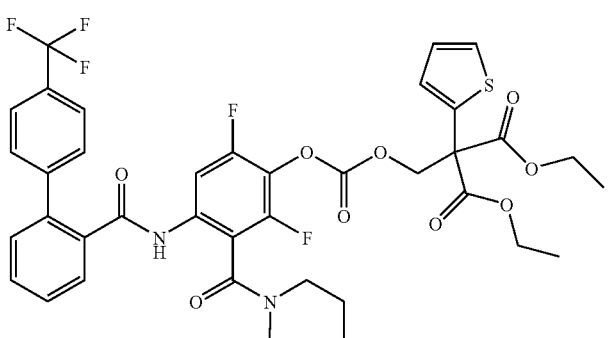 mp 158-166 | 1.29 (6H, t, J=7.1Hz), 1.45-1.96 (4H, m), 2.75-4.18 (5H, m), 4.31 (4H, q, J=7.1Hz), 4.99 (1H, d, J=10.5Hz), 5.03 (1H, d, J=10.5Hz), 6.97-7.03 (1H, m), 7.08-7.13 (1H, m), 7.32-7.70 (9H, m), 8.10-8.24 (1H, m), 8.87 (1H, d, J=8.3Hz). |

TABLE 14-continued
| Example | Structure | NMR (δ, 300MHz, CDCl₃) |
|---|---|---|
| 2-48 | 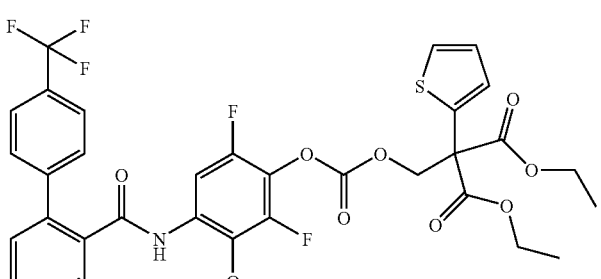 mp 147-155° C. | 1.29 (6H, t, J=7.1Hz), 3.52 (3H, s), 4.21-4.36 (4H, m), 5.00 (2H, s), 6.99-7.10 (2H, m), 7.30-7.71 (9H, m), 7.80 (1H, d, J=7.6Hz), 8.24 (1H, dd, J=12.1, 1.5Hz). |
| 2-49 | 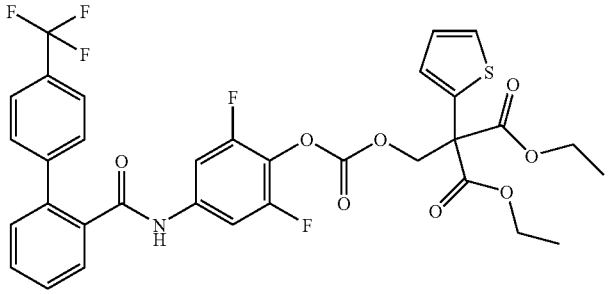 mp 160-161 | 1.29 (6H, t, J=7.1Hz), 4.29 (2H, q, J=7.1Hz), 4.31 (2H, q, J=7.1Hz), 5.00 (2H, s), 6.86-7.04 (4H, m), 7.09-7.13 (1H, m), 7.29-7.81 (9H, m). |
| 2-50 | 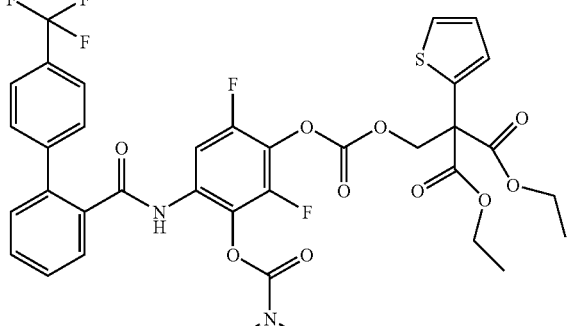 | 1.29 (6H, t, J=7.2Hz), 2.96 (3H, s), 2.99 (3H, s), 4.26-4.36 (4H, m), 5.00 (2H, s), 7.01 (1H, dd, J=5.3, 3.8Hz), 7.11 (1H, dd, J=3.8, 1.1Hz), 7.35 (1H, dd, J=5.3, 1.1Hz), 7.41-7.81 (9H, m), 8.03-8.07 (1H, m). |
TABLE 15
| Example | Structure | NMR (δ, 300MHz, CDCl₃) |
|---|---|---|
| 2-51 | 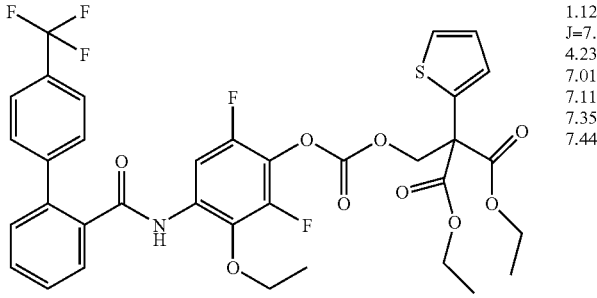 mp 113-116° C. | 1.12 (3H, t, J=7.2Hz), 1.29 (6H, t, J=7.2Hz), 3.72 (2H, q, J=7.2Hz), 4.23-4.36 (4H, m), 5.00 (2H, s), 7.01 (1H, dd, J=5.3, 3.8Hz), 7.11 (1H, dd, J=3.8, 1.1Hz), 7.35 (1H, dd, J=5.3, 1.1Hz), 7.44-7.77 (9H, m), 8.24-8.28 (1H, m). |

TABLE 15-continued

| Example | Structure | NMR (δ, 300MHz, CDCl₃) |
|---|---|---|
| 2-52 | 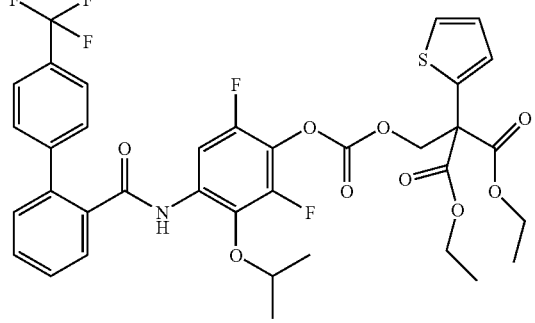 mp 103-111° C. | 1.05 (6H, d, J=6.1Hz), 1.29 (6H, t, J=7.1Hz), 4.24-4.35 (5H, m), 5.00 (2H, s), 7.01 (1H, dd, J=4.9, 3.8Hz), 7.10-7.33 (1H, m), 7.33-7.73 (10H, m), 8.24-8.27 (1H, m). |

Example 3

2-Ethoxycarbonyl-2-phenylpentanedioic acid 5-{3-dimethylcarbamoyl-4-[(4'-trifluoromethylbiphenyl-2-carbonyl)amino]phenyl}ester 1-ethyl ester a) 2-Ethoxycarbonyl-2-phenylpentanedioic acid diethyl ester

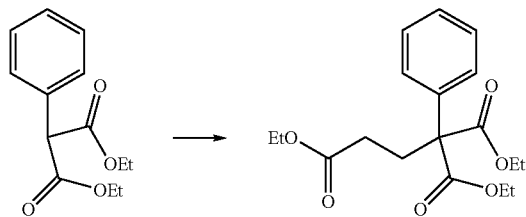

Sodium hydride (520 mg) was dissolved in THF (7 ml), and the solution was cooled to 0° C. and thereto were added diethyl 2-phenylmalonate (2.36 g) and tetrabutyl ammonium iodide (6 mg). The resulting mixture was stirred at room temperature for 0.5 hour and ethyl 3-bromopropionate (1.3 g) was added. The mixture was stirred at room temperature for 4 hours. The reaction solution was filtered through a Celite, and the filtrate was concentrated and purified by column chromatography on silica gel (ethyl acetate:hexane=1:7) to give 2-ethoxycarbonyl-2-phenylpentanedioic acid diethyl ester (2.65 g).

b) 2-Ethoxycarbonyl-2-phenylpentanedioic acid 1-ethyl ester

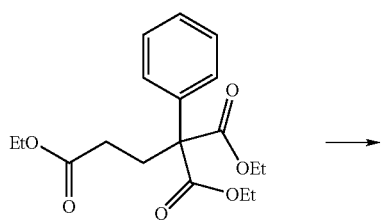

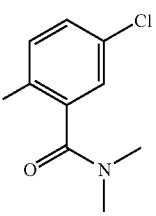

2-Ethoxycarbonyl-2-phenylpentanedioic acid diethyl ester (670 mg) was dissolved in THF (2 mL) and EtOH (2 mL), and thereto was added 1N sodium hydroxide (2 mL). The solution was stirred at room temperature for 1 hour and concentrated. The residue was acidified with 2N hydrochloric acid and extracted with ethyl acetate. The extract was washed with water and concentrated to give 2-ethoxycarbonyl-2-phenyl-pentanedioic acid 1-ethyl ester (517 mg).

c) 5-Benzyloxy-N,N-dimethyl-2-nitrobenzamide

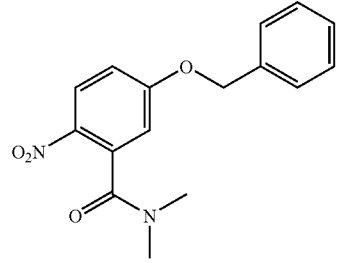

Sodium hydride (210 mg) was suspended in DMF (10 mL), and the suspension was cooled to 0° C. and thereto were added benzyl alcohol (568 mg) and a solution of 5-chloro-N,N-dimethyl-2-nitrobenzamide (1.00 g) in DMF (2 mL). The mixture was stirred at 50° C. for 0.5 hour and then concentrated. The residue was acidified with 2N hydrochloric acid and extracted with ethyl acetate. The extract was washed with water and concentrated. The residue was purified by column chromatography on silica gel (ethyl acetate:hexane=1:2→2:3) to give 5-benzyloxy-N,N-dimethyl-2-nitrobenzamide (1.18 g)

d) 2-Amino-5-benzyloxy-N,N-dimethylbenzamide

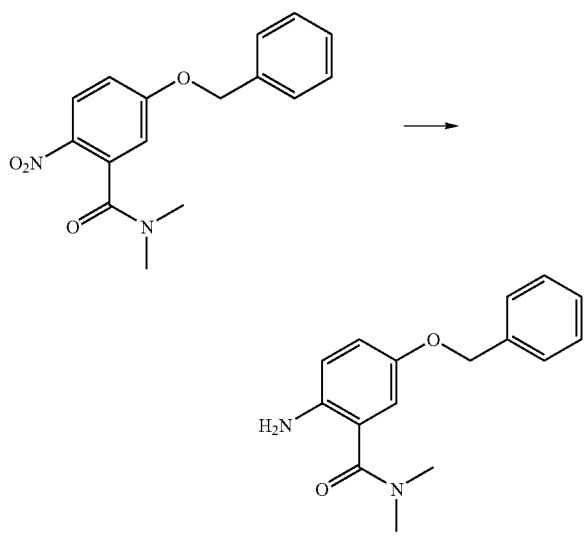

5-Benzyloxy-N,N-dimethyl-2-nitrobenzamide (1.18 g) was dissolved in a mixed solvent of THF (10 mL), EtOH (10 mL) and acetic acid (2 mL), and reduced iron (3.72 g) was added thereto, followed by stirring at 100° C. for 4.5 hours. The reaction solution was cooled and filtered through a Celite. The filtrate was concentrated and diluted with ethyl acetate. The extract was washed successively with saturated aqueous sodium bicarbonate, water and saturated brine, dried over sodium sulfate, and concentrated to give 2-amino-5-benyzloxy-N,N-dimethylbenzamide (950 mg).

e) 4'-Trifluoromethylbiphenyl-2-carboxylic acid (4-benzyloxy-2-dimethylcarbamoylphenyl)amide

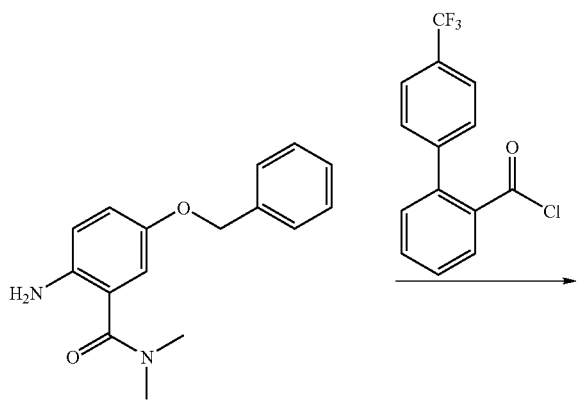

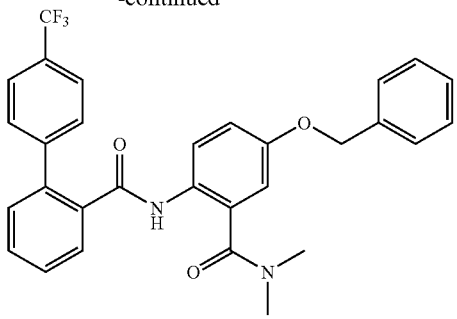

2-Amino-5-benzyloxy-N,N-dimethylbenzamide (950 mg) was dissolved in ethyl acetate (10 mL), and thereto was added triethylamine (533 mg). The solution was cooled to 0° C. and 4'-trifluoromethylbiphenyl-2-carbonyl chloride (synthesized from 0.934 g of corresponding carboxylic acid) was added. The mixture was stirred overnight at room temperature. After removal of the insoluble materials by filtration, the filtrate was concentrated and purified by column chromatography on silica gel to give 4'-trifluoromethylbiphenyl-2-carboxylic acid (4-benzyloxy-2-dimethylcarbamoylphenyl)amide (1.23 g).

f) 4'-Trifluoromethylbiphenyl-2-carboxylic acid (2-dimethylcarbamoyl-4-hydroxyphenyl)amide

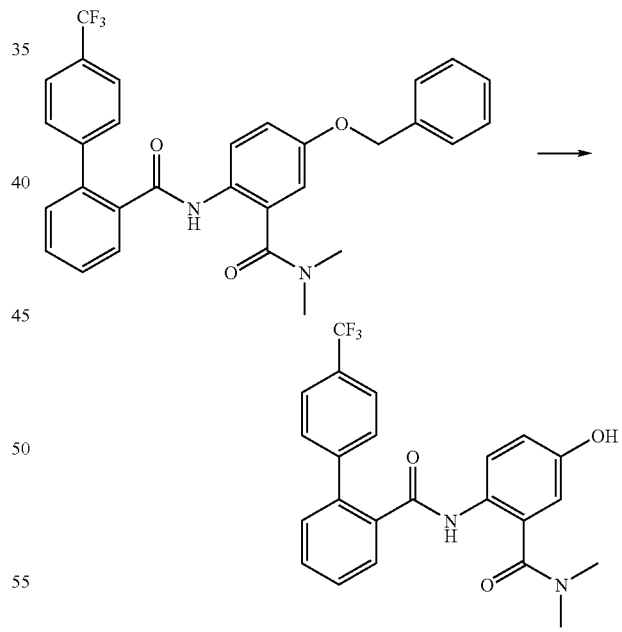

4'-Trifluoromethylbiphenyl-2-carboxylic acid (4-benzyloxy-2-dimethylcarbamoylphenyl)amide (1.2 g) was dissolved in MeOH (25 mL)-THF (25 mL), and thereto was added 7.5% palladium carbon (250 mg). The mixture was stirred for 5 hours under hydrogen atmosphere. The reaction solution was filtered through a Celite and the filtrate was concentrated to give 4'-trifluoromethylbiphenyl-2-carboxylic acid (2-dimethylcarbamoyl-4-hydroxyphenyl)amide (1.05 g).

165 g) 2-Ethoxycarbonyl-2-phenylpentanedioic acid 5-{3-dimethylcarbamoyl-4-[(4'-trifluoromethylbiphenyl-2-carbonyl)amino]phenyl}ester 1-ethyl ester

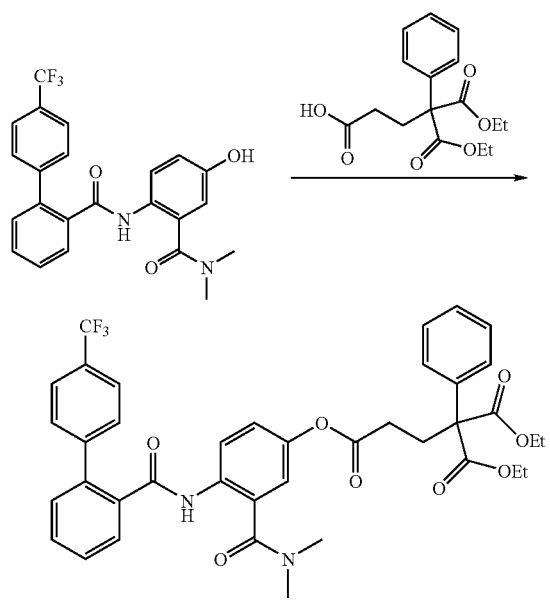

4-Dimethylaminopyridine (106 mg), 2-ethoxycarbonyl-2-phenylpenanedioic acid 1-ethyl ester (185 mg) and 4'-trifluoromethylbiphenyl-2-carboxylic acid (2-dimethylcarbamoyl-4-hydroxyphenyl)amide (214 mg) were dissolved in acetone (5 mL), and thereto was added WSC (173 mg). The mixture was stirred at room temperature for 1 day, concentrated and diluted with ethyl acetate. The extract was washed successively with saturated aqueous sodium bicarbonate, water and saturated brine, dried over sodium sulfate, concentrated and purified by column chromatography on silica gel (ethyl acetate:hexane=1:1) 2-ethoxycarbonyl-2-phenylpentanedioic acid 5-{3-dimethylcarbamoyl-4-[(4'-trifluoromethylbiphenyl-2-carbonyl)amino]phenyl}ester 1-ethyl ester (0.240 g).

Example 3-2

2-(2-{3-Dimethylcarbamoyl-4-[(4'-trifluoromethylbiphenyl-2-carbonyl)amino]phenoxy}acetoxymethyl)-2-phenylmalonic acid diethyl ester a) {3-Dimethylcarbamoyl-4-[(4'-trifluoromethylbiphenyl-2-carbonyl)amino]phenoxy}acetic acid benzyl ester

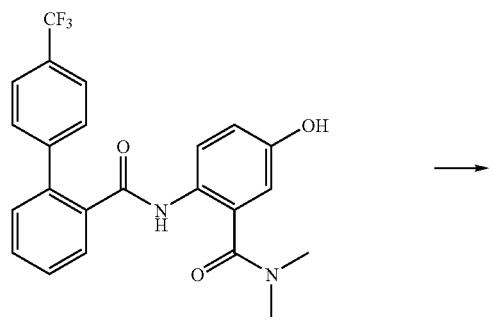

166

-continued

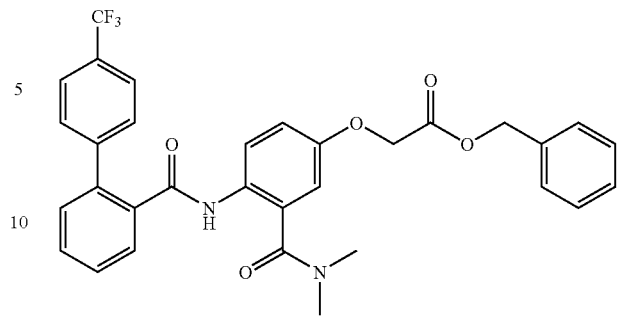

Sodium hydride (34 mg) was dissolved in THF (9 ml), and the solution was cooled to 0° C. and thereto were added 4'-trifluoromethylbiphenyl-2-carboxylic acid (2-dimethylcarbamoyl-4-hydroxyphenyl)amide (300 mg) and tetrabutyl ammonium iodide (10 mg). After addition of benzyl bromoacetate (160 mg), the resulting mixture was stirred at 40° C. for 1 hour. The mixture was stirred at room temperature for 4 hours. The reaction solution was filtered through a Celite, and the filtrate was concentrated and purified by column chromatography on silica gel (ethyl acetate:hexane=1:1) to give {3-dimethylcarbamoyl-4-[(4'-trifluoromethylbiphenyl-2-carbonyl)amino]phenoxy}acetic acid benzyl ester (226 mg).

b) {3-Dimethylcarbamoyl-4-[(4'-trifluoromethylbiphenyl-2-carbonyl)amino]phenoxy}acetic acid

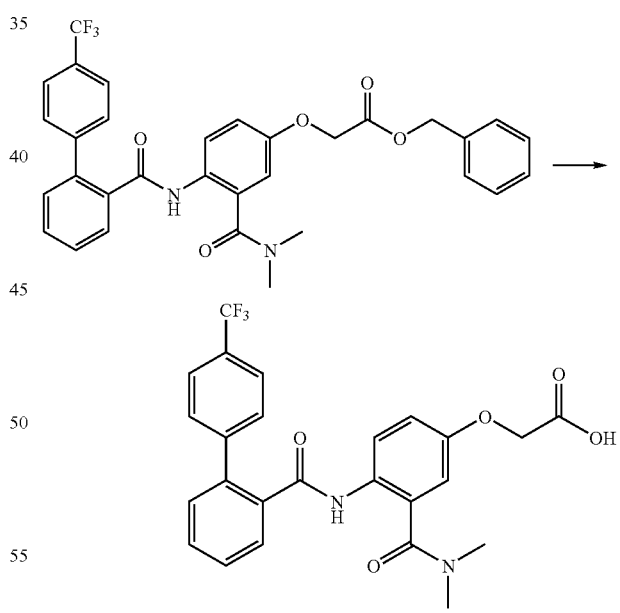

{3-Dimethylcarbamoyl-4-[(4'-trifluoromethylbiphenyl-2-carbonyl)amino]phenoxy}acetic acid benzyl ester (260 mg) was dissolved in ethyl acetate (5 mL), and thereto was added 7.5% palladium carbon (250 mg). The mixture was stirred for 1 hour under hydrogen atomosphere. The reaction solution was filtered through a Celite and the filtrate was concentrated to give {3-dimethylcarbamoyl-4-[(4'-trifluoromethylbiphenyl-2-carbonyl)amino]phenoxy}acetic acid (118 mg).

c) 2-(2-{3-Dimethylcarbamoyl-4-[(4'-trifluoromethylbiphenyl-2-carbonyl)amino]phenoxy}acetoxymethyl)-2-phenylmalonic acid diethyl ester

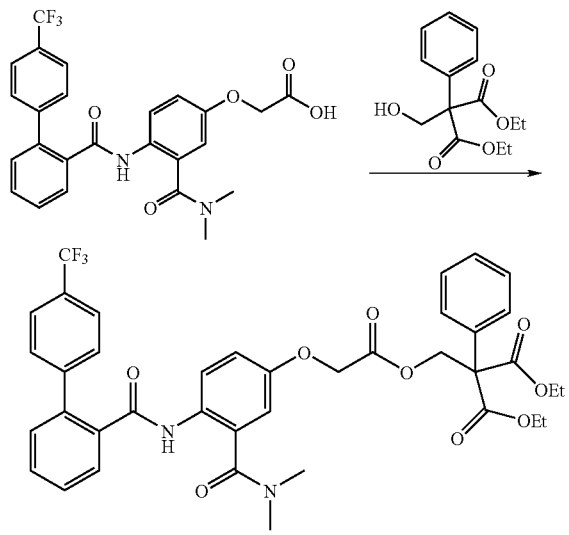

4-Dimethylaminopyridine (53 mg), 2-hydroxymethyl-2-phenylmalonic acid diethyl ester (116 mg) and {3-dimethylcarbamoyl-4-[(4'-trifluoromethylbiphenyl-2-carbonyl)amino]phenoxy}acetic acid (176 mg) were dissolved in acetone (5 mL), and to the solution was added WSC (104 mg). The mixture was stirred at room temperature for 3 hours and then concentrated. The residue was purified by column chromatography on silica gel (ethyl acetate:hexane=1:1) to give 2-(2-{3-dimethylcarbamoyl-4-[(4'-trifluoromethylbiphenyl-2-carbonyl)amino]phenoxy}acetoxymethyl)-2-phenylmalonic acid diethyl ester (133 mg) as a colorless solid (m.p. 132-138° C.).

Example 3-3

3-(2,2'-Bisethylcarbamoyl-2-phenylethoxy)propionic acid 3-dimethylcarbamoyl-4-[(4'-trifluoromethylbiphenyl-2-carbonyl)amino]phenyl ester a) 3-(2,2'-Bisethylcarbamoyl-2-phenylethoxy)propionic acid methyl ester

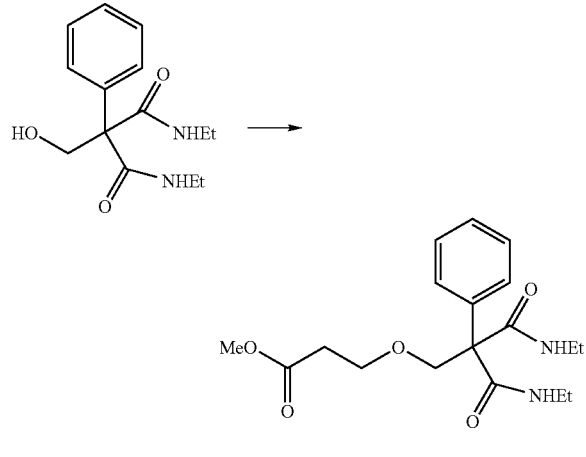

Sodium hydride (89 mg) was dissolved in THF (5 ml), and the solution was cooled to 0° C. and thereto were added a THF solution (1 ml) of N,N'-diethyl-2-hydroxymethyl-2-phenylmalonamide (400 mg) and tetrabutyl ammonium iodide (10 mg). After addition of a THF solution (2 mL) of methyl 3-bromopropionate (314 mg), the resulting mixture was stirred overnight at room temperature, and further at 60° C. for 0.5 hour. The reaction solution was filtered through a Celite, and the filtrate was concentrated and purified by column chromatography on silica gel (ethyl acetate:hexane=1:1) to give 3-(2,2'-bisethylcarbamoyl-2-phenylethoxy)propionic acid methyl ester (175 mg).

b) 3-(2,2'-Bisethylcarbamoyl-2-phenylethoxy)propionic acid

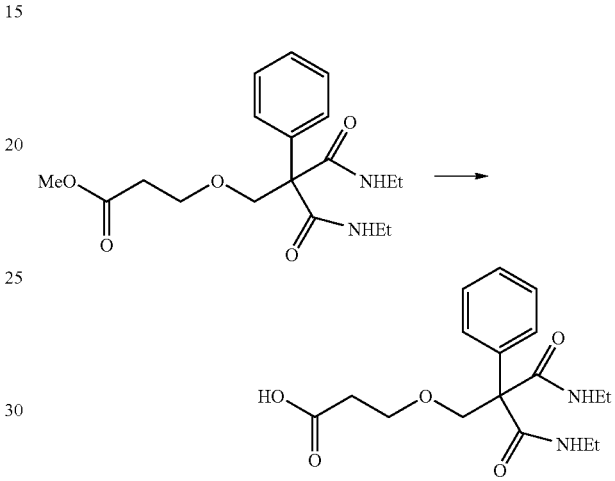

3-(2,2'-Bisethylcarbamoyl-2-phenylethoxy)propionic acid methyl ester (125 mg) was dissolved in THF (0.5 mL) and MeOH (0.5 mL), and 1N sodium hydroxide (0.5 mL) was added thereto. The solution was stirred at room temperature for 1 hour and then concentrated. The residue was acidified with 1N hydrochloric acid and extracted with ethyl acetate. The extract was washed with water and concentrated to give 3-(2,2'-bisethylcarbamoyl-2-phenylethoxy)propionic acid (115 mg).

c) 3-(2,2'-Bisethylcarbamoyl-2-phenylethoxy)propionic acid 3-dimethylcarbamoyl-4-[(4'-trifluoromethylbiphenyl-2-carbonyl)amino]phenyl ester

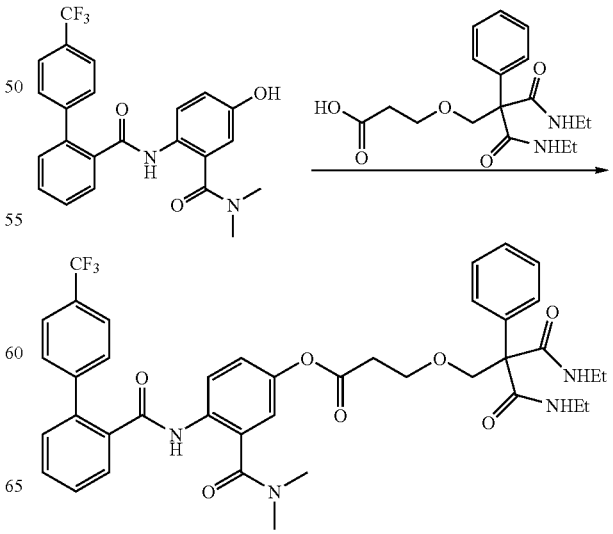

4-Dimethylaminopyridine (55 mg), 3-(2,2'-bisethylcarbamoyl-2-phenylethoxy)propionic acid (115 mg) and 4'-trifluoromethylbiphenyl-2-carboxylic acid (2-dimethylcarbamoyl-4-hydroxyphenyl)amide (161 mg) were dissolved in acetone (5 mL), and thereto was added WSC (86 mg). The mixture was stirred at room temperature for 3 hours and then concentrated. The residue was purified by column chromatography on silica gel (ethyl acetate:hexane=4:1→1:0) to give 3-(2,2'-bisethylcarbamoyl-2-phenylethoxy)propionic acid 3-dimethylcarbamoyl-4-[(4'-trifluoromethylbiphenyl-2-carbonyl)amino]phenyl ester (150 mg).

Examples 3-4 to 3-24

Compounds of Exampes 3-4 to 3-24 shown in Tables 16 to 20 were prepared in a similar manner to Example 3, 3-2 or 3-3, or by the conventional method.

TABLE 16

| Example | Structure | NMR (δ, 300MHz, CDCl₃) |
| --- | --- | --- |
| 3 | 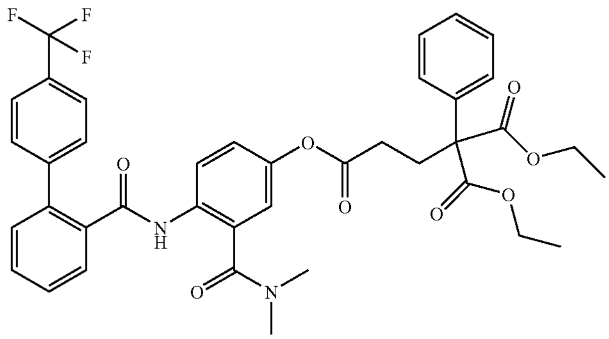 | 1.28 (6H, t, J=7.5Hz), 2.48-2.78 (4H, m), 2.92 (6H, brs), 4.27 (4H, q, J=7.5Hz), 6.90-6.96 (1H, m), 7.04-7.13 (1H, m), 7.23-7.73 (13H, m), 8.42 (1H, d, J=9.0Hz), 9.15 (1H, brs). |
| 3-2 | mp 132-138 | 1.24 (6H, t, J=7.0Hz), 2.82 (3H, brs), 2.93 (3H, brs), 4.24 (4H, q, J=7.0Hz), 4.51 (2H, s), 4.93 (2H, s), 6.69 (1H, d, J=2.4Hz), 6.84 (1H, dd, J=2.4Hz, J=9.0Hz), 7.28-7.70 (13H, m), 8.23 (1H, d, J=9.0Hz), 8.82 (1H, brs). |
| 3-3 | 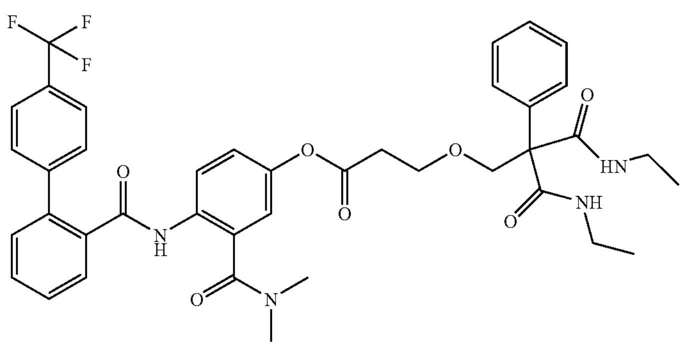 | 1.09 (6H, t, J=7.3Hz), 2.80 (2H, t, J=5.8Hz), 2.88 (3H, brs), 2.94 (3H, brs), 3.28 (2H, q, J=7.3Hz), 3.30 (2H, q, J=7.3Hz), 3.84 (2H, t, J=5.8Hz), 4.07-4.17 (4H, m), 6.92 (1H, d, J=2.9Hz), 7.07 (1H, dd, J=2.9Hz, J=9.0Hz), 7.22-7.82 (15H, m), 8.43 (1H, d, J=9.0Hz), 9.12 (1H, brs). |

TABLE 16-continued
| Example | Structure | NMR (δ, 300MHz, CDCl₃) |
|---|---|---|
| 3-4 | 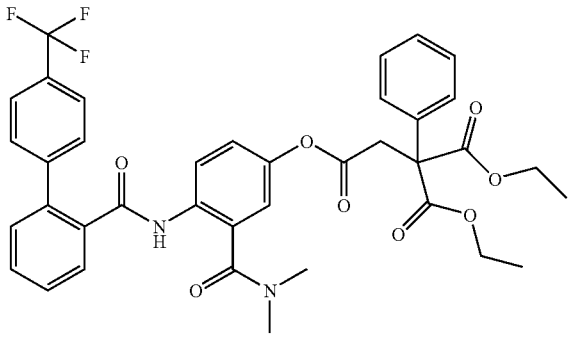 mp 139-142 | 1.24 (6H, t, J=7.4Hz), 2.86 (3H, brs), 2.92 (3H, brs), 3.51 (2H, s), 4.20-4.34 (4H, m), 6.93 (1H, d, J=2.6Hz), 7.08 (1H, dd, J=2.6Hz, J=9.0Hz), 7.29-7.71 (13H, m), 8.41 (1H, d, J=9.0Hz), 9.14 (1H, brs). |
| 3-5 | 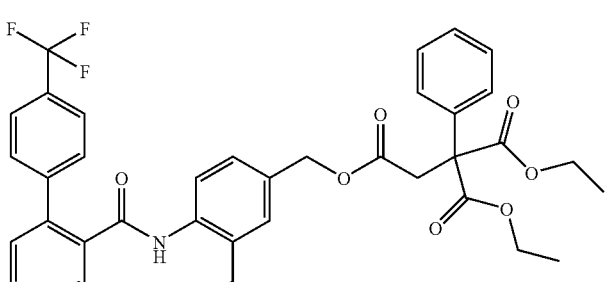 mp 116-119 | 1.20 (6H, t, J=7.0Hz), 2.80 (3H, brs), 2.94 (3H, brs), 3.34 (2H, s), 4.20 (2H, q, J=7.0Hz), 4.21 (2H, q, J=7.0Hz), 5.04 (2H, s), 7.14 (1H, d, J=1.7Hz), 7.27-7.57 (9H, m), 7.61 (4H, s), 7.70 (1H, dd, J=1.7Hz, J=8.3Hz), 8.41 (1H, d, J=8.3Hz), 9.19 (1H, brs). |
TABLE 17
| Example | Structure | NMR (δ, 300MHz, CDCl₃) |
|---|---|---|
| 3-6 | 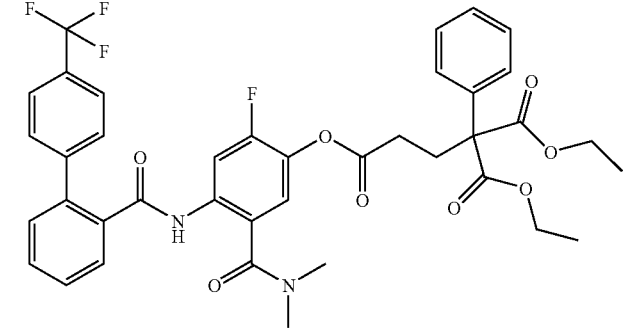 | 1.25 (6H, t, J=7.1Hz), 2.57-2.61 (2H, m), 2.69-2.73 (2H, m), 2.89 (6H, brs), 4.20-4.28 (4H, m), 6.93 (1H, d, J=7.9Hz), 7.26-7.62 (12H, m), 7.69 (1H, dd, J=7.6, 1.4Hz), 8.43 (1H, d, J=12.5Hz), 9.39 (1H, s). |
| 3-7 | 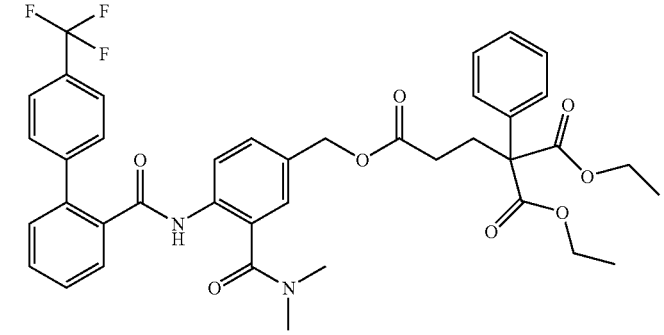 | 1.23 (6H, t, J=7.1Hz), 2.29-2.33 (2H, m), 2.58-2.62 (2H, m), 2.83 (3H, brs), 2.94 (3H, brs), 4.17-4.25 (4H, m), 4.98 (2H, s), 7.13 (1H, d, J=2.1Hz), 7.26-7.39 (7H, m), 7.47-7.69 (7H, m), 8.38 (1H, d, J=8.3Hz), 9.15 (1H, s). |

TABLE 17-continued

| Example | Structure | NMR (δ, 300MHz, CDCl₃) |
|---|---|---|
| 3-8 | 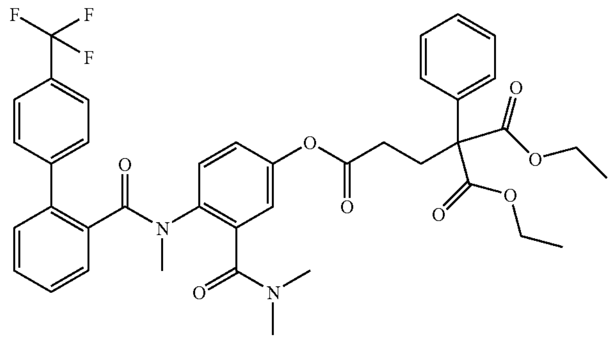 | 1.24-1.28 (6H, m), 2.50-2.58 (2H, m), 2.65-2.73 (2H, m), 2.92-3.26 (9H, m), 4.21-4.31 (4H, m), 6.60-6.73 (2H, m), 7.00-7.13 (2H, m), 7.30-7.52 (8H, m), 7.62-7.72 (4H, m). |
| 3-9 | mp 105-108 | 1.26 (6H, t, J=7.1Hz), 2.61-2.73 (4H, m), 2.76 (3H, d, J=3.4Hz), 2.95 (3H, s), 4.23-4.29 (4H, m), 7.31-7.68 (13H, m), 8.26 (1H, d, J=10.9Hz), 8.91 (1H, s). |
| 3-10 | 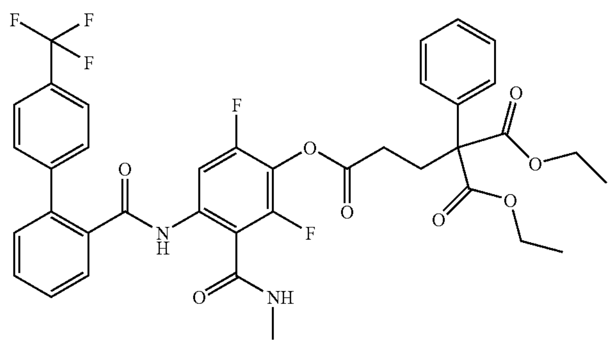 | 1.24-1.29 (6H, m), 2.34-2.39 (1H, m), 2.60-2.73 (3H, m), 2.87-2.89 (3H, m), 4.20-4.32 (4H, m), 6.47 (1H, brs), 7.31-7.73 (13H, m), 8.37-8.54 (1H, m), 11.36-11.69 (1H, m). |

TABLE 18

| Example | Structure | NMR (δ, 300MHz, CDCl₃) |
|---|---|---|
| 3-11 | mp 104-108° C. | 1.26 (6H, t, J=7.2Hz), 2.59-2.74 (4H, m), 2.88 (3H, s), 2.95 (3H, s), 4.22-4.29 (4H, m), 6.86 (1H, s), 7.28-7.73 (13H, m), 8.71 (1H, s), 9.38 (1H, s). |

TABLE 18-continued

| Example | Structure | NMR (δ, 300MHz, CDCl$_3$) |
|---|---|---|
| 3-12 | 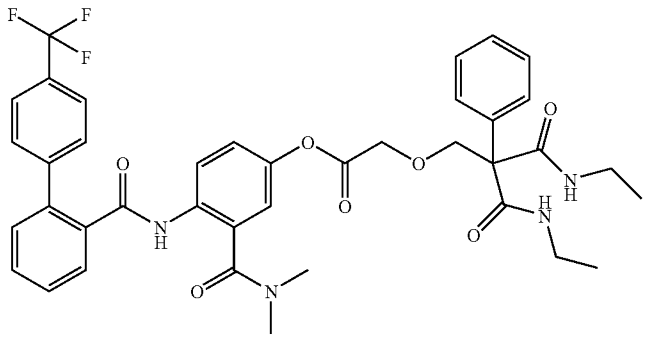 | 1.15 (6H, t, J=7.3Hz), 2.89 (3H, brs), 2.94 (3H, brs), 3.36 (2H, q, J=7.3Hz), 3.38 (2H, q, J=7.3Hz), 4.19 (2H, s), 4.39 (2H, s), 6.95 (1H, d, J=2.8Hz), 7.14 (1H, dd, J=2.8Hz, J=8.8Hz), 7.23-7.72 (13H, m), 8.20 (2H, t, J=4.8Hz), 8.46 (1H, d, J=8.8Hz), 9.13 (1H, brs). |
| 3-13 | 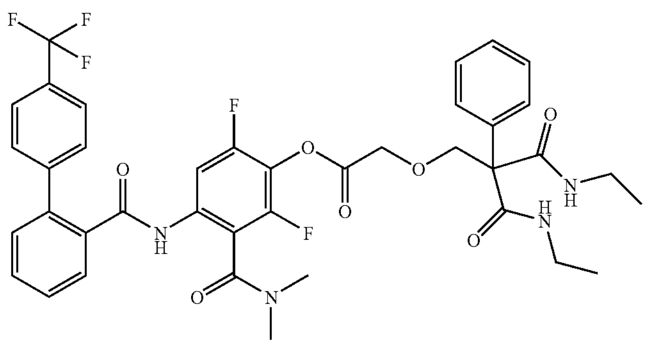 | 1.15 (6H, t, J=7.1Hz), 2.77 (3H, d, J=3.4Hz), 2.97 (3H, s), 3.32-3.41 (4H, m), 4.19 (1H, d, J=12.8Hz), 4.23 (1H, d, J=12.8Hz), 4.50 (2H, s), 7.28-7.69 (13H, m), 8.08-8.09 (2H, m), 8.31 (1H, dd, J=12.0, 1.8Hz), 8.93 (1H, s). |
| 3-14 | 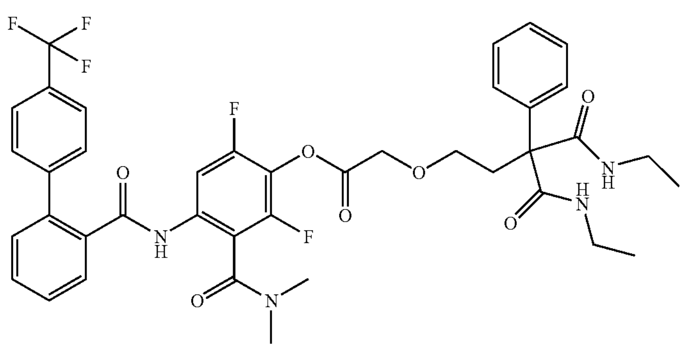 | 1.11 (6H, t, J=7.1Hz), 2.63 (2H, t, J=6.4Hz), 2.77 (3H, d, J=3.0Hz), 2.96 (3H, s), 3.25-3.34 (4H, m), 3.69 (2H, t, J=6.4Hz), 4.35 (2H, s), 7.28-7.69 (15H, m), 8.27-8.32 (1H, m), 8.94 (1H, s). |
| 3-15 | 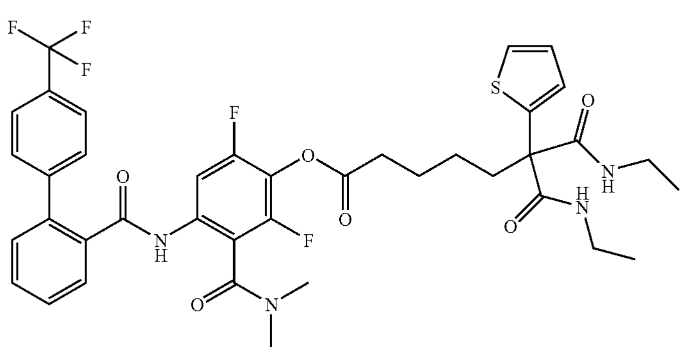 | 1.09 (6H, t, J=7.1Hz), 1.36-1.43 (2H, m), 1.77 (2H, tt, J=7.5, 7.5Hz), 2.36-2.42 (2H, m), 2.59 (2H, t, J=7.5Hz), 2.77 (3H, d, J=3.4Hz), 2.95 (3H, s), 3.27 (4H, dt, J=7.1, 7.1Hz), 6.85-7.04 (4H, m), 7.30-7.69 (9H, m), 8.27 (1H, dd, J=12.1, 1.5Hz), 8.92 (1H, s). |

TABLE 19
| Example | Structure | NMR (δ, 300MHz, CDCl₃) |
|---------|-----------|------------------------|
| 3-16 | 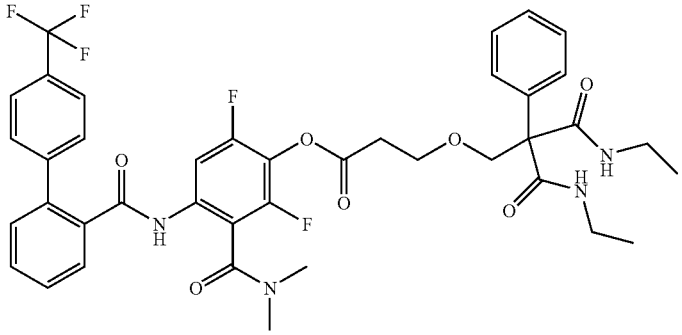 | 1.10 (6H, t, J=7.1Hz), 2.76 (3H, d, J=3.3Hz), 2.88 (2H, d, J=3.3Hz), 2.96 (3H, brs), 3.21-3.38 (4H, m), 3.86 (2H, t, J=5.6Hz), 4.10 (2H, t, J=5.8Hz), 7.20-7.71 (15H, m), 7.78 (2H, t, J=4.8Hz), 8.29 (1H, dd, J=1.8Hz, J=12.0Hz), 8.90 (1H, brs). |
| 3-17 | 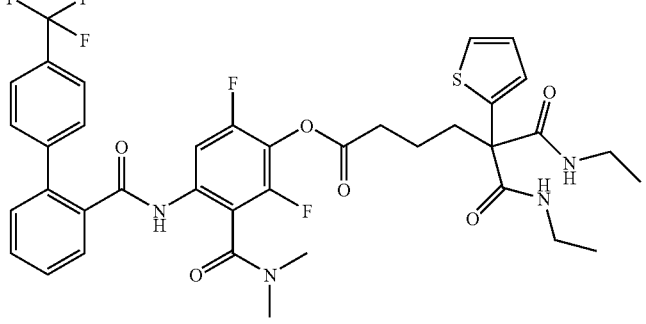 | 1.10 (6H, t, J=7.2Hz), 1.66-1.76 (2H, m), 2.42-2.47 (2H, m), 2.68 (2H, t, J=6.4Hz), 2.77 (3H, d, J=3.3Hz), 2.96 (3H, s), 3.28 (4H, dt, J=7.2, 7.2Hz), 6.97-7.29 (5H, m), 7.39-7.68 (8H, m), 8.28 (1H, d, J=12.0Hz), 8.92 (1H, s). |
| 3-18 | 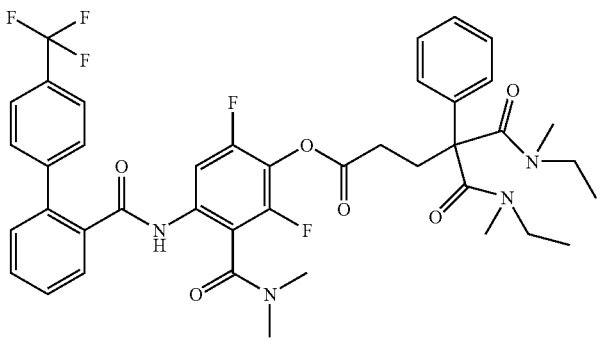 | 1.18-1.27 (6H, m), 2.40-2.58 (4H, m), 2.73 (3H, d, J=3.4Hz), 2.87-2.97 (9H, m), 3.22-3.53 (4H, m), 7.27-7.67 (13H, m), 8.20-8.24 (1H, m), 8.90 (1H, s). |
| 3-19 | 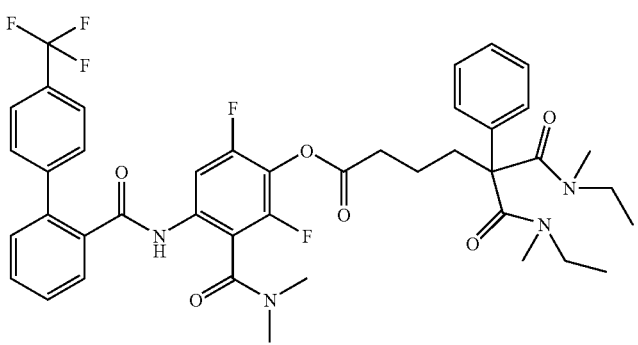 | 0.80-1.15 (6H, m), 1.45-1.20 (2H, m), 2.18-2.70 (2H, m), 2.51 (2H, t, J=6.7Hz), 2.75 (3H, d, J=3.4Hz), 2.84-2.95 (9H, m), 3.20-3.55 (4H, m), 7.21-7.68 (13H, m), 8.24 (1H, dd, J=12.1, 1.5Hz), 8.91 (1H, s). |

TABLE 19-continued
| Example | Structure | NMR (δ, 300MHz, CDCl₃) |
|---|---|---|
| 3-20 | 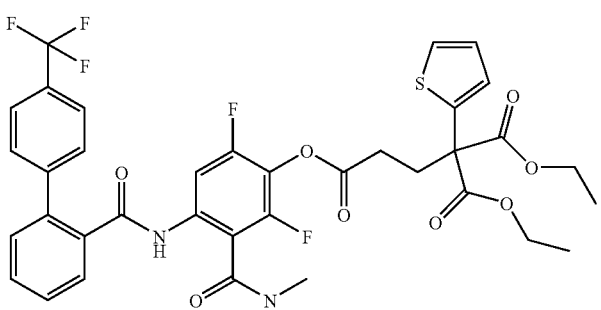 mp 100-107° C. | 1.27 (6H, t, J=7.2Hz), 2.23-2.40 (11H, m), 6.97-7.09 (2H, m), 7.32-7.68 (9H, m), 8.24-8.28 (1H, m), 8.92 (1H, s). |
TABLE 20
| Example | Structure | NMR (δ, 300MHz, CDCl₃) |
|---|---|---|
| 3-21 | 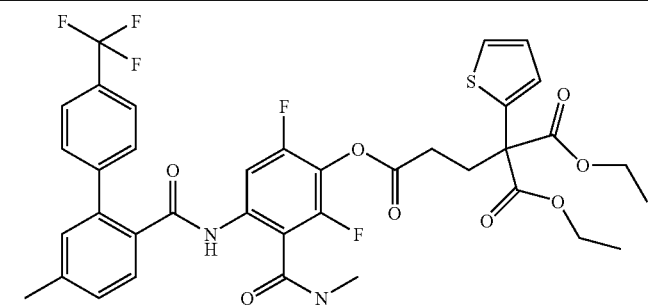 mp 109-116° C. | 1.27 (6H, t, J=7.2Hz), 2.25-4.20 (10H, m), 4.23-4.30 (4H, m), 6.97-7.09 (2H, m), 7.20-7.33 (3H, m), 7.54-7.65 (5H, m), 8.24-8.28 (1H, m), 8.89 (1H, s). |
| 3-22 | 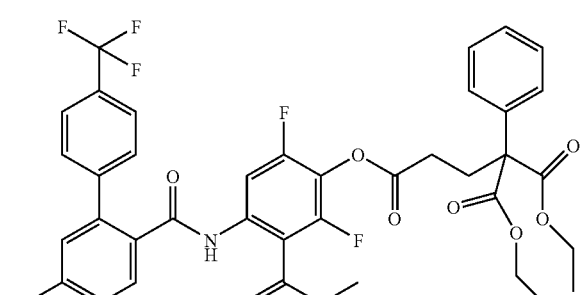 mp 127-130° C. | 1.26 (6H, t, J=7.2Hz), 2.44 (3H, s), 2.62-2.73 (4H, m), 2.76 (3H, d, J=3.4Hz), 2.95 (3H, s), 4.21-4.31 (4H, m), 7.20-7.37 (7H, m), 7.54-7.65 (5H, m), 8.26 (1H, dd, J=11.6, 1.5Hz), 8.89 (1H, s). |
| 3-23 | 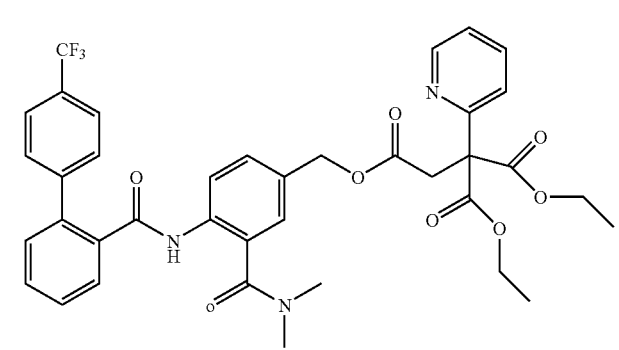 | 1.21 (6H, t, J=7.2Hz), 2.78 (3H, brs), 2.94 (3H, brs), 3.50 (2H, s), 4.21 (4H, q, J=7.2Hz), 5.04 (2H, s), 7.11-7.19 (2H, m), 7.30-7.73 (11H, m), 8.32-8.42 (2H, m), 9.19 (1H, brs). |

TABLE 20-continued

| Example | Structure | NMR (δ, 300MHz, CDCl₃) |
|---|---|---|
| 3-24 | 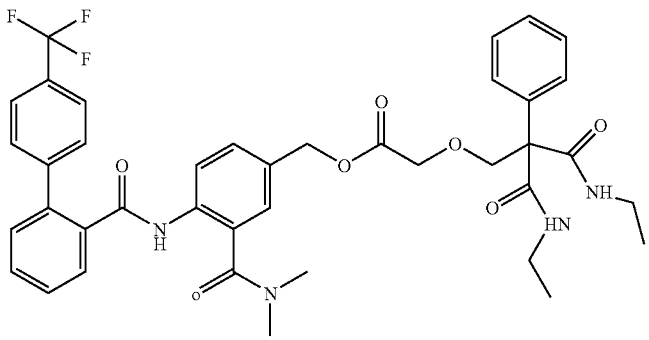 | 1.18 (6H, t, J=7.3Hz), 2.84 (3H, brs), 2.94 (3H, brs), 3.37 (2H, q, J=7.3Hz), 3.39 (2H, q, J=7.3Hz), 4.10 (2H, s), 4.15 (2H, s), 5.11 (2H, s), 7.15 (1H, d, J=1.9Hz), 7.21-7.73 (14H, m), 8.30 (2H, t, J=4.7Hz), 8.43 (1H, d, J=9.0Hz), 9.13 (1H, brs). |

Example 4

Compounds shown in the following Tables 21 to 23 can be prepared similarly according to the procedures of Examples 1 to 3.

TABLE 21

| No. | Structure |
|---|---|
| 1 | 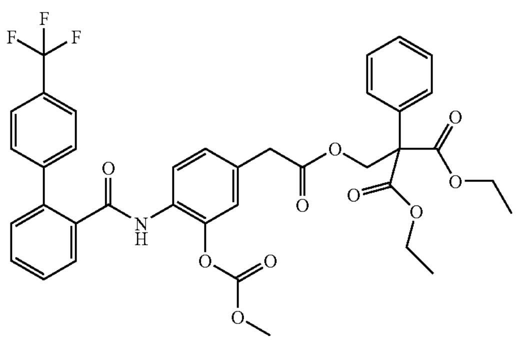 |
| 2 | 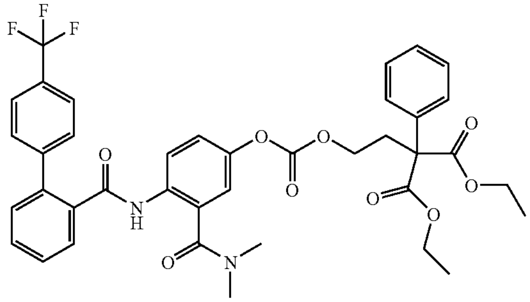 |
| 3 | |
| 4 | |

TABLE 21-continued

| No. | Structure |
|-----|-----------|
| 5 | 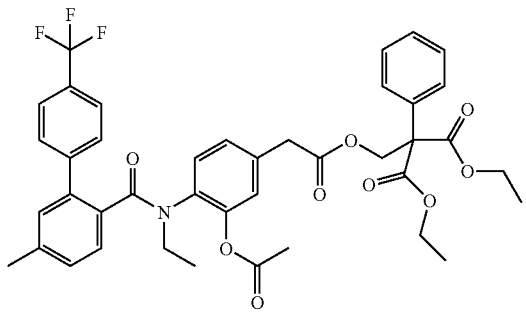 |
| 6 | 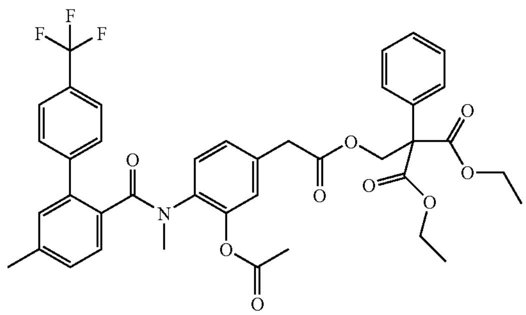 |
| 7 | 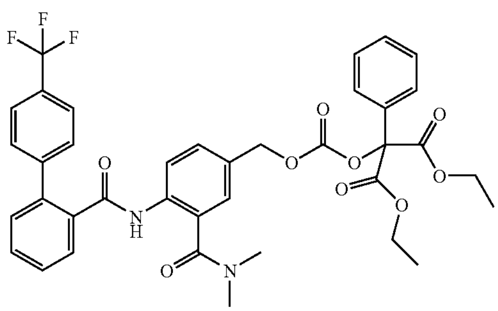 |
| 8 | 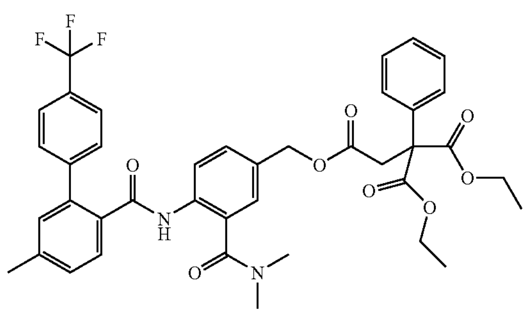 |
| 9 | 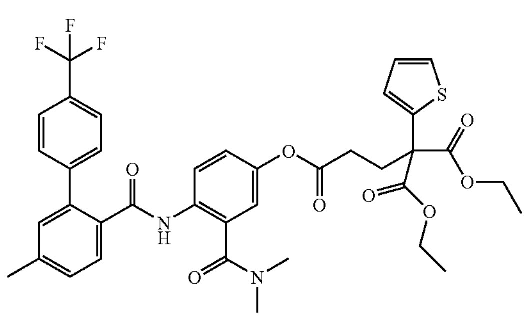 |
| 10 | |

TABLE 22

| No. | Structure |
|-----|-----------|
| 11 | 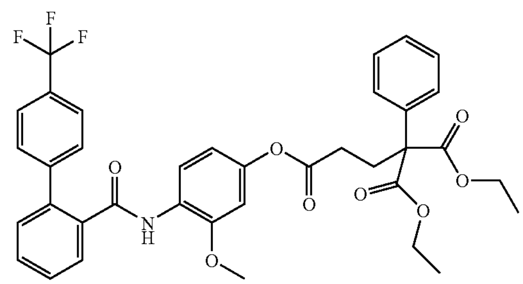 |
| 12 | 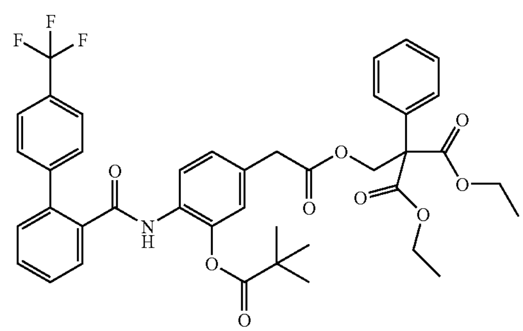 |
| 13 | 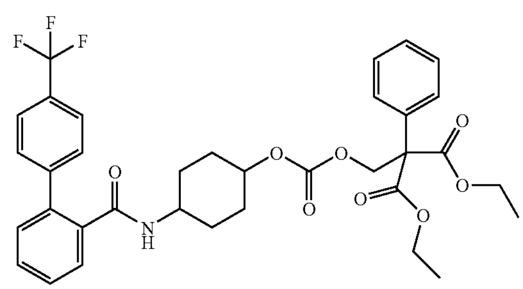 |
| 14 | 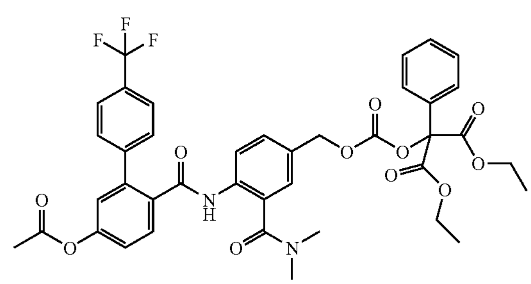 |

185
TABLE 22-continued
| No. | Structure |
|---|---|
| 15 | 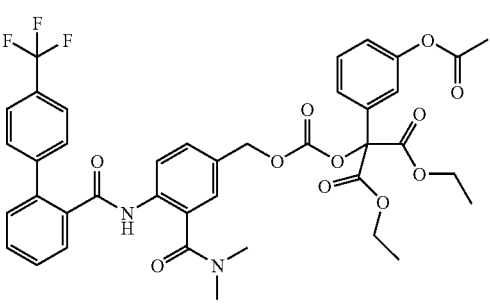 |
| 16 | 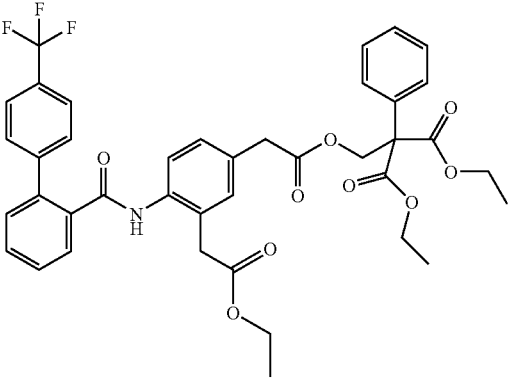 |
TABLE 23
| No. | Structure |
|---|---|
| 17 | 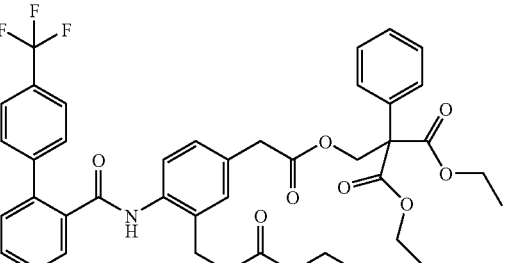 |
| 18 | 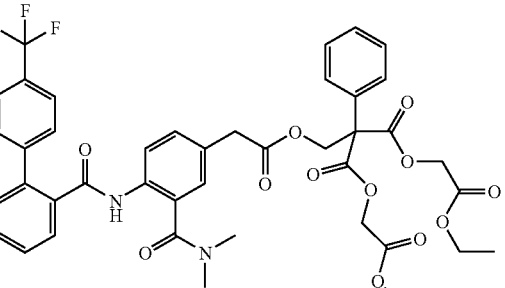 |
186
TABLE 23-continued
| No. | Structure |
|---|---|
| 19 | 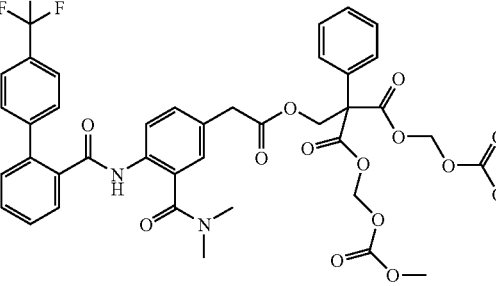 |
| 20 | 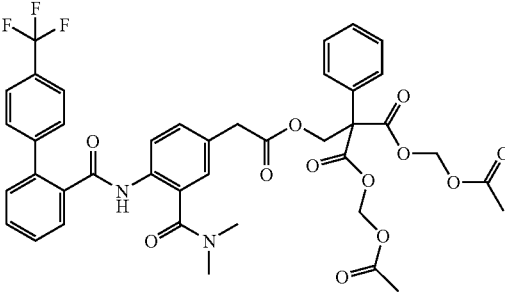 |
| 21 | 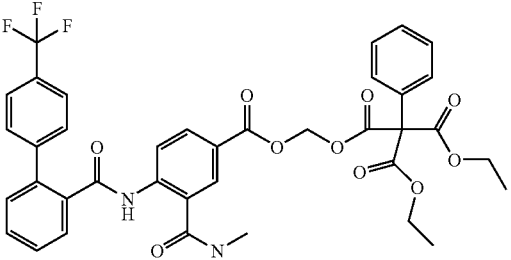 |
| 22 | 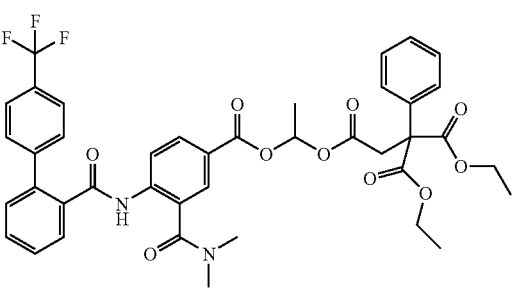 |
| 23 | 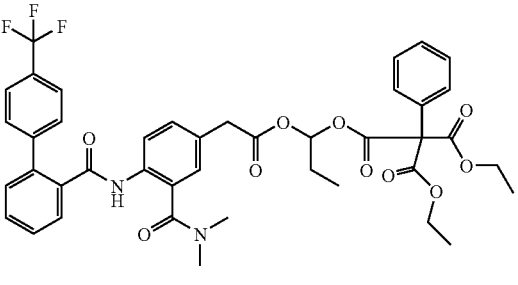 |

TABLE 23-continued

| No. | Structure |
|---|---|
| 24 | (structure) |
| 25 | (structure) |
| 26 | (structure) |

Formulation

Hereinafter, the present invention will be illustrated specifically by references of formulations.

Formulation 1

A film with a controlled thickness was prepared by use of a gelatin shell composition (a) in accordance with the conventional method. Two sheets of the film were inserted into a rotating left-right symmetric metallic die rolls and molded into outer shells of soft capsules, while a filling solution (b) was injected into the outer shells of the soft capsules, and simultaneously the outer shells of the soft capsules were melted and sealed by the rotation of the die rolls, then the capsules were cut from the film. The capsules were dried in a rotary dryer, and allowed to dry for 4 days to give soft capsules. Hereinafter, specific examples of formulations were given.

Formulation 1-1

(a) film composition

| | |
|---|---|
| gelatin | 100 parts |
| sugar alcohol solution derived from corn starch | 30 parts |
| purified water | 100 parts |

(b) filling solution (per capsule)

| | |
|---|---|
| compound of Example 1-3 | 5 mg |
| propylene glycol fatty acid ester | 295 mg |
| ethanol | 105 mg |

Formulation 1-2

(a) film composition

| | |
|---|---|
| gelatin | 100 parts |
| sugar alcohol solution derived from corn starch | 30 parts |
| purified water | 100 parts |

(b) filling solution (per capsule)

| | |
|---|---|
| compound of Example 2-5 | 5 mg |
| propylene glycol fatty acid ester | 291 mg |
| ethanol | 104 mg |

Formulation 1-3

(a) film composition

| | |
|---|---|
| gelatin | 100 parts |
| sugar alcohol solution derived from corn starch | 30 parts |
| purified water | 100 parts |

(b) filling solution (per capsule)

| | |
|---|---|
| compound of Example 2-5 | 5 mg |
| propylene glycol fatty acid ester | 277 mg |
| ethanol | 148 mg |

Formulation 2

The compound of Example 2-22, an excipient and a binder were mixed in a usual method to prepare granulated powder. The powder obtained was blended with a disintegrator and a lubricant to prepare a powder for tablets in a usual method. The powder was compressed to give tablets in a usual method. Specific examples of formulations were hereinafter given.

Formulation 2-1

| | |
|---|---|
| compound of Example 2-22 | 5 mg |
| lactose | 133.06 mg |
| crystalline cellulose | 18 mg |
| hydroxypropyl methylcellulose 2910 | 5.4 mg |
| crospovidone | 18 mg |
| magnesium stearate | 0.54 mg |

Formulation 2-2

| compound of Example 2-22 | 5 mg |
| --- | --- |
| lactose | 92.44 mg |
| corn starch | 15 mg |
| hydroxypropyl methylcellulose 2910 | 3.6 mg |
| carboxymethyl starch | 3.6 mg |
| magnesium stearate | 0.36 mg |

Formulation 2-3

| compound of Example 2-22 | 5 mg |
| --- | --- |
| D-mannitol | 158.4 mg |
| hydroxypropyl methylcellulose 2910 | 6 mg |
| calcium silicate | 20 mg |
| crospovidone | 10 mg |
| magnesium stearate | 0.6 mg |

Pharmacological Test

Test Example 1

Inhibition of Interliposomal Triglyceride (TG) Transfer Activity by MTP

Microsomal triglyceride transfer protein (MTP) from bovine liver was partially purified in such a way described below. A buffer (50 mM Tris, 250 mM sucrose, 1 mM EDTA, 0.02% NaN$_3$ (pH 7.4)) for making a homogenate preparation was added to bovine liver, and the mixture was homogenated under ice-cooling, then centrifuged at 10,000×g (4° C., 30 minutes) The supernatant was adjusted to pH 5.1 with hydrochloric acid, and stirred for 30 minutes. The solution was further centrifuged at 10,000×g (4° C., 30 minutes), and 1 mM Tris buffer was added to the precipitated residue, and the mixture was adjusted to pH 8.6 with sodium hydroxide. After addition of 2.7 M ammonium sulfate solution, the mixture was stirred for 30 minutes, then centrifuged at 10,000×g (4° C., 40 minutes). The resulting supernatant was served as a crude extraction fraction of MTP and stored at −80° C. under freezing. In its practical use, the crude extraction fraction of MTP was purified by column chromatography on diethylaminoethyl (DEAE) Sepharose using FPLC (Fast Performance Liquid Chromatography) system, and the purified MTP was used for the test.

Small unilamellar-vesicle (SUV) liposome (donor, 0.25 mol % triolein, 5 mol % cardiolipin) labeled with $^{14}$C-triolein and non-labeled SUV liposome (acceptor, 0.25 mol % triolein) were prepared. A fixed amount of donor and acceptor, and MTP were mixed with a sample dissolved in DMSO or with DMSO. The mixture was incubated in a 15 mM Tris hydrochloride buffer (pH 7.4) containing 40 mM sodium chloride, 1 mM EDTA (ethylenediaminetetraacetic acid), 0.02% NaN$_3$ and 0.5% bovine serum albumin at 37° C. for one hour. After completion of the incubation, a suspension of DEAE cellulose (50% v/v) in 15 mM Tris hydrochloride buffer (pH 7.4) was added to the above solution, and the mixture was centrifuged to separate the donor and the acceptor. The radioactivity in the acceptor was measured by liquid scintillation counter. The value obtained by subtracting the radioactivity in the blank from the amount of radioactivity in the acceptor of a DMSO group was determined as MTP-mediated TG transfer activity, and it was compared with the value obtained by subtracting the radioactivity in the blank from the radioactivity in a sample group. The blank was prepared by adding 15 mM Tris-HCl buffer (pH 7.4) in place of MTP. Inhibition rate (%) was calculated from the values obtained according to the following equation.

Inhibition rate (%)=100×(1 minus ((radioactivity of sample group minus radioactivity of blank group)/(radioactivity of DMSO group minus radioactivity of blank group))).

50% Inhibition rate (IC$_{50}$) was determined on the basis of the above equation. The results were shown in Table 30. In the Table 30, "+++" shows IC$_{50}$ value is less than 10 nM, "++" shows IC$_{50}$ value is 10 nM to less than 100 nM, and "+" shows IC$_{50}$ value is 100 nM to 1000 nM.

TABLE 30

| Example No. | IC$_{50}$ | Example No. | IC$_{50}$ | Example No. | IC$_{50}$ | Example No. | IC$_{50}$ |
| --- | --- | --- | --- | --- | --- | --- | --- |
| 1 | +++ | 1-2 | +++ | 1-3 | +++ | 1-4 | ++ |
| 1-5 | +++ | 1-6 | +++ | 1-7 | +++ | 1-8 | +++ |
| 2 | +++ | 2-2 | +++ | 2-3 | ++ | 2-4 | +++ |
| 2-5 | +++ | 2-6 | +++ | 2-7 | +++ | 2-8 | +++ |
| 2-9 | +++ | 2-10 | +++ | 2-11 | + | 2-12 | +++ |
| 2-13 | +++ | 2-14 | +++ | 2-15 | +++ | 2-16 | +++ |
| 2-17 | + | 2-18 | +++ | 2-19 | +++ | 2-20 | ++ |
| 2-22 | +++ | 2-23 | +++ | 2-25 | +++ | 2-26 | +++ |
| 2-27 | ++ | 2-28 | +++ | 2-29 | +++ | 2-30 | +++ |
| 2-31 | ++ | 2-32 | +++ | 2-33 | +++ | 2-34 | +++ |
| 2-35 | ++ | 2-36 | +++ | 2-37 | ++ | 2-38 | ++ |
| 2-39 | +++ | 2-40 | +++ | 2-41 | +++ | 2-42 | ++ |
| 2-43 | ++ | 2-44 | ++ | 2-45 | + | 2-46 | + |
| 2-47 | + | 2-48 | +++ | 2-49 | +++ | 2-50 | ++ |
| 2-51 | +++ | 2-52 | +++ | 3 | +++ | 3-1 | +++ |
| 3-2 | +++ | 3-3 | +++ | 3-4 | +++ | 3-5 | +++ |
| 3-6 | +++ | 3-7 | +++ | 3-8 | +++ | 3-9 | +++ |
| 3-10 | +++ | 3-12 | +++ | 3-15 | + | 3-16 | +++ |
| 3-17 | ++ | 3-18 | ++ | 3-19 | + | 3-20 | +++ |
| 3-21 | +++ | 3-22 | +++ | 3-23 | +++ | 3-24 | +++ |

Test Example 2

Inhibition of Apolipoprotein B Secretion from HepG2 Cells

HepG2 cells were suspended in Dulbecco's Modified Eagle's Medium (DMEM) (containing 10% fetal bovine serum, 100 units/mL penicillin and 100 µg/mL streptomycin), and placed on a 96-well plate (4×10$^4$ cells/well), then incubated for 24 hours. After removal of the medium, DMEM was replaced by a medium containing a sample dissolved in DMSO or a medium containing DMSO (concentration of DMSO: 0.5%) and incubation was further performed for about 20 hours, after which the supernatant was recovered, and concentration of apo B in the supernatant was assayed by Enzyme-Linked Immunosorbent Assay (ELISA)

ELISA was carried out as follows. Anti-human apo B monoclonal antibody (0.5 µg/well) diluted with a 50 mM sodium carbonate/sodium bicarbonate buffer was placed in a 96-well plate for ELISA, and allowed to stand at room temperature for 15 hours. After washing the plate, a blocking solution (250 µL/well) was placed in the well, and allowed to stand at room temperature for 1.5 hours. After washing the plate, a standard and a sample (100 µL/well) were placed in the well and allowed to stand at room temperature for 1.5 hours. The standard was prepared by adjusting the concentration of the purified human apo B with the DMEM to 0 to 250 ng/mL. After washing the plate, an anti-human apo B polyclonal antibody labeled with a horse radish peroxidase which was diluted in 1:1000 with DEME (100 µL/well) was added, and allowed to stand at room temperature for 1.5 hours. After washing the plate, 2,2-azinobis(3-ethylbenzothiazoline-6-sulfonic acid) solution (100 μL/well) was placed in the well, and allowed to stand at room temperature for 0.5 hour. The reaction was stopped by addition of 2% oxalic acid (100 μL/well), and absorbency at 405 nm was measured. Concentration of apo B in the sample was calculated on the basis of a standard curve of the standard. Inhibition rate (%) was calculated from the assayed values in accordance with the following equation.

Inhibition rate (%)=100×(1 minus (concentration of apo B in sample group/concentration of apo B in DMSO group).

Based on the above equation, 50% inhibition concentration ($IC_{50}$) was determined.

The results were shown in Table 31.

TABLE 31

| Compound of Example (Test Compound) | Inhibition of apolipoprotein B secretion $IC_{50}(\mu M)$ |
|---|---|
| Example 1 | <1 |
| Example 1-2 | <1 |
| Example 1-3 | <1 |
| Example 1-4 | <10 |

Test Example 3

Olive Oil-Loading Test

Syrian hamsters (9-11 weeks of age) under non-fasted conditions were used in the test. Blood was collected previously from orbital venous plexus, and a sample was suspended in 0.5% methyl cellulose (vehicle) and the suspension was forced to be administered orally to the hamsters at a dose of 0.3, 1, 3 or 10 mg/2 mL/kg. Only vehicle in the same volume was administered to the control group. Olive oil (2 mL/kg) was forced to be administered orally 30 minutes after the administration of the sample, and blood was collected from orbital venous plexus 4 hours later. Plasma was recovered from the blood, and the amount of triglyceride (TG) in the plasma was determined by automatic analyzer (Hitachi Co.). The data was expressed in terms of ΔTG(mg/dL)=the value at $4^{th}$ hr minus the value before administration. Inhibition rate (%) was calculated from the data obtained on the basis of the following equation.

Inhibition rate (%)=100×(1 minus ΔTG of sample group/ΔTG of control group).

Test Example 4

Liver TG Release Inhibition Test

Syrian hamsters (9 to 11 weeks of age) which were fasted for one day were used in the test. Blood was collected previously from orbital venous plexus, and a sample was forced to be administered orally to the hamsters at a dose of 30, 100 or 300 mg/2 mL/kg, and the same amount of vehicle was administered to the control group. Triton WR 1339 (2 mL/kg) was intravenously administered to the hamsters 30 minutes after the above administration. Two hours later, blood was collected from orbital venous plexus, and plasma was separated from the blood. The amount of TG in the plasma was determined by automatic analyzer (Hitachi Co.). The data was expressed in terms of TG release velocity (mg/dL/min)= (value at $2^{nd}$ hour minus value before administration)/120.

Inhibition rate (%) was calculated from the data obtained on the basis of the following equation.

Inhibition rate (%)=100×(1 minus TG release velocity of sample/TG release velocity of control group).

Test Example 5

Combination use Test

Japanese white rabbits (male, 19 weeks of age, JW, purchased from Kitayama Labes Co., Ltd.) were fed previously in such a way that they were fed a high cholesterol diet (0.3% cholesterol+3% peanut oil-added RC-4, Product of Oriental Yeast Co., Ltd.) of 70 g/day under limited feeding for one day. The rabbits thus fed were used as a cholesterol-loaded rabbit model, and the grouping of such model was carried out in such a way that there might be no variation in the amount of plasma cholesterol among each group (five rabbits/group). After collection of blood from auricular artery, compound of Example, simvastatin, and compound of Example plus simvastatin were added to a high cholesterol diet and the rabbits were fed using such diet. The rabbits were fed 70 g of each diet every morning. Blood was collected from auricular artery 6 hours after the feeding on the $4^{th}$ day of the administration, and cholesterol level in plasma was assayed.

Test Example 6

Determination of the Concentration in Plasma

Syrian hamsters (9-15 weeks of age) under non-fasted conditions were used in the test. A sample was suspended in 0.5% methyl cellulose (vehicle), and the suspension was forced to be administered orally to the hamsters at a dose of 30 or 100 mg/2 mL/kg. After a fixed period of time, blood was partly collected from orbital venous plexus, and the hamsters were subjected to laparotomy under ether anesthesia, and then blood was collected from portal vein. The blood was immediately cooled with ice to separate plasma. A portion of the plasma was extracted with an organic solvent and the supernatant was recovered. Concentration of the sample (unchanged form) and that of the metabolite in the supernatant were determined quantitatively by high performance liquid chromatography/mass spectrometry (LC/MS) comparing with chromatogram of synthetic standard.

Test Example 7

Metabolic Stability Test in Liver S9 and Small Intestine S9

Human and hamster liver S9 (final concentration: 2 mg protein/mL), and human and hamster small intestine S9 (final concentration: 2 mg protein/mL) were each suspended in 100 mM potassium phosphate buffer (pH 7.4, containing β-nicotinamide adenine dinucleotide phosphate: 1.3 mM, D-glucose-6-phosphate: 3.3 mM, magnesium chloride: 3.3 mM, and glucose-6-phosphate dehydrogenase: 0.4 U/mL). The suspensions were mixed with a solution of a sample (Example 1) in DMSO. The solutions were incubated at 37° C. for 0, 10 and 60 minutes, and an organic solvent was added thereto. The solutions were centrifuged, and the concentration of the sample (unchanged form) in the supernatant was determined by high performance liquid chromatography/mass spectrometry (LC/MS). Based on the data obtained, remaining rate (%) was calculated according to the following equation.

Remaining rate(%)=amount of sample 10 or 60 minutes after incubation/amount of sample at zero time after incubation×100

The results were shown in Table 32.

TABLE 32

|  | Human | | Hamster | |
| --- | --- | --- | --- | --- |
|  | Remaining rate (%) after 10 minutes | Remaining rate (%) after 60 minutes | Remaining rate (%) after 10 minutes | Remaining rate (%) after 60 minutes |
| Small intestine S9 | 7.5 | 1.1 | 4.1 | 0.0 |
| Liver S9 | 6.2 | 1.8 | 1.6 | 0.0 |

It is apparent from the above Test Example 1 that novel compounds and their pharmaceutically acceptable salts of the present invention possess excellent MTP inhibitory activity and also strongly inhibit absorption of triglyceride. Also, as is apparent from Test Example 2, compounds and their pharmaceutically acceptable salts of the present invention have excellent inhibitory activity against apo lipoprotein B secretion. In addition, it is shown from Test Example 4 that even when the compounds of the present invention are administered at high dose, they inhibit little of liver TG release. Further, it is deduced from Test Example 7 that a small amount of active compound which has reached the liver is metabolized rapidly to a metabolite. In addition, since the ester moiety of these metabolites is cleaved by hydrolysis, they have little or no MTP inhibitory activity. Further, Test Example 6 reveals that active compounds after absorption in the small intestine are present in portal vein in a very small amount, and since most of such active compounds are converted into metabolites, they almost do not reach the liver. Furthermore, it is revealed from Test Example 5 that combination use of the compounds of the present invention with other agents for treating hyperlipidemia (statin type agents) can remarkably inhibit the increase of cholesterol and exhibit extremely excellent synergistic effect. These facts elucidate that the compounds of the present invention can be used in combination with other agents, particularly other agents for treating hyperlipidemia, arteriosclerosis, coronary artery diseases, obesity, diabetes or hypertension.

From the fact as mentioned above, it is understood that novel compounds of the present invention and their pharmaceutically acceptable salts can strongly inhibit lipid absorption in the small intestine and further do not inhibit TG release in the liver. This means that the compounds of this invention do not inhibit MTP in the liver, but selectively inhibit MTP in the small intestine.

Therefore, selective inhibition of MTP activity in the small intestine by the compounds of the present invention results in reduction of lipid absorption, which makes it possible to control lipoproteins such as triglyceride, cholesterol and LDL, etc. in blood or to control lipid in cells. Further, since the compounds of the present invention do not affect liver MTP, accumulation of triglyceride does not occur in the liver. Consequently, prevention of fatty liver generation as an adverse effect might be expected. Therefore, the compounds of the present invention can be said novel MTP inhibitors having no side effects such as fatty liver, etc. or, in other words, they are novel agents for the treatment or prophylaxis of hyperlipidemia, arteriosclerosis, coronary artery diseases, obesity, diabetes or hypertension, and further for the treatment or prophylaxis of pancreatitis, hypercholesterolemia, hypertriglyceridemia, etc., which rarely act on MTP in the liver and do substantially inhibit only MTP in the small intestine.

INDUSTRIAL APPLICABILITY

The present invention is useful for the treatment or prophylaxis of hyperlipidemia, arteriosclerosis, coronary artery diseases, obesity, diabetes, or hypertension, and further for the treatment or prophylaxis of pancreatitis, hypercholesterolemia, hypertriglyceridemia, and the like.

The invention claimed is:

1. An ester compound of the formula (1):

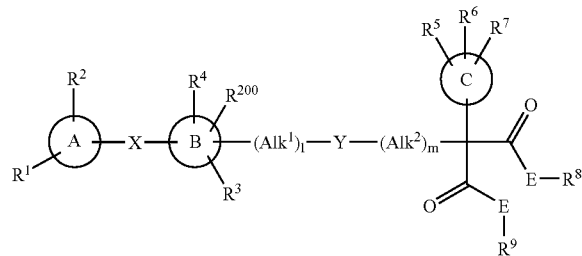

(1)

wherein
$R^1$ is hydrogen or $C_1$-$C_6$ alkyl;
ring A is phenyl;
X is —CON($R^{10}$)—$(CH_2)_n$— (wherein $R^{10}$ is hydrogen, $C_1$-$C_6$ alkyl or $C_3$-$C_7$ cycloalkyl, and n is 0 or an integer of 1 to 3);
$R^2$ is optionally substituted phenyl;
$R^3$, $R^4$ and $R^{200}$ are each independently hydrogen, hydroxy, halogen, optionally substituted $C_1$-$C_6$ alkyl, $C_1$-$C_6$ alkoxy, halo-$C_1$-$C_6$ alkyl, $C_1$-$C_6$ acyl, $C_3$-$C_{10}$ alkoxycarbonylalkyl, —CON($R^{11}$)($R^{12}$)
(wherein $R^{11}$ and $R^{12}$ are each independently hydrogen, optionally substituted $C_1$-$C_6$ alkyl or $C_1$-$C_6$ alkoxy, or $R^{11}$ and $R^{12}$ taken together with the nitrogen atom to which they are attached may form

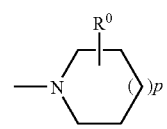

(wherein $R^0$ is hydrogen and p is 0));
—$(CH_2)_{q'}$—N($R^{13}$)($R^{14}$)
(wherein $R^{13}$ and $R^{14}$ are each independently hydrogen, $C_1$-$C_6$ alkyl, $C_2$-$C_7$ alkoxycarbonyl; or $C_1$-$C_6$ acyl; or $R^{13}$ and $R^{14}$ taken together with the nitrogen atom to which they are attached may form

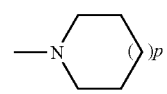

(wherein p has the same meaning as defined above) and q' is 0 or an integer of 1 to 3));
—CO—($R^{15}$)
(wherein $R^{15}$ is hydroxy, $C_1$-$C_6$ alkyl, $C_1$-$C_6$ alkoxy, optionally substituted $C_6$-$C_{14}$ aryloxy or $C_7$-$C_{16}$ aralkyloxy); or
—$(CH_2)_{r'}$—O—CO—$R^{100'}$
(wherein $R^{100'}$ is $C_1$-$C_6$ alkyl, $C_1$-$C_6$ alkoxy, $C_2$-$C_{12}$ alkoxyalkyl or —N($R^{40}$)($R^{41}$) (wherein $R^{40}$ and $R^{41}$ are each independently hydrogen, $C_1$-$C_6$alkyl or optionally substituted $C_6$-$C_{14}$aryl, and r' is 0 or an integer of 1 to 3));

ring B is

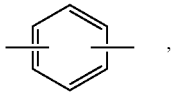

Alk$^1$ is methylene;
Alk$^2$ is methylene;
l is 0 or an integer of 1 to 3;
m is 0 or an integer of 1 to 3;
ring C is

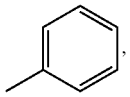

$R^5$, $R^6$ and $R^7$ are each independently hydrogen or $C_1$-$C_6$ alkyl;

$R^8$ and $R^9$ are each independently hydrogen or $C_1$-$C_6$ alkyl;

E is —O— or —N($R^{90}$)— wherein $R^{90}$ is hydrogen or $C_1$-$C_6$ alkyl; and Y is —O—CO—O—, —O—CO—, —CO—O—, —CO—O—C($R^{110}$)($R^{111}$)—O—CO—, —CO—O—C($R^{110}$)($R^{111}$)—O—CO—O—, —O—CO—O—C($R^{110}$)($R^{111}$)—O—CO—, —O—CO—C($R^{110}$)($R^{111}$)—O—, —O—CO—C($R^{110}$)($R^{111}$)—C($R^{110}$)($R^{111}$)—O— or —O—C($R^{110}$)($R^{111}$)—CO—O—

(wherein $R^{110}$ and $R^{111}$ are each independently hydrogen or $C_1$-$C_6$ alkyl), provided that when Y is —CO—O—, then $R^3$ is —(CH$_2$)$_{r'}$—O—CO—$R^{100'}$ wherein $R^{100'}$ and r' each has the same meaning as defined above;

or a pharmaceutically acceptable salt thereof.

2. The ester compound according to claim 1, which is represented by the formula (1'):

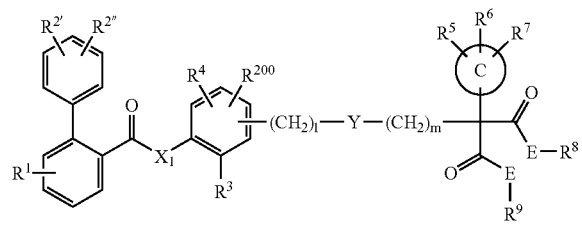

wherein $R^{2'}$ and $R^{2''}$ are each independently hydrogen, $C_1$-$C_6$ alkyl, $C_3$-$C_7$ cycloalkyl, $C_1$-$C_6$ alkoxy, halogen, halo-$C_1$-$C_6$ alkyl, halo-$C_1$-$C_6$ alkyloxy, $C_1$-$C_6$ acyl, $C_2$-$C_6$ alkenyl, or cyano, $X_1$ is —NR$^{10}$, provided that when Y is —CO—O—, then $R^3$ is —(CH$_2$)$_{r'}$—O—CO—R$^{100'}$; or a pharmaceutically acceptable salt thereof.

3. An ester compound represented by the formula:

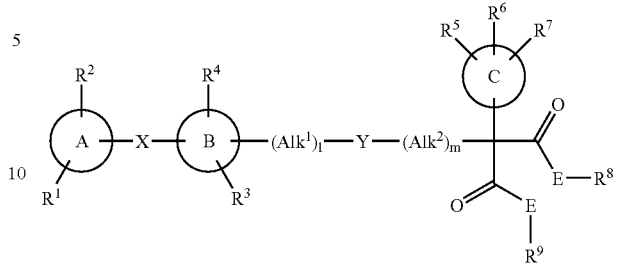

wherein
$R^1$ is hydrogen, or $C_1$-$C_6$ alkyl;
ring A is phenyl;
X is —CON($R^{10}$)—(CH$_2$)$_n$— (wherein $R^{10}$ is hydrogen, $C_1$-$C_6$ alkyl or $C_3$-$C_7$ cycloalkyl, and n is 0 or an integer of 1 to 3);
$R^2$ is optionally substituted phenyl;
$R^3$ and $R^4$ are each independently hydrogen, hydroxy, halogen, optionally substituted $C_1$-$C_6$ alkyl, $C_1$-$C_6$ alkoxy, halo-$C_1$-$C_6$ alkyl, $C_1$-$C_6$ acyl, $C_3$-$C_{10}$ alkoxycarbonylalkyl, —CON($R^{11}$)($R^{12}$)
(wherein $R^{11}$ and $R^{12}$ are each independently hydrogen, $C_1$-$C_6$ alkyl, or $C_1$-$C_6$ alkoxy, or $R^{11}$ and $R^{12}$ taken together with the nitrogen atom to which they are attached may form

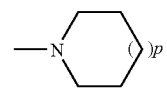

(wherein p is 0));
—(CH$_2$)$_q$—N($R^{13}$)($R^{14}$)
(wherein $R^{13}$ and $R^{14}$ are each independently hydrogen, $C_1$-$C_6$ alkyl, $C_2$-$C_7$ alkoxycarbonyl or $C_1$-$C_6$ acyl or $R^{13}$ and $R^{14}$ taken together with the nitrogen atom to which they are attached may form

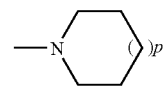

(wherein p has the same meaning as defined above), and q is 0 or an integer of 1 to 3));
—CO—($R^{15}$)
(wherein $R^{15}$ is hydroxy, $C_1$-$C_6$ alkoxy, optionally substituted $C_6$-$C_{14}$ aryloxy, optionally substituted $C_7$-$C_{16}$ aralkyloxy or optionally substituted $C_1$-$C_6$ alkyl); or
—(CH$_2$)$_{r'}$—O—CO—$R^{\Phi'}$
(wherein $R^{100'}$ is $C_1$-$C_6$ alkyl, $C_1$-$C_6$ alkoxy or $C_2$-$C_{12}$ alkoxyalkyl, and r' is 0 or an integer of 1 to 3);

ring B is

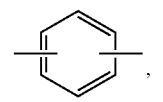

Alk$^1$ is methylene;
Alk$^2$ is methylene;
l is 0 or an integer of 1 to 3;
m is 0 or an integer of 1 to 3;
ring C is

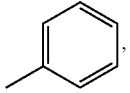

R$^5$, R$^6$ and R$^7$ are each independently hydrogen, C$_1$-C$_6$ alkyl
R$^8$ and R$^9$ are each independently hydrogen or C$_1$-C$_6$ alkyl;
E is —O— or —NH—; and
Y is —O—CO—O—, —O—CO—, —CO—O—, —CO—O—C(R$^{110}$)(R$^{111}$)—O—CO—, —CO—O—C(R$^{110}$)(R$^{111}$)—O—CO—O—, or —O—CO—O—C(R$^{110}$)(R$^{111}$)—O—CO—, (wherein R$^{110}$ and R$^{111}$ are each independently hydrogen or C$_1$-C$_6$ alkyl, provided that when Y is —CO—O—, then R$^3$ is —(CH$_2$)$_{r'}$—O—CO—R$^{100'}$ wherein R$^{100'}$ and r' each has the same meaning as defined above;
or a pharmaceutically acceptable salt thereof.

4. The ester compound according to claim 3, which is represented by the formula:

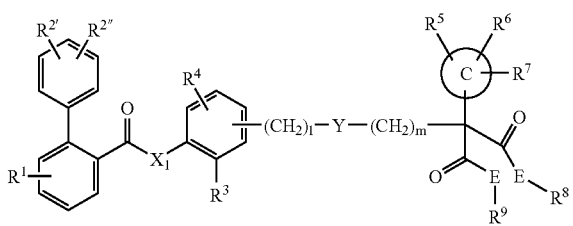

wherein R$^{2'}$ and R$^{2''}$ are each independently hydrogen, C$_1$-C$_6$ alkyl, C$_3$-C$_7$ cycloalkyl, C$_1$-C$_6$ alkoxy, halogen, halo-C$_1$-C$_6$ alkyl, halo-C$_1$-C$_6$ alkyloxy, C$_1$-C$_6$ acyl, C$_2$-C$_6$ alkenyl or cyano; and
X$_1$ is —O— or —NR$^{10}$;
or a pharmaceutically acceptable salt thereof.

5. A pharmaceutical composition, which comprises the ester compound or a pharmaceutically acceptable salt thereof according to claim 1, and a pharmaceutically acceptable carrier.

6. An MTP (microsomal triglyceride transfer protein) inhibitor, which comprises the ester compound or a pharmaceutically acceptable salt thereof according to claim 1 as an active ingredient.

7. A method for the treatment of hyperlipidemia, which comprises administering to a host in need thereof an effective amount of the ester compound or a pharmaceutically acceptable salt thereof according to claim 1.

8. A method for the treatment of arteriosclerosis, which comprises administering to a host in need thereof an effective amount of the ester compound or a pharmaceutically acceptable salt thereof according to claim 1.

9. A method for the treatment of obesity, which comprises administering to a host in need thereof an effective amount of the ester compound or a pharmaceutically acceptable salt thereof according to claim 1.

10. A biphenyl compound of the formula (100):

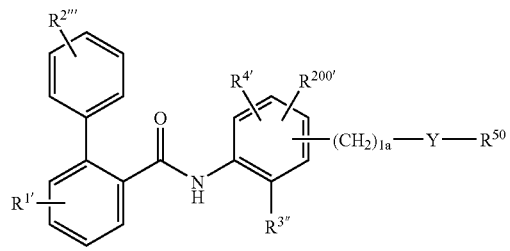

wherein
R$^{1'}$ is hydrogen, C$_1$-C$_6$ alkyl, halogen, halo-C$_1$-C$_6$ alkyl, C$_1$-C$_6$ alkoxy or —(CH$_2$)$_r$—O—CO—R$^{100}$ (wherein R$^{100}$ is C$_1$-C$_6$ alkyl, C$_1$-C$_6$ alkoxy or C$_2$-C$_{12}$ alkoxyalkyl, and r is 0 or an integer of 1 to 3;
R$^{2'''}$ is hydrogen, C$_1$-C$_6$ alkyl, halogen, halo-C$_1$-C$_6$ alkyl or C$_2$-C$_6$ alkenyl;
R$^{3''}$ is —CON(R$^{11a}$)(R$^{12a}$) wherein R$^{11a}$ and R$^{12a}$ are each independently hydrogen, C$_1$-C$_6$alkyl or C$_1$-C$_6$ alkoxy or R$^{11a}$ and R$^{12a}$ may be taken together with the nitrogen to which they are attached to form

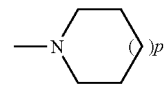

(in which p is 0 or an integer of 1 to 2) or —(CH$_2$)$_{r'}$—O—CO—R$^{100'}$ (wherein R$^{100'}$ is C$_1$-C$_6$ alkyl, C$_1$-C$_6$ alkoxy or C$_2$-C$_{12}$ alkoxyalkyl, and r' is 0 or an integer of 1 to 3);
R$^{4'}$ and R$^{200'}$ are each independently hydrogen, halogen, C$_1$-C$_6$ alkyl or halo-C$_1$-C$_6$ alkyl;
R$^{50}$ is hydrogen, C$_1$-C$_6$ alkyl, optionally substituted C$_6$-C$_{14}$ aryl or optionally substituted C$_7$-C$_{16}$ aralkyl;
Y is —O—CO—O—, —O—CO—, —CO—O—, —O—CO—C(R$^{110}$)(R$^{111}$)—O—, —O—CO—C(R$^{110}$)(R$^{111}$)—C(R$^{110}$)(R$^{111}$)—O— or —O—C(R$^{110}$)(R$^{111}$)—CO—O— (wherein R$^{110}$ and R$^{111}$ are each independently hydrogen or C$_1$-C$_6$ alkyl), provided that when Y is —CO—O—, then R$^{3''}$ is —(CH$_2$)$_{r'}$—O—CO—R$^{100'}$ wherein R$^{100'}$ and r' each has the same meaning as defined above; and
1a is an integer of 1 to 3;
or a pharmaceutically acceptable salt thereof.

11. A biphenyl compound of the formula:

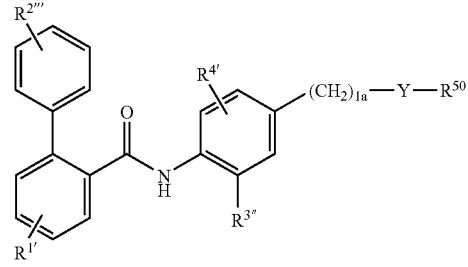

wherein
R$^{1'}$ is hydrogen, C$_1$-C$_6$ alkyl, halogen, halo-C$_1$-C$_6$ alkyl, C$_1$-C$_6$ alkoxy or —(CH$_2$)$_r$—O—CO—R$^{100}$ (wherein $R^{100}$ is $C_1$-$C_6$ alkyl, $C_1$-$C_6$ alkoxy or $C_2$-$C_{12}$ alkoxyalkyl, and r is 0 or an integer of 1 to 3);

$R^{2'''}$ is hydrogen, $C_1$-$C_6$ alkyl, halogen, halo-$C_1$-$C_6$ alkyl or $C_2$-$C_6$ alkenyl;

$R^{3''}$ is —CON($R^{11a}$)($R^{12a}$) (wherein $R^{11a}$ and $R^{12a}$ are each independently hydrogen, $C_1$-$C_6$ alkyl or $C_1$-$C_6$ alkoxy or $R^{11a}$ and $R^{12a}$ may be taken together with the nitrogen to which they are attached to form

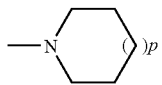

(wherein p is 0 or an integer of 1 to 2) or —$(CH_2)_{r'}$—O—CO—$R^{100'}$ (wherein $R^{100'}$ is $C_1$-$C_6$ alkyl, $C_1$-$C_6$ alkoxy or $C_2$-$C_{12}$ alkoxyalkyl, and r' is 0 or an integer of 1 to 3);

$R^{4'}$ is hydrogen, halogen, $C_1$-$C_6$ alkyl or halo-$C_1$-$C_6$ alkyl;

$R^{50}$ is hydrogen, $C_1$-$C_6$ alkyl, optionally substituted $C_6$-$C_{14}$ aryl or optionally substituted $C_7$-$C_{16}$ aralkyl;

Y is —O—CO—O—, —O—CO— or —CO—O—, C($R^{110}$)($R^{111}$)—O—provided that when Y is —CO—O—, then $R^{3''}$ is —$(CH_2)_{r'}$—O—CO—$R^{100'}$ (wherein $R^{100'}$ and r' each has the same meaning as defined above); and 1a is an integer of 1 to 3;

or a pharmaceutically acceptable salt thereof.

\* \* \* \* \*